US012760328B2

(12) United States Patent
Dowen et al.

(10) Patent No.: US 12,760,328 B2
(45) Date of Patent: Oct. 13, 2026

(54) COMPOSITIONS AND METHODS FOR ALTERING GENE EXPRESSION

(71) Applicant: Whitehead Institute for Biomedical Research, Cambridge, MA (US)

(72) Inventors: Jill M. Dowen, Chapel Hill, NC (US); Zi Peng Fan, Waltham, MA (US); Denes Hnisz, Cambridge, MA (US); Tong Ihn Lee, Somerville, MA (US); Richard A. Young, Boston, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 15/282,905

(22) Filed: Sep. 30, 2016

(65) Prior Publication Data

US 2017/0130247 A1 May 11, 2017

Related U.S. Application Data

(60) Provisional application No. 62/234,770, filed on Sep. 30, 2015.

(51) Int. Cl.
*C12N 15/63* (2006.01)
*C12N 15/06* (2006.01)
*C12N 15/90* (2006.01)
*A01K 67/00* (2006.01)

(52) U.S. Cl.
CPC ........... *C12N 15/907* (2013.01); *C12N 15/90* (2013.01); *C12N 2800/80* (2013.01)

(58) Field of Classification Search
CPC ...... C12N 15/907; C12N 15/90; C12N 9/226; C12N 2800/80; C12N 2310/20
See application file for complete search history.

(56) References Cited

U.S. PATENT DOCUMENTS

2002/0114788 A1* 8/2002 Isacson .................. A61K 35/30 424/93.21
2014/0287932 A1* 9/2014 Hnisz ................. C12N 15/1034 506/2
2016/0215280 A1* 7/2016 Fanucchi ................. C12N 9/22
2017/0224843 A1* 8/2017 Deglon .................... C12N 9/52

FOREIGN PATENT DOCUMENTS

WO WO-2017011710 A2 * 1/2017 ............... C12Q 1/68

OTHER PUBLICATIONS

Sander et al. CRISPR-Cas systems for editing, regulating and targeting genomes. Nature Biotechnology 32:347-355, (Year: 2014).*
Katainen et al. CTCF/cohesin-binding sites are frequently mutated in cancer. Nature Genetics 47: 818-821 plus 2—page Online Methods; (Year: 2015).*
Zhang et al. Off-target effects in CRISPR/Cas9-mediated genome engineering. Molecular Therapy 4, e264; doi:10,1038/mtna.2015. 37, 8 pages, (Year: 2015).*
Wu et al. Target specificity of the CRISPR-Cas9 system. Quant Biol. 2:59-70; doi:10.1007/s40484-014-0030-x, 19 pages, (Year: 2014).*
Dowen, Jill M. et al., Control of Cell Identity Genes Occurs in Insulated Neighborhoods in Mammalian Chromosomes, *Cell*, vol. 159 , Issue 2, 374-387.
Dixon, Jesse, Topological domains in mammalian genomes identified byinteractions, *Nature* 485, 376-380, May 17, 2012.
Hnisz, D., Abraham, et al., Super-enhancers in the control of cell identity and disease, *Cell* 155, 934-947, (2013).
Whyte, W.A., et al. Master transcription factors and mediator establish super-enhancers at key cell identity genes, *Cell* 153, 307-319, (2013).
Phillips-Cremins, J.E., et al., Chromatin insulators: linking genome organization to cellular function. *Mol. Cell* 50, 461-474, (2013).
Kagey, M.H., et al., Mediator and cohesin connect gene expression and chromatin architecture. *Nature* 467, 430-435, (2010).
Handoko, L., et al., CTCF-mediated functional chromatin interactome in pluripotent cells. *Nat. Genet.* 43, 630-638, (2011).
Shen, Y., et al., A map of the cis-regulatory sequences in the mouse genome. *Nature* 488, 116-120, (2012).
Sofueva, S., et al., Cohesin-mediated interactions organize chromosomal domain architecture. *EMBO J.* 32, 3119-3129, (2013).
DeMare, L.E., at al., The genomic landscape of cohesin-associated chromatin interactions. *Genome Res.* 23, 1224-1234, (2013).
Hawkins, R.D., et al., Dynamic chromatin states in human ES cells reveal potential regulatory sequences and genes involved in pluripotency. *Cell Res.* 21, 1393-1409, (2011).
Zhang, Yong, et al. "Model-based analysis of ChIP-Seq (MACS)." *Genome biology* 9.9 (2008): R137.
De Wit, Elzo, et al. "The pluripotent genome in three dimensions is shaped around pluripotency factors." *Nature* 501.7466: 227-231 (2013).

* cited by examiner

*Primary Examiner* — Quang Nguyen
(74) *Attorney, Agent, or Firm* — Morse, Barnes-Brown & Pendleton, P.C.; Lisa M. Warren, Esq.; Erin E. Bryan, Esq.

(57) ABSTRACT

Provided herein are improved compositions and methods for the directed control of gene expression.

8 Claims, 43 Drawing Sheets

Specification includes a Sequence Listing.

A.

B.

C.

D

A.

B.

C.

D.

A.

B.

C.

D.

E.

A.

B.

C.

D.

E.

A.

B.

C.

D.

E.

F.

A.

B.

C.

Figure 7 (Figure S1)
A.
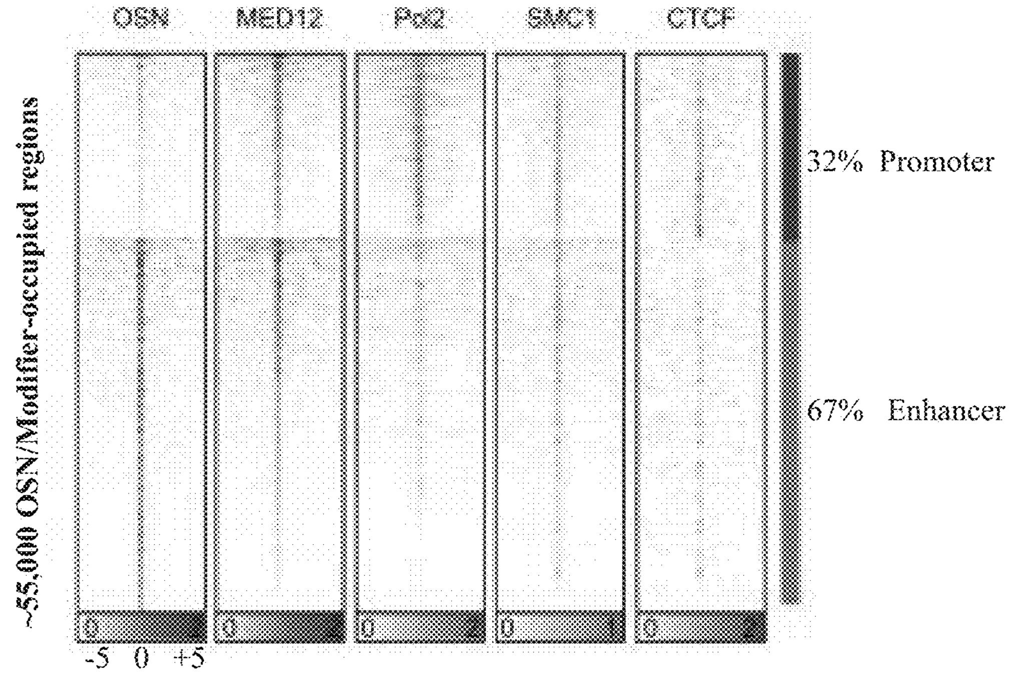

Figure 7 (Figure S1)
B.
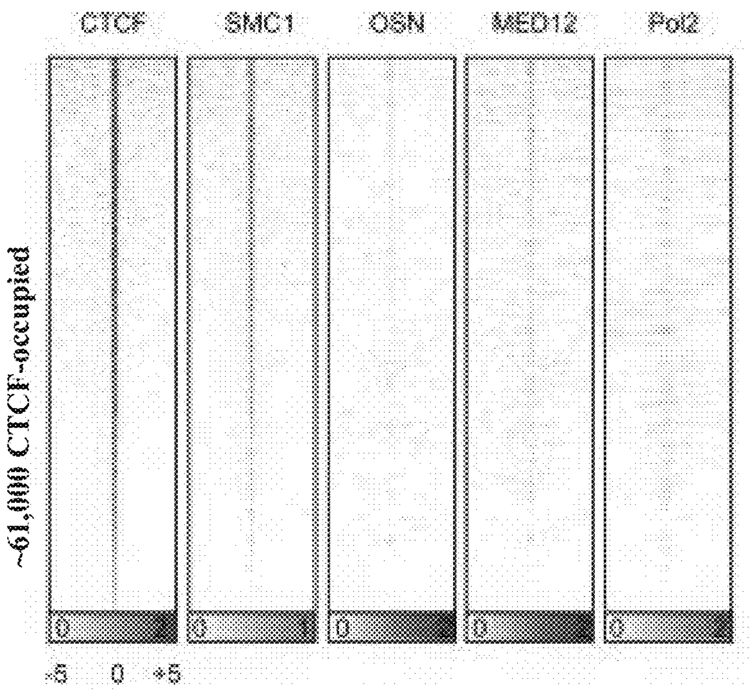

Figure 7 (Figure S1)
C.
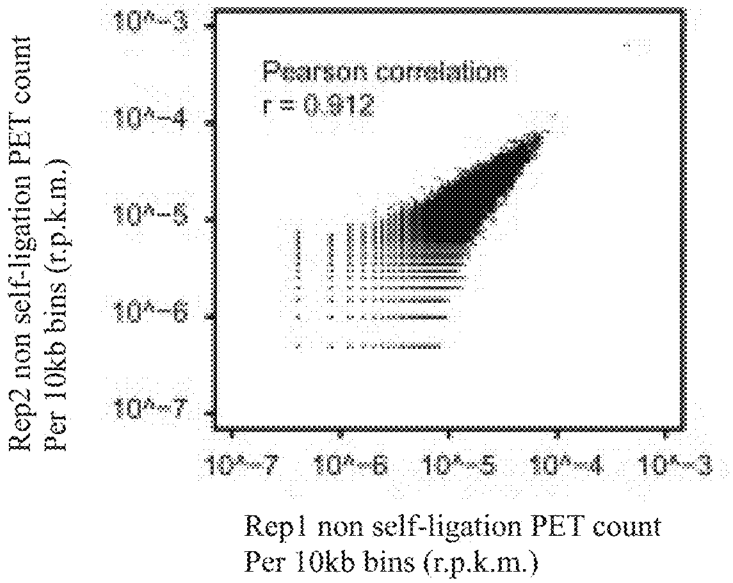
D.
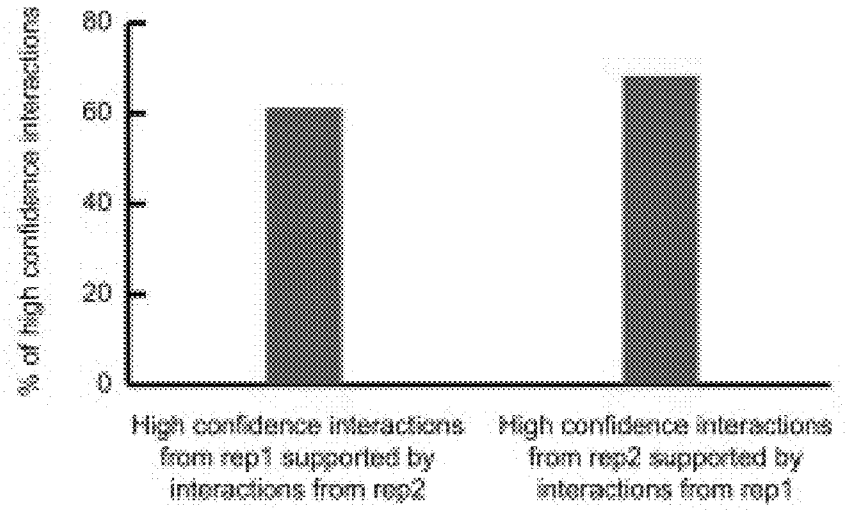

Figure 7 (Figure S1)
E.
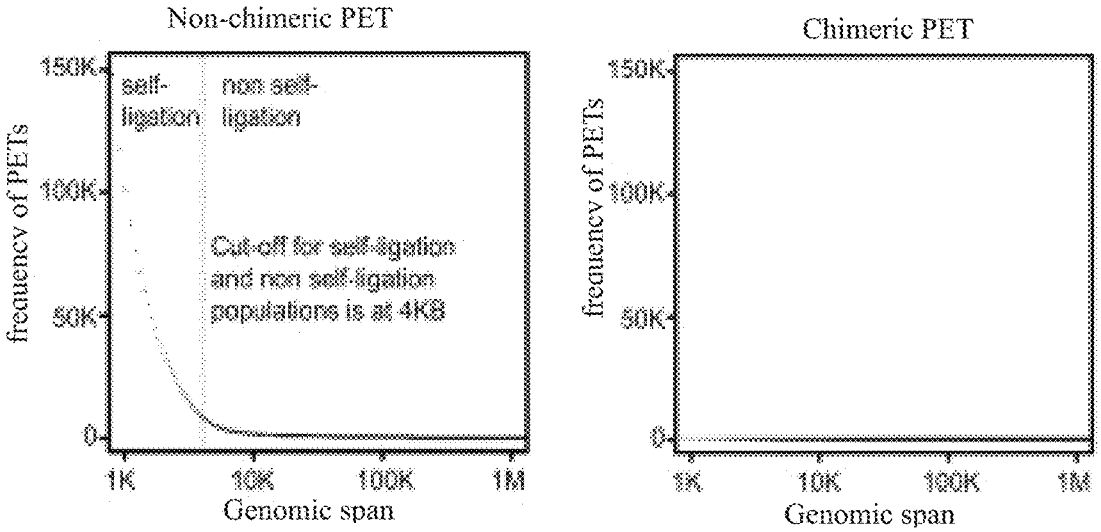
F.
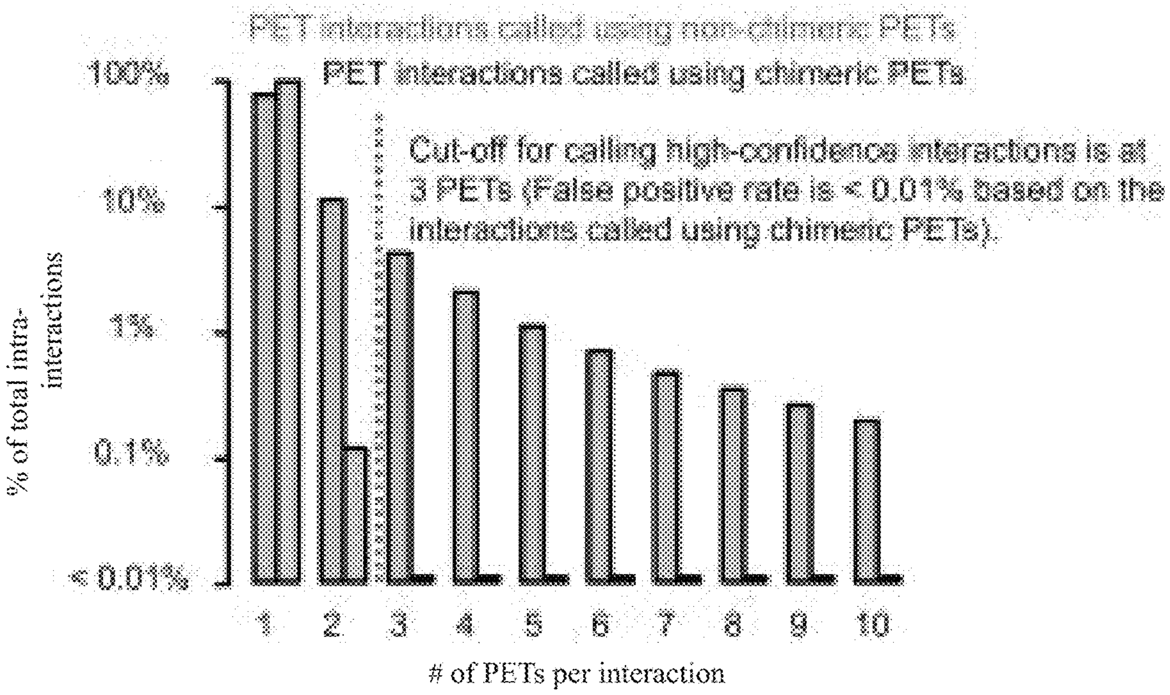

Figure 7 (Figure S1)
G.
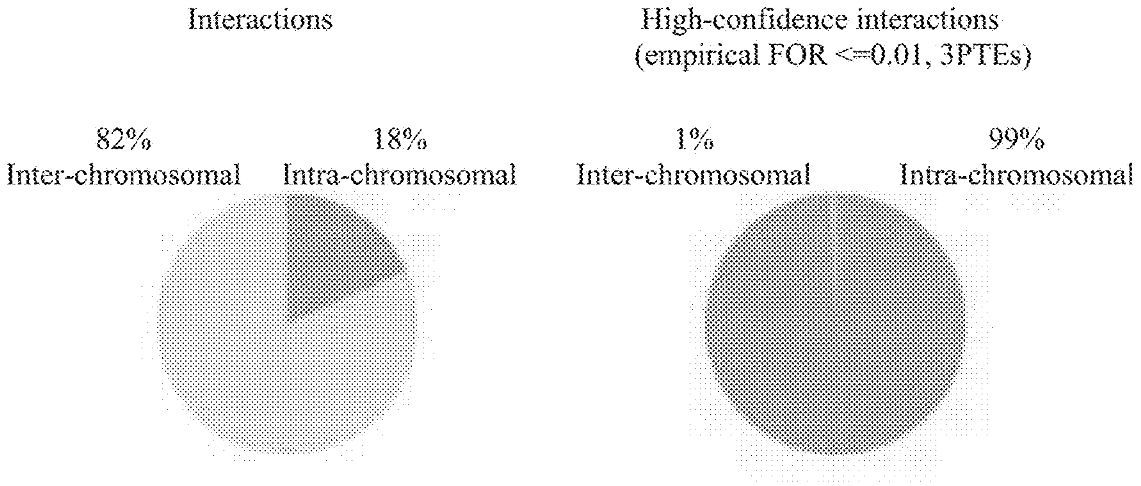
H.
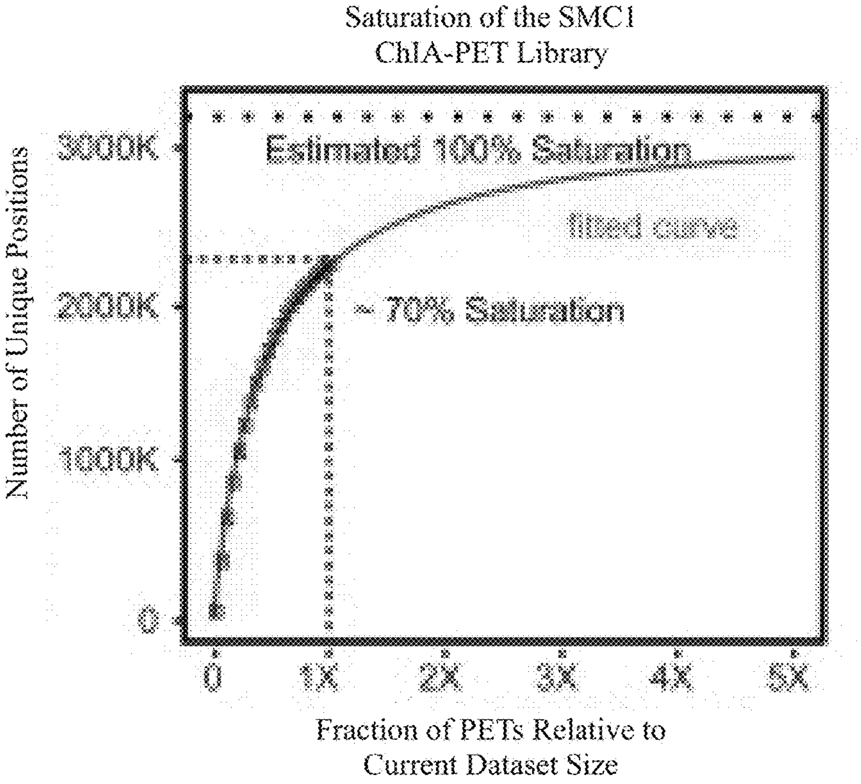

Figure 8 (Figure S2)
A.
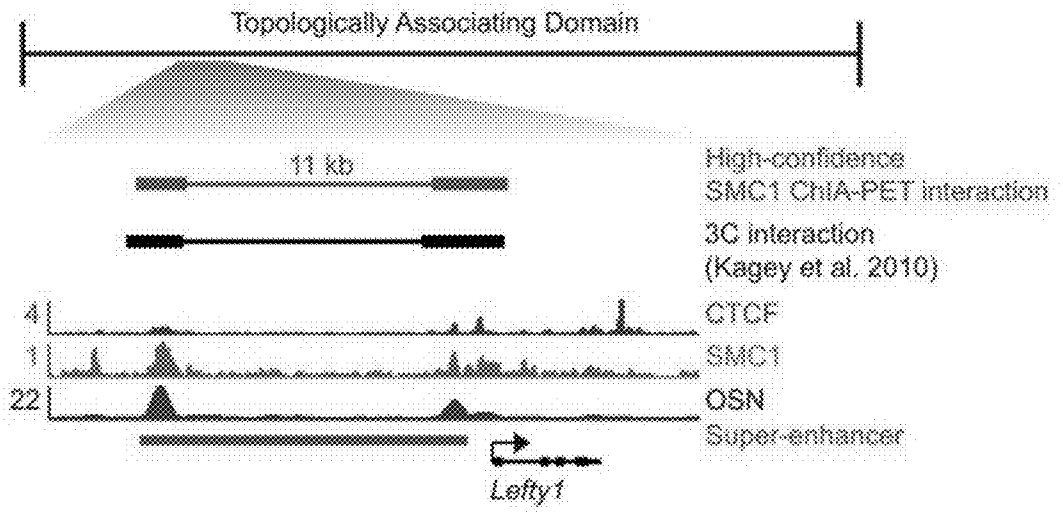
B.
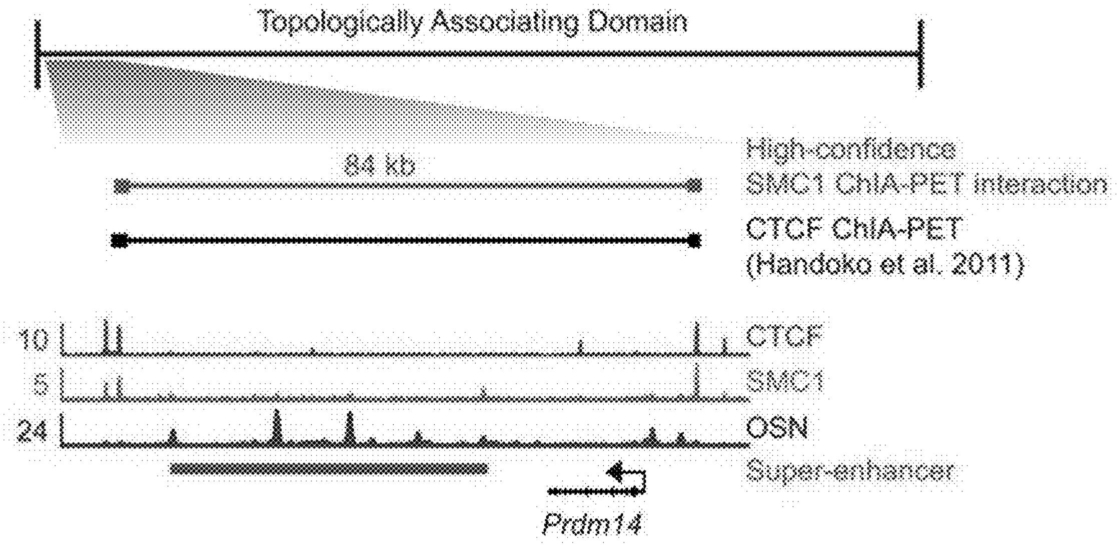

Figure 8 (Figure S2)
C.
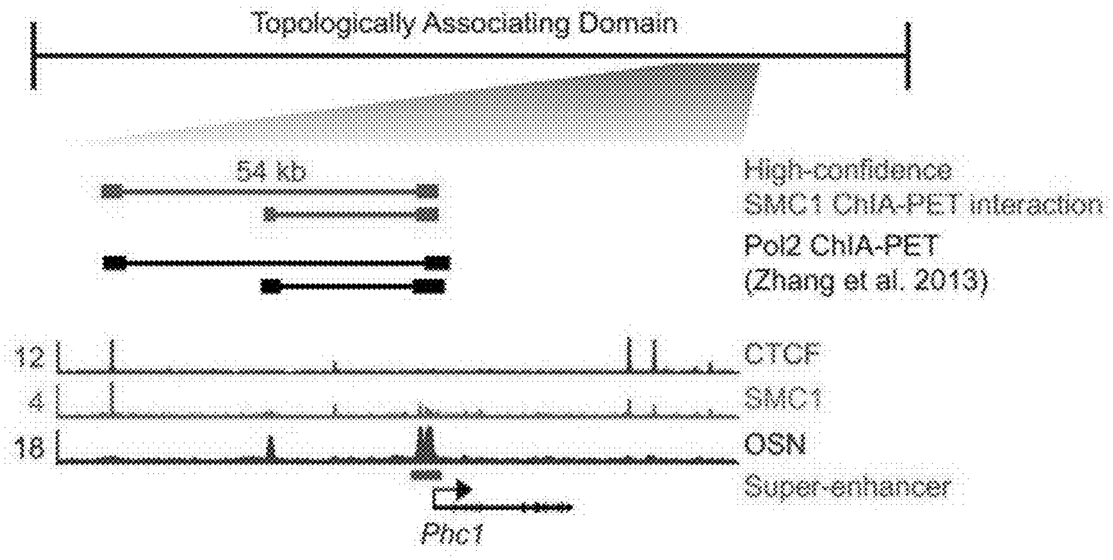
D.
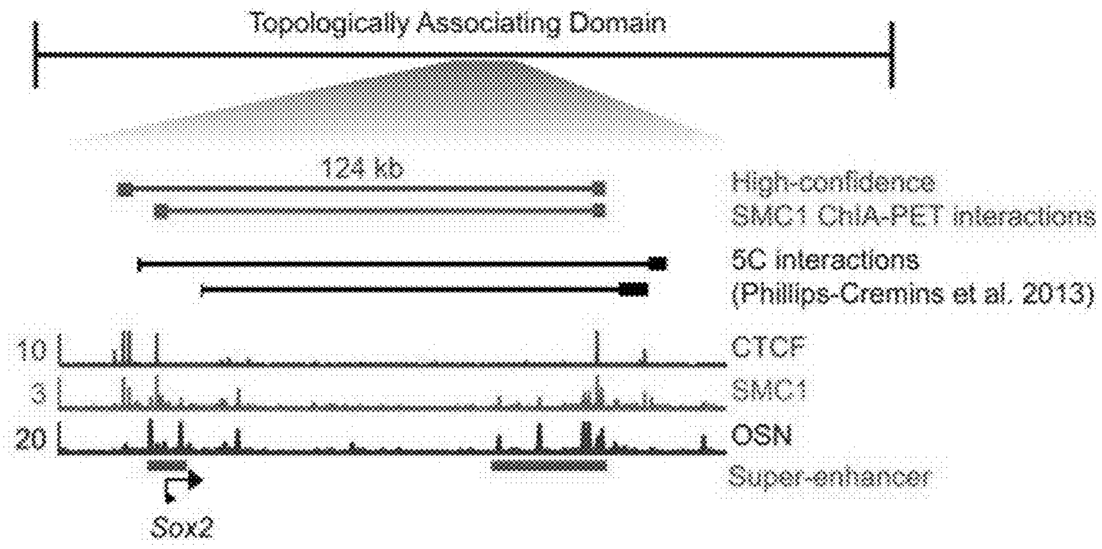

Figure 9 (Figure S3)
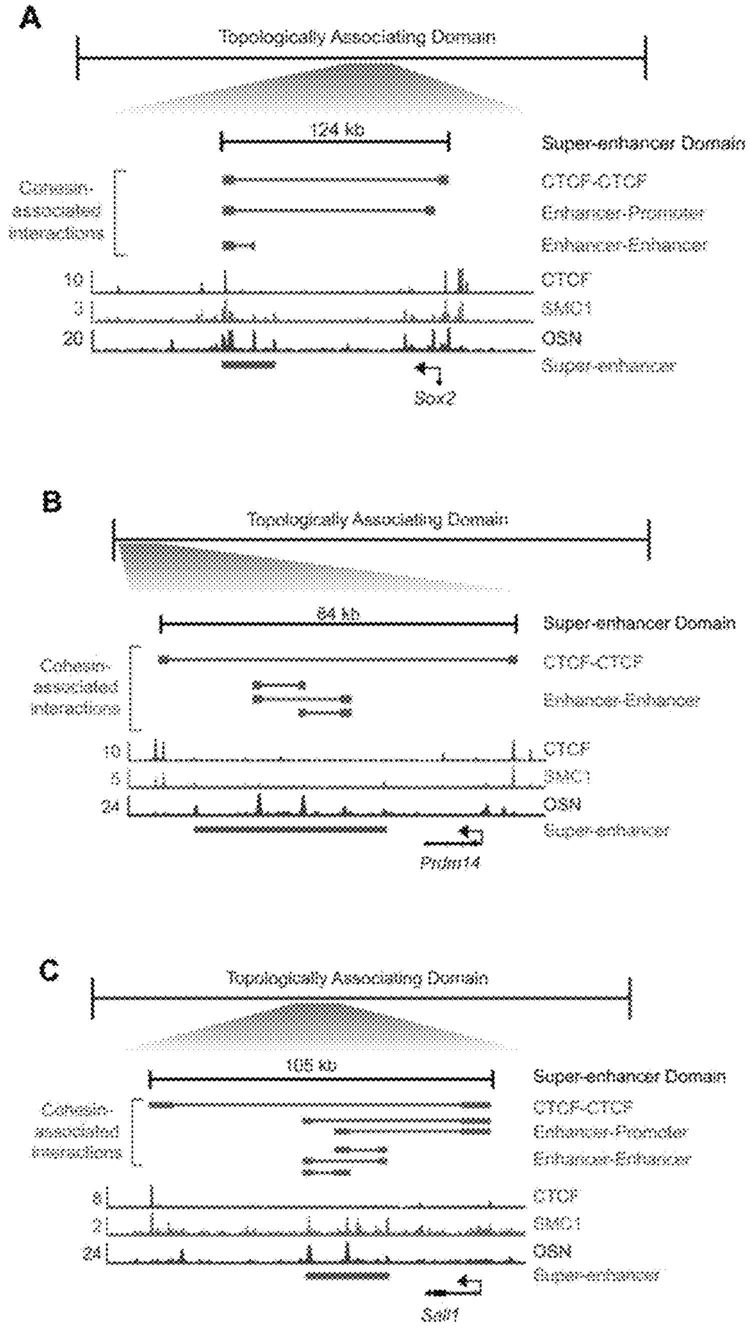

Figure 9 (Figure S3)
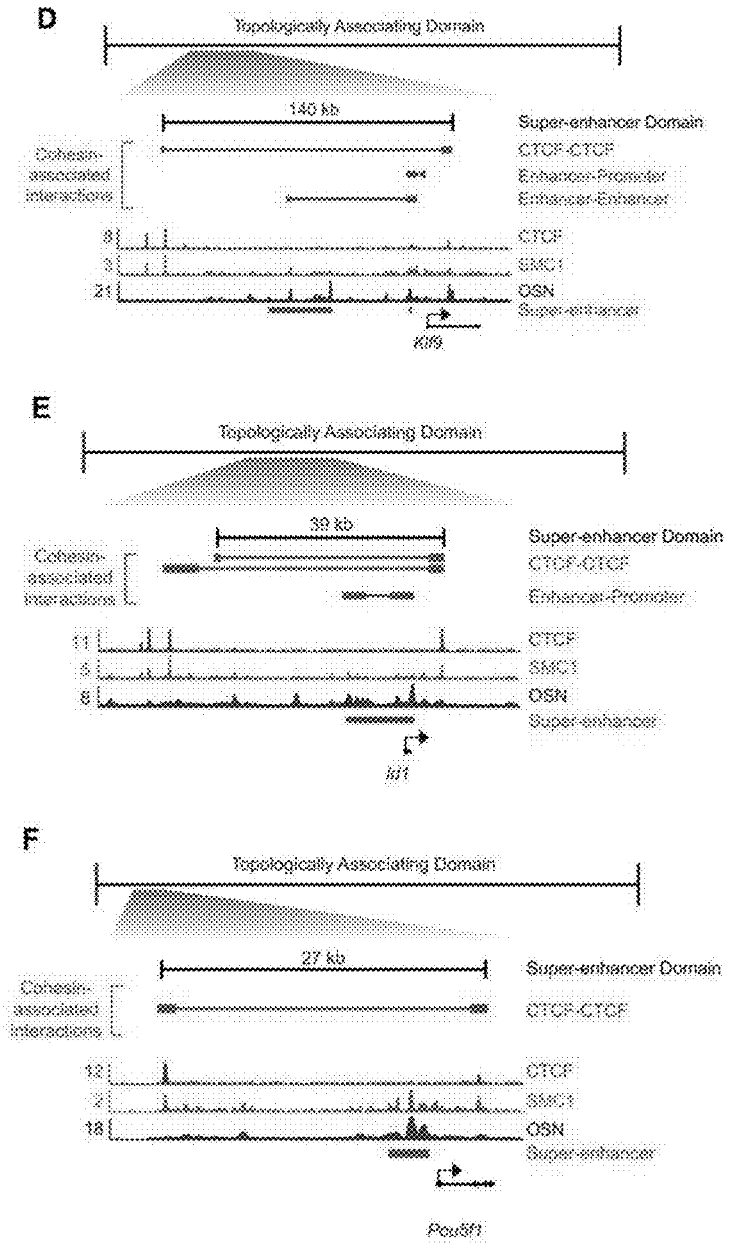

Figure 9 (Figure S3)
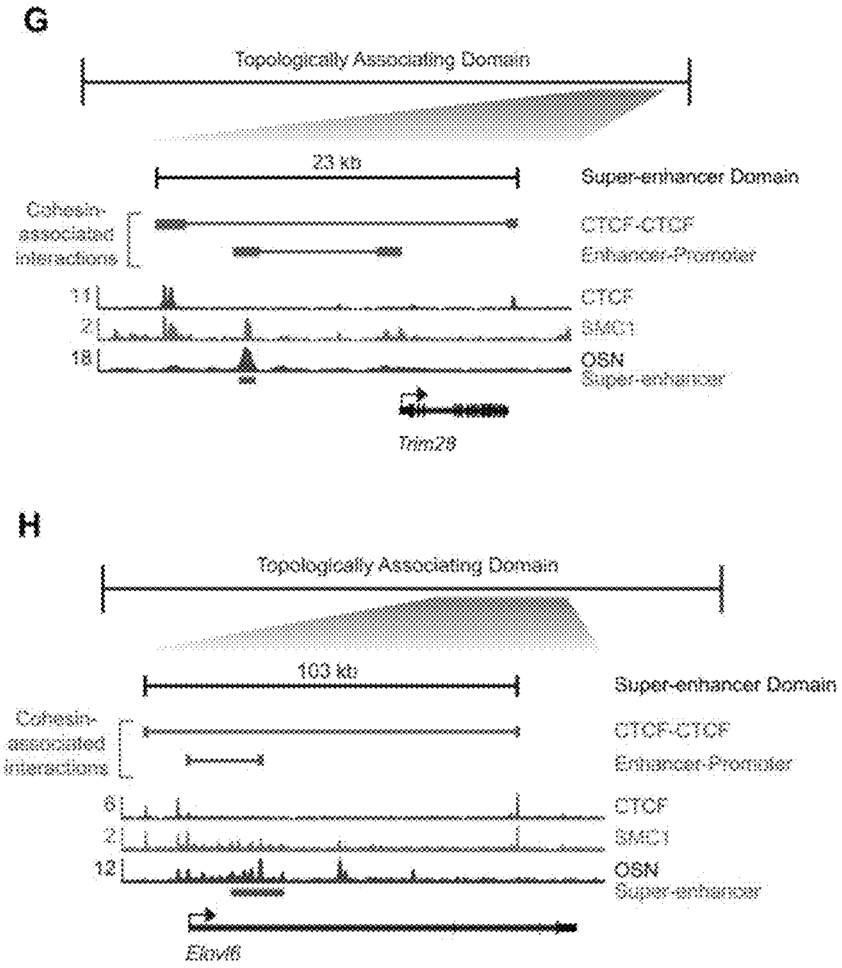

Figure 9 (Figure S3)
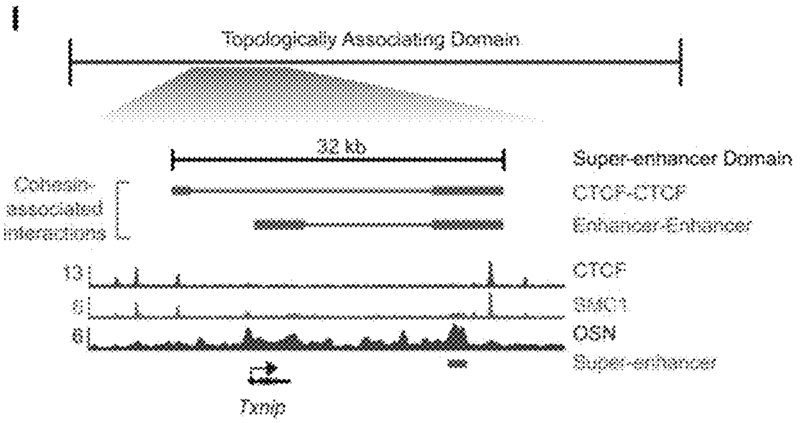
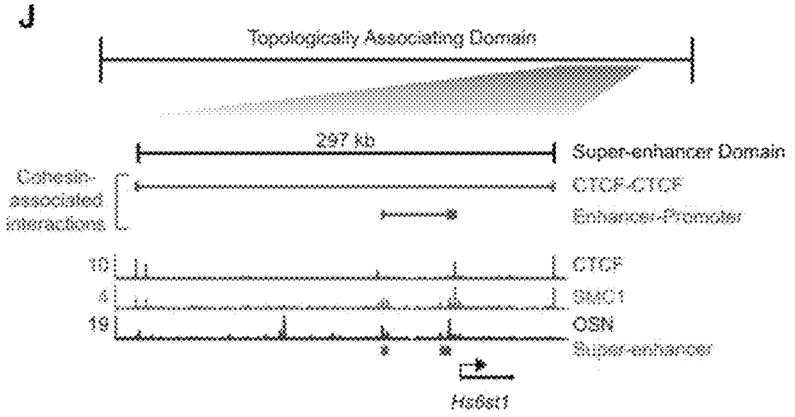

Figure 10 (Figure S4)
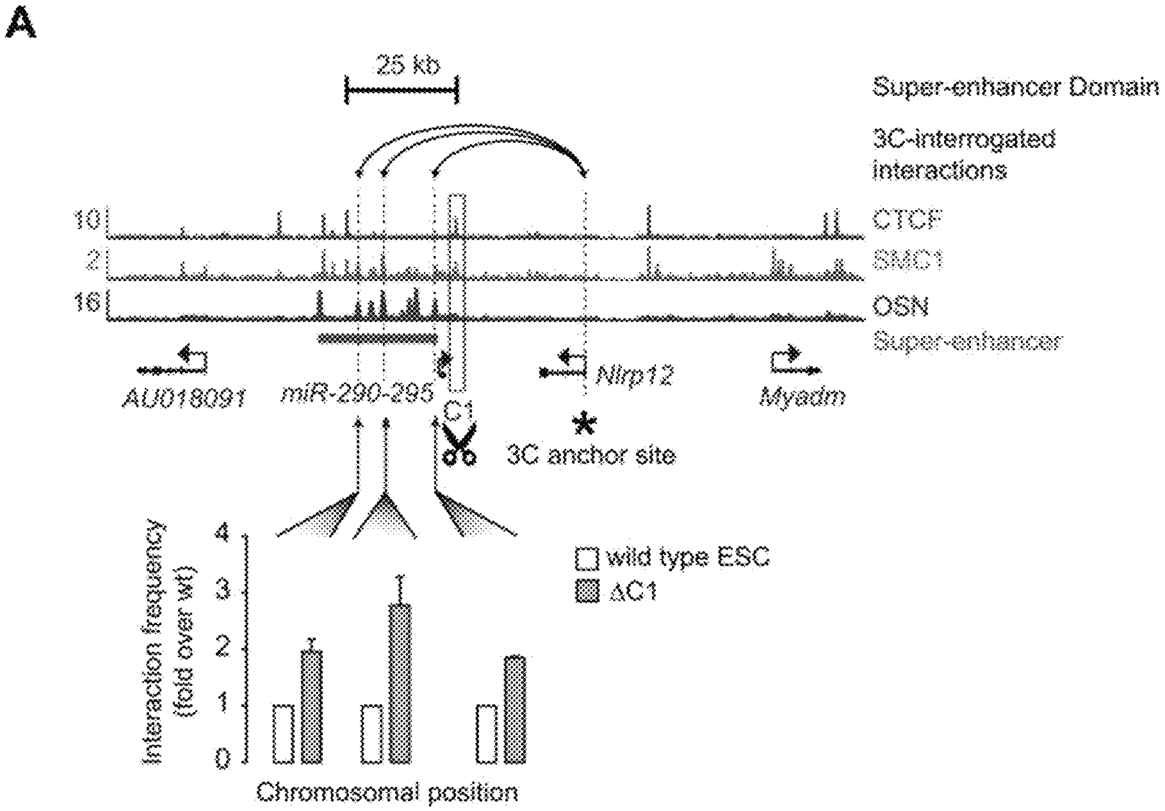

Figure 10 (Figure S4)
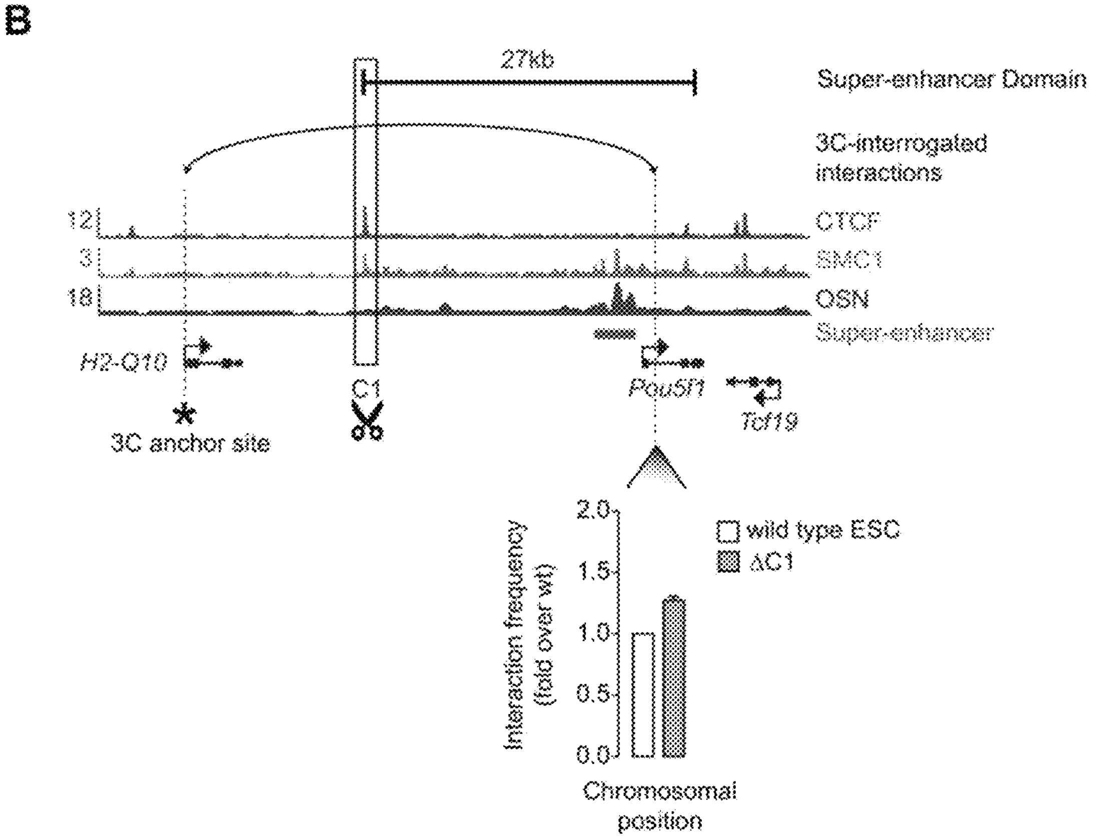

Figure 10 (Figure S4)
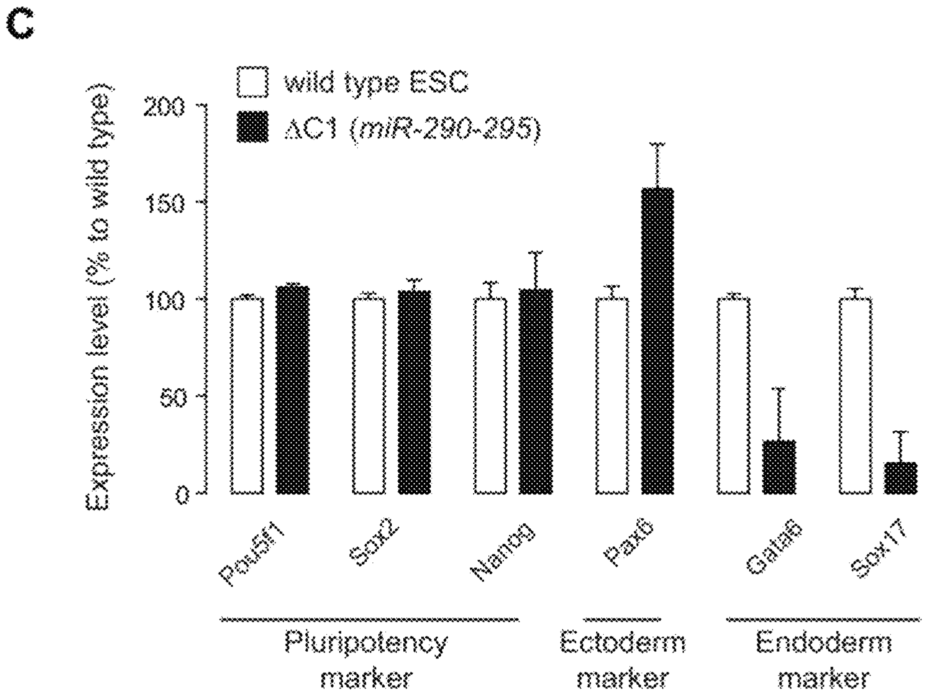

Figure 11 (Figure S5)
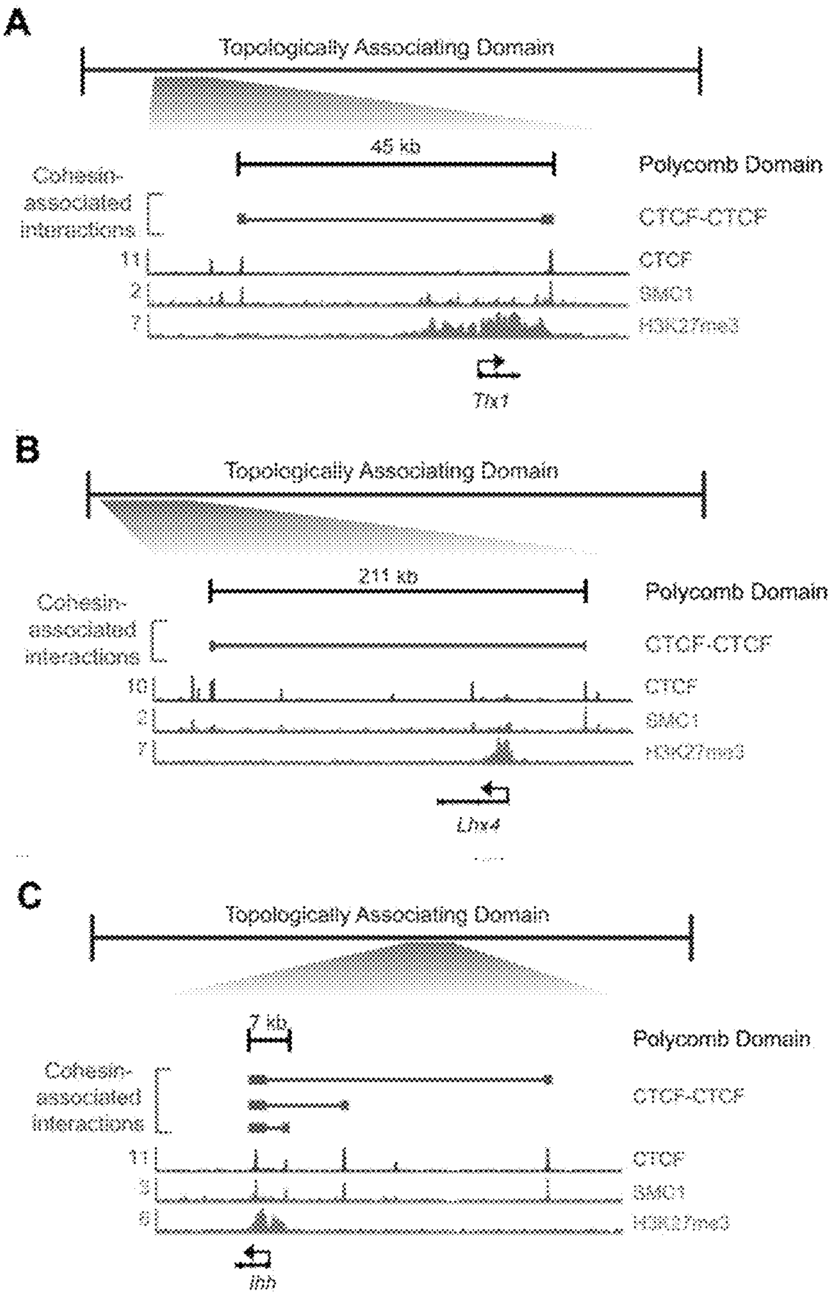

Figure 11 (Figure S5)
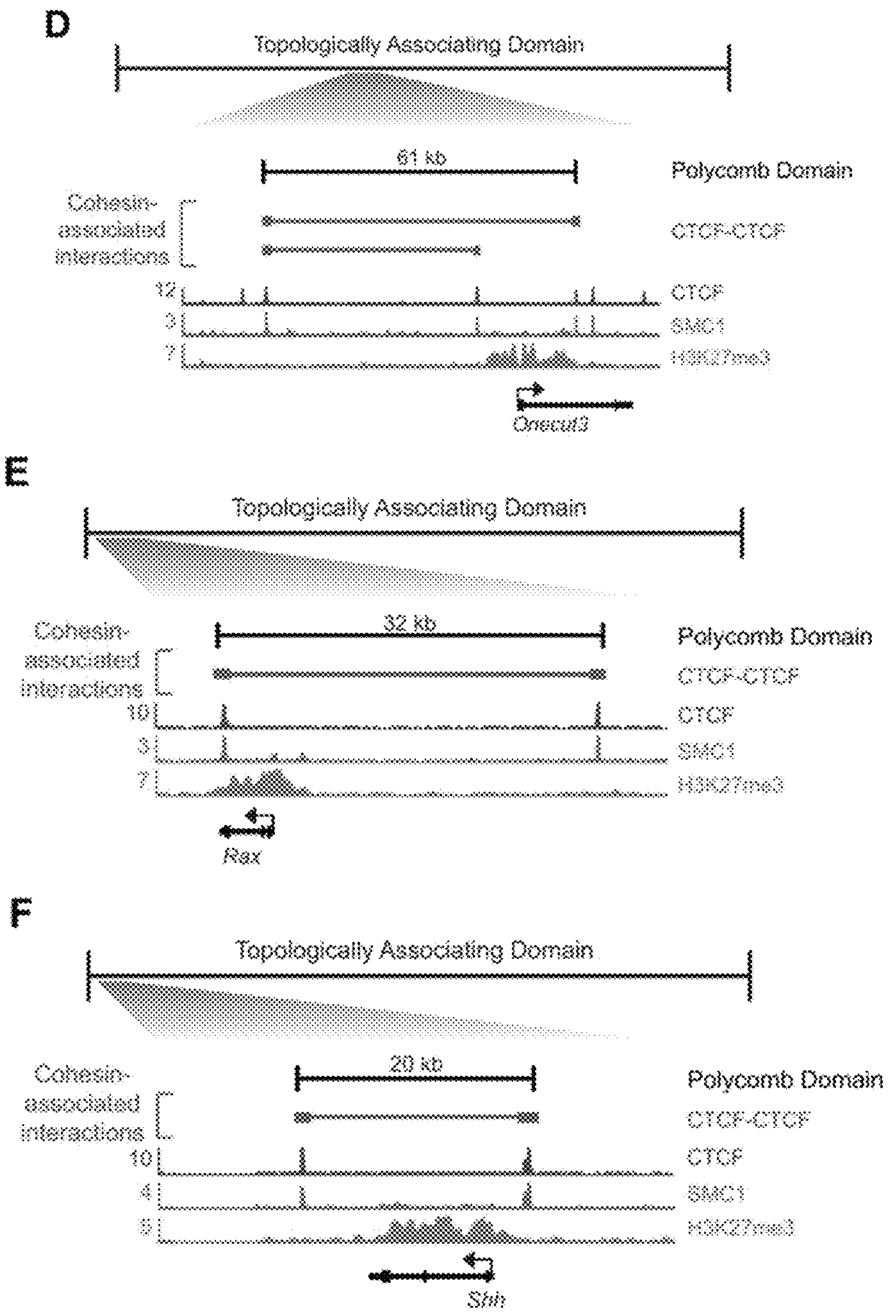

Figure 11 (Figure S5)
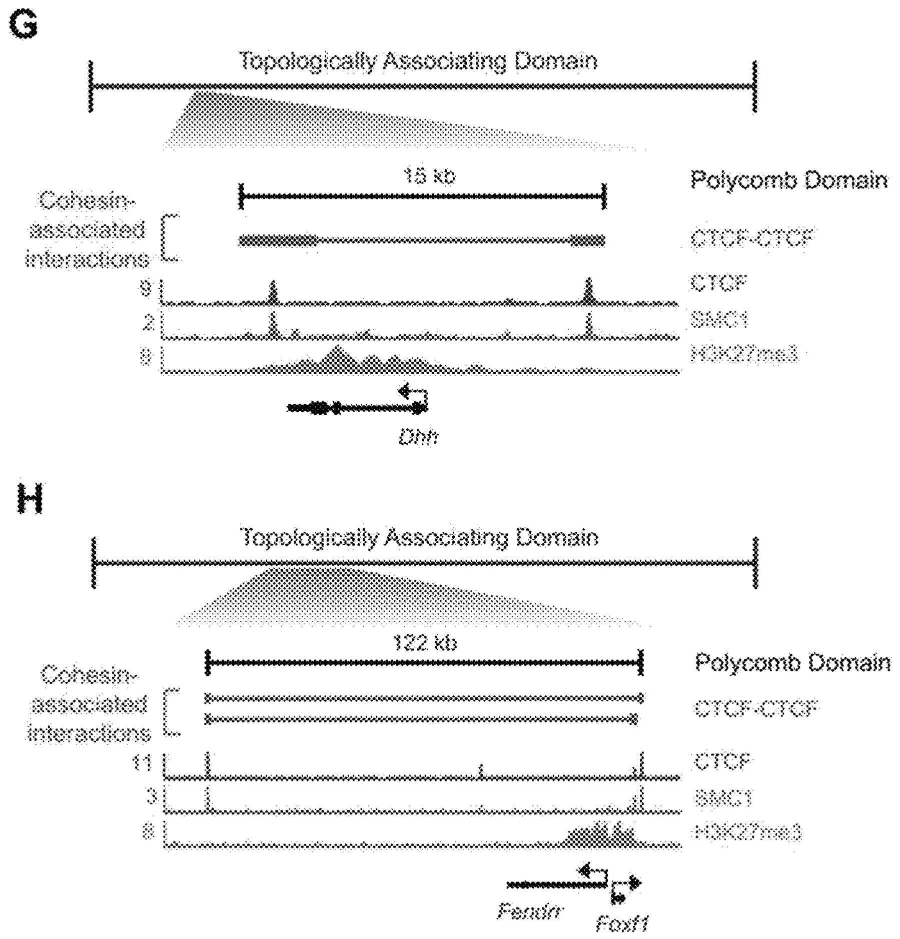

Figure 11 (Figure S5)
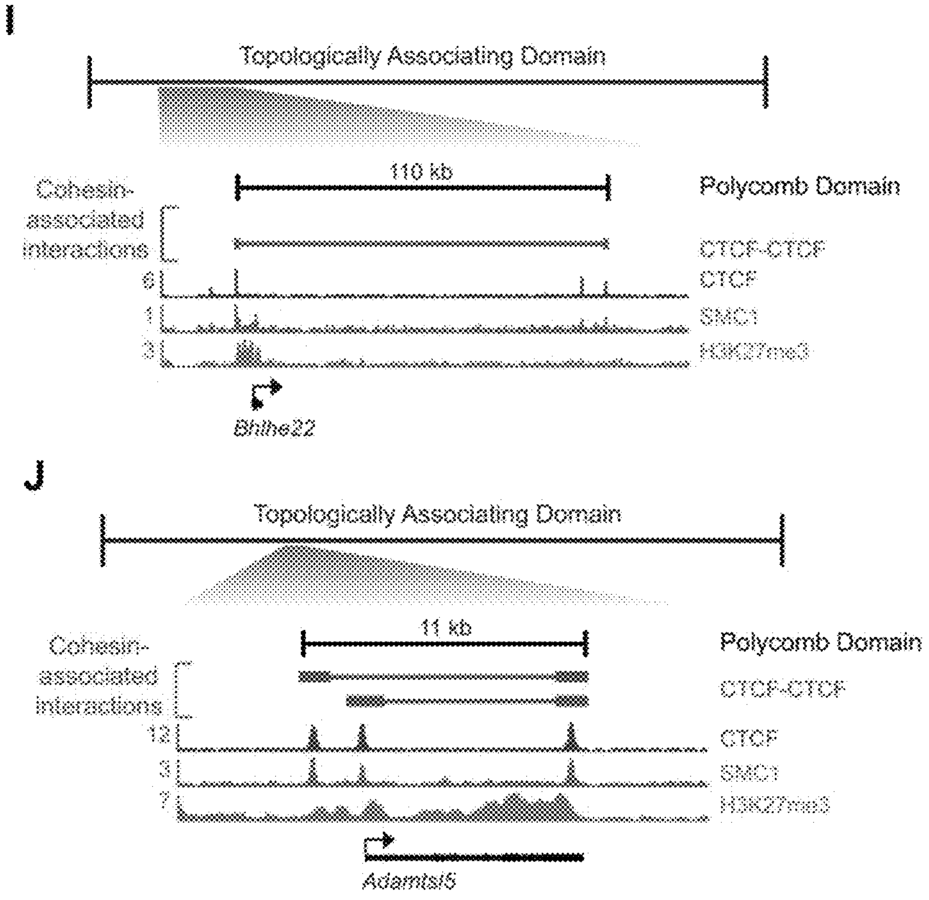

Figure 12 (Figure S6)
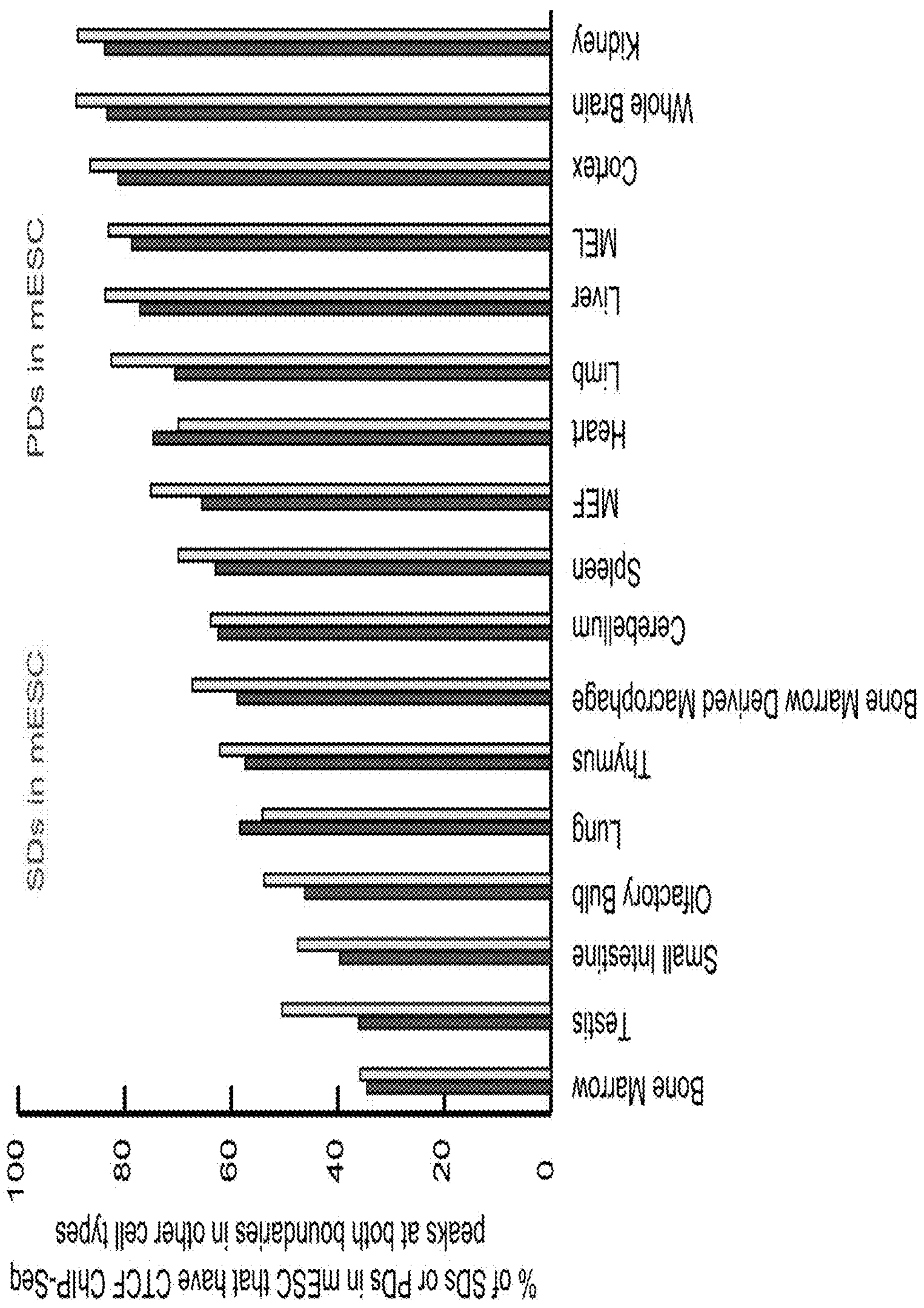

COMPOSITIONS AND METHODS FOR ALTERING GENE EXPRESSION

CROSS-REFERENCE TO RELATED APPLICATION(S)

This application claims the benefit of U.S. Provisional Application No. 62/234,770, filed Sep. 30, 2015. The entire teachings of the above application is incorporated herein by reference.

GOVERNMENT SUPPORT

This invention was made with government support under Grant Number HG002668 awarded by the National Institutes of Health. The government has certain rights in the invention.

FIELD OF THE INVENTION

The present invention generally relates to methods of selectively altering gene expression within, for example, insulated neighborhoods formed by the looping of two CTCF interaction sites occupied by cohesion.

REFERENCE TO LENGTHY TABLE

The specification includes lengthy Tables: Table S1E and Table S2A. Lengthy Table S1E has been submitted via EFS-Web in electronic format as follows: File name: S1ETBL.txt, Date created: Sep. 30, 2016; File size: 2,482,827 Bytes and is incorporated herein by reference in its entirety. Lengthy Table S2 has been submitted via EFS-Web in electronic format as follows: File name: S2ATBL.txt, Date created: Sep. 30, 2016; File size: 360,209 Bytes and is incorporated herein by reference in its entirety.

Please refer to the end of the specification for access instructions.

BACKGROUND OF THE INVENTION

Embryonic stem cells depend on active transcription of genes that play prominent roles in pluripotency (ES cell identity genes) and on repression of genes encoding lineage-specifying developmental regulators (Ng and Surani, 2011; Orkin and Hochedlinger, 2011; Young, 2011). The master transcription factors (TFs) OCT4, SOX2, and NANOG (OSN) form super-enhancers at most cell identity genes, including those encoding the master TFs themselves; these super-enhancers contain exceptional levels of transcription apparatus and drive high-level expression of associated genes (Hnisz et al., 2013; Whyte et al., 2013).

Maintenance of the pluripotent ESC state also requires that genes encoding lineage-specifying developmental regulators remain repressed, as expression of these genes can stimulate differentiation and thus loss of ESC identity. These repressed lineage specifying genes are occupied by polycomb group proteins in ESCs (Boyer et al., 2006; Lee et al., 2006; Margueron and Reinberg, 2011; Squazzo et al., 2006). The ability to express or repress these key genes in a precise and sustainable fashion is thus essential to maintaining ESC identity.

Recent pioneering studies of mammalian chromosome structure have suggested that they are organized into a hierarchy of units, which include topologically associating domains (TADs) and gene loops (FIG. 1A) (Dixon et al., 2012; Filippova et al., 2014; Gibcus and Dekker, 2013; Naumova et al., 2013; Nora et al., 2012).

TADs, also known as topological domains, are defined by DNA-DNA interaction frequencies, and their boundaries are regions across which relatively few DNA-DNA interactions occur (Dixon et al., 2012; Nora et al., 2012). TADs average 0.8 Mb, contain approximately seven protein-coding genes, and have boundaries that are shared by the different cell types of an organism (Dixon et al., 2012; Smallwood and Ren, 2013). The expression of genes within a TAD is somewhat correlated, and thus some TADs tend to have active genes and others tend to have repressed genes (Cavalli and Misteli, 2013; Gibcus and Dekker, 2013; Nora et al., 2012).

Gene loops and other structures within TADs are thought to reflect the activities of transcription factors (TFs), cohesin, and CTCF (Baranello et al., 2014; Gorkin et al., 2014; Phillips-Cremins et al., 2013; Seitan et al., 2013; Zuin et al., 2014). The structures within TADs include cohesin-associated enhancer-promoter loops that are produced when enhancer-bound TFs bind cofactors such as Mediator that, in turn, bind RNA polymerase II at promoter sites (Lee and Young, 2013; Lelli et al., 2012; Roeder, 2005; Spitz and Furlong, 2012). The cohesin-loading factor NIPBL binds Mediator and loads cohesin at these enhancer-promoter loops (Kagey et al., 2010). Cohesin also becomes associated with CTCF-bound regions of the genome, and some of these cohesin-associated CTCF sites facilitate gene activation while others may function as insulators (Dixon et al., 2012; Parelho et al., 2008; Phillips-Cremins and Corces, 2013; Seitan et al., 2013; Wendt et al., 2008).

The chromosome structures anchored by Mediator and cohesin are thought to be mostly cell-type-specific, whereas those anchored by CTCF and cohesin tend to be larger and shared by most cell types (Phillips-Cremins et al., 2013; Seitan et al., 2013). Despite this picture of cohesin-associated enhancer-promoter loops and cohesin-associated CTCF loops, we do not yet understand the relationship between the transcriptional control of cell identity and the sub-TAD structures of chromosomes that may contribute to this control. Furthermore, there is limited evidence that the integrity of sub-TAD structures is important for normal expression of genes located in the vicinity of these structures.

To gain insights into the cohesin-associated chromosome structures that may contribute to the control of pluripotency in ESCs, we generated a large cohesin ChIA-PET data set and integrated this with other genome-wide data to identify local structures across the genome.

The results show that super enhancer-driven cell identity genes and repressed genes encoding lineage-specifying developmental regulators occur within insulated neighborhoods formed by the looping of two CTCF interaction sites occupied by cohesin.

Perturbation of these structures demonstrates that their integrity is important for normal expression of genes located in the vicinity of the neighborhoods.

SUMMARY OF THE INVENTION

The present disclosure provides compositions and methods for regulating gene expression in a directed fashion.

In one embodiment is provided a method of altering the expression of a gene in an insulated neighborhood (IN) of the genome of a cell comprising contacting an organism comprising said cell with a gene modulatory molecule. Such molecules include, but are not limited to, small molecules, lipid, proteins, peptides, nucleic acids, such as RNA, DNA or any modified version thereof, and combinations thereof.

In one embodiment, expression of the gene is increased.

In one embodiment, the cell is selected from the group consisting of stem cells, bone marrow cells, testis cells, olfactory cells, lung cells, thymus cells, cells of the central nervous system, cells of the brain, spleen cells, MEF cells, MEL cells, heart cells, somatic cells of the limbs, liver cells, and kidney cells.

In one embodiment, the cells are stem cells and said stem cells are embryonic stem cells.

In one embodiment, the insulated neighborhood comprises a topologically active domain (TAD).

In one embodiment, the topologically active domain is a super-enhancer domain (SD) and such SDs may be selected from any known SD or any disclosed herein such as those in Table S4A and S4B.

In one embodiment, the gene is selected from the group consisting of those in Table S4C.

In one embodiment is provided a method of altering the expression of a gene located in an insulated neighborhood (IN) of the genome of a cell comprising altering the sequence of one or more of the CTCF boundaries of said insulated neighborhood.

In one embodiment, the CTCF boundary is altered via CRISPR technology.

Such alteration may involve either or both of the boundaries of the insulated neighborhood.

Additional embodiments of the present compositions and methods, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

for CTCF, cohesin (SMC1), and OCT4, SOX2, and NANOG (OSN) in ESCs at the respective loci. The super enhancer is indicated as a red bar. The bottom of each panel shows gene expression level of the indicated genes in wild-type and CTCF site-deleted cells measured by qRT-PCR. Transcript levels were normalized to GAPDH. Gene expression was assayed in triplicate in at least two biological replicate samples and is displayed as mean+SD. All p values were determined using the Student's t test. (A) CRISPR-mediated genome editing of a CTCF site at the miR-290-295 locus ($p<0.001$, Pri-miR-290-295, and Nlrp12 in wild-type versus CTCF site-deleted). (B) CRISPR-mediated genome editing of a CTCF site at the Nanog locus ($p<0.05$, Nanog in wild-type versus CTCF site-deleted). (C) CRISPR-mediated genome editing of a CTCF site at the Tdgf1 locus ($p<0.001$, Gm590; $p<0.01$, Lrrc2) in wild-type versus CTCF site-deleted). (D) CRISPR-mediated genome editing of a CTCF site at the Pou5f1 locus ($p<0.012$, H2Q-10 in wild-type versus CTCF site-deleted). (E) CRISPR-mediated genome editing of CTCF sites at the Prdm14 locus ($p<0.001$, Slco5a1 in wild-type versus CTCF site-deleted). The CTCF-deletion lines at the Pou5f1 and Prdm14 (C1-2) loci are heterozygous, whereas the CTCF-deletion lines at the Nanog, Tdgf1, and miR-290-295 loci are homozygous for the mutation. See also Figure S4.

Figure 5:
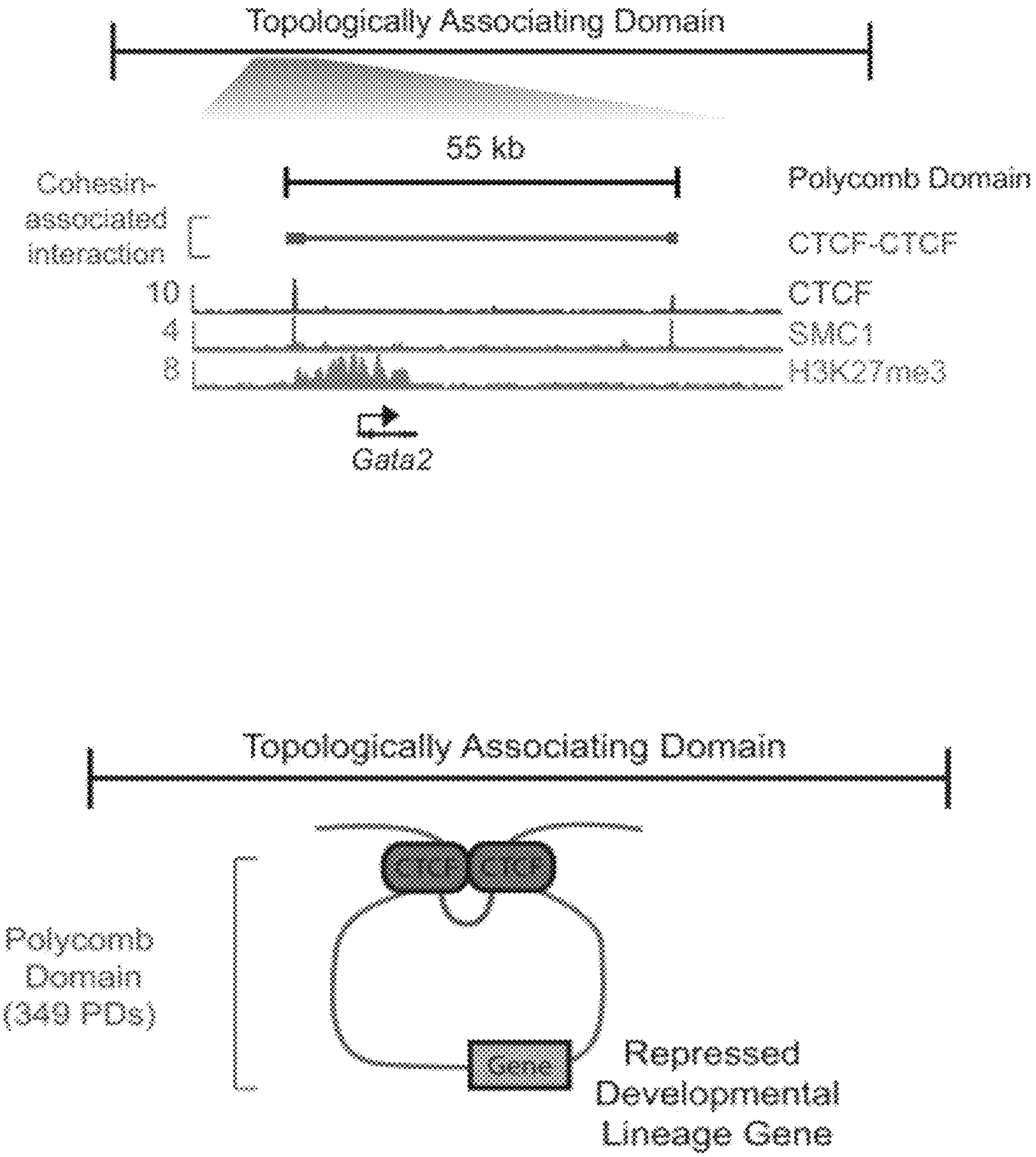
Figure 5:
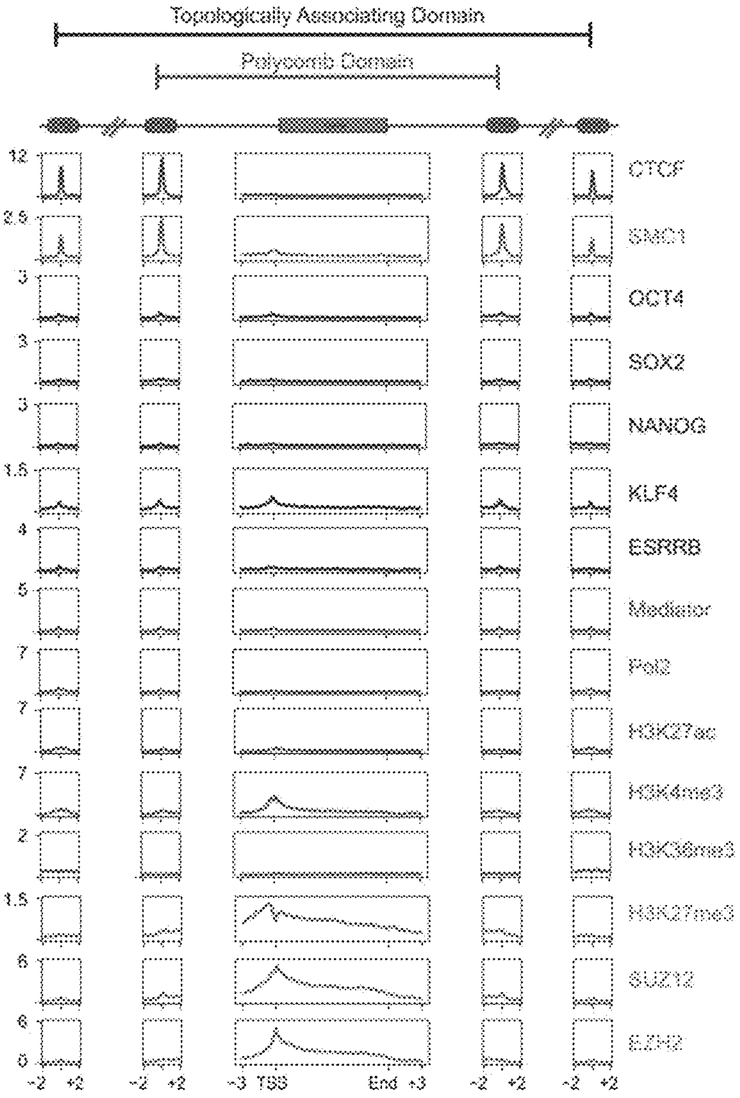
Figure 5:
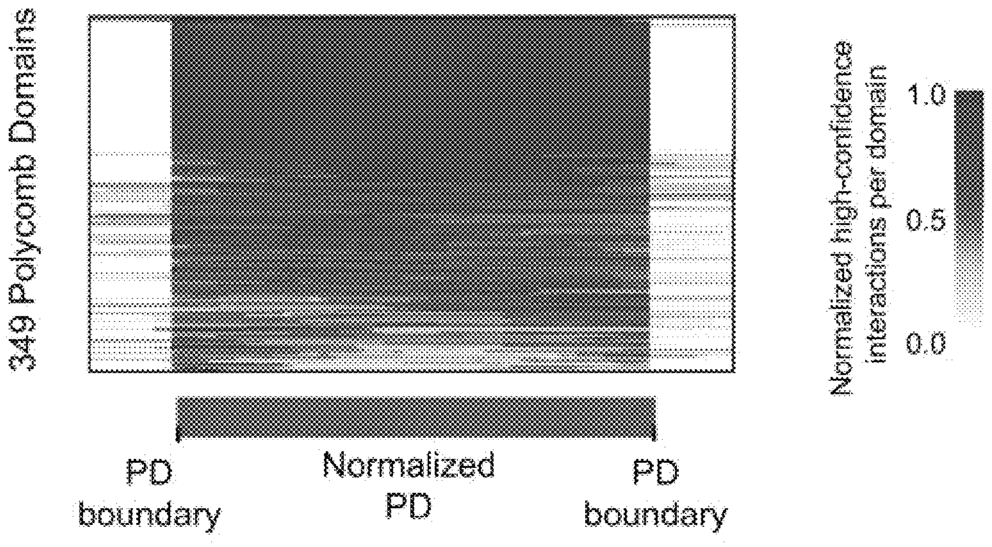
Figure 5:
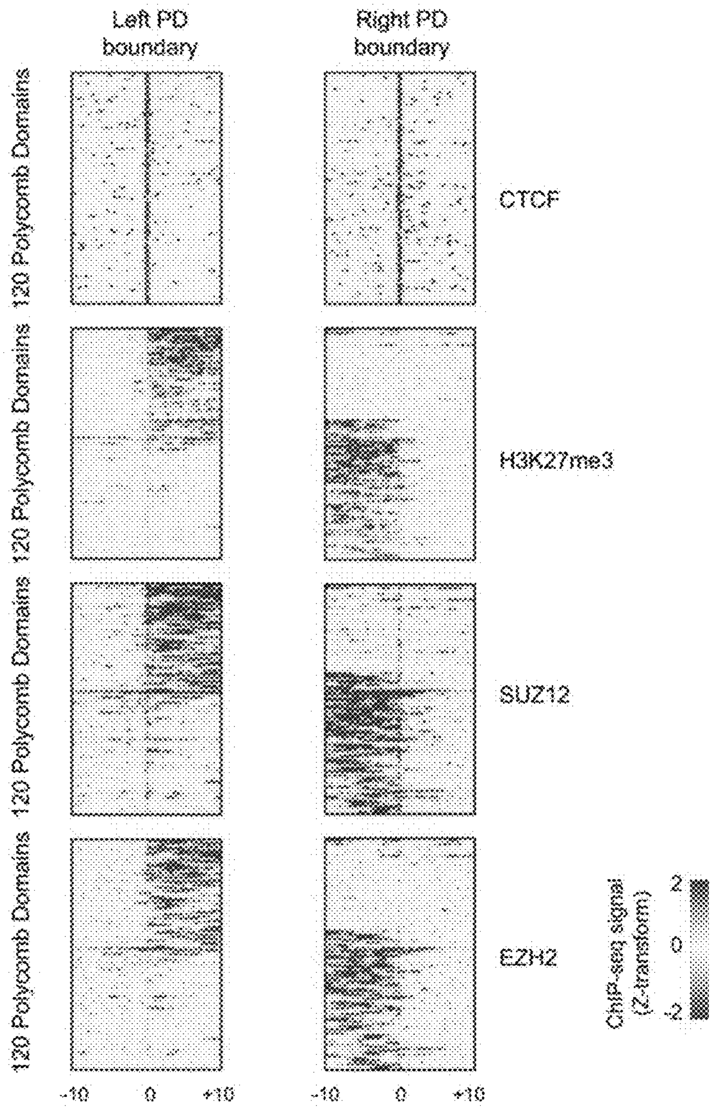
Figure 5:
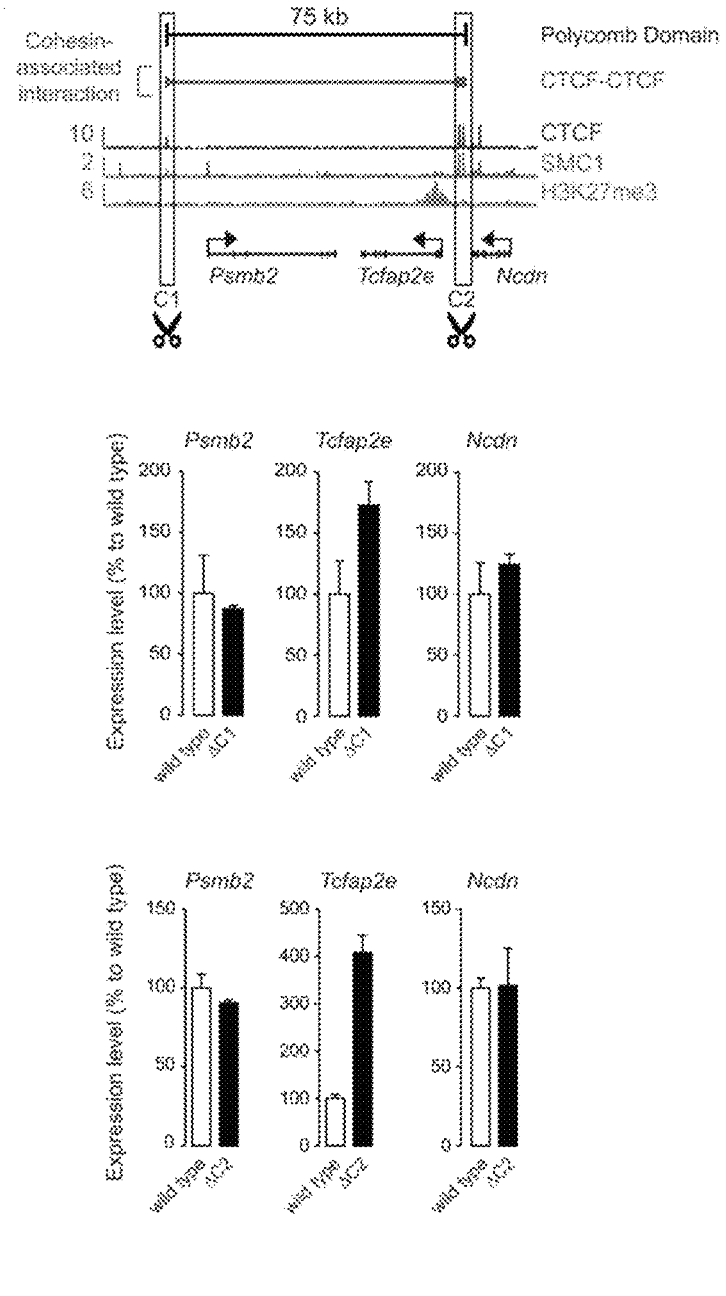

FIG. 5 Polycomb Domain Structure. (A) An example polycomb domain (PD) within a TAD. A high-confidence interaction is depicted as the blue line. ChIP-seq binding profiles (reads per million per base pair) for CTCF, cohesin (SMC1), and H3K27me3 at the Gata2 locus in ESCs. (B) Model of PD structure. The 349 PDs have interactions (blue) between CTCF sites that serve as putative boundaries of the domain structure. (C) Metagene analysis reveals the occupancy of various factors at the key elements of TADs and PDs: CTCF sites and target genes. ChIP-seq profiles are shown in reads per million per base pair. Boundary site metagenes are centered on the CTCF peak, and ±2 kb is displayed. The metagenes depicting genes are centered on the 380 polycomb target genes in PDs, and ±3 kb is displayed. (D) Heatmap showing that high-confidence interactions are largely constrained within PDs. The density of high-confidence interactions is shown across a normalized PD length for the 349 PDs. (E) Heatmap showing that polycomb proteins are contained within boundary sites of PDs. The occupancy of CTCF, H3K27me3, SUZ12, and EZH2 is indicated within a 20 kb window centered on the left, and right CTCF-occupied boundary region is shown for the 120 PDs with this transition pattern. (F) CRISPR-mediated genome editing of a CTCF site at the Tcfap2e locus. (Top) A high-confidence interaction is depicted by a blue line, and ChIP-seq binding profiles (reads per million per base pair) for CTCF, cohesin (SMC1), and H3K27me3 are shown in ESCs. (Bottom) Expression level of the indicated genes in wildtype and CTCF site-deleted cells measured by qRT-PCR. Transcript levels were normalized to GAPDH. Gene expression was assayed in triplicate in at least two biological replicate samples and is displayed as mean+SD ($p<0.05$, Tcfap2e in C1 deletion cells; $p<0.001$, Tcfap2e in C2 deletion cells in wild-type versus CTCF site-deleted). p values were determined using the Student's t test. See also Figure S5 and Table S5.

Figure 6:
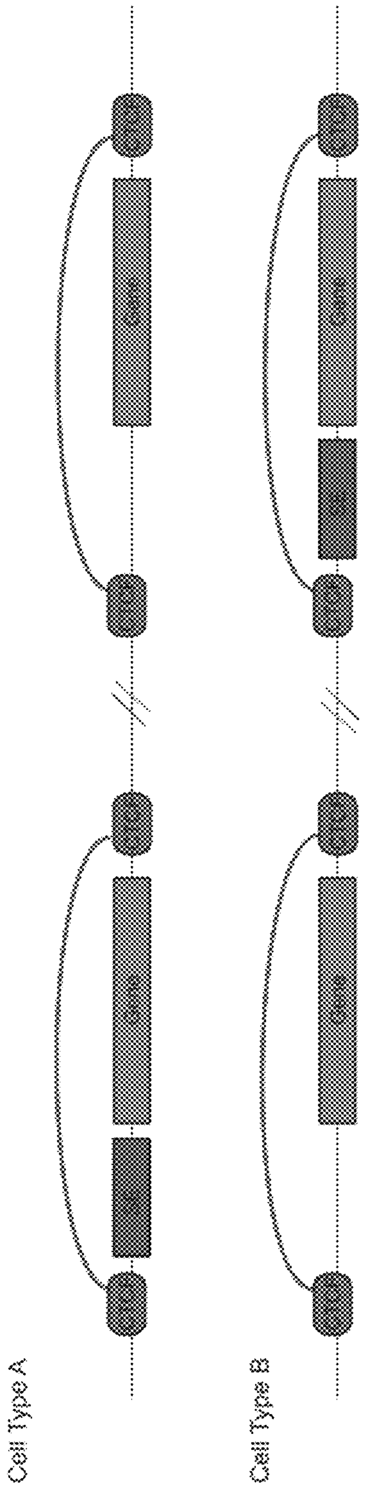
Figure 6:
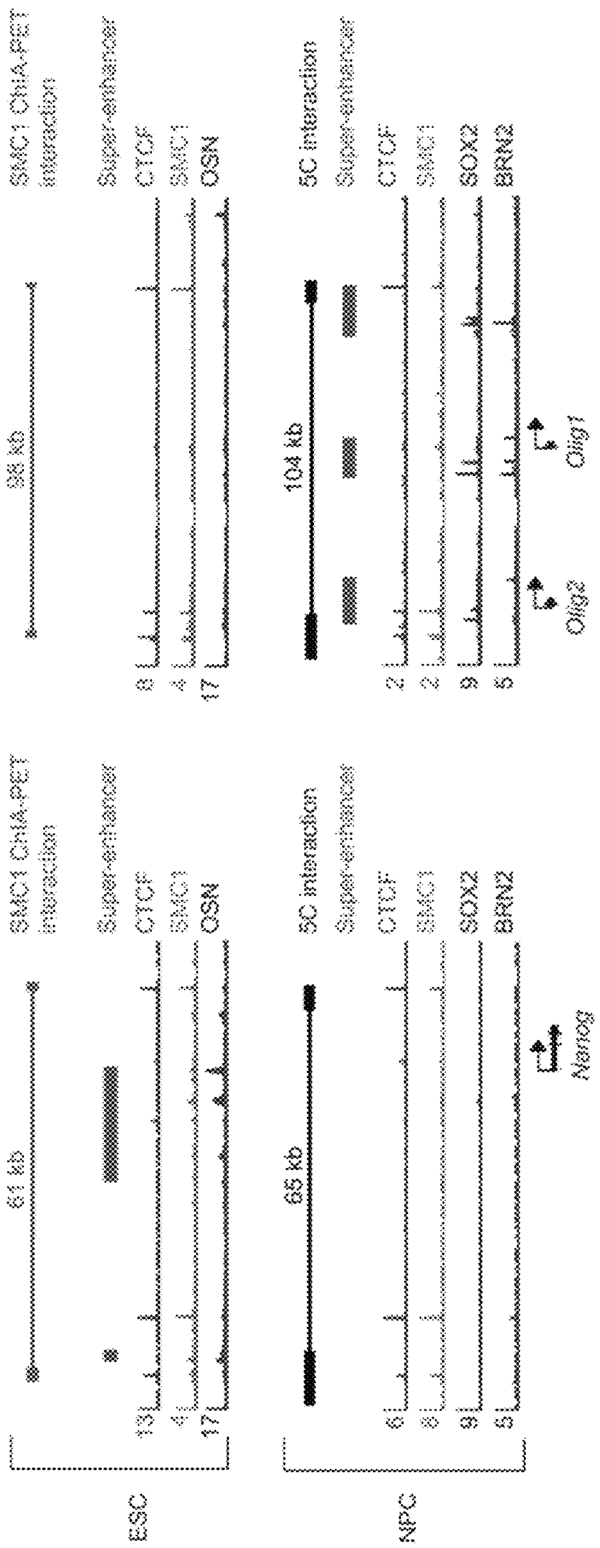
Figure 6:
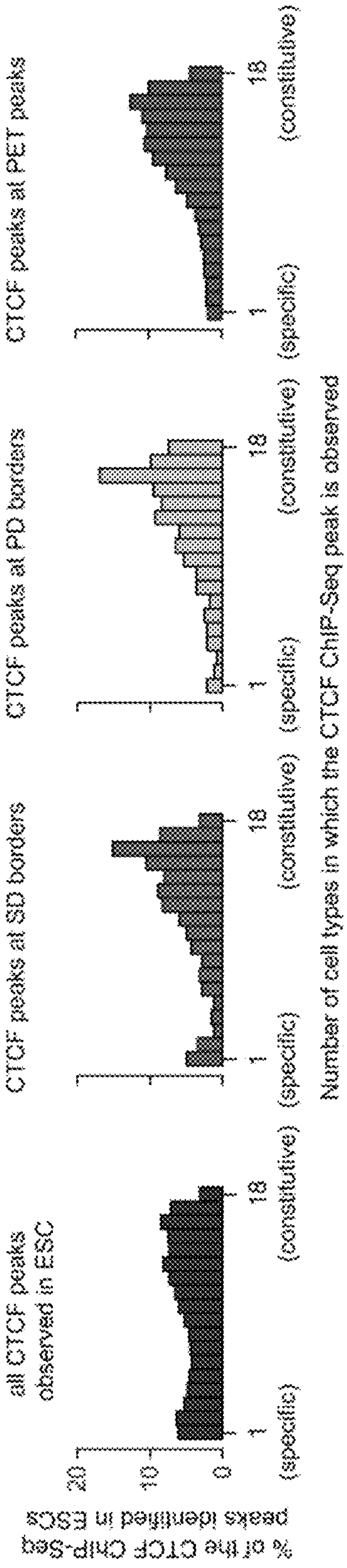

FIG. 6 Insulated Neighborhoods Are Preserved in Multiple Cell Types. (A) Model depicting constitutive domain organization, mediated by interaction of two CTCF sites co-occupied by cohesin, in two cell types. (B) An example SD in ESCs and a domain in NPCs. High-confidence interactions from the SMC1 ChIA-PET data set are depicted by blue lines, and 5C interactions from Phillips-Cremins et al. (2013) are depicted by black lines. Super-enhancers are indicated by red bars. ChIP-seq binding profiles (reads per million per base pair) for CTCF, cohesin (SMC1), OCT4, SOX2, NANOG (OSN), SOX2, and BRN2 are shown at the Nanog locus and the Olig1/Olig2 locus in ESCs and NPCs. (C) Occupancy of CTCF peaks across 18 cell types. The CTCF peaks used for the analysis are the CTCF peaks found in ESCs. The percentage of these peaks that are observed in the indicated number of cell types is shown for four groups of CTCF sites: all CTCF peaks identified in ESCs, CTCF peaks at SD boundaries in ESCs, CTCF peaks at PD boundaries in ESCs, and CTCF peaks at PET peaks (identified by SMC1 ChIA-PET in ESCs). See also Figure S6 and Table S3B.

FIG. 7 (Figure S1). PET Quality Assessment and Interactions, Related to FIG. 1. (A) Heatmap representation of ESC ChIP-seq data for the combination of the master transcription factors OCT4, SOX2 and NANOG (OSN), MED12, RNA polymerase II (Pol2), CTCF, and SMC1 at promoters and enhancers in ESCs. Read density is displayed within a 10 kb window and color scale intensities are shown in rpm/bp. (B) Heatmap representation of ESC ChIP-seq data for the combination of the master transcription factors OCT4, SOX2 and NANOG (OSN), MED12, RNA polymerase II (Pol2), CTCF, and SMC1 at CTCF-bound sites in ESCs. Read density is displayed within a 10 kb window and color scale intensities are shown in rpm/bp. (C) Scatter plot showing the number of non self-ligation PETs in 10 kb windows in replicates in reads per million mapped reads per kilobase. (D) Bar graph showing the percentage of high confidence interactions from one replicate of the SMC1 ChIA-PET supported by interactions in the other replicate. (E) Left, scatter plot showing the frequency of non-chimeric PETs with homodimeric linkers against PET genomic span in increments of 100 bp. The curve suggests a distance cut-off at 4 kb, below which the PETs may originate from self-ligation of DNA ends from a single chromatin fragment in the ChIA-PET protocol. Right, scatter plot showing chimeric PET frequencies with heterodimeric linkers against PET genomic span in increments of 100 bp, suggesting chimeric PETs were more uniformly distributed across different genomic spans. (F) Bar graph showing the percentage of interactions called by requiring different numbers of chimeric and non-chimeric PETs. All PET interactions called using chimeric PETs that are supported by at least 3 PETs have a false positive likelihood<1% (see Extended Experimental Procedures). (G) Diagram showing the frequency of intrachromosomal and interchromosomal interactions in the interaction (left) and high confidence interaction data set (right). (H) Saturation analysis of the SMC1 ChIA-PET data set. Subsampling of various fractions of PETs within the merged ChIA-PET data set was performed, and the number of unique genomic positions of intrachromosomal PETs beyond the self-ligation distance cutoff of 4 kb was plotted. The solid line depicting the non-linear least-squares regression fitting of the data to the Michaelis-Menten model suggests that we have sampled approximately 70% of the available intrachromosomal PETs beyond 4 kb in the current library. The dashed line indicates the estimated 100% saturation.

Figure 1:
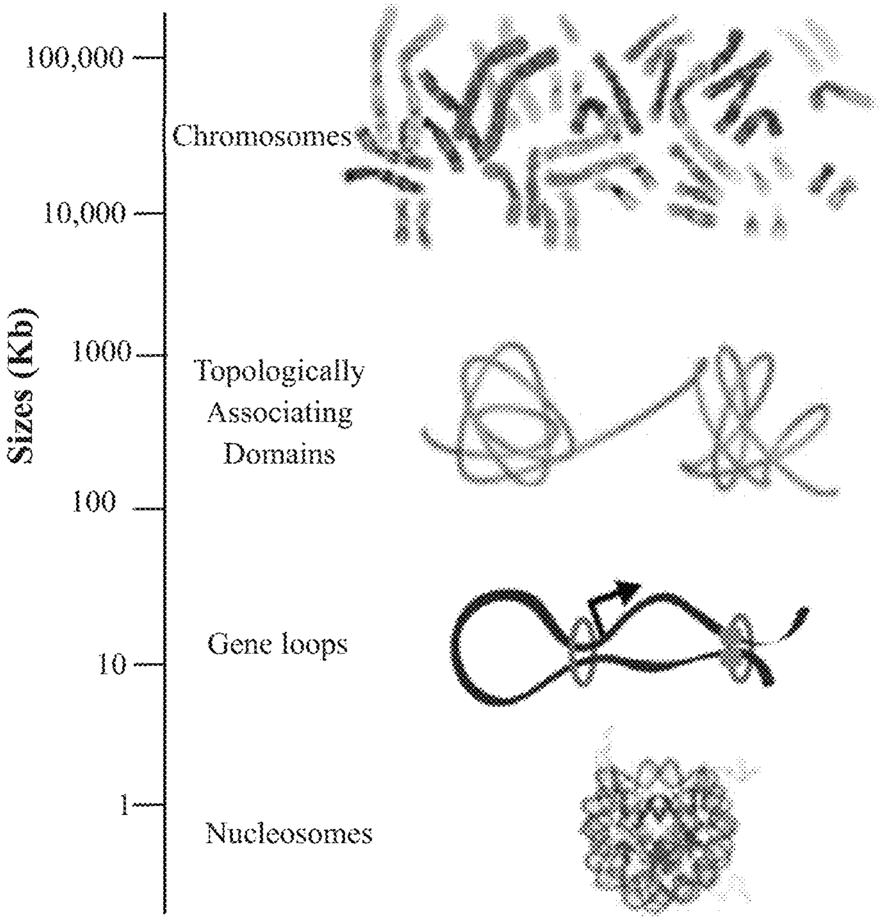
FIG. 1 DNA Interactions Involving Cohesin (A) Units of chromosome organization. Chromosomes consist of multiple topologically associating domains (TADs). TADs (image adapted from Dixon et al., 2012) contain multiple genes with DNA loops involving interactions between enhancers, promoters, and other regulatory elements, which are mediated by cohesin (blue ring) and CTCF (purple balls). Nucleosomes represent the smallest unit of chromosome organization. (B) Heatmap representation of ESC ChIP-seq data for SMC1, a merged data set for the transcription factors OCT4, SOX2, and NANOG (OSN), MED12, RNA polymerase II (Pol2), H3K27me3, and CTCF at SMC1-occupied regions. Read density is displayed within a 10 kb window, and color scale intensities are shown in rpm/bp. Cohesin occupies three classes of sites: enhancer-promoter sites, polycomb-occupied sites, and CTCF-occupied sites. (C) ESC cohesin (SMC1) ChIA-PET data analysis at the Mycn locus. The algorithm used to identify paired-end tags (PETS) is described in detail in the Extended Experimental Procedures. PETs and interactions involving enhancers and promoters within the window are displayed at each step in the analysis pipeline: unique PETs, PET peaks, interactions between PET peaks, and high-confidence interactions supported by at least three independent PETs and with a false positive likelihood of <1% (see Extended Experimental Procedures). (D) Summary of the major classes of interactions and high-confidence interactions identified in the cohesin ChIA-PET data. Enhancers, promoters, and CTCF sites where interactions occur are displayed as blue circles, and the size of the circle is proportional to the number of regions. The interactions between two sites are displayed as gray lines, and the thickness of the gray line is proportional to the number of interactions. The diagram on the left was generated using the interactions, and the diagram on the right was generated using the high-confidence interactions. See also Figures S1 and S2 and Tables S1 and S2.
Figure 1:
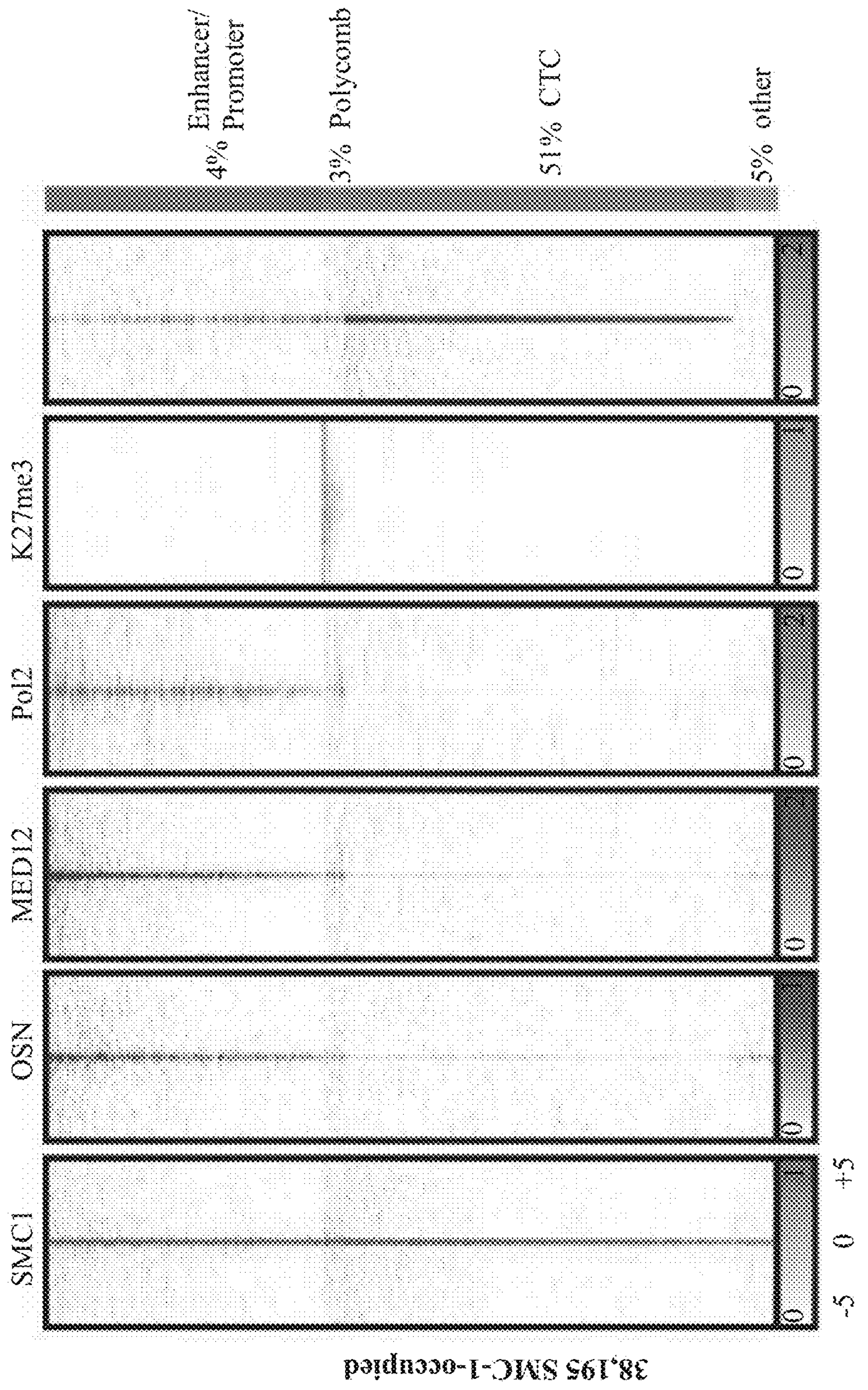
Figure 1:
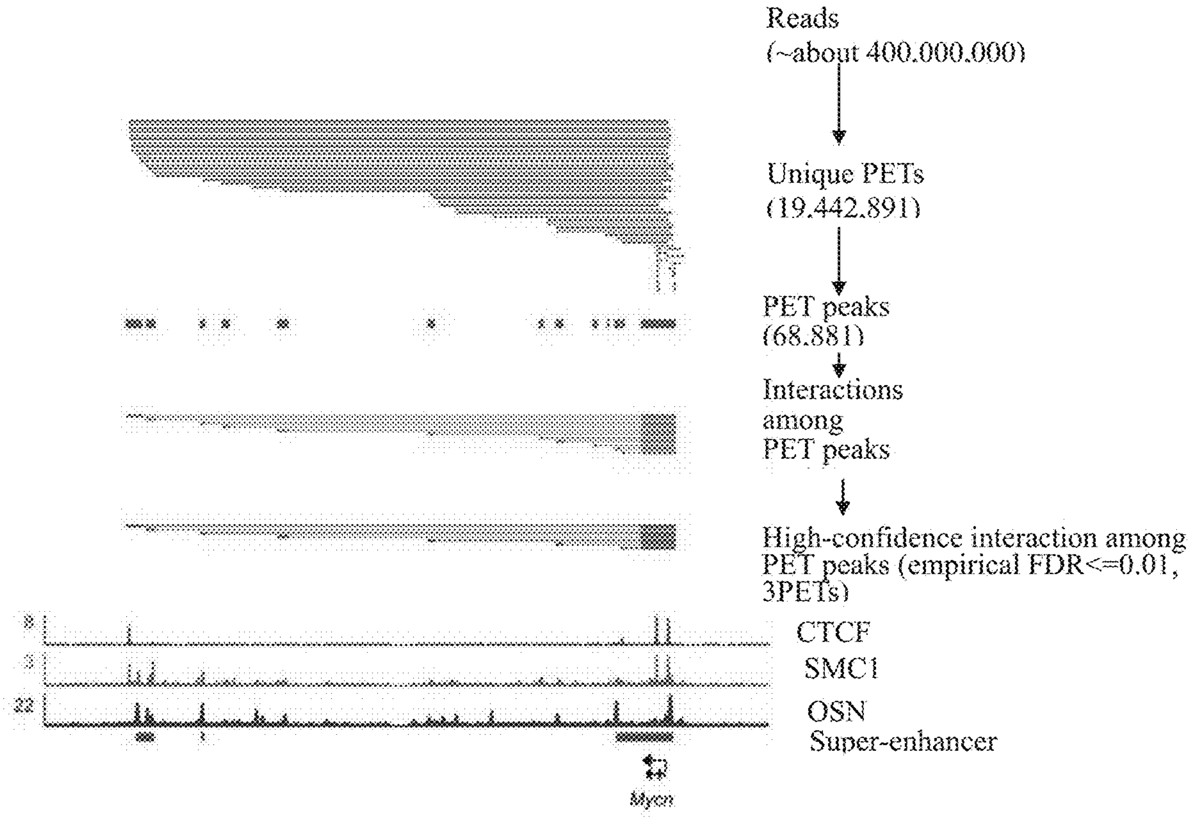
Figure 1:
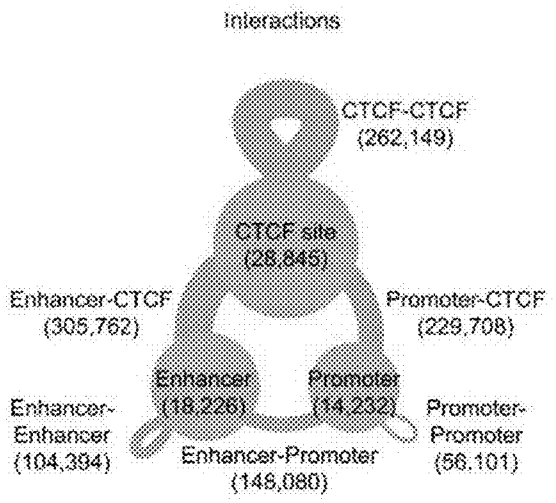

FIG. 8 (Figure S2) High-Confidence SMC1 ChIA-PET Interactions Are Consistent with Previously Identified Interactions, Related to FIG. 1. High-confidence SMC1 ChIA-PET interactions are depicted as blue lines. Interactions from other published data sets are depicted as black lines. ChIP-seq binding profiles (reads per million per base pair) for CTCF, cohesin (SMC1), and OCT4, SOX2, and NANOG (OSN) are shown at the indicated loci in ESCs. (A) A high-confidence SMC1 ChIA-PET interaction is supported by 3C from (Kagey et al., 2010). Genomic coordinates for the Lefty1 TAD are chr1:182,760,000-183,160,000. Genomic coordinates for the Lefty1 ChIP-seq binding profiles are chr1:182,851,700-182,871,500. (B) A high-confidence SMC1 ChIA-PET interaction is supported by a CTCF ChIA-PET PET from (Handoko et al., 2011). Genomic coordinates for the Prdm14 TAD are chr1:13,040,000-13,680,000. Genomic coordinates for the Prdm14 ChIP-seq binding profiles are chr1:13,034,300-13,131,900. (C) A high-confidence SMC1 ChIA-PET interaction is supported by a Pol2 ChIA-PET PET in (Zhang et al., 2013). Genomic coordinates for the Phc1 TAD are chr6:121,160,000-122,600,000. Genomic coordinates for the Phc1 ChIP-seq binding profiles are chr6:122,241,500-122,350,700. (D) A high-confidence SMC1 ChIA-PET interaction is supported by 5C in (Phillips-Cremins et al., 2013). Genomic coordinates for the Sox2 TAD are chr3:33,680,000-35,520,000. Genomic coordinates for the Sox2 ChIP-seq binding profiles are chr3:34,522,100-34,691,600.

Figure 3:
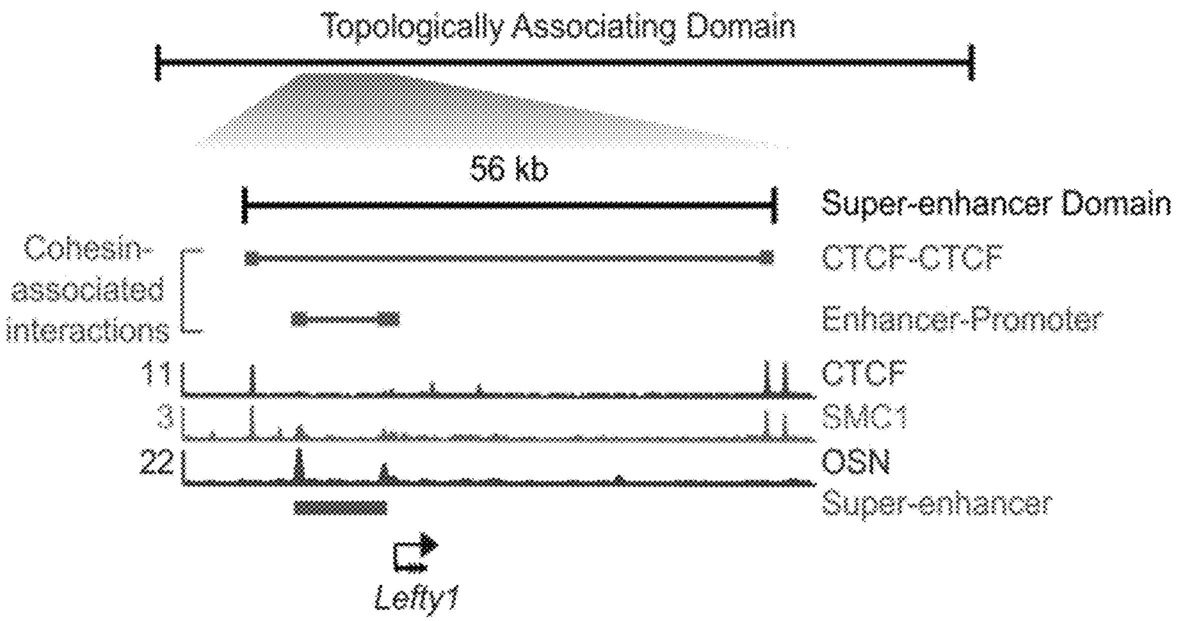
FIG. 3 Super-Enhancer Domain Structure. (A) An example super-enhancer domain (SD) within a TAD. High-confidence SMC1 ChIA-PET interactions are depicted as blue lines. ChIP-seq binding profiles (reads per million per base pair) for CTCF, cohesin (SMC1), and the master transcription factors OCT4, SOX2, and NANOG (OSN) are shown at the Lefty1 locus in ESCs. The super-enhancer is indicated by a red bar. (B) Model of SD structure. The 197 SDs have interactions (blue) between cohesin-occupied CTCF sites that may serve as outer boundaries of the domain structure. SDs also contain interactions between super-enhancers and the promoters of their associated genes. (C) Metagene analysis showing the occupancy of various factors at the key elements of TADs and SDs, including CTCF sites, super-enhancers, and super enhancer-associated genes. ChIP-seq profiles are shown in reads per million per base pair. Boundary site metagenes are centered on the CTCF peak, and ±2 kb is displayed. Super-enhancer metagenes are centered on the 197 super-enhancers in SDs, and ±3 kb is displayed. The data for associated genes are centered on the 219 super-enhancer-associated genes in SDs, and ±3 kb is displayed. (D) Heatmap showing that cohesin ChIA-PET high-confidence interactions occur predominantly within the SDs. The density of high-confidence interactions is shown across a normalized SD length for the 197 SDs. (E) Heatmap showing that transcriptional proteins are contained within boundary sites of SDs. The occupancy of Mediator (MED12), H3K27ac, and RNA polymerase II (Pol2) at super-enhancers and associated genes is shown across a normalized SD length for the 197 SDs. See also Figure S3 and Table S4.
Figure 3:
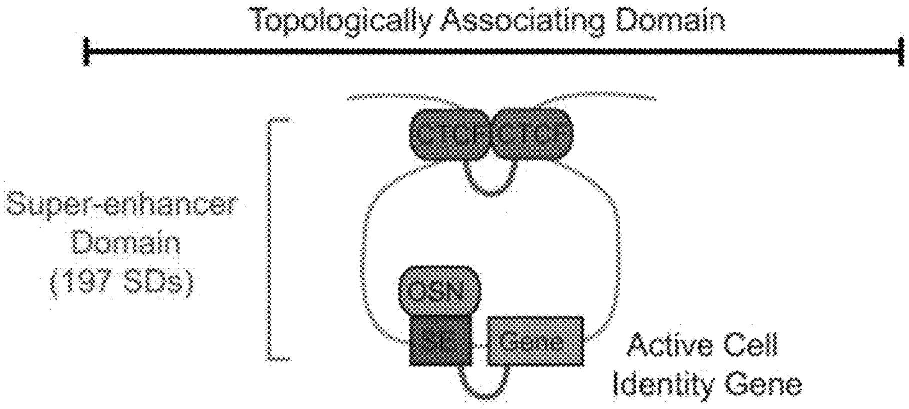
Figure 3:
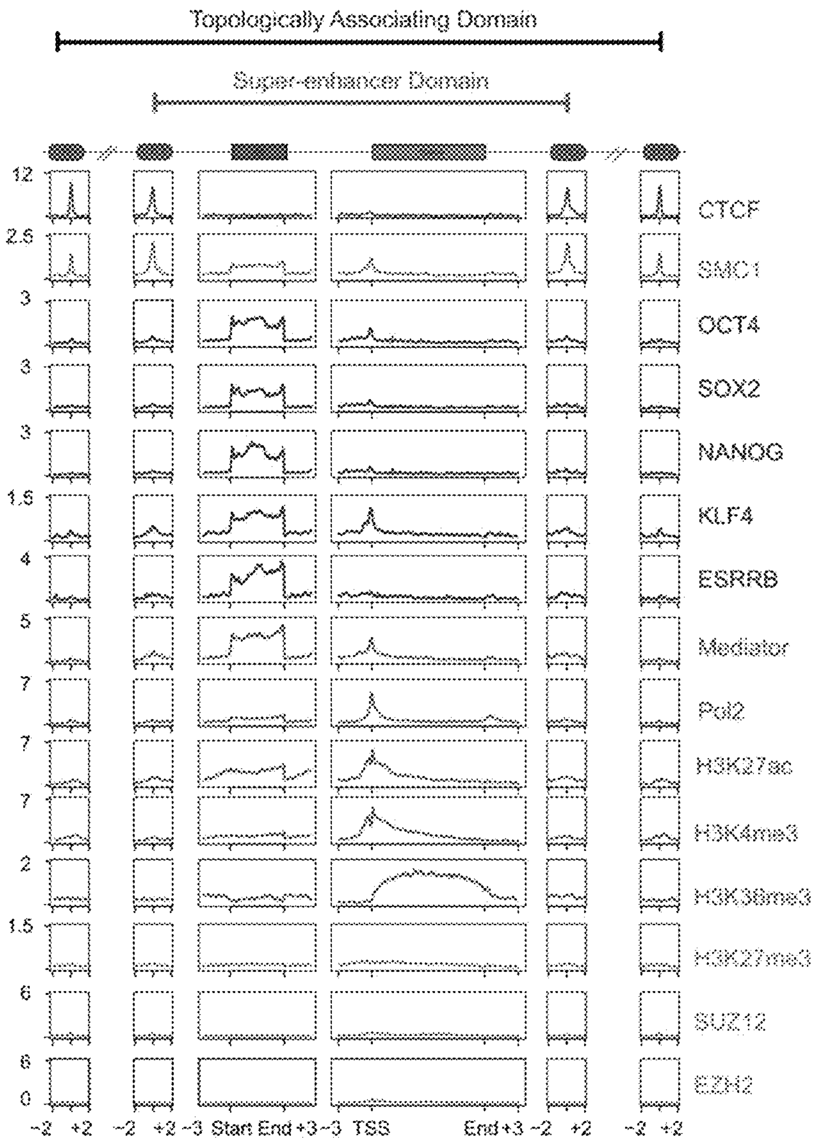
Figure 3:
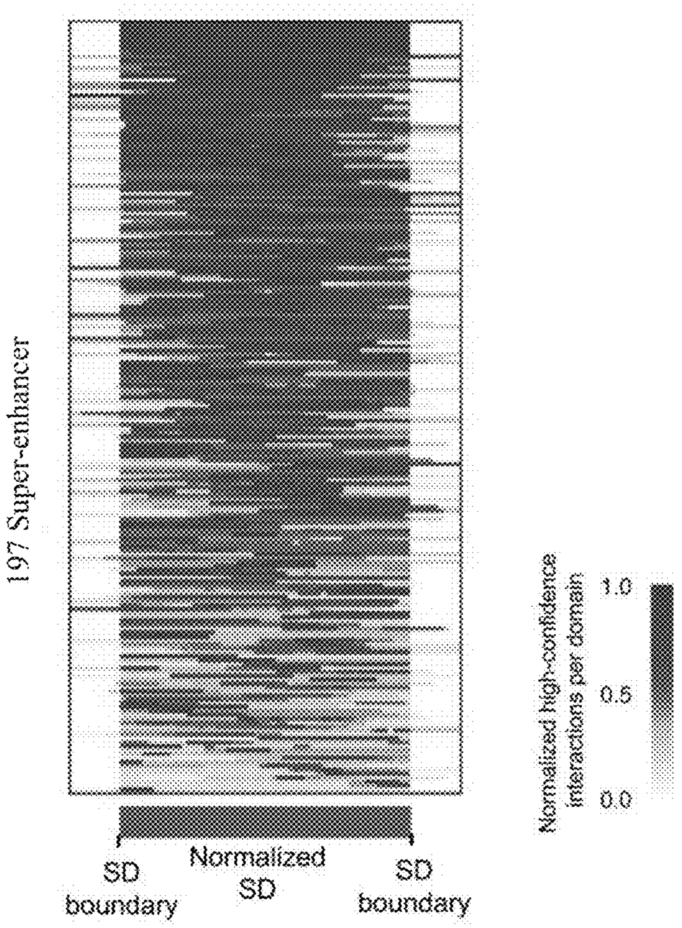
Figure 3:
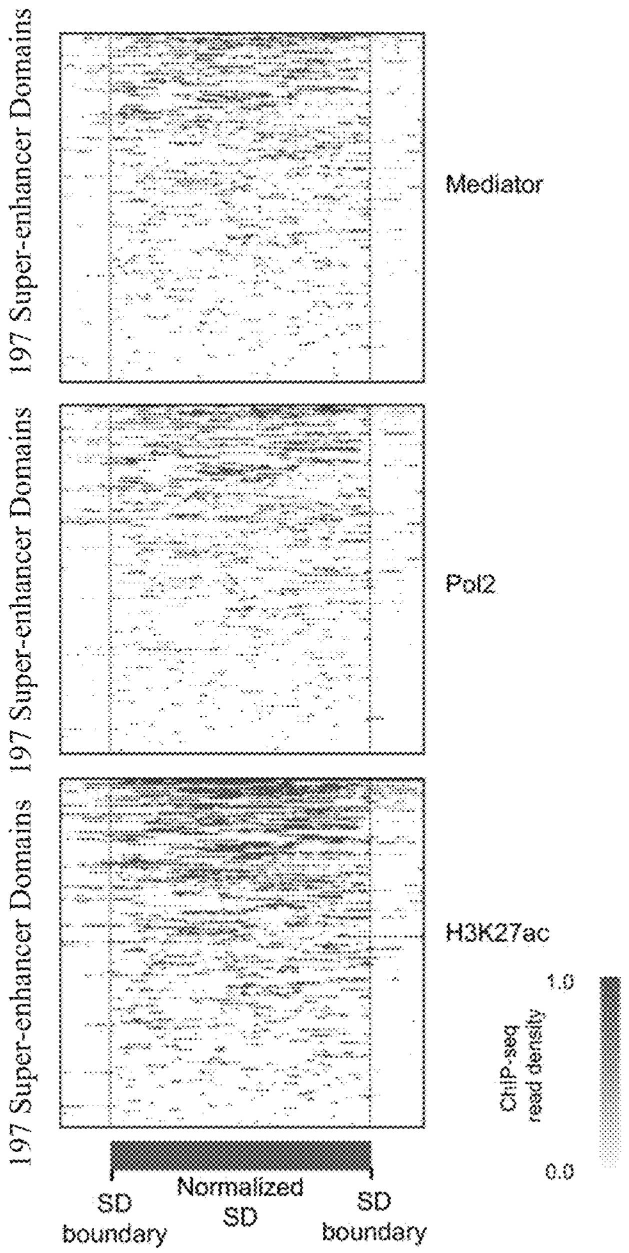

FIG. 9 (Figure S3) Super-Enhancer Domains, Related to FIG. 3. Active cell identity genes reside in Super-enhancer Domains (SD). Shown are example SDs within Topologically Associating Domains (TADs) in ESCs. High confidence SMC1 ChIA-PET interactions are depicted as blue lines. ChIP-seq binding profiles (reads per million per base pair) for CTCF, cohesin (SMC1), and the master transcription factors OCT4, SOX2, and NANOG (OSN) are shown at the example SDs in ESCs. Super-enhancer regions are indicated by a red bar. (A) Genomic coordinates for the Sox2 TAD are chr3:35,520,000-33,680,000. Genomic coordinates for the Sox2 binding profiles are chr3:34,724,900-34,502,100. (B) Genomic coordinates for the Prdm14 TAD are chr1:13,040,000-13,680,000. Genomic coordinates for the Prdm14 binding profiles are chr1:13,034,300-13,131,900. (C) Genomic coordinates for the Sall1 TAD are chr8:90,920,000-92,360,000. Genomic coordinates for the Sall1 binding profiles are chr8:91,455,200-91,581,300. (D) Genomic coordinates for the Klf9 TAD are chr19:22,920,000-24,360,000. Genomic coordinates for the Klf9 and binding profiles are chr19:23,068,300-23,273,400. (E) Genomic coordinates for the Id1 TAD are chr2:152,440,000-152,680,000. Genomic coordinates for the Id1 binding profiles are chr2:152,511,000-152,581,000. (F) Genomic coordinates for the Pou5f1 TAD are chr17: 35,600,000-36,080,000. Genomic coordinates for the Pou5f1 binding profiles are chr17:35,617,300-35,649,800. (G) Genomic coordinates for the Trim28 TAD are chr7:13,000,000-13,640,000. Genomic coordinates for the Trim28 binding profiles are chr7:13,590,396-13,620,304. (H) Genomic coordinates for the Elovl6 TAD are chr3:128,920,000-129,480,000. Genomic coordinates for the Elovl6 binding profiles are chr3:129,217,096-129,348,924. (I) Genomic coordinates for the Txnip TAD are chr3:96,320,000-96,520,000. Genomic coordinates for the Txnip binding profiles are chr3:96,347,300-96,391,100. (J) Genomic coordinates for Hs6st1 TAD are chr1:34,520,000-36,360,000. Genomic coordinates for Hs6st1 binding profiles are chr1:35,883,900-36,200,400.

Figure 4:
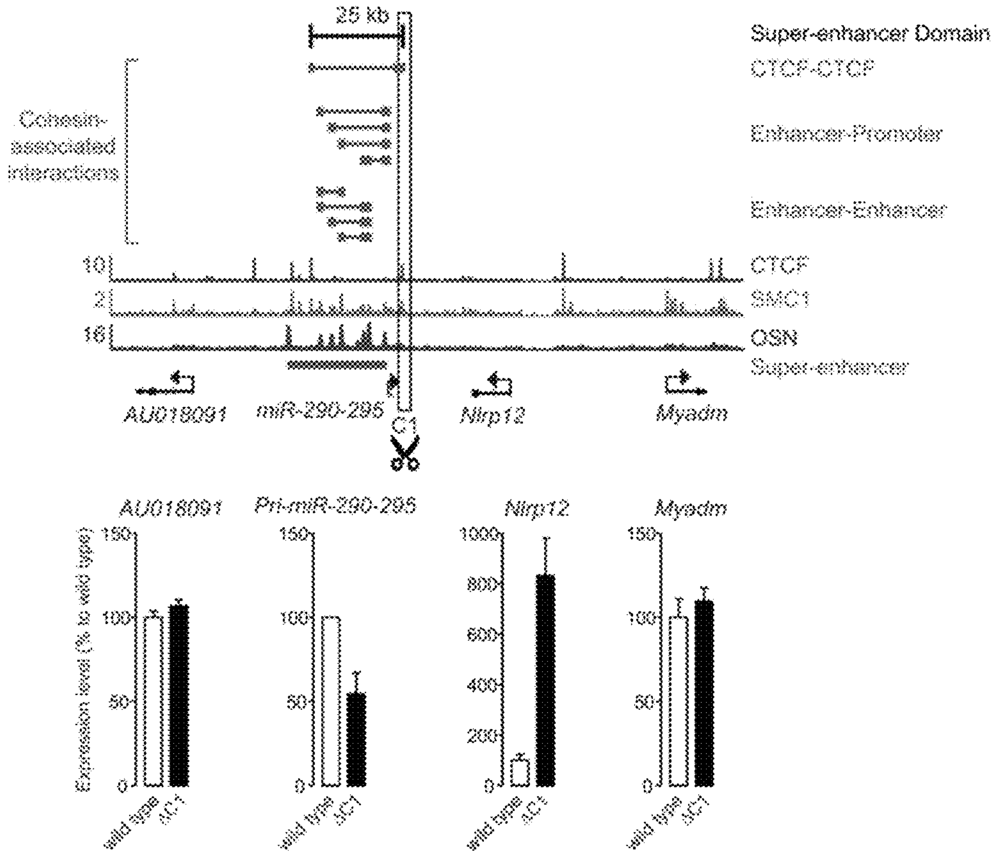
FIG. 4 Super-Enhancer Domains Are Functionally Linked to Gene Expression. CRISPR-mediated genome editing of CTCF sites at five loci. The top of each panel shows high-confidence interactions depicted as blue lines and ChIP-seq binding profiles (reads per million per base pair)
Figure 4:
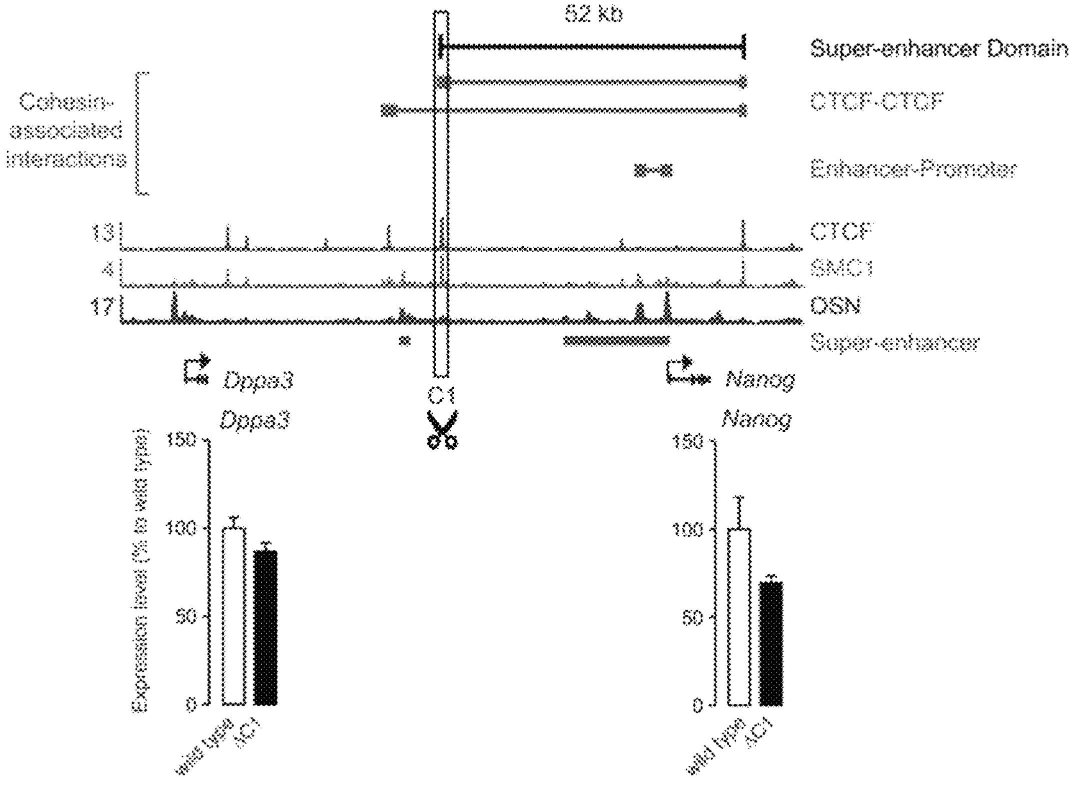
Figure 4:
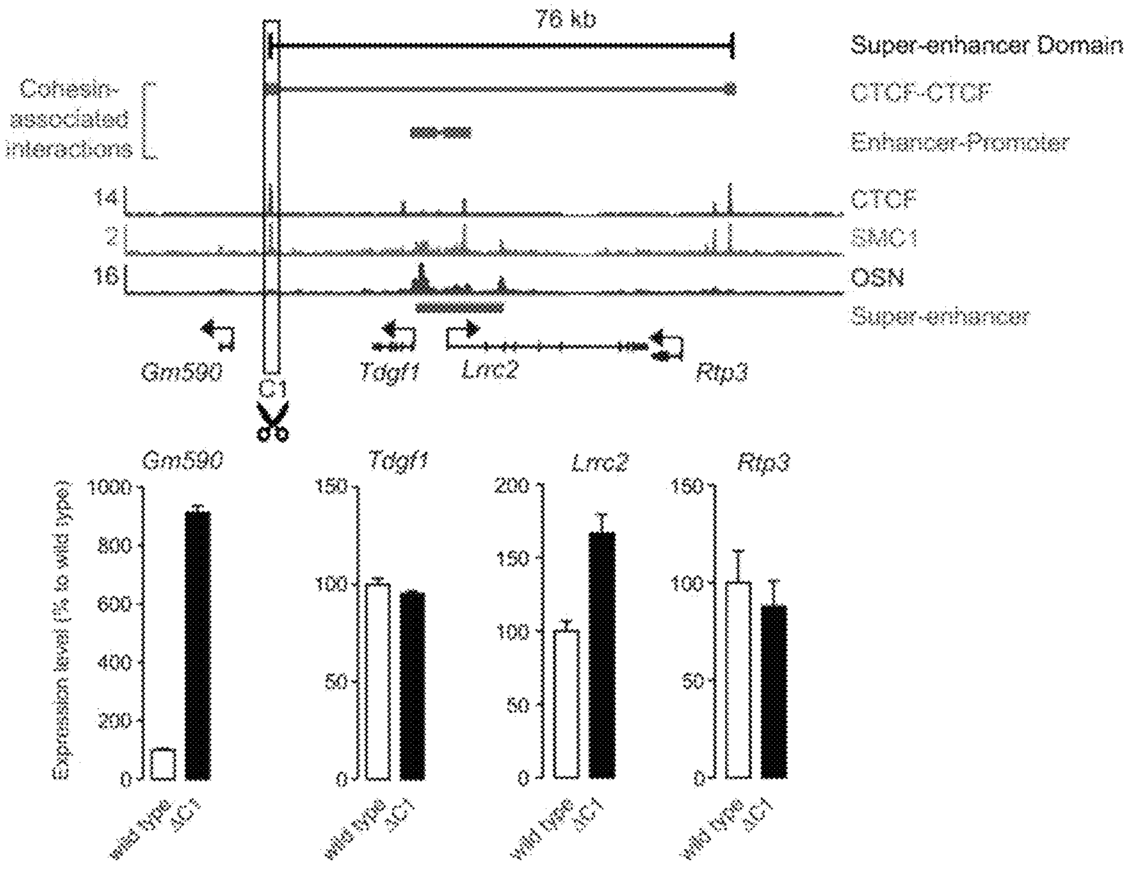
Figure 4:
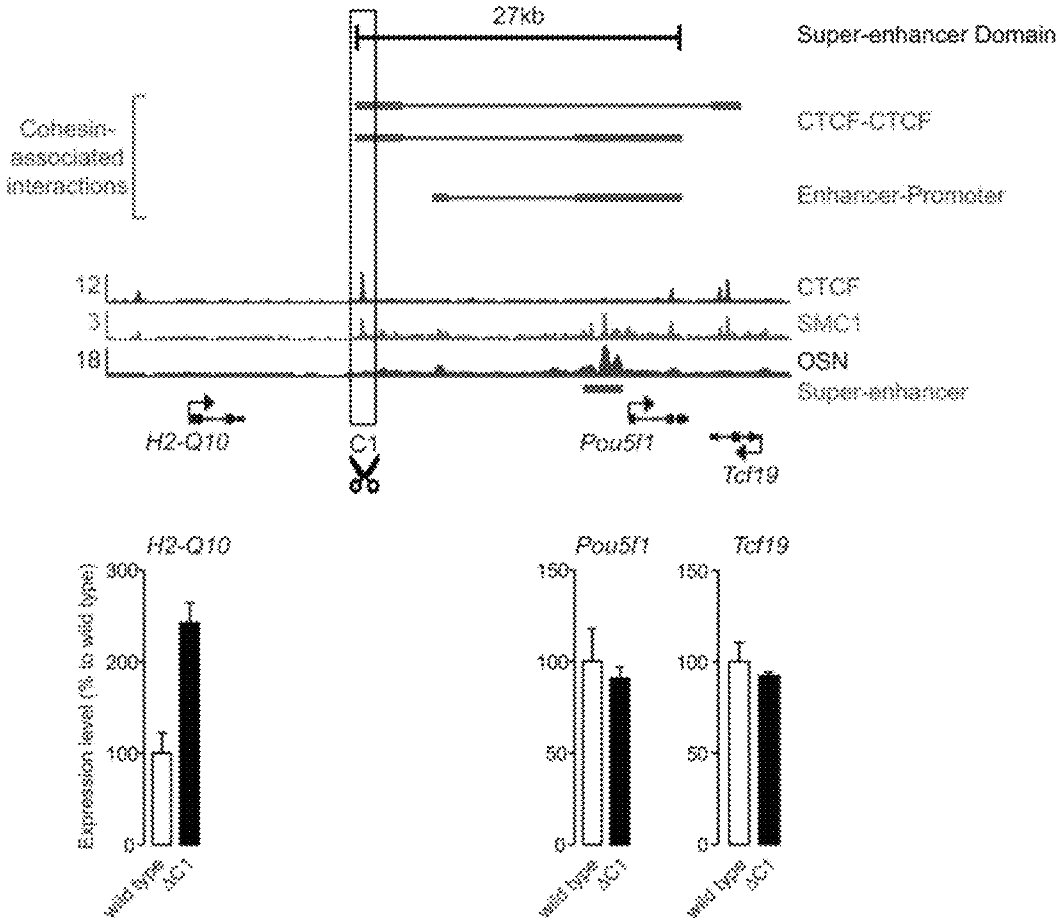
Figure 4:
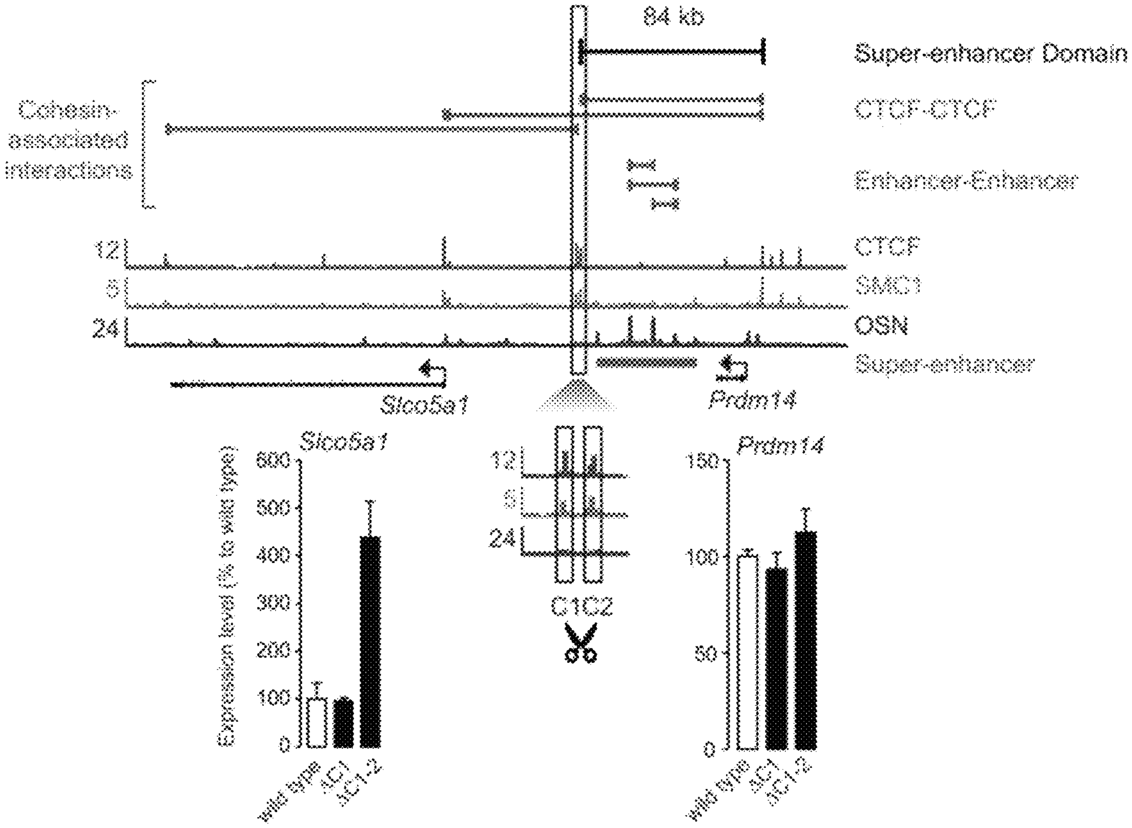

FIG. 10 (Figure S4) Super-Enhancer Domain Functions, Related to FIG. 4. (A) Quantitative 3C analysis at the miR-290-295 locus. The super-enhancer domain is indicated as a black bar. The deleted CTCF site is highlighted with a box. Arrows indicate the chromosomal positions between which the interaction frequency was assayed. Asterisk indicates the 3C anchor site. ChIP-seq binding profiles (reads per million per base pair) for CTCF, cohesin (SMC1), and the master transcription factors OCT4, SOX2, and NANOG (OSN) are also shown. The super-enhancer is indicated as a red bar. The interaction frequencies between the indicated chromosomal positions and the 3C anchor sites are displayed as a bar chart (mean+SD) on the bottom panel. qPCR reactions were run in duplicates, and values are normalized against the mean interaction frequency in wild-type cells. ($p<0.05$ for all three regions; Student's t test.) (B) Quantitative 3C analysis at the Pou5f1 locus. The super-enhancer domain is indicated as a black bar. The deleted CTCF site is highlighted with a box. Arrow indicates the chromosomal positions between which the interaction frequency was assayed. Asterisk indicates the 3C anchor site. ChIP-seq binding profiles (reads per million per base pair) for CTCF, cohesin (SMC1), and the master transcription factors OCT4, SOX2, and NANOG (OSN) are also shown. The super enhancer is indicated as a red bar. The interaction frequencies between the indicated chromosomal positions and the 3C anchor sites are displayed as a bar chart (mean SD) on the bottom panel. qPCR reactions were run in duplicates, and values are normalized against the mean interaction frequency in wild-type cells. ($p<0.05$; Student's t test.) (C) Expression level of the indicated germ layer markers in wild-type cells and a cell line where the SD boundary CTCF site was deleted at the miR-290-295 locus. Gene expression was measured by qRT-PCR. Gene expression was assayed in triplicate reactions in at least two biological replicate samples and is displayed as mean+SD (p value<0.003, PAX6, GATA6 and Sox17 in wild-type versus CTCF site-deleted). p value was calculated using the Student's t test.

FIG. 11 (Figure S5) Polycomb Domain Interactions, Related to FIG. 5. Repressed developmental lineage genes reside in chromosome structures termed Polycomb Domains (PD). Example PDs within Topologically Associating Domains (TADs) are shown with high-confidence PET interactions depicted by blue lines. ChIP-seq binding profiles (reads per million per base pair) for CTCF, cohesin (SMC1), and H3K27me3 are shown at the example PDs in ESCs. (A) Genomic coordinates for the Tlx1 TAD are chr19:45,120,000-45,840,000. Genomic coordinates for the Tlx1 binding profiles are chr19:45,178,400-45,246,700. (B) Genomic coordinates for the Lhx4 TAD are chr1:157,400,000-158,640,000. Genomic coordinates for the Lhx4 binding profiles are chr1:157,392,000-157,657,700. (C) Genomic coordinates for the Ihh TAD are chr1:74,240,000-75,600,000. Genomic coordinates for the Ihh binding profiles are chr1:74,978,200-75,060,400. (D) Genomic coordinates for the Onecut3 TAD are chr10:79,200,001-81,040,000. Genomic coordinates for the Onecut3 binding profiles are chr10:79,892,959-79,985,160. (E) Genomic coordinates for the Rax TAD are chr18:66,080,001-66,680,000. Genomic coordinates for the Rax binding profiles are chr18:66,089,130-66,130,404. (F) Genomic coordinates for the Shh TAD are chr5:28,760,001-29,680,000. Genomic coordinates for the Shh binding profiles are chr5:28,766,181-28,808,422. (G) Genomic coordinates for the Dhh TAD are chr15:98,360,001-100,560,000. Genomic coordinates for the Dhh binding profiles are chr15:98,718,426-98,738,916. (H) Genomic coordinates for the Fendrr/Foxf1 TAD are chr8:123,160,001-124,360,000. Genomic coordinates for the Fendrr/Foxf1 binding profiles are chr8:123,482,102-123,627,553. (I) Genomic coordinates for the Bhlhe22 TAD are chr3:17,800,001-19,120,000. Genomic coordinates for the Bhlhe22 binding profiles are chr3:17,927,749-18,082,958. (J) Genomic coordinates for the Adamtsl5 TAD are chr10:

79,200,001-81,040,000. Genomic coordinates for the Adamtsl5 binding profiles are chr10:79,797,646-79,818,602.

FIG. 12 (Figure S6) SD and PD Boundary Sites Are Constitutively Occupied by CTCF across Multiple Cell Types, Related to FIG. 6. The proportions of SDs and PDs identified in ESCs for which CTCF ChIP-seq peaks at both boundaries are observed in other mouse cell types. Occupancy of CTCF peaks across the cell types was determined from publicly available CTCF ChIP-seq data (Shen et al., 2012). MEF cells are murine embryonic fibroblasts and MEL cells are murine erythroleukemia cells.

DETAILED DESCRIPTION

Provided herein are compositions and methods for the controlled or selected regulation of gene expression such as those genes found in insulated neighborhoods within the genome.

As used herein, an "insulated neighborhood" is a region of a chromosome bounded by one or more markers.

Modulation of gene expression in an insulated neighborhood can be effected by administration of a gene modulatory compound.

In one embodiment, administration of a gene modulatory compound increases the level of gene expression by 5%, 10%, 15%, 20%, 25%, 30%, 33%, 35%, 40%, 45%, 50%, 52% 55%, 60%, 65%, 67%, 69%, 70%, 74%, 75%, 76%, 77%, 80%, 85%, 90%, 95% or more than 95%.

In one embodiment, gene expression may be increased by 1, 2, 3, 4, 5, 6, 7, 8, 9, 10, 11, 12, 13, 14, 15, 16, 17, 18, 19, 20 21, 22, 23, 24, 15, 26, 27, 28, 29, 30, 31, 32, 33, 34, 35, 36, 37, 38, 39, 40, 41, 42, 43, 44, 45, 46, 47, 48, 49, 50, 51, 52, 53, 54, 1-5, 1-10, 1-20, 1-30, 1-40, 1-50, 2-5, 2-10, 2-20, 2-30, 2-40, 2-50, 3-5, 3-10, 3-20, 3-30, 3-40, 3-50, 4-6, 4-10, 4-20, 4-30, 4-40, 4-50, 5-7, 5-10, 5-20, 5-30, 5-40, 5-50, 6-8, 6-10, 6-20, 6-30, 6-40, 6-50, 7-10, 7-20, 7-30, 7-40, 7-50, 8-10, 8-20, 8-30, 8-40, 8-50, 9-10, 9-20, 9-30, 9-40, 9-50, 10-20, 10-30, 10-40, 10-50, 20-30, 20-40, 20-50, 30-40, 30-50 or 40-50 times the wild type level or such level as is presented by a subject having a disease or disorder associated with the aberrant expression of that gene.

Discussion of Results

Understanding how the ESC pluripotency gene expression program is regulated is of considerable interest because it provides the foundation for understanding gene control in all cells. There is much evidence that cohesin and CTCF have roles in connecting gene regulation and chromosome structure in ESCs (Cavalli and Misteli, 2013; Dixon et al., 2012; Gibcus and Dekker, 2013; Gorkin et al., 2014; Merkenschlager and Odom, 2013; Phillips-Cremins and Corces, 2013; Phillips-Cremins et al., 2013; Sanyal et al., 2012; Sofueva et al., 2013) but limited knowledge of these structures across the genome and scant functional evidence that specific structures actually contribute to the control of important ESC genes.

We describe here organizing principles that explain how a key set of cohesin-associated chromosome structures contributes to the ESC gene expression program. To gain insights into the relationship between transcriptional control of cell identity and control of chromosome structure, we carried out cohesin ChIA-PET and focused the analysis on loci containing super-enhancers, which drive expression of key cell identity genes.

We found that the majority of super enhancers and their associated genes occur within large loops that are connected through interacting CTCF sites co-occupied by cohesin. These super-enhancer domains, or SDs, typically contain one super-enhancer that loops to one gene within the SD. The SDs appear to restrict super-enhancer activity to genes within the SD because the cohesin ChIA-PET interactions occur primarily within the SD and loss of a CTCF boundary tends to cause inappropriate activation of nearby genes located outside that boundary.

The proper association of super-enhancers and their target genes in such "insulated neighborhoods" is of considerable importance, as the mistargeting of a single super enhancer is sufficient to cause leukemia (Groschel et al., 2014). The cohesin ChIA-PET data and perturbation of CTCF sites suggest that genes that encode repressed, lineage-specifying, developmental regulators also occur within insulated neighborhoods in ESCs. Maintenance of the pluripotent ESC state requires that genes encoding lineage-specifying developmental regulators are repressed, and these repressed lineage-specifying genes are occupied by nucleosomal histones that carry the polycomb mark H3K27me3 (Boyer et al., 2006; Bracken et al., 2006; Lee et al., 2006; Ne'gre et al., 2006; Schwartz et al., 2006; Squazzo et al., 2006; Tolhuis et al., 2006).

The majority of these genes were found to be located within a cohesion-associated CTCF-CTCF loop, which we call a polycomb domain (PD). The perturbation of CTCF PD boundary sites caused derepression of the polycomb-bound gene within the PD, suggesting that these boundaries are important for maintenance of gene repression within the PD. CTCF has previously been shown to be associated with boundary formation, insulator activity, and transcriptional regulation (Bell et al., 1999; Denholtz et al., 2013; Felsenfeld et al., 2004; Handoko et al., 2011; Kim et al., 2007; Phillips and Corces, 2009; Schwartz et al., 2012; Sexton et al., 2012; Soshnikova et al., 2010; Valenzuela and Kamakaka, 2006).

Previous report shave also demonstrated that cohesin and CTCF are associated with large loop substructures within TADs, whereas cohesin and Mediator are associated with smaller loop structures that sometimes form within the CTCF-bound loops (de Wit et al., 2013; Phillips-Cremins et al., 2013; Sofueva et al., 2013). CTCF-bound domains have been proposed to confine the activity of enhancers to specific target genes, thus yielding proper tissue-specific expression of genes (DeMare et al., 2013; Handoko et al., 2011; Hawkins et al., 2011).

Our genome-wide study extends these observations by connecting such structures with the transcriptional control of specific super-enhancer-driven and polycomb-repressed cell identity genes and by showing that these structures can contribute to the control of genes both inside and outside of the insulated neighborhoods that contain key pluripotency genes.

The organization of key cell identity genes into insulated neighborhoods may be a property common to all mammalian cell types. Indeed, several recent studies have identified CTCF-bound regions whose function is consistent with ESC SDs (Guo et al., 2011; Wang et al., 2014).

For example, in T cell acute lymphocytic leukemia, Notch1 activation leads to increased expression of a super-enhancer-driven gene found between two CTCF sites that are structurally connected but does not affect genes located outside of the two CTCF sites (Wang et al., 2014).

Future studies addressing the mechanisms that regulate loop formation should provide additional insights into the relationships between transcriptional control of cell identity genes and control of local chromosome structure.

The following examples of the related art and limitations related therewith are intended to be illustrative and not exclusive. Other limitations of the related art will become apparent to those of skill in the art upon a reading of the specification and a study of the drawings.

Compounds useful in the invention include those described herein in any of their pharmaceutically acceptable forms, including isomers such as diastereomers and enantiomers, salts, solvates, and polymorphs, as well as racemic mixtures and pure isomers of the compounds described herein, where applicable.

While a number of exemplary aspects and embodiments have been discussed herein, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

All patents, patent applications, patent publications, scientific articles and the like, cited or identified in this application are hereby incorporated by reference in their entirety in order to describe more fully the state of the art to which the present application pertains.

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

REFERENCES

Baranello, L., Kouzine, F., and Levens, D. (2014). CTCF and cohesin cooperate to organize the 3D structure of the mammalian genome. Proc. Natl. Acad. Sci. USA 111, 889-890.

Bell, A. C., West, A. G., and Felsenfeld, G. (1999). The protein CTCF is required for the enhancer blocking activity of vertebrate insulators. Cell 98, 387-396.

Boyer, L. A., Plath, K., Zeitlinger, J., Brambrink, T., Medeiros, L. A., Lee, T. I., Levine, S. S., Wernig, M., Tajonar, A., Ray, M. K., et al. (2006). Polycomb complexes repress developmental regulators in murine embryonic stem cells. Nature 441, 349-353.

Bracken, A. P., Dietrich, N., Pasini, D., Hansen, K. H., and Helin, K. (2006). Genome-wide mapping of Polycomb target genes unravels their roles in cell fate transitions. Genes Dev. 20, 1123-1136.

Cavalli, G., and Misteli, T. (2013). Functional implications of genome topology. Nat. Struct. Mol. Biol. 20, 290-299.

Chepclev, I., Wei, G., Wangsa, D., Tang, Q., and Zhao, K. (2012). Characterization of genome-wide enhancer-promoter interactions reveals co-expression of interacting genes and modes of higher order chromatin organization. Cell Res. 22, 490-503.

Cuddapah, S., Jothi, R., Schones, D. E., Roh, T. Y., Cui, K., and Zhao, K. (2009). Global analysis of the insulator binding protein CTCF in chromatin barrier regions reveals demarcation of active and repressive domains. Genome Res. 19, 24-32.

de Wit, E., Bouwman, B. A., Zhu, Y., Klous, P., Splinter, E., Verstegen, M. J., Krijger, P. H., Festuccia, N., Nora, E. P., Welling, M., et al. (2013). The pluripotent genome in three dimensions is shaped around pluripotency factors. Nature 501, 227-231.

DeMare, L. E., Leng, J., Cotney, J., Reilly, S. K., Yin, J., Sarro, R., and Noonan, J. P. (2013). The genomic landscape of cohesin-associated chromatin interactions. Genome Res. 23, 1224-1234.

Denholtz, M., Bonora, G., Chronis, C., Splinter, E., de Laat, W., Ernst, J., Pellegrini, M., and Plath, K. (2013). Long-range chromatin contacts in embryonic stem cells reveal a role for pluripotency factors and polycomb proteins in genome organization. Cell Stem Cell 13, 602-616.

Dixon, J. R., Selvaraj, S., Yue, F., Kim, A., Li, Y., Shen, Y., Hu, M., Liu, J. S., and Ren, B. (2012). Topological domains in mammalian genomes identified by analysis of chromatin interactions. Nature 485, 376-380.

Dowen, J. M., Bilodeau, S., Orlando, D. A., Hu"bner, M. R., Abraham, B. J., Spector, D. L., and Young, R. A. (2013). Multiple structural maintenance of chromosome complexes at transcriptional regulatory elements. Stem Cell Rev. 1, 371-378.

Essafi, A., Webb, A., Berry, R. L., Slight, J., Burn, S. F., Spraggon, L., Velecela, V., Martinez-Estrada, O. M., Wiltshire, J. H., Roberts, S. G., et al. (2011). A wt1-controlled chromatin switching mechanism underpins tissue-specific wnt4 activation and repression. Dev. Cell 21, 559-574.

Felsenfeld, G., Burgess-Beusse, B., Farrell, C., Gaszner, M., Ghirlando, R., Huang, S., Jin, C., Litt, M., Magdinier, F., Mutskov, V., et al. (2004). Chromatin boundaries and chromatin domains. Cold Spring Harb. Symp. Quant. Biol. 69, 245-250.

Filippova, D., Patro, R., Duggal, G., and Kingsford, C. (2014). Identification of alternative topological domains in chromatin. Algorithms Mol. Biol. 9, 14.

Fullwood, M. J., Liu, M. H., Pan, Y. F., Liu, J., Xu, H., Mohamed, Y. B., Orlov, Y. L., Velkov, S., Ho, A., Mei, P. H., et al. (2009). An oestrogen-receptor-alpha-bound human chromatin interactome. Nature 462, 58-64.

Gibcus, J. H., and Dekker, J. (2013). The hierarchy of the 3D genome. Mol. Cell 49, 773-782. Goh, Y., Fullwood, M. J., Poh, H. M., Peh, S. Q., Ong, C. T., Zhang, J., Ruan, X., and Ruan, Y. (2012). Chromatin interaction analysis with paired-end tag sequencing (ChIA-PET) for mapping chromatin interactions and understanding transcription regulation. J. Vis. Exp. http://dx.doi.org/10.3791/3770.

Gorkin, D. U., Leung, D., and Ren, B. (2014). The 3D genome in transcriptional regulation and pluripotency. Cell Stem Cell 14, 762-775.

Groschel, S., Sanders, M. A., Hoogenboezem, R., de Wit, E., Bouwman, B. A., Erpelinck, C., van der Velden, V. H., Havermans, M., Avellino, R., van Lom, K., et al. (2014). A single oncogenic enhancer rearrangement causes concomitant EVI1 and GATA2 deregulation in leukemia. Cell 157, 369-381.

Guo, C., Yoon, H. S., Franklin, A., Jain, S., Ebert, A., Cheng, H. L., Hansen, E., Despo, O., Bossen, C., Vettermann, C., et al. (2011). CTCF-binding elements mediate control of V(D)J recombination. Nature 477, 424-430.

Handoko, L., Xu, H., Li, G., Ngan, C. Y., Chew, E., Schnapp, M., Lee, C. W., Ye, C., Ping, J. L., Mulawadi, F., et al. (2011). CTCF-mediated functional chromatin interactome in pluripotent cells. Nat. Genet. 43, 630-638.

Hawkins, R. D., Hon, G. C., Yang, C., Antosiewicz-Bourget, J. E., Lee, L. K., Ngo, Q. M., Klugman, S., Ching, K. A., Edsall, L. E., Ye, Z., et al. (2011). Dynamic chromatin states in human ES cells reveal potential regulatory sequences and genes involved in pluripotency. Cell Res. 21, 1393-1409.

Hnisz, D., Abraham, B. J., Lee, T. I., Lau, A., Saint-Andre, V., Sigova, A. A., Hoke, H. A., and Young, R. A. (2013). Super-enhancers in the control of cell identity and disease. Cell 155, 934-947.

Kagey, M. H., Newman, J. J., Bilodeau, S., Zhan, Y., Orlando, D. A., van Berkum, N. L., Ebmeier, C. C., Goossens, J., Rahl, P. B., Levine, S. S., et al. (2010). Mediator and cohesin connect gene expression and chromatin architecture. Nature 467, 430-435.

Kaspi, H., Chapnik, E., Levy, M., Beck, G., Hornstein, E., and Soen, Y. (2013). Brief report: miR-290-295 regulate embryonic stem cell differentiation propensities by repressing Pax6. Stem Cells 31, 2266-2272.

Kieffer-Kwon, K. R., Tang, Z., Mathe, E., Qian, J., Sung, M. H., Li, G., Resch, W., Baek, S., Pruett, N., Grøntved, L., et al. (2013). Interactome maps of mouse gene regulatory domains reveal basic principles of transcriptional regulation. Cell 155, 1507-1520.

Kim, T. H., Abdullaev, Z. K., Smith, A. D., Ching, K. A., Loukinov, D. I., Green, R. D., Zhang, M. Q., Lobanenkov, V. V., and Ren, B. (2007). Analysis of the vertebrate insulator protein CTCF-binding sites in the human genome. Cell 128, 1231-1245.

Lee, T. I., and Young, R. A. (2013). Transcriptional regulation and its misregulation in disease. Cell 152, 1237-1251.

Lee, T. I., Jenner, R. G., Boyer, L. A., Guenther, M. G., Levine, S. S., Kumar, R. M., Chevalier, B., Johnstone, S. E., Cole, M. F., Isono, K., et al. (2006). Control of developmental regulators by Polycomb in human embryonic stem cells. Cell 125, 301-313.

Lelli, K. M., Slattery, M., and Mann, R. S. (2012). Disentangling the many layers of eukaryotic transcriptional regulation. Annu. Rev. Genet. 46, 43-68.

Li, G., Fullwood, M. J., Xu, H., Mulawadi, F. H., Velkov, S., Vega, V., Ariyaratne, P. N., Mohamed, Y. B., Ooi, H. S., Tennakoon, C., et al. (2010). ChIA-PET tool for comprehensive chromatin interaction analysis with paired-end tag sequencing. Genome Biol. 11, R22.

Li, G., Ruan, X., Auerbach, R. K., Sandhu, K. S., Zheng, M., Wang, P., Poh, H. M., Goh, Y., Lim, J., Zhang, J., et al. (2012). Extensive promoter-centered chromatin interactions provide a topological basis for transcription regulation. Cell 148, 84-98.

Margueron, R., and Reinberg, D. (2011). The Polycomb complex PRC2 and its mark in life. Nature 469, 343-349.

Merkenschlager, M., and Odom, D. T. (2013). CTCF and cohesin: linking gene regulatory elements with their targets. Cell 152, 1285-1297.

Meuleman, W., Peric-Hupkes, D., Kind, J., Beaudry, J. B., Pagie, L., Kellis, M., Reinders, M., Wessels, L., and van Steensel, B. (2013). Constitutive nuclear lamina-genome interactions are highly conserved and associated with A/Trich sequence. Genome Res. 23, 270-280.

Naumova, N., Imakaev, M., Fudenberg, G., Zhan, Y., Lajoie, B. R., Mirny, L. A., and Dekker, J. (2013). Organization of the mitotic chromosome. Science 342, 948-953.

Negre, N., Hennetin, J., Sun, L. V., Lavrov, S., Bellis, M., White, K. P., and Cavalli, G. (2006). Chromosomal distribution of PcG proteins during *Drosophila* development. PLoS Biol. 4, e170.

Ng, H. H., and Surani, M. A. (2011). The transcriptional and signalling networks of pluripotency. Nat. Cell Biol. 13, 490-496. Nora, E. P., Lajoie, B. R., Schulz, E. G., Giorgetti, L., Okamoto, I., Servant, N., Piolot, T., van Berkum, N. L., Meisig, J., Sedat, J., et al. (2012). Spatial partitioning of the regulatory landscape of the X-inactivation centre. Nature 485, 381-385.

Ong, C. T., and Corces, V. G. (2014). CTCF: an architectural protein bridging genome topology and function. Nat. Rev. Genet. 15, 234-246.

Orkin, S. H., and Hochedlinger, K. (2011). Chromatin connections to pluripotency and cellular reprogramming. Cell 145, 835-850.

Parelho, V., Hadjur, S., Spivakov, M., Leleu, M., Sauer, S., Gregson, H. C., Jarmuz, A., Canzonetta, C., Webster, Z., Nesterova, T., et al. (2008). Cohesins functionally associate with CTCF on mammalian chromosome arms. Cell 132, 422-433.

Phillips, J. E., and Corces, V. G. (2009). CTCF: master weaver of the genome. Cell 137, 1194-1211.

Phillips-Cremins, J. E., and Corces, V. G. (2013). Chromatin insulators: linking genome organization to cellular function. Mol. Cell 50, 461-474.

Phillips-Cremins, J. E., Sauria, M. E., Sanyal, A., Gerasimova, T. I., Lajoie, B. R., Bell, J. S., Ong, C. T., Hookway, T. A., Guo, C., Sun, Y., et al. (2013). Architectural protein subclasses shape 3D organization of genomes during lineage commitment. Cell 153, 1281-1295.

Roeder, R. G. (2005). Transcriptional regulation and the role of diverse coactivators in animal cells. FEBS Lett. 579, 909-915.
Rubio, E. D., Reiss, D. J., Welcsh, P. L., Disteche, C. M., Filippova, G. N., Baliga, N. S., Aebersold, R., Ranish, J. A., and Krumm, A. (2008). CTCF physically links cohesin to chromatin. Proc. Natl. Acad. Sci. USA 105, 8309-8314.
Sanyal, A., Lajoie, B. R., Jain, G., and Dekker, J. (2012). The long-range interaction landscape of gene promoters. Nature 489, 109-113.
Schaaf, C. A., Misulovin, Z., Gause, M., Koenig, A., Gohara, D. W., Watson, A., and Dorsett, D. (2013). Cohesin and polycomb proteins functionally interact to control transcription at silenced and active genes. PLoS Genet. 9, e1003560.
Schwartz, Y. B., Kahn, T. G., Nix, D. A., Li, X. Y., Bourgon, R., Biggin, M., and Pirrotta, V. (2006). Genome-wide analysis of Polycomb targets in *Drosophila melanogaster*. Nat. Genet. 38, 700-705.
Schwartz, Y. B., Linder-Basso, D., Kharchenko, P. V., Tolstorukov, M. Y., Kim, M., Li, H. B., Gorchakov, A. A., Minoda, A., Shanower, G., Alekseyenko, A. A., et al. (2012). Nature and function of insulator protein binding sites in the *Drosophila* genome. Genome Res. 22, 2188-2198.
Seitan, V. C., Faure, A. J., Zhan, Y., McCord, R. P., Lajoie, B. R., Ing-Simmons, E., Lenhard, B., Giorgetti, L., Heard, E., Fisher, A. G., et al. (2013). Cohesin based chromatin interactions enable regulated gene expression within preexisting architectural compartments. Genome Res. 23, 2066-2077.
Sexton, T., Yaffe, E., Kenigsberg, E., Bantignies, F., Leblanc, B., Hoichman, M., Parrinello, H., Tanay, A., and Cavalli, G. (2012). Three-dimensional folding and functional organization principles of the *Drosophila* genome. Cell 148, 458-472.
Shen, Y., Yue, F., McCleary, D. F., Ye, Z., Edsall, L., Kuan, S., Wagner, U., Dixon, J., Lee, L., Lobanenkov, V. V., and Ren, B. (2012). A map of the cis-regulatory sequences in the mouse genome. Nature 488, 116-120.
Smallwood, A., and Ren, B. (2013). Genome organization and long-range regulation of gene expression by enhancers. Curr. Opin. Cell Biol. 25, 387-394.
Sofueva, S., Yaffe, E., Chan, W. C., Georgopoulou, D., Vietri Rudan, M., Mira-Bontenbal, H., Pollard, S. M., Schroth, G. P., Tanay, A., and Hadjur, S. (2013). Cohesin-mediated interactions organize chromosomal domain architecture. EMBO J. 32, 3119-3129.
Soshnikova, N., Montavon, T., Leleu, M., Galjart, N., and Duboule, D. (2010). Functional analysis of CTCF during mammalian limb development. Dev. Cell 19, 819-830.
Spitz, F., and Furlong, E. E. (2012). Transcription factors: from enhancer binding to developmental control. Nat. Rev. Genet. 13, 613-626.
Squazzo, S. L., O'Geen, H., Komashko, V. M., Krig, S. R., Jin, V. X., Jang, S. W., Margueron, R., Reinberg, D., Green, R., and Farnham, P. J. (2006). Suz12 binds to silenced regions of the genome in a cell-type-specific manner. Genome Res. 16, 890-900.
Tolhuis, B., de Wit, E., Muijrers, I., Teunissen, H., Talhout, W., van Steensel, B., and van Lohuizen, M. (2006). Genome-wide profiling of PRC1 and PRC2 Polycomb chromatin binding in *Drosophila melanogaster*. Nat. Genet. 38, 694-699.
Valenzuela, L., and Kamakaka, R. T. (2006). Chromatin insulators. Annu. Rev. Genet. 40, 107-138. Van Bortle, K., Ramos, E., Takenaka, N., Yang, J., Wahi, J. E., and Corces, V. G. (2012). *Drosophila* CTCF tandemly aligns with other insulator proteins at the borders of H3K27me3 domains. Genome Res. 22, 2176-2187.
Wang, H., Zang, C., Taing, L., Arnett, K. L., Wong, Y. J., Pear, W. S., Blacklow, S. C., Liu, X. S., and Aster, J. C. (2014). NOTCH1-RBPJ complexes drive target gene expression through dynamic interactions with superenhancers. Proc. Natl. Acad. Sci. USA 111, 705-710.
Wen, B., Wu, H., Shinkai, Y., Irizarry, R. A., and Feinberg, A. P. (2009). Large histone H3 lysine 9 dimethylated chromatin blocks distinguish differentiated from embryonic stem cells. Nat. Genet. 41, 246-250.
Wendt, K. S., Yoshida, K., Itoh, T., Bando, M., Koch, B., Schirghuber, E., Tsutsumi, S., Nagae, G., Ishihara, K., Mishiro, T., et al. (2008). Cohesin mediates transcriptional insulation by CCCTC-binding factor. Nature 451, 796-801.
Whyte, W. A., Bilodeau, S., Orlando, D. A., Hoke, H. A., Frampton, G. M., Foster, C. T., Cowley, S. M., and Young, R. A. (2012). Enhancer decommissioning by LSD1 during embryonic stem cell differentiation. Nature 482, 221-225.
Whyte, W. A., Orlando, D. A., Hnisz, D., Abraham, B. J., Lin, C. Y., Kagey, M. H., Rahl, P. B., Lee, T. I., and Young, R. A. (2013). Master transcription factors and mediator establish super-enhancers at key cell identity genes. Cell 153, 307-319.
Young, R. A. (2011). Control of the embryonic stem cell state. Cell 144, 940-954.
Zuin, J., Dixon, J. R., van der Reijden, M. I., Ye, Z., Kolovos, P., Brouwer, R. W., van de Corput, M. P., van de Werken, H. J., Knoch, T. A., van IJcken, W. F., et al. (2014). Cohesin and CTCF differentially affect chromatin architecture and gene expression in human cells. Proc. Natl. Acad. Sci. USA 111, 996-1001.
Benjamini, Y., Hochberg, Y. (1995). Controlling the false discovery rate: a practical and powerful approach to multiple testing. J R Statist Soc B 57, 280-300.
Boyer, L. A., Plath, K., Zeitlinger, J., Brambrink, T., Medeiros, L. A., Lee, T. I., Levine, S. S., Wernig, M., Tajonar, A., Ray, M. K., et al. (2006). Polycomb complexes repress developmental regulators in murine embryonic stem cells. Nature 441, 349-353.
Chen, X., Xu, H., Yuan, P., Fang, F., Huss, M., Vega, V. B., Wong, E., Orlov, Y. L., Zhang, W., Jiang, J., et al. (2008). Integration of external signaling pathways with the core transcriptional network in embryonic stem cells. Cell 133, 1106-1117.
Chepelev, I., Wei, G., Wangsa, D., Tang, Q., and Zhao, K. (2012). Characterization of genome-wide enhancer-promoter interactions reveals coexpression of interacting genes and modes of higher order chromatin organization. Cell research 22, 490-503.
Dixon, J. R., Selvaraj, S., Yue, F., Kim, A., Li, Y., Shen, Y., Hu, M., Liu, J. S., and Ren, B. (2012). Topological domains in mammalian genomes identified by analysis of chromatin interactions. Nature 485, 376-380.
Fuglede, B., and Topsoe, F. (2004). Jensen-Shannon Divergence and Hilbert space embedding. Information theory, 31.
Fullwood, M. J., Liu, M. H., Pan, Y. F., Liu, J., Xu, H., Mohamed, Y. B., Orlov, Y. L., Veikov, S., Ho, A., Mei, P. H., et al. (2009). An oestrogen-receptor-alpha-bound human chromatin interactome. Nature 462, 58-64.
Goh, Y., Fullwood, M. J., Poh, H. M., Peh, S. Q., Ong, C. T., Zhang, J., Ruan, X., and Ruan, Y. (2012). Chromatin Interaction Analysis with Paired-End Tag Sequencing (ChIA-PET) for mapping chromatin interactions and understanding transcription regulation. Journal of visualized experiments: JoVE.

Guenther, M. G., Levine, S. S., Boyer, L. A., Jaenisch, R., and Young, R. A. (2007). A chromatin landmark and transcription initiation at most promoters in human cells. Cell 130, 77-88.

Handoko, L., Xu, H., Li, G., Ngan, C. Y., Chew, E., Schnapp, M., Lee, C. W., Ye, C., Ping, J. L., Mulawadi, F., et al. (2011). CTCF-mediated functional chromatin interactome in pluripotent cells. Nature genetics 43, 630-638.

Hnisz, D., Abraham, B. J., Lee, T. I., Lau, A., Saint-Andre, V., Sigova, A. A., Hoke, H. A., and Young, R. A. (2013). Super-enhancers in the control of cell identity and disease. Cell 155, 934-947.

Kagey, M. H., Newman, J. J., Bilodeau, S., Zhan, Y., Orlando, D. A., van Berkum, N. L., Ebmeier, C. C., Goossens, J., Rahl, P. B., Levine, S. S., et al. (2010). Mediator and cohesin connect gene expression and chromatin architecture. Nature 467, 430-435.

Kent, W. J., Sugnet, C. W., Furey, T. S., Roskin, K. M., Pringle, T. H., Zahler, A. M., and Haussler, D. (2002). The human genome browser at UCSC. Genome Res 12, 996-1006.

Kieffer-Kwon, K. R., Tang, Z., Mathe, E., Qian, J., Sung, M. H., Li, G., Resch, W., Baek, S., Pruett, N., Grontved, L., et al. (2013). Interactome maps of mouse gene regulatory domains reveal basic principles of transcriptional regulation. Cell 155, 1507-1520.

Langmead, B., Trapnell, C., Pop, M., and Salzberg, S. L. (2009). Ultrafast and memory-efficient alignment of short DNA sequences to the human genome. Genome biology 10, R25.

Lee, T. I., Jenner, R. G., Boyer, L. A., Guenther, M. G., Levine, S. S., Kumar, R. M., Chevalier, B., Johnstone, S. E., Cole, M. F., Isono, K., et al. (2006). Control of developmental regulators by Polycomb in human embryonic stem cells. Cell 125, 301-313.

Lehoczky, J. A., Williams, M. E., and Innis, J. W. (2004). Conserved expression domains for genes upstream and within the HoxA and HoxD clusters suggests a long-range enhancer existed before cluster duplication. Evolution & development 6, 423-430.

Lettice, L. A., Heaney, S. J., Purdie, L. A., Li, L., de Beer, P., Oostra, B. A., Goode, D., Elgar, G., Hill, R. E., and de Graaff, E. (2003). A long-range Shh enhancer regulates expression in the developing limb and fin and is associated with preaxial polydactyly. Human molecular genetics 12, 1725-1735.

Li, G., Fullwood, M. J., Xu, H., Mulawadi, F. H., Velkov, S., Vega, V., Ariyaratne, P. N., Mohamed, Y. B., Ooi, H. S., Tennakoon, C., et al. (2010). ChIA-PET tool for comprehensive chromatin interaction analysis with paired-end tag sequencing. Genome biology 11, R22.

Li, G., Ruan, X., Auerbach, R. K., Sandhu, K. S., Zheng, M., Wang, P., Poh, H. M., Goh, Y., Lim, J., Zhang, J., et al. (2012). Extensive promoter-centered chromatin interactions provide a topological basis for transcription regulation. Cell 148, 84-98.

Lieberman-Aiden, E., van Berkum, N. L., Williams, L., Imakaev, M., Ragoczy, T., Telling, A., Amit, I., Lajoie, B. R., Sabo, P. J., Dorschner, M. O., et al. (2009). Comprehensive mapping of long-range interactions reveals folding principles of the human genome. Science 326, 289-293.

Loven, J., Hoke, H. A., Lin, C. Y., Lau, A., Orlando, D. A., Vakoc, C. R., Bradner, J. E., Lee, T. I., and Young, R. A. (2013). Selective inhibition of tumor oncogenes by disruption of super-enhancers. Cell 153, 320-334.

Meuleman, W., Peric-Hupkes, D., Kind, J., Beaudry, J. B., Pagie, L., Kellis, M., Reinders, M., Wessels, L., and van Steensel, B. (2013). Constitutive nuclear lamina-genome interactions are highly conserved and associated with A/T-rich sequence. Genome Res 23, 270-280.

Noble, W. S. (2009). How does multiple testing correction work? Nature biotechnology 27, 1135-1137.

Phillips-Cremins, J. E., Sauria, M. E., Sanyal, A., Gerasimova, T. I., Lajoie, B. R., Bell, J. S., Ong, C. T., Hookway, T. A., Guo, C., Sun, Y., et al. (2013). Architectural protein subclasses shape 3D organization of genomes during lineage commitment. Cell 153, 1281-1295.

Shen, Y., Yue, F., McCleary, D. F., Ye, Z., Edsall, L., Kuan, S., Wagner, U., Dixon, J., Lee, L., Lobanenkov, V. V., et al. (2012). A map of the cis-regulatory sequences in the mouse genome. Nature 488, 116-120.

Spitz, F., Gonzalez, F., and Duboule, D. (2003). A global control region defines a chromosomal regulatory landscape containing the HoxD cluster. Cell 113, 405-417.

Wen, B., Wu, H., Shinkai, Y., Irizarry, R. A., and Feinberg, A. P. (2009). Large histone H3 lysine 9 dimethylated chromatin blocks distinguish differentiated from embryonic stem cells. Nature genetics 41, 246-250.

Whyte, W. A., Bilodeau, S., Orlando, D. A., Hoke, H. A., Frampton, G. M., Foster, C. T., Cowley, S. M., and Young, R. A. (2012). Enhancer decommissioning by LSD1 during embryonic stem cell differentiation. Nature 482, 221-225.

Whyte, W. A., Orlando, D. A., Hnisz, D., Abraham, B. J., Lin, C. Y., Kagey, M. H., Rahl, P. B., Lee, T. I., and Young, R. A. (2013). Master transcription factors and mediator establish super-enhancers at key cell identity genes. Cell 153, 307-319.

Xu, Z., Wei, G., Chepelev, I., Zhao, K., and Felsenfeld, G. (2011). Mapping of INS promoter interactions reveals its role in long-range regulation of SYT8 transcription. Nature structural & molecular biology 18, 372-378.

Zhang, Y., Liu, T., Meyer, C. A., Eeckhoute, J., Johnson, D. S., Bernstein, B. E., Nusbaum, C., Myers, R. M., Brown, M., Li, W., et al. (2008). Model-based analysis of ChIP-Seq (MACS). Genome biology 9, R137.

EXAMPLES

The following examples are illustrative in nature and are in no way intended to be limiting.

Example 1. Experimental Procedures

A. Experimental Procedures

Cell Culture

V6.5 murine ESCs were grown on irradiated murine embryonic fibroblasts (MEFs) under standard ESC conditions, as described previously (Whyte et al., 2012). V6.5 murine ESCs were grown on irradiated murine embryonic fibroblasts (MEFs). Cells were grown under standard ESC conditions as described previously (Whyte et al., 2012). Cells were grown on 0.2% gelatinized (Sigma, G1890) tissue culture plates in ESC media; DMEM-KO (Invitrogen, 10829-018) supplemented with 15% fetal bovine serum (Hyclone, characterized SH3007103), 1,000 U/ml LIF (ESGRO, ESG1106), 100 μM nonessential amino acids (Invitrogen, 11140-050), 2 mM L-glutamine (Invitrogen, 25030-081), 100 U/ml penicillin, 100 μg/ml streptomycin (Invitrogen, 15140-122), and 8 nl/ml of 2-mercaptoethanol (Sigma, M7522).

Genome Editing

The CRISPR/Cas9 system was used to create ESC lines with CTCF site deletions. Target-specific oligonucleotides were cloned into a plasmid carrying a codon-optimized version of Cas9 (pX330, Addgene: 42230). The genomic sequences complementary to guide RNAs in the genome editing experiments were:

| Name | Sequence | SEQ ID NO |
|---|---|---|
| PRDM14_C1_up | ATGACATAATGAGATTCACG | |
| PRDM14_C1_down | ACTGAAGTGGAAGGTGAGTG | |
| PRDM14_C2_down | CGACCCACCTCCTAACCTTA | |
| MIR290_C1_up | CATTGGCTGTCAACTATACC | |
| MIR290_C1_down | CCCGTCCTAAATTATCTGCG | |
| POU5F1_C1_up | CAGAAGCTGACAACACCAAG | |
| POU5F1_C1_down | ACACTCAAACTCGAGGACTC | |
| NANOG_C1_up | TTAAACACATCATAAGATGA | |
| NANOG_C1_down | TGAACTACGTAGCAAGTTCC | |
| TDGF1_C1_up | CAGTCTGAACTGCACATAGC | |
| TDGF1_C1_down | AAAGCTAAACTCTCCCAAGT | |
| TCFAP2E_C1_up | CCACGTGGGAAATCTAACTC | |
| TCFAP2E_C1_down | GAAGTGAAGCCTTCTCGTTA | |
| TCFAP2E_C2_up | GAAGAGTGTGACTGAAAAGA | |
| TCFAP2E_C2_down | TCTCACGGAGCCTCAGGAGA | |

Cells were transfected with two plasmids expressing Cas9 and sgRNA targeting regions around 200 base pairs up- and downstream of the CTCF binding site, respectively. A plasmid expressing PGK-puroR was also cotransfected, using X-fect reagent (Clontech) according to the manufacturer's instructions. One day after transfection, cells were replated on DR4 MEF feeder layers. One day after replating, puromycin (2 ug/ml) was added for 3 days. Subsequently, puromycin was withdrawn for 3-4 days. Individual colonies were picked and genotyped by PCR.

For the Prdm14 (C1-2), mir-290-295, Pou5f1 and Nanog SDs and Tcfap2e (C1) PD boundary CTCF site deletions, at least two independent clones were expanded and analyzed. Data on FIGS. 4, 5 and S4 were obtained from the analysis of a single representative clone for each genotype. The sequences of the deletion alleles in the used cell lines are listed below.

PRDM14 locus reference sequence (SEQ ID NO: 16):

```
CCGTTTCCCTAGCACAGAGCCACCCAGGACCAGAAATAACAGCTTCACAA
AAGAGCTCGCTCTGTACACATGGGTCCCAAGGAAGAAGTGAGATTCTTTC
CCCCTCACTGAGGAAAGGGGGCCGTCTTTCCTGCTAAAGAGAAAGAAAGT
GAAGTTTCCTGGAATCTTCTTTTTCTCCTCGTGAATCTCATTATGTCATC
GAAATTCTAGGCTTAATCGATGCTTCTGCCCCAGCTTCTCAATTATCTGA
GATTTCAGATGCCCACCGCGTCCAGCTCAGAAAATCAAATTGTGGTTACT
ATTCTAGACATTTCCAGCAGAGGGCGCTTCGGTGCAGGTAGCCAGAACAC
```

-continued

```
CGAAGTCATCCAGTTTCTGGCCGCAAACTCAGATTACTAGATTGCCAACA
GGGTTTCCAGAACGTGGGTAAAAGAGACTGAAGTGGCAATCCCCACGAAA
ACAAAAAAAACAAAACAAAACGGTCAAGGGTGCTTCGTACTGAAGTGGAA
GGTGAGTGAGGCTGTGTGGGCAGATCGCAACCGTCATTTAGAACAAACCT
GAAGCAGAGCGGTGTAAATGACTGTATTCCCAGCACTCAAGAGAATAGCT
GGAGCTTTGGCCAGCCTACAGAGGAGACCCTGTGCTGTTCTCAGTATTCA
GTTATGCTACCCTCTAATGAAGTACATTGTACTTCCTGGTAATTTCATTT
TTATGAAAGGCAATACTGGATTCCTGCCTTTCTTCCTTTCTGCCTGTAGT
CCGTTTTTAGGTTGATCAACAGGTTGACATTACACTTGTGACAATTCTCT
TGCCTCACGGAACGATAACGTTTCAAAGGGGAAGACTAATTAGGATTGGT
ACCGTTAGTTTTTTGTCAACACAGCCAGAGTCATCTGGGAAGAGGGAACC
TGAGCTGGGGGTTTACCTCCATCAGATCGTTTGTGAGTATGTCTGTAGGA
AATGTTCTTAATCATTAATATCGGAGAGCCAGACCATCCCCGGTGGTGCC
ACTGCTGGGCCGGTAGTCCTGGGTGATACAAGGAGGCAGGTTTACTGGCT
AGTAAGCAGCACTCCTTTGCAGGCTCTGCTCCACTCTCTCCTTCCTCCCT
TCTGCCTTGAGTTCCTGTCTTGACTTCCCTCGGTGATGAGCTGTACCCTG
AAAACCAGATAACTTGTCCTTAATTTACTTTTGGTCATGGTAGACTTTTT
ATTATTGTTGTTTTGTTGTTGTTGTTGTTGTTGTTGTTTTTATGTGTATG
GGTGTTTTGCTTACAAGTATGTCTGGGCACCATATTCATGCACAGTGATG
CCCAATGATTCCAGAAAAGGGCCGAGGATTCCCTGGGACTGGAGTTACAG
AAAGTTAGGAGCTGCCATGTGTGTGCAGCGAATCAAACTCTGGCCTTCTG
GAAGAGCAGCCAGTGCTCTTAACTGCTGATCCATCTTTCTAGCCCACTTC
GTCACGTTGTTTATCACAGCAGTCGAAAGCAGACTAGGACATGATGGAAA
GGAGTCAAAAGCTTGGTCAAGGGATCTTTAGAGATGGGAAGGGGAACTTT
TTAAACGTTGGTCCTGCCATGCTCTCCCAGAGGCATGGTGCCTTCTCTGT
CTTTCCTAGTGCTTTCCTTTGCAAAGCAAGCAAATATCATCTACTTTGGT
GTTTTAAGAAATAGTACGGGGGGGCTGGTGAGATGGCTCAGTGGGTTAGA
GCACCCGACTGCTCTTCCGAAGGTCCAGAGTTCAAATCCCAGCAACCACA
TGGTGGCTCACAACCATCCGTAACGAGATCTGACTCCCTCTTCTGGTGTG
TCTGAAGACAGCTACAATGTACTTACATATAATAAATAAATAAATCTTTA
AAAAAAAAAAAAAAAAAAAAAAAAAGAAATAGTACGGGGCTGGTGAGATGG
CTTAGTGGGTAAAAGCACCCGACTGCTCTTCCGAAGGTTCAAAGTTCAAA
TCCCAGCAACCACATGGTGGCTCACAATCACCCGTAATGAGATCTGACTC
CCTCTTCTGAAGTGTCTAAAGACAGCTACAGTGTACATTATATGTAATAA
ATAAATGTTTTTTTMAAAAAGAAAGAAATAGTACATTTCTCAATGGCCTC
GAGAATTAACCTGCAGGAAAAGGAAAATGCTGTGTTTCTTCTCCAAAAAT
CCTATAGGTGGCGCACAGACACCGGTTTCAAGTGATGGGTCCCAGCTTTG
ACCTTTCTGCCCAAGTCCGGTTTGTCGGGAACTCTTCTTCCTTCTGCCTC
TACCCCCTGCCAGAATTACAGGGCTGCTCTTGGCTCTGAGTTGTTCGGTG
TAAGTGAGAAAGCAAGCAGCACCTGCAGTCCTGAGGTGTCACCTAGCAGC
```

-continued

```
TCCCTTCTAACAAGGCTGCGCTCCTCTTGGGAGGACATAGCCAAGAGTCA
CTGAAGGGCAAGCTCCCTCAAAGCTCCTCTCTAAGGTTAAATAGCAGCAT
GACCTCGACCCACCTCCTAACCTTAAGGTTCATATTCTCTCTGCAAAACA
TCAAGGGGGTCTGGAGGAACACTGAAGTCCCTCCTGCCGCATG
```

PRDM14 C1-2 Deletion allele sequence (SEQ ID NO: 17):

```
TCTCCTGCTAAAGAGAAAGAAAGTGAAGTTTCCTGGAATCTTCTTTTTCT
CCTCCACCTCCTAACCTTAAGGTTCATATTCTCTCTGCAAAACATCAAGG
GGGTCTGGAGGAACACTG
```

MIR290 locus reference sequence (SEO ID NO: 18):

```
CCAGGCCTCACTAGTGTCAGGTCGTGAGTCATGCACAGCCATGATTTCTG
CATCCTTGGCCACCTTGCTCAGTTTTCTGGAGTGTTGAGATTCAATGCGA
ACACCACCACAGCTGGGCAAAATCTAATAACCCAGGATAGGATGGGAGCA
TTGGCTGTCAACTATACCAGGTGTGCAAATCTTGGGTTTTGAGGCCTCAT
TTGTAAGGTGCCTTATACCTTTAGCCCCAGCCCACTTTTTTTTCCCCCTG
CTGTATAAAATTCAGGTGTGAGTACAATTTTTCTTTTTAAAGATTTATAA
GTGTTCTGTAGCTATCTTCAGATTCACCCAAAGAAGGCATTGGATCCCAT
TACAGATGATTGCAAGCCACCATGTAGTTGCTGGGAATTGAACTCAGGAC
CTCTGACTTAACCACTCCAGCCCTTGAGTACAATTTTTGAAAAATTACCT
TGTGGGTCTTTATGCTGTGACTTGGCCAGTAGATGGCAGTCTTGGTCCAT
GGAAATGTCTAGGACTCTGGATATTTTTCCTTTTCTGTGGTCTTTACTGA
TCTTCAAACCTGCTAACCAGCCAATCCCCGTCCTAAATTATCTGCGTGGA
ATCTACATCAAACCCAGTGAGCTCCATCAAAGGTTGAGTGTTTAGGTCTC
AAGCAGAACAATTTTGTCAACCTGCACTTACTGGGCCTCCTGACCTAAGA
CGGTCCCATGTAACAGGATGACCTTGAGTGATCTTGTCTCCACCTCACCA
TATACCAGAGGCTGGCCTTTAAAAGTTCCACCTCAAGTGCTTCAAAGCA
```

MIR290 C1 deletion allele sequence (SEQ ID NO: 19):

```
AAATCTAATAACCCAGGATAGGATGGGAGCATTGGCTGTCAATCTATATC
AAACCCAGTGAGCTCCATCAAAGGTTGAGTGTTTAGGTCTCAAGTAGAAC
AATTTTGTCAACCTGCACTTACTGGGCCTCCTGACCTAAGACGGTCCCAT
GTAACAGGAT
```

POU5F1 locus reference sequence (SEQ ID NO: 20):

```
CTCAGCCATCTCCCTGTTGAGCTGTCAAGCAGAGAGGCCCCAACAACAAC
ACAGGAAATTGCCAGTGTTCTTGATTGCCCAAAAGAACCAGATGACCAGA
AGCTGACAACACCAAGAGGCTAGGGGTCTTCCAGTTGGCCTTGTACTGTT
GCAACTGTCAGGGAAAGGATGTAACCAGAGGGCCTCTGGGACTCCTCTCA
CCCTTGATAGTTTGAGGGATATGAGCAAATTACACGGTTATCAGAAGGTG
GCCATAGTGACACTGAAAATTGGCCCATTGGCTTCAAAGATTTACCAAAG
```

-continued

```
TACCGTCCGTATTTTCTACCTACGGTGTGCTGGAGCCTAGAGGACACTAG
GGGGCGCGCTGAGCTCGCGGAAGCCACCCAGAGTCCTTCCAGGAGACTCC
CTTAAAGGTTGATCAAATTGTTCTTTGCCAAACTGAATTTATCATAAAAA
TTATACTTTATTTTGTATTACTTTGTGTACATGGGTGTTTTGCCTTCACA
GATGCGTCTGGTGCACCTGAGAAGCCAGAAAAGAGAACAGGAGTGAACAG
GTTTGTGGGGGCTGACACTCAAACTCGAGGACTCTGGGAAAGCATCGAGT
GCTCTTAACCATTGAGCCATCTCTCCAGCCCATCTGTTTTCTTTTGCCGG
AGGAAGGGGCTCTGAGAAAGGATCTTACCTGTAGCCCAGGCTGGCCCAGT
TCACCATGTGATGAAGGCTCCTTTCAAATCCAAGCTA
```

POU5F1 C1 deletion allele sequence (SEQ ID NO: 21):

```
AATTGCCAGTGTTCTTGATTGCCCAAAAGAACCAGATGACCAGAAGCTGA
CAACAAATTATACTTTATTTTGTATTACTTTGTGTACATGGGTGTTTTGC
CTTCACAGATGCGTCTGGTGCACCTGAGAAGCCAGAAAAGAGAACAGGAG
TGAACAGGTTTGT
```

NANOG locus reference sequence (SEQ ID NO: 22):

```
TCAGTTGTGTGTGGGGTAGGCCATGTGTGCCTTGGTGCACATGTGCAGGT
CAGAACAACTTGGGTGAGAGTCTGCTTCCTTTTTCTGCTCTGTATGGGTT
GTAGGGATAGAATTCAAGTTTCGCATTTGAATTCTATGGTTTAGCACTTA
AACATCAAAACCTTTCCCAGAACGTCACACTTCAATGCCATTGAGGAAGG
TGTCTGTAACGCTGTGTGTGTGTTGTTAGTTAAACACATCATAAGATGAA
GGAAAGCTGGGAGTGTCCTTAACACAGCAGCGAGCAGCAAAAGCTACTTT
CTCCTCAAGCCTGGAGGAGTCTGGTCCGACAGTCCACCAACAGGGGGCGT
TATTTCCCAGCCCTCGTGAAGCGTTGAACTGTCCTGGTGAGAAGGGTGAT
GTGCAGTTCCTTGTCTCAGCAGCAGATGGAGCCATAGGGACGAGAACAAG
TTCCTAGGTGAAGGAAGGAGTGGGGGGAGACGAAGCGGAAGAAGCTGAAG
TGCATCTTGGTCGGTCAAATTTTTCTTATTGATGAAAAAGATGATTAAAG
GACACTGTGAATTTGAGACTATTCTGAACTACGTAGCAAGTTCCAGGACA
GCCAGTGTTACAAATCAAGACCCGATTTTGGAAGAAGATGGGGGCTGGGG
AAGGCGCCATGTTCCCCCCCCCACCCCCCACCCCCAGCTCCCATCTCATC
TGTTGCTACATTTACTAGACTGCCAAGAATTTTCTCTCTCAGAAATTAAA
AAAATAGTAAAGAAATAAAGAAAAAAGCCAGGCATGATGGTTCACTCTCA
TAATCCCATAATTCCATTACGTAAGAGAATCTCTCTACC
```

NANOG C1 deletion allele sequence (SEQ ID NO: 23):

```
GTCTGTAACGCTGTGTGTGTGTTGTTAGTTAAACACATCATAAGATCCAG
GACAGCCAGTGTTACAAATCAAGACCCGATTTTGGAAGAAGATGGGGGCT
G
```

TDGF1 locus reference sequence (SEQ ID NO: 24):

TGAGCAACAAGATGTCTGCACCATCTTTTCATCCCTCGGATTTTTCTTTA

TAGTCGTGGCTTGTACTGAGTAGACAGGTTCCTGTCTCTGACAAAAACGG

AGGACAGAAACCCCACTCTTCTCCAAAGAAGCATGCTGATAAAAAGTGGA

CACAAACCATGAACTGCCGTGTGACAGTCTGAACTGCACATAGCCGGATG

AGGCTTTCGGGTAAAGACTAGAATTGCAAGATTACTAACACTGTTAAACT

CTTTGTTTTCTGCAGTCCTTGGTTTAGACTCAAGACTCTGAAACCTAGAA

ACTGAGCTCAAGGCTTCCGAGGCTTTGACATCGAAACACCTGATCTCCAG

TAGGGGGCGCTGCAGCCTAGCAGGGCGGAGCTGACTCTTCTGGCCAGTTT

TTTCTCCTGATGGTCCCAGTAAAACTCATGTCAGGCTCAGATTTTAGACT

AAGGGACTGGAAAGGGGGAATTCTGAGAATTAGAGCTAAAGAATTAGAGG

GGTTAAAGAGTGAAGCCCAGGAAAATATATTTGAACAAATAAAAGCTAAA

CTCTCCCAAGTTGGACAAACAAAAACAAAACAAAAACCCTCCATAAATCC

TCAATCTTTAGCTTCAAGAAATTGAATCCAAAGGAACCCATATCCAGACC

CGGTGCTCAGCGTGGAAAAGGCCAGAGTGCTGAAAGCAGCTGACTCTTCA

GTACACATGGACAAACCCTGGCAGAGCTGGGCAAGAAAACAGACACACCT

GGGTGTGATAATGACTT

TDGF1 C1 deletion allele sequence (SEQ ID NO: 25):

AGACAGGTTCCTGTCTCTGACAAAAACGGAGGACAGAAACCCCACTCTTC

TCCAAAGAAGCATGCTGATAAAAAGTGGACACAAACCATGAACTGCCGTG

TGACAGTCTGAACTGGACAAACAAAAACAAAACAAAAACCCTCCATAAAT

CCTCAATCTTTAGCTTCAAGAAATTGAATCCAAAGGAACCCATATCCAGA

CCCGGTGCTCAGCGTGGAAAAGG

TCFAP2E locus reference sequence (C1) (SEQ ID NO: 26):

GCTATCTTGCATCTAGAAGTGGAAAGACAGTTCTTTAAATGCCTAGGCAG

TGTACATTAACCTATGACAAGCAAACACTCCCCTGTGGATTTTGCTCTTC

AGTTTGCCTGTATGTATGTGTGCTTGTATTTGCACTGCATGTGTTTCTGG

TGCCCTTGAAGATCAGAAGAAACATCAAACCCCCTAGGACTAGAGTTACA

GATGGCTGTGAATCACCACGTGGGAAATCTAACTCTGGACTTGGGGGGGT

GTGTATTGAGAGAGTAATTTTTAGAAGAAAGAAGACAAGCAGGGTAGGAC

AGAAAATTTTTAAAAAGCTGGAAAGAATGTAATCTCATATGATTTTATAG

GATAAAATTTTAAGGTACAAATGGGACCACAGAATTAGTTCCCCACATGA

GCAAGATGGTCTTCTGTATTATTATTTTTTTTCCTTTTATGGTGTTTTGT

CTGCATGTGTGTCTGTGCACCATGTGCATGAAGTGCCTGAGAAGGCCAGC

AGAGGGCATCAGATCCCTTGAGATGAGTTACAGGTGGTTGAGAGACACCT

TATGAGTCCTGGAAATTATACCTGGGTACTCTGGAAGAGCAGCCAGGATT

CTTAACCTCTGAGCCATCTCCCTGGCCCCAATCTTTTGCATTCTTCTGTC

CGTCAGCTATTCAATCCATTTCAAAGTGGAAGTGAAGCCTTCTCGTTAAG

-continued

GATGACAGTTATCCGGAAGGGAGCATGAAAATGTTCCAGGGCCTTTTCTT

GCTTTATGCACACTCAAAGCTGAAAATCTTTCCCATGTCAATGGATGAGA

CCATCACTCAATACCTAAACAGAAAACTATGAAGCCTAATTGCTTGTGTG

CTTGCTTAAGTATATACTGGTTGGTGACAGCTTCCACCAAGAAAGGCATA

CCACTGATTGATAACATTGGTAACAACATGAACTTCAGGTATTGATAGGT

T

TCFAP2E C1 deletion allele sequence (SEQ ID NO: 27):

TGCACTGCATGTGTTTCTGGTGCCCTTGAAGATCAGAAGAAACATCAAAC

CCCCTAGGACTAGAGTTACAGATGGCTGTGAATCACCACGTGGGATGACA

GTTATCCGGAAGGGAGCATGAAAATGTTCCAGGGCCTTTTCTTGCTTTAT

GCACACTCAAAGCTGAAAATCTTTCCCATGTCAATGGATGAGACCATCAC

TCAATACCTAAACAGAAAACTAT

TCFAP2E locus reference sequence (C2) (SEQ ID NO: 28):

TGATCCACTTCCAGCTCCTTGGTTCATTCAGCATCTTTCACCTGGCCCAT

GCCCCTCCCCTTATGCAAAATGCCTCCGGGATCATGGCCTTGGCCCACTC

CAGGAATGAAGCTGACTAGCACTCCAGGACTCCTGGTTACTTTTCCTTTC

TTGCTCTGTGAGTCGCTTCACCAGAAGTCTAAAGTTGGGGGGGAGGGGGG

GGGGGAAGAGTGTGACTGAAAAGATGGCTCAGAGGCTACGAGAACCGGCT

GCTCTTTCAAAGGAGTCAGGTTTCATCCCCAGTACCCACATGGCAGGAAT

GGCTATCTGTAATTCCAGTTCTGATGGATCTGGTGAGTCTGACGCCCTCT

TCTGGCCCCCACAGGCATTGCGCTGCACAGACAGGCTGGCAGAACACCCC

ACACATAAAACAATAAAGGAATCTTTAAAAAAAAAAAAAAAGTCTAAAGAA

GTCACAAGTCGGGCTGGTGAGATGGCTCAGTGGGTAAGAGCACCCGACTG

CTCTTCCAAAGGTCCGGAGTTCAAATCCCAGCAACCACATGGTGGCTCAC

AACCATCCATAATGAGATCTGACGCCCTCTTAAGTGTCTGAAGACAGCTA

CAGTGTACTTACATATAATAAATAAATAAATCTAAAAAAAAAAAAAGTCAA

AAGTCTATTTAGTACTTTGCTTGGAGTGGGTCAAGCAGCCAACAAATAGC

TACTAAATAAATAAGTAACCAAAAAGATAATTACAGTTTTCCAAATCTGT

TAGGGGACTCTTTGGAAGGGCTCTTATGTGACCTTGACCTAGCATAGCTA

CACATAAGGCCCAGTTATAAGTGAGCACAAACGAGCAACTGTGCTTATTT

CTTCTAGGAGGGACATGTGCTTCATGAGCTACTTCTCTGGAGACCAGCAG

AGCTGTGGAATACCAGGGTTTCAGACTGGGCCCTTCTGTTTCAGGGGCAA

GGGTTCTTCACATTGTAAGCATGCAGGTGATGATTTCTTATGGTTTTATT

TTATTTTTTTTTTTTAGATACAGACACCTGGATGAAGGCATGAGGAAGGC

AGAGAGATACCCCTGGGAAAACGGAGACCACAACAGGCACAGATACACTG

ATAAGACATATATACACATCGGTATGCATGCTCAAATACACATGGACTCT

CAGTTGACATTCTTGGCTTATTCTCTTCCAAGGCTCACGTTTTCTCCTCT

TTAAAACAAAACAAAACGAAACGAAACGAAACAAAACAAACAAACAAACC

CCAAACTTTTTTGTCCTCCTTTGTTGACAGAGCCGGATTCCTCTTCCTAA

-continued

```
CAGGTCTGTCTGCAAATGTTTGAGATGAAATCTCGCAAAAGATACTGACG

CCCCATCTAGTGGCCGGAGCTTACCACTGCAGCTCAACACTCCCCTGCCT

GTCTCAGTGGAGGCACCCAGACAGAGCCAGCCCTGCCTTGCAAGCTTCCG

CTTAGCCCCTTGCTCACTCTGGAGTCTGGAACCCTCTCACGGAGCCTCAG

GAGAAGGCAGGTTTCAGTCTGCCTTCTGTTCTCAAGCTTCGCTGGCCTTG

GCATGCAGGAGAGCAACTCAACCGCAAGGACCGTGGACAGTAATCATTTG

CTTTGTGGCCTTTCCCTCACTTCCCCAGACTACCCGTTACTCCCATGATT

CCAAAGAACACTTGACAGCTCCCAAATCTGCCTC
```

TCFAP2E C2 deletion allele sequence (SEQ ID NO: 29):

```
GGGGGGGAAGAGTGTGACTGCCTTCTGTTCTCAAGCTTCGCTGGCCTTGG

CATGCAGGAGAGCAACTCAACCGCAAGGACCGTGGACAGTAATCATT
```

The CTCF-deletion lines at the Pou5f1 and Prdm14 (C1-2) loci are heterozygous, while the CTCF-deletion lines at the Nanog, Tdgf1, Prdm14 (C1) and miR-290-295 loci are homozygous for the mutation. Gene Expression Analysis ESC lines were split off MEFs for two passages. RNA was isolated using Trizol reagent (Invitrogen) or RNeasy purification kit (Promega), and reverse transcribed using oligo-dT primers and SuperScript III reverse transcriptase (Invitrogen) according to the manufacturers' instructions. Quantitative real-time PCR was performed on a 7000 AB Detection System using the following Taqman probes, according to the manufacturer's instructions (Applied Biosystems).

| |
|---|
| Gapdh: Mm99999915_g1 |
| Prdm14: Mm01237814_m1 |
| Slco5a1: Mm00556042_m1 |
| Pou5f1: Mm00658129_gH |
| H2-Q10: Mm01275264_g1 |
| Tcf19: Mm00508531_m1 |
| Mmu-mir-292b: Mm03307733_pri |
| Nlrp12: Mm01329688_m1 |
| Myadm: Mm01329822_m1 |
| AU018091: Mm01329669_m1 |
| Nanog: Mm02019550_s1 |
| Dppa3: Mm01184198_g1 |
| Tdgf1: Mm03024051_g1 |
| Gm590: Mm01250263_m1 |
| Lrrc2: Mm01250173_m1 |
| Rtp3: Mm00462169_m1 |
| Tcfap2e: Mm01179789_m1 |
| Psmb2: Mm00449477_m1 |
| Ncdn: Mm00449525_m1 |
| Sox2: Mm03053810_s1 |
| Pax6: Mm00443081_m1 |
| Gata6: Mm00802636_m1 |
| Sox17: Mm00488363_m1 |

Based on RNA-seq data (Shen et al., 2012), the genes are expressed at the following levels prior to deletion of the CTCF site:

Pou5f1: 79.4 RPKM (rank among 24,827 Refseq transcripts: 232, top 1%)

Prdm14: 2.21 RPKM (rank: 9,745, 39th %)

Slco5a1: 0.93 RPKM (rank: 12,277, 50th %)

miR-295: 18.9 RPKM (rank: 1,902, 8th %)

H2-Q10: 0.48 RPKM (rank: 13,782, 56th %)

Tcf19: 1.03 RPKM (rank: 12,011, 49th %)

Nlrp12: 0.06 RPKM (17,108, 69th %)

AU018091: 17.1 RPKM (rank: 2,150, 9th %)

Myadm: 14.6 RPKM (mean of multiple splice isoforms) (rank: 2610, 11th %)

Dppa3: 25 RPKM (rank: 1,320, 5th %)

Tdgf1: 92 RPKM (rank: 167, top 1%)

Lrrc2: 1.2 RPKM (rank: 10,292, 42nd %)

Rtp3: 0.01 RPKM (rank: 14,587 59th)

Sox2: 122 RPKM (rank: 100, top 1%)

Nanog: 122 RPKM (rank: 99, top 1%)

Pax6: 0.07 RPKM (rank: 16,941, 68th %)

Gata6: 0.25 RPKM (rank: 14,981, 60th %)

Sox17: 0.15 RPKM (rank: 15,754, 64th %)

Psmb2: 85 RPKM (rank: 203, top 1%)

Tcfap2e: 0.19 RPKM (rank: 15,402, 62nd %)

Ncdn: 3.19 RPKM (rank: 8,388, 24th %)

ChIP-Seq Illumina Sequencing and Library Generation

Purified DNA from a H3K27me3 ChIP was used to prepare a library for Illumina sequencing. The library was prepared following the Illumina TruSeq DNA Sample Preparation v2 kit protocol as previously described (Whyte et al., 2012).

Bioinformatics Analysis—ChIP-seq Data Analysis

All ChIP-Seq data sets were aligned using Bowtie (version 0.12.2) (Langmead et al., 2009) to build version MM9 of the mouse genome with parameter -k 1 -m 1 -n 2. Data sets used in this manuscript can be found in Table S6. We used the MACS version 1.4.2 (model-based analysis of ChIP-seq) (Zhang et al., 2008) peak finding algorithm to identify regions of ChIP-seq enrichment over input DNA control. A p value threshold of enrichment of 1e-09 was used for all data sets. For the histone modification H3K27me3 whose signal tends to be broad across large genomic regions, we used MACS (Zhang et al., 2008) with the parameter "-p 1e-09 -no-lambda -no-model". UCSC Genome Browser (Kent et al., 2002) tracks were generated using MACS wiggle outputs with parameters "-w -S -space=50".

SMC1 ChIP-Seq

Enrichment Heatmap FIG. 1B, S1A, and S1B shows the average ChIP-seq read density (r.p.m./bp) of different factors at the indicated sets of regions. The average ChIP-seq reads in 50 bp bin were calculated and drawn using bamToGFF (https://github.com/BradnerLab/pipeline). In FIG. 1B, +/−5 kb from the center of the SMC1-enriched region was interrogated. In Figure S1A, the enriched regions of OSN, MED1, and MED12 were merged together if overlapping by at least 1 bp. For each of the merged regions, +/−5 kb from the center of the merged region was interrogated. On Figure S1B, +/−5 kb from the center of the CTCF enriched region was interrogated.

Gene Sets and Classification of Gene Transcriptional State in ESCs

All gene-centric analyses in ESCs were performed using mouse (mm9/NCBI37) RefSeq annotations downloaded from the UCSC genome browser (genome.ucsc.edu). For counting purposes and for assignment of enhancers to target genes (Table S2A-C), we collapsed multiple identical TSS into one gene level TSS. Genes were separated into classes of activity as follows: A gene was defined as active if an enriched region for either H3K4me3 or RNA Pol II was located within +/−2.5 kb of the TSS and lacked an enriched region for H3K27me3 therein. H3K4me3 is a histone modification associated with transcription initiation (Guenther et al., 2007). A gene was defined as Polycomb-occupied if an enriched region for H3K27me3 (representing Polycomb complexes) but not RNA Pol II was located within +/−2.5 kb of the TSS. H3K27me3 is a histone modification associated with Polycomb complexes (Boyer et al., 2006; Lee et al., 2006). A gene was defined as silent if H3K4me3, H3K27me3, or RNA Pol II enriched regions was absent from +/−2.5 kb of the TSS. Remaining genes to which we were unable to assign a state were left as unclassified. Overall, there were 15,312 unique active TSSs, 1,091 unique Polycomb-occupied TSSs, 8,477 unique silent TSSs, and 616 unclassified TSSs in mouse ES cells.

Defining Active Enhancers in ESCs

Co-occupancy of ESC genomic sites by the OCT4, SOX2, and NANOG transcription factors is highly predictive of enhancer activity (Chen et al., 2008) and Mediator is typically associated with these sites (Kagey et al., 2010). We first pooled the reads of ChIP-seq profiles of transcription factors OCT4, SOX2, and NANOG, which were performed in parallel, to create a merged "OSN" ChIP-seq experiment (Whyte et al., 2013). These reads were processed by MACS to create an OSN binding profile for visualization. To define active enhancers, we first identified enriched regions for the merged "OSN" ChIP-seq read pool, and for both Mediator complex components MED1 and MED12 using MACS. Then we used the union of these five sets of enriched ChIP-Seq regions that fell outside of promoters (e.g., a region not overlapping with ±2.5 kb region flanking the RefSeq transcriptional start sites) as putative enhancers.

SMC1 ChIA-PET Processing

All ChIA-PET datasets were processed with a method adapted from a previous computational pipeline (Li et al., 2010). The raw sequences were analyzed for linker barcode composition and separated into non-chimeric PETs with homodimeric linkers (AA or BB linkers) derived from specific ligation products, or chimeric PETs (AB linkers) with heterodimeric linker derived from nonspecific ligation products. We trimmed the PETs immediately before a perfect match of the first 10 nt of the linker sequences (Linker A with CTGCTGTCCG; Linker B with CTGCTGTCAT). After removing the linkers, only the 5' ends of the trimmed PETs of at least 27 bp were retained, because the restriction enzyme EcoP151 cuts 27 bp away from its recognition sequence.

The sequences of the two ends of PETs were separately mapped to the mm9 mouse genome using the bowtie algorithm with the option "-k 1 -m 1 -v 1" (Langmead et al., 2009). These criteria retained only the uniquely mapped reads, with at most a single mismatch for further analysis. Aligned reads were paired with mates using read identifiers and, to remove PCR bias artifacts, were filtered for redundancy. PETs with identical genomic coordinates and strand information at both ends were collapsed into a single PET. The PETs were further categorized into intrachromosomal PETs, where the two ends of a PET were on the same chromosome, and interchromosomal PETs, where the two ends were on different chromosomes. The two ends of all non-chimeric PETs were used to call PET peaks that represent local enrichment of the PET sequence coverage by using MACS 1.4.2 (Zhang et al., 2008) with the parameters "-p 1e-09 -no-lambda -no-model -keepdup=2".

Chimeric Versus Non-Chimeric PET Quality Assessment

Chimeric PETs with heterodimeric linkers can be used to estimate the degree of noise in the ChIA-PET dataset. 7% of paired-end ligations involved heterodimeric linkers (AB linkers Table S1A). Since the frequency of ligations involved heterodimeric linkers (AB linkers) gave an estimate of non-specific homodimeric ligations (AA or BB linkers), we estimated that less than 14% of total homodimeric ligations (AA and BB linkers) were nonspecific. We also counted the chimeric PETs that overlapped with PET peaks at both ends by at least 1 bp. These chimeric PETs represented "non-specific" chromatin interactions. We found that more than 99.8% "non-specific" chromatin interactions derived from chimeric PETs overlapping with PET peaks had only 1 chimeric PET; 0.1% "nonspecific" interactions had 2 chimeric PETs. We thus used a 3 PET cut-off for our high-confidence interactions (Figure S1F). Since contact frequency is expected to inversely scale with genomic distance, we examined the relationship between PET frequencies over genomic distance between the two ends of intrachromosomal PETs. The frequency of non-chimeric PETs with homodimeric linkers was plotted over genomic span in increments of 100 bp (Figure S1E). The scatter plot suggested two populations within intra-chromosomal PETs and showed that the vast majority of these PETs were within 4 kb (Figure S1E). We thus used a 4 kb cutoff to remove those PETs that may originate from self ligation of DNA ends from a single chromatin fragment in the ChIA-PET procedure. In contrast, chimeric PETs with heterodimeric linkers did not show an inverse relationship with genomic distance (Figure S1E, Table S1A).

Creation of High-Confidence ChIA-PET Interactions

To identify long-range chromatin interactions, we first removed intrachromosomal PETs of length<4 kb because these PETs may originate from self-ligation of DNA ends from a single chromatin fragment in the ChIA-PET procedure (Figure S1E). We next identified PETs where each end overlapped with a different PET peak (overlap of at least 1 bp).

Operationally, these PETs were defined as putative interactions. Applying a statistical model based upon the hypergeometric distribution identified high-confidence interactions, representing high-confidence physical linking between the PET peaks. Specifically, we first counted the number of PETs originating from each PET peak. We then asked, given the numbers of PETs originating from any two PET peaks, what was the likelihood of seeing the observed number of PETs linking the two PET peaks, using a hypergeometric distribution to generate a p value for each potential interaction. To correct for multiple hypothesis testing, we derived a background distribution for p-values of interactions through random shuffling of the links between PET ends. Using this background distribution, we controlled the number of false positives in our interaction set by setting a p-value cutoff threshold such that only the top 1% of simulated interactions from the background dataset would be called significant. This threshold, which we term the false positive likelihood in figure legends, was then applied to the actual data. This method did not make any assumption of the distribution of p-values as the Benjamini-Hochberg procedure (Benjamini, 1995); both methods for multiple hypothesis testing yielded similar number of interactions (Noble, 2009). For each of the two SMC1 ChIA-PET replicates, two independent PETs were required to call high-confidence interactions between pairs of interacting sites (Table S1C, S1D (not shown); merged data in Table S1E). For the merged SMC1 ChIA-PET dataset, non-chimeric PETs from two replicates were pooled together and three independent PETs were required to call high-confidence interactions (Table S1E).

Saturation Analysis of ChIA-PET Library

To determine the degree of saturation within our ChIA-PET library (Figure S1H), we modeled the number of sampled genomic positions as a function of sequencing depth by the Michaelis-Menten model. Intrachromosomal PETs with a distance span above our self-ligation cutoff of 4 kb were subsampled at varying depths, and the number of unique genomic positions (defined as the start and end coordinates of the paired PETs) that they occupy were counted. Model fitting using non-linear least-squares regression suggested that we have sampled approximately 70% of the available intrachromosomal PET space, encompassing 2.22/3.17 million positions (Figure S1H).

We considered whether ChIA-PET data limitations might limit detection of longer range interactions. If sparseness of data were a significant problem, resulting in under-calling of long-range interactions, we would likely miss previously detected long-range interactions. Instead, we detect previously known long-range interactions, e.g. the interaction between Sonic Hedgehog (Shh) and its enhancer in the intron of the nearby Lmbr1 gene (1 Mb away), interactions between the HoxD gene cluster and its distal regulatory sequences (>300 kb away), and interactions between the HoxA gene cluster and its distal regulatory sequences (>500 kb away) (Lehoczky et al., 2004; Lettice et al., 2003; Spitz et al., 2003).

Reproducibility Analysis of SMC1 ChIA-PET Replicates

Saturation analysis suggested that each of the two SMC1 ChIA-PET replicates sampled only ~50% of the available intrachromosomal PET space (data not shown). We thus investigated the reproducibility of SMC1 ChIA-PET replicates by examining how often high-confidence interactions from one of the two SMC1 ChIA-PET replicates were supported by PET interactions from the other replicate. Operationally, we counted the percentage of high-confidence interactions from one replicate whose individual end reads overlapped with those from high-confidence interactions identified in the other replicate by at least 1 bp (Figure S1D).

To compare the replicates' genome-wide interaction frequency (Figure S1C), inter-chromosomal PETs and intra-chromosomal PETs below the self-ligation cutoff (4 kb) were filtered. Each chromosome was partitioned into 10 kb bins and 21 symmetric two-dimensional matrices (all bins× all bins) were constructed for each replicate. These matrices were populated such that bin ai,j represented the number of PETs in that replicate with one end in bin i and the other in bin j. PET counts were separately normalized by the number of mapped reads in each replicate as well as the bin size*1000.

This resulted in an RPKM-like metric for all bins in both matrices. Figure S1C represents the relationships between each replicate where the X axis represents bin ai.j in replicate 1 and the Y axis represents bin ai,j in replicate 2. This relationship was also analyzed using the Pearson r.

Assignment of Interactions to Regulatory Elements

To identify the association of long-range chromatin interactions to different regulatory elements, we assigned the PET peaks of interactions to different regulatory elements, including active enhancers, promoters (+/−2.5 kb of the Refseq TSS), and CTCF ChIP-seq binding sites. Operationally, an interaction was defined as associated with the regulatory element if one of the two PET peaks of the interaction overlapped with the regulatory element by at least 1 base-pair.

Assignment of Enhancers to Genes

Our analysis identified 2,921 high-confidence interactions involving an enhancer (contains an OCT4/SOX2/NANOG or MED1 or MED12 enriched region and is not located within +/−2.5 kb of an annotated TSS) and a promoter (+/−2.5 kb of an annotated TSS) (FIG. 1D, Table S1E). Each high-confidence interaction, as defined above, is required to be connected by three PET peaks. A large majority (81%) of these enhancer-promoter interactions (2071/2921 interactions) involved an active gene (H3K4me3 or RNA Pol II but not H3K27me3 enriched regions), while 302 interactions involved a Polycomb-occupied gene (H3K27me3) and 229 interactions involved a silent gene (absence of H3K4me3, RNA Pol II and H3K27me3 enriched regions).

We identified 216 enhancer-promoter interactions that involved super-enhancers (Table S2B), as defined in (Whyte et al., 2013). The high-confidence enhancer-promoter interactions were used to assign super enhancers and typical enhancers to their target genes (Table S2B, S2C). Multiple enhancer constituents that are in close proximity can be computationally stitched together into enhancer regions (true for typical and super-enhancers) as described previously (Hnisz et al., 2013; Whyte et al., 2013).

We identified high confidence interactions overlapping with a super-enhancer or typical enhancer region at one end and a promoter (+/−2.5 kb of a TSS) at the other end (Table S2B, S2C). For 151 super-enhancers with sufficient interaction data, we found that 83% of enhancer assignments to the nearest active gene (including Polycomb-occupied genes) were confirmed/supported by high-confidence interactions.

For typical enhancers with 1477 sufficient interaction data, we found that 87% of enhancer assignments to the nearest active gene (including Polycomb-occupied genes) were confirmed/supported by high-confidence interaction data.

Heatmap Representation of High-Confidence ChIA-PET Interactions at Topologically Associating Domains (TADS)

Genome-wide average representations of ChIA-PET interactions at TADs were created by mapping high-confidence ChIA-PET interactions across TADs (Dixon et al., 2012) (FIG. 2D). All 2,200 TADs plus their upstream and downstream flanking regions (10% of the size of the domain) were aligned and each split into 60 equally-sized bins. To calculate interaction density in each TAD, we first filtered high-confidence interactions by requiring they were completely contained within the genomic region of the TAD and its flanking regions defined above.

We next counted the interaction frequency between any two bins in each TAD to produce a 60 by 60 interaction matrix using a method as previously described in Dixon et al., 2012 The numbers in the interaction matrices represent interaction frequencies at the diagonals originating from two bins on the x- and y-axis. Average interaction frequencies across 2,200 TAD interaction matrices were calculated. The upper triangular matrix of the average interaction frequencies was displayed in the units of interactions per bin in FIG. 2D.

Definition of Super-Enhancer Domains and Polycomb Domains

Typical enhancer and super-enhancer regions in murine embryonic stem cells were described previously (Hnisz et al., 2013; Whyte et al., 2013), and their genomic coordinates were downloaded (Table S2B, S2C). The 231 super enhancers were assigned to genes with a combination of ChIA-PET interactions and proximity to their nearest active transcriptional start sites (TSSs). We first used high-confidence SMC1 PET interactions (FDR 0.01, 3 PETs) between super-enhancers and TSS regions (+/−2.5 kb of a TSS) to identify their target genes.

When super-enhancers did not have PET interactions to any TSS regions, they were assigned the nearest active TSSs (including Polycomb occupied genes) by proximity. Super-enhancers and the TSS regions (+/−2.5 kb of a TSS) of their target genes are considered as SE-gene units. All 231 super enhancers were assigned to target genes with this method.

This approach resulted in a total of 302 SE-gene units because a SE occasionally interacted with multiple genes.

We next identified SMC1 PET interactions between two CTCF-enriched regions (regardless of whether these CTCF regions were at promoters or enhancers) that encompass these SE-gene units, which we called super-enhancer domains—we call these regions "CTCF-CTCF PET interactions." The CTCF-CTCF PET interactions defining super-enhancer domains were required to encompass the TSS regions (+/−2.5 kb of a TSS) and the super enhancer for each SE-gene unit. When multiple nested CTCF-CTCF PET interactions encompassed a SE-gene unit, we used the smallest CTCF-CTCF PET interactions for simplicity.

We identified 193 Super-enhancer Domains (SDs) containing a total of 191 super-enhancers. We noted that the boundaries of super-enhancer are sensitive to the algorithm that computationally defines super enhancers. For 4 super-enhancers, one super-enhancer constituent out of multiple constituent enhancers that define the super enhancers fall outside of the CTCF-CTCF PET interactions. These 4 CTCF-CTCF PET interactions encompass the target gene TSS regions (+/−2.5 kb of a TSS) and more than 50% of the genomic space covered by the super-enhancer. Therefore, we qualified these 4 CTCF-CTCF PET interactions as Super-enhancer Domains.

Thus, we identified a total of 197 Super-enhancer Domains (SDs) containing a total of 197 boundary CTCF-CTCF PET interactions and 195 super-enhancers (Table S4A, S4B). For the ~15% super-enhancers that did not qualify for occurrence within a SD by using the high confidence ChIA-PET data, the interaction dataset (not the high confidence data) shows that all but one of these super-enhancers are located within CTCF-CTCF loops co-bound by cohesin.

We also performed the same computational analyses for the 8,563 typical enhancers. We found that only 48% (4128/8563) typical-enhancers are contained in CTCF-CTCF topological structures similar to SDs. Developmental regulators in embryonic stem cells frequently exhibit extended binding of Polycomb complex at their promoters spanning 2-35 kb from their promoters (Boyer et al., 2006; Lee et al., 2006). We thus focused on those Polycomb-occupied TSSs that showed enrichment of H3K27me3 spanning greater than 2 kb in size. This distance cutoff was based on analyses performed in (Lee et al., 2006). We noted that ~60% H3K27me3 regions called by MACS had neighboring H3K27me3 regions within 2 kb. In order to accurately capture the large genomic regions that show enrichment of H3K27me3 signal, we first merged the H3K27me3 regions that were within 2 kb of each other. 546 genes, including 203 encoding transcription factors, showed enrichment of H3K27me3 spanning greater than 2 kb at their promoters.

We next identified high confidence CTCF-CTCF PET interactions that encompassed the H3K27me3 regions of these 546 genes at promoters. When multiple nested CTCF-CTCF PET interactions encompassed the H3K27me3 regions, we took the smallest CTCFCTCF PET interactions for simplicity. We identified 349 Polycomb Domains (PDs) containing a total of 349 boundary CTCF-CTCF PET interactions and 380 Polycomb-associated genes (Table S5A, S5B).

Support for SD and PD Structures from Published Datasets

The existence of Super-enhancer Domains and Polycomb Domains was supported by evidence from published CTCF ChIA-PET datasets (GSE28247) (Handoko et al., 2011). We applied our ChIA-PET processing method to the published CTCF ChIA-PET dataset to identify unique PETs. We then counted the instances where a high-confidence CTCF-CTCF boundary interaction from our ChIA-PET dataset showed a minimum 80% reciprocal overlap with the span of a unique PET from the CTCF ChIA-PET dataset, i.e. 80% of a high-confidence SD boundary interaction region is in common with a CTCF ChIA-PET unique PET and vice versa. To accomplish this, we used BEDtools (https://github.com/arq5x/bedtools2) intersect with parameters -f 0.8 -r -u.

We found that 34% (6770/20080) of our CTCF-CTCF interactions were confirmed by a unique PET within the CTCF ChIA-PET dataset, 33% (65/197) of our SD boundary interactions were confirmed by a unique PET within the CTCF ChIAPET dataset, and 33% (115/349) of our PD boundary interactions were confirmed by a unique PET within the CTCF ChIA-PET dataset (Table S3A). Most Super-enhancer Domains and Polycomb Domains are distinct from the previously described Topologically Associating Domains (TADS).

We compared Super-enhancer Domains and Polycomb Domains to TADs by counting the instances where a Super-enhancer Domain or a Polycomb Domain showed a minimum 80% reciprocal overlap with a TAD. 3% (5/197) of our SDs and 4% (13/349) of our PD have an 80% reciprocal overlap with a TAD (Dixon et al., 2012). 8% (16/197) of our SDs and 9% (30/349) of our PD have an 80% reciprocal overlap with a TAD (Filippova et al., 2014) (Table S3A).

The existence of enhancer-promoter and enhancer-enhancer interactions was supported by evidence from published RNA Pall ChIA-PET datasets (Kieffer-Kwon et al., 2013). We applied our ChIA-PET processing method to the published Pol2 ChIA-PET dataset to identify unique PETs. We then counted the instances where a high-confidence enhancer-promoter or enhancer-enhancer interaction from our Smc1 ChIA-PET dataset showed a minimum 80% reciprocal overlap with a unique PET from the Pol2 ChIA-PET dataset, e.g. 80% of an enhancer-promoter interaction region is in common with a Pol2 ChIA-PET unique PET and vice versa. We found that 82% (2,402/2,921) of our enhancer-promoter interactions were confirmed by a unique PET within the Pol2 ChIA-PET dataset, and 73% (1,969/2,700) of our enhancer-enhancer interactions were confirmed by a unique PET within the Pol2 ChIA-PET dataset (Table S3A).

Several types of structural domains have been previously described, and we expect our interactions to occur largely within their boundaries. Thus, we determined how many of our interactions spanned a boundary. Topologically Associating Domains (TADs) (Dixon et al., 2012) were determined using Hi-C in mouse ESCs; 6% (1,354/23,739) of high-confidence intrachromosomal cohesion-mediated interactions cross a TAD boundary. LOCK (large organized chromatin K9 modification) domains were determined using ChIP data (Wen et al., 2009); 4% (1,053/23,739) of high-confidence, intrachromosomal cohesin-mediated interactions cross a LOCK boundary. Lamin-associated domains (LADS) were determined using DamID (Meuleman et al., 2013); 5% (1,180/23,739) of high confidence intrachromosomal cohesin-mediated interactions cross a LAD boundary (Table S3A).

Meta Representations of ChIP-Seq Occupancy at Super-Enhancer Domains and Polycomb Domains Genome-wide average "meta" representations of ChIP-seq occupancy of different factors were created by mapping ChIP-seq read density to different sets of regions (FIG. 3C, FIG. 5C). All regions within each set were aligned and the average ChIP-Seq factor density in each bin was calculated to create a meta genome-wide average in units of rpm/bp.

For super-enhancers, each super enhancer or their corresponding flanking region (+/−3 kb) was split into 100 equally-sized bins. This split all super-enhancer regions, regardless of their size, into 300 bins. For the target genes within SDs or PDs, we created three regions: upstream, gene body and downstream. 80 equally-sized bins divided the 2000 to 0 promoter region, 200 equally-sized bins divided the length of the gene body, and 80 equally-sized bins divided the 0 to +2 kb downstream region. For SMC1 and CTCF ChIP-Seq binding sites at the SD, PD, and TAD borders, flanking regions (+/−2 kb) around the center of CTCF ChIP-Seq binding sites were aligned and split into 40 equally-sized bins.

Heatmap representations of ChIP-seq read density of different factors were created by mapping the reads within super-enhancers and/or their target genes across super-enhancer domains (FIG. 3E). We first filtered reads for those contacting (>=1 bp) super-enhancers and/or their target genes. Then we created three types of regions: SD and their corresponding flanking regions (+/−10 kb). We divided the upstream and downstream flanking regions into 10 equally-sized bins each. We divided the SD into 50 equally-sized bins. The average filtered ChIP-seq read density (r.p.m./bp) of different factors in each bin was calculated and drawn.

Heatmap Representation of High-Confidence ChIA-PET Interactions Superenhancer Domains and Polycomb Domains Heatmap representations of ChIA-PET interactions were created by mapping high-confidence ChIA-PET interactions across Super-enhancer Domains (SD) and Polycomb Domains (PD), which are defined above. We created three types of regions: upstream, SD or PD, and downstream. Upstream and downstream regions are 20% of the SD's or PD's length each. We divided the upstream and downstream regions into 10 equally-sized bins each. We divided the SD or PD into 50 equally-sized bins. To calculate interactions in each bin, we filtered high-confidence interactions in two ways. 1) We required high-confidence interactions to have at least one end in the interrogated region. This removed interactions that are anchored outside of our region of interest. 2) We removed interactions that are not related to the internal structure of the domain. This removed interactions that have one end at an SD or PD border PET peak and the other end outside of the SD or PD.

We considered the whole span of each filtered high-confidence ChIA-PET interaction. The density of such spans in each bin was calculated, where all bins contacting an interaction were incremented by 1. Per row counts were normalized by dividing each bin count by the row maximum and displayed in Heatmaps in FIGS. 3D and 5D.

Definition of Putative Chromatin Insulator Elements at the Boundaries of Polycomb Domains An entropy-based measure of Jensen-Shannon Divergence (JSD) was adopted to identify putative SMC1- and CTCF-bound chromatin insulator elements at PD domain boundaries (FIG. 5E). We divided 20 kb regions centered on CTCF enriched regions within SDs or PDs into 100 equally-sized bins. We used H3K27me3 and SUZ12 ChIP-seq profiles to identify putative insulator elements at PD boundaries. For each 20 kb region, the average ChIP-seq read density within each bin was calculated and the density in each bin was divided by the sum of the row so the new normalized vector sums to 1. Since we expect high ChIP-seq signal at one side of insulator elements and low ChIP-seq signal at other side of insulator elements, we defined two vectors to represent the chromatin patterns at insulator elements at the left or right borders of PDs: one vector has 50 0s followed by 50 1s, and the other has 50 1s followed by 50 0s. These vectors were normalized so their sum was 1.

We next used JSD as described in (Fuglede and Topsoe, 2004) to quantify the similarity between normalized ChIP-seq patterns and the two pre-defined patterns, which results in a similarity score between each normalized ChIP-seq vector and the ideal vectors described above. We took the top 15 percent of our 20 kb regions ranked by their similarity score and extracted those that were at the boundaries of Polycomb Domains (PD). For robustness, only PD border regions whose average ChIP-seq signal (H3K27me3) within the 20 kb window was above the 60 percentile of all CTCF enriched regions at the side within the domain and below 50 percentile of all CTCF enriched regions at the side outside of the domain were considered as putative chromatin insulator elements.

FIG. 5E show normalized ChIP-seq density at these putative chromatin insulator elements by standard Z-transform across all CTCF enriched regions.

Conservation of CTCF Binding Across Cell Types

CTCF peaks in 18 tissues/cell types from ENCODE were downloaded from the UCSC table browser (http://genome.ucsc.edu/cgibin/hgFileUi?db=mm9&g=wgEncodeLicrTfbs).

We restricted our analysis to autosomal CTCF sites, because these 18 cell types could be derived from mice of different sex or strains. We first took the intersection of our autosomal CTCF peaks in murine V6.5 ESC 129-057Bl/6 line and autosomal CTCF peaks in the murine ESC Bruce4 line from ENCODE to account for differences in cells and experimental technique. We next quantified how frequently these autosomal CTCF peaks from ESCs were occupied by CTCF ChIP-Seq peaks in 18 tissues/cell types (including ESC Bruce4 cells) from ENCODE. The histogram of CTCF occupancy across 18 tissues/cell types were plotted in FIG. 6C.

Super-Enhancers in NPCs

Super-enhancers were identified in mouse neural progenitor cells (NPCs) using ROSE (https://bitbucket.org/young_computation/rose). This code is an implementation of the method used in (Hnisz et al., 2013; Loven et al., 2013).

Briefly, regions enriched in H3K27ac signal were identified using MACS with background control, -keep-dup=auto, and -p 1e-9. These regions were stitched together if they were within 12.5 kb of each other and enriched regions entirely contained within +/−2 kb from a TSS were excluded from stitching. Stitched regions were ranked by H3K27ac signal therein.

ROSE identified a point at which the two classes of enhancers were separable. Those stitched enhancers falling above this threshold were considered super-enhancers.

5C CTCF-CTCF Interactions in NPCs

Phillips-Cremins et al. performed 5C at 7 genomic loci (Phillips-Cremins et al., 2013). We filtered for statistically significant 5C interactions in mouse NPC by requiring a p value for both replicates<0.05, resulting in 674 interactions. We filtered for CTCF-CTCF interactions by requiring an overlap with a CTCF ChIPSeq enriched region in NPC on both ends resulting in 32 CTCF-positive 5C interactions. 34% (11/32)

CTCF 5C interactions in NPCs have an 80% reciprocal overlap with a SMC1 ChIA-PET interactions in mouse ESCs (Table S3B).

3C Assays

For each sample, 2×107 ESCs cells were crosslinked with 1% formaldehyde for 20 min at RT. The reaction was quenched by the addition of 125 mM glycine for 5 min at RT. Crosslinked ESCs were washed with PBS and resuspended in 10 ml lysis buffer (10 mM Tris-HCl, pH 8.0, 10 mM NaCl, 0.2% NP40 and proteinase inhibitors) and lysed with a Dounce homogenizer. Following BglII digestion overnight, 3C-ligated DNA was prepared as previously described (Lieberman-Aiden et al., 2009).

The 3C interactions at the miR-290-295 and Pou5f1 loci (Figure S4A, S4B) were analyzed by quantitative real-time PCR using custom Taqman probes as previously described (Xu et al., 2011). The amount of DNA in the qPCR reactions was normalized across 3C libraries using a custom Taqman probe directed against the Actb locus. Primer sequences are listed below.

Target region Primer name Sequence (5'-3')

| Target, Region, primer name | Sequence (5'-3') | SEQ ID NO |
|---|---|---|
| N1rp12, promoter, N1rp12 R | CACATCTTCAAAGCAAACACTATTGTT | |
| N1rp12, Taqman probe, N1rp12 Probe | TCTCCTACCCATTGCTTCTCTGCTACCTGC | |
| SE, region 1, N1rp12 eF1 | TTCCTGGAACCTGGGCAA | |
| SE, region 2, N1rp12 eF2 | TGATACAGCACAGCTTTCCTTCA | |
| SE, region 3, N1rp12 eF3 | CAGATTTTTTATTTCCTTCAGTTCTGTG | |
| H2-Q10, promoter, H2Q10 F | AGGATGGCTCAGCGGTTAAG | |
| SE region, H2Q10 R | AGGGCTCACCTTCAGTCAAGTT | |
| H2-Q10, Taqman probe, H2Q10 probe | CGGCCTGTCTACTTTAGCCTCAGACTCCA | |
| Actin, Actin-F | GGGAGTGACTCTCTGTCCATTCA | |
| Actin, Actin-R | ATTTGTGTGGCCTCTTGTTTG A | |
| Actin, Taqman probe, Actin probe | TCCAGGCCCCGCGTGTCC | |

F, and R denote forward and reverse primers, respectively.

ChIA-PET

In brief, murine ESCs (up to $13\times10^{8}$ cells) were treated with 1% formaldehyde at room temperature for 10 min and then neutralized using 0.2 M glycine. The crosslinked chromatin was fragmented by sonication to size lengths of 300-700 bp. The anti-SMC1 antibody (Bethyl, A300-055A) was used to enrich SMC1-bound chromatin fragments. A portion of ChIP DNA was eluted from antibody-coated beads for concentration quantification and for enrichment analysis using quantitative PCR. For ChIA-PET library construction, ChIP DNA fragments were end repaired using T4 DNA polymerase (NEB) and ligated to either linker A or linker B. After linker ligation, the two samples were combined for proximity ligation in diluted conditions. Following proximity ligation, the paired-end tag (PET) constructs were extracted from the ligation products and the PET templates were subjected to 50 3 50 paired-end sequencing using Illumina HiSeq 2000.

ChIA-PET Library Construction

ChIA-PET was performed as previously described (Chepelev et al., 2012; Fullwood et al., 2009; Goh et al., 2012; Li et al., 2012). Briefly, ES cells (up to $1\times10^{8}$ cells) were treated with 1% formaldehyde at room temperature for 20 min and then neutralized using 0.2M glycine. The crosslinked chromatin was fragmented by sonication to size lengths of 300-700 bp. The anti-SMC1 antibody (Bethyl, A300-055A) was used to enrich SMC1-bound chromatin fragments. A portion of ChIP DNA was eluted from antibody-coated beads for concentration quantification and for enrichment analysis using quantitative PCR.

For ChIA-PET library construction ChIP DNA fragments were end-repaired using T4 DNA polymerase (NEB). ChIP DNA fragments were divided into two aliquots and either linker A or linker B was ligated to the fragment ends. The two linkers differ by two nucleotides which are used as a nucleotide barcode (Linker A with CG; Linker B with AT) (Table S1A). After linker ligation, the two samples were combined and prepared for proximity ligation by diluting in a 20 ml volume to minimize ligations between different DNA-protein complexes. The proximity ligation reaction was performed with T4 DNA ligase (Fermentas) and incubated without rocking at 22 degrees Celsius for 20 hours.

During the proximity ligation DNA fragments with the same linker sequence were ligated within the same chromatin complex, which generated the ligation products with homodimeric linker composition. However, chimeric ligations between DNA fragments from different chromatin complexes could also occur, thus producing ligation products with heterodimeric linker composition. These heterodimeric linker products were used to assess the frequency of nonspecific ligations and were then removed bioinformatically.

As shown in Figure S1E, all heterodimeric linker ligations, giving rise to chimeric PETs, are by definition nonspecific. Because random intermolecular associations in the test tube are expected to be comparable for linkers A and B, the frequency of random homo and heterodimeric linker ligations should also be equivalent. In our SMC1 ChIA-PET library, only 7% of pair-end ligations involved heterodimeric linkers (Table S1A). Thus, we estimate that less than 14% of total homodimeric ligations are nonspecific.

Following proximity ligation, samples were treated with Proteinase K and DNA was purified. An EcoP15I (NEB) digestion was performed at 37 degrees Celsius for 17 hours to linearize the ligated chromatin fragments. The chromatin fragments were then immobilized on Dynabeads M280 Streptavidin beads. An End-Repair reaction was performed (Epicentre #ER81050), then As were added to the ends with Klenow treatment by rotating at 37 degrees Celsius for 35 minutes. Next, Illumina paired-end sequencing adapters were ligated on the ends and 18 cycles of PCR was performed. The Paired-End-Tag (PET) constructs were extracted from the ligation products and the PET templates were subjected to 50×50 paired-end sequencing using Illumina HiSeq 2000. SMC1 ChIA-PET was performed as previously described (Chepelev et al., 2012; Fullwood et al., 2009; Goh et al., 2012; Li et al., 2012).

Data Analysis

ChIA-PET data analysis was performed as previously described (Li et al., 2010), with modifications described in the Extended Experimental Procedures. The high-confidence interactions for the two biological replicate SMC1

ChIAPET experiments and for the merged data set are listed in Tables S1C, S1D (not shown) but merged into Table S1E, respectively. All data sets used in this study are listed in Table S6.

Example 2: Accession Numbers

Raw and processed sequencing data were deposited in GEO under accession number GSE57913 (http://www.ncbi.nlm.nih.gov/geo/).

The GEO accession ID for aligned and raw data is GSE57913 (www.ncbi.nlm.nih.gov/geo/).

Results of Experimentals

Cohesin ChIA-PET in ESCs

The organization of mammalian chromosomes involves structural units with various sizes and properties, and cohesin, a structural maintenance of chromosomes (SMC) complex, participates in DNA interactions that include enhancer-promoter loops and larger loop structures that occur within topologically associating domains (TADs) (FIG. 1A). ESC ChIP-seq data indicate that ~40% of cohesin-occupied sites involve active enhancers and promoters, ~3% involve genes with polycomb modifications, and ~50% involve CTCF sites that are not associated with enhancers, promoters, or polycomb-occupied sites (FIG. 1B and Figures S1A and S1B available online). We employed cohesin ChIA-PET to further investigate the relationship between control of the ESC pluripotency program and control of local chromosome structure. We selected cohesin because it is a relatively well-studied SMC complex that is loaded at enhancer-promoter loops and can thus identify those interactions and can also migrate to CTCF sites and thus identify those interactions as well Kagey et al., 2010; Parelho et al., 2008; Rubio et al., 2008; Schaaf et al., 2013; Wendt et al., 2008).

The ChIA-PET technique was used because it yields high-resolution (~4 kb) genome-wide interaction data, which is important because most loops involved in transcriptional regulation are between 1 and 100 kb (Gibcus and Dekker, 2013). We hoped to extend previous findings that mapped interactions among regulatory elements across portions of the ESC genome (Denholtz et al., 2013; Phillips-Cremins et al., 2013; Seitan et al., 2013) and gain a detailed understanding of the relationship between transcriptional control of ESC identity genes and control of local chromosome structure. To identify interactions between cohesin-occupied sites, we generated biological replicates of SMC1 ChIA-PET data sets in ESCs totaling ~400 million reads (Table S1A). The two biological replicates showed a high degree of correlation (Pearson's r>0.91, Figures S1C and S1D), so we pooled the replicate data and processed it using an established protocol (Li et al., 2010), with modifications described in the Extended Experimental Procedures (Figure S1 and Table S1A). The data set contained ~19 million unique paired-end tags (PETs) that were used to identify PET peaks (FIG. 1C). Interactions between PET peaks were identified and filtered for length and significance (FIG. 1C, S1E, and S1F, Table S1B, and Extended Experimental Procedures). The analysis method produced 1,234,006 cohesin-associated DNA interactions (FIG. 1C and Table S1B). The vast majority (92%) of these interacting cohesin-occupied sites occurred at enhancers, promoters, and CTCF-binding sites, consistent with the known roles of cohesin at these regulatory elements (FIG. 1D).

Genomic data of any type are noisy, and our confidence in the interpretation of DNA interaction data is improved by identifying PETs that represent independent events in the sample and pass statistical significance tests. For this reason, we generated a high-confidence interaction data set (described in Extended Experimental Procedures) by requiring that at least three independent PETs support the identified interaction between two PET peaks. The high-confidence data set consisted of 23,835 interactions that were almost entirely intrachromosomal (99%) and included 2,921 enhancer-promoter interactions, 2,700 enhancer-enhancer interactions, and 7,841 interactions between non-enhancer, non-promoter CTCF sites (FIGS. 1C, 1D, S1G, and S2 and Table S1B). Unless stated otherwise, the high-confidence data set was used for further quantitative analysis. We used the interaction data sets to create a table of enhancer-promoter assignments for ESCs (Tables S2A-S2C).

We found that the interaction data supported 83% of superenhancer assignments to the proximal active gene and 87% of typical enhancer assignments to the proximal active gene (Tables S2B and S2C), with approximately half of the remainder assigned to the second most proximal gene. The interaction data most frequently assigned super-enhancers and typical enhancers to a single gene, with 76% of super-enhancers and 84% of typical enhancers showing evidence of interaction with a single gene. Prior studies have suggested that there can be more frequent interactions between enhancers and genes (Kieffer-Kwon et al., 2013; Sanyal et al., 2012; Shen et al., 2012); our high-confidence data are not saturating and do not address the upper limits of these interactions (Figure S1H and Extended Experimental Procedures).

Figure 2:
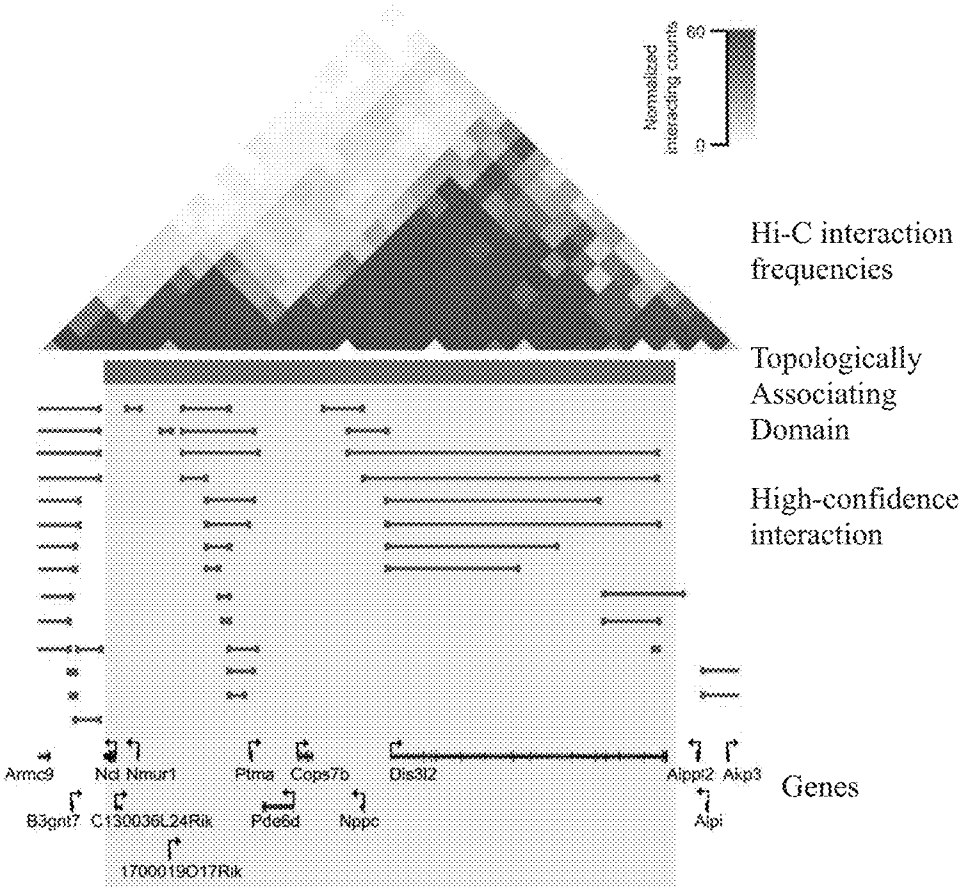
FIG. 2 DNA Interactions Frequently Occur within Topologically Associating Domains. (A) An example TAD shown with normalized Hi-C interaction frequencies is displayed as a two-dimensional heat map (Dixon et al., 2012), and the TAD is indicated as a gray bar. High-confidence SMC1 ChIA-PET interactions are depicted as blue lines. (B) Enrichment of CTCF, cohesin (SMC1), and PET peaks at TAD boundary regions. The metagene representation shows the number of regions per 10 kb window centered on the TAD boundary, and ±500 kb is displayed. (C) Pie chart of high-confidence interactions that either fall within TADs (88%) or across TAD boundaries (12%). (D) High-confidence interactions are displayed as a two-dimensional heatmap across a normalized TAD length for the ~2,200 TADs (Dixon et al., 2012). The display is centered on the normalized TAD and extends beyond each boundary to 10% of the size of the domain. See also Table S3A.
Figure 2:
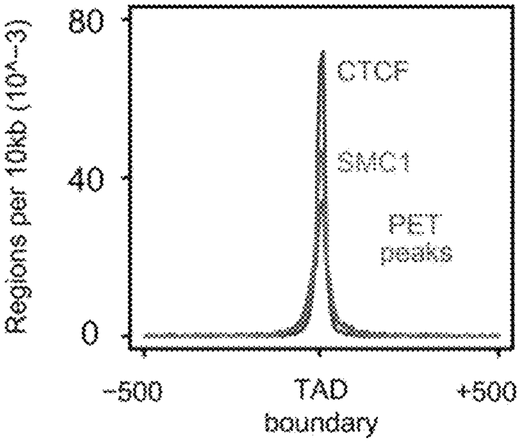
Figure 2:
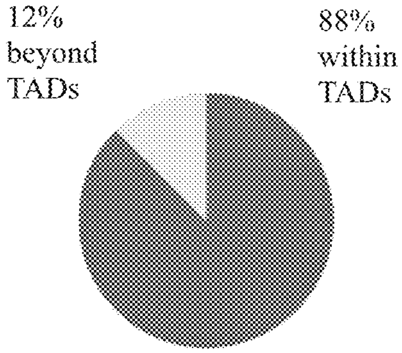
Figure 2:
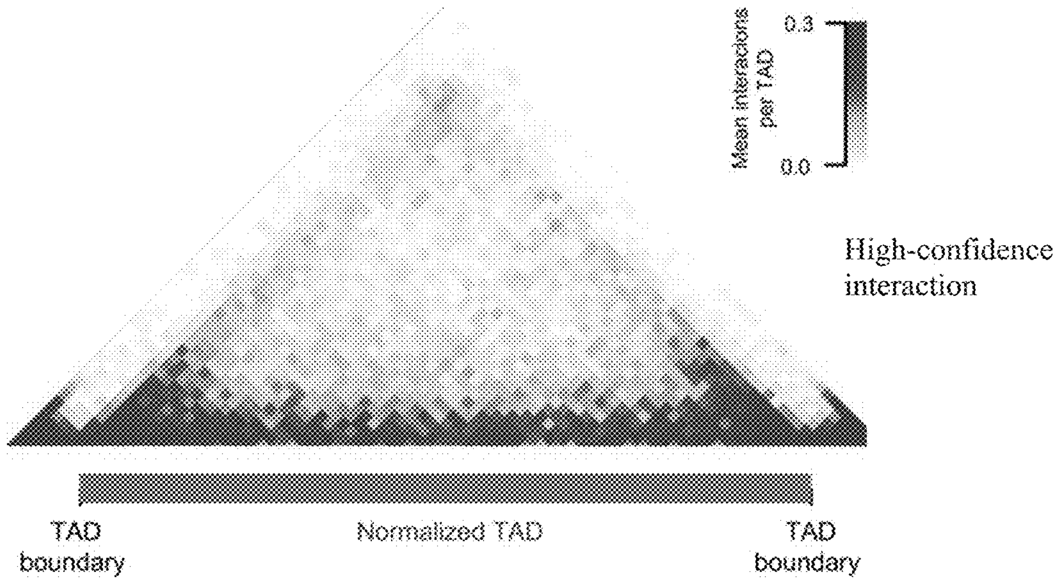

The catalog of enhancer-promoter assignments provided by these interaction data should prove useful for future studies of the roles of ESC enhancers and their associated factors in control of specific target genes. The majority of cohesin ChIA-PET interactions did not cross the boundaries of previously defined TADs (Dixon et al., 2012; Filippova et al., 2014; Meuleman et al., 2013; Wen et al., 2009) (FIG. 2 and Table S3A). FIG. 2A shows a representative example of a TAD, in which the majority (96%) of interactions occur within the domain. As expected from previous studies, the TAD boundaries are enriched for cohesin and CTCF and thus cohesin ChIA-PET peaks (FIG. 2B). Genome-wide analysis shows that 88% of all interactions are contained within TADs (FIG. 2C) and are somewhat enriched near the boundaries of TADs (FIG. 2D). The majority of cohesin ChIA-PET interactions did not cross lamin-associated domains (LADs), which are associated with repression at the nuclear periphery, or LOCK domains, which are large regions of chromatin marked with histone H3K9 modifications (Table S3A) (Meuleman et al., 2013; Wen et al., 2009). These results are consistent with properties previously described for TAD, LAD, and LOCK domain structures.

Super-Enhancer Domain Structure

Super-enhancers drive expression of key cell identity genes and are densely occupied by the transcription apparatus and its cofactors, including cohesin (Dowen et al., 2013; Hnisz et al., 2013). Analysis of high-confidence cohesin ChIA-PET interaction data revealed a striking feature common to loci containing super-enhancers and their associated genes (FIG. 3). This feature consisted of a super-enhancer and its associated gene located within a loop connected by two interacting CTCF sites co-occupied by cohesin (FIGS. 3A, 3B, and S3A-S3J). The vast majority of ESC super-enhancers (84%) are contained within these structures, which we call super-enhancer domains (SDs) (FIG. 3B, Tables S4A and S4B, and Extended Experimental Procedures).

In contrast, only 48% of typical enhancers were found to occur within comparable loops between two CTCF sites. The 197 SDs average 106 kb and most frequently contain one or two genes (Tables S4A and S4C). It was evident that there were cohesin-associated interactions between individual enhancer elements (constituents) of super-enhancers as well as interactions between super-enhancers and the promoters of their associated genes (Figures S3A-S3J).

Indeed, the results suggest that super-enhancer constituents have cohesin-associated interactions with one another (345 interactions) even more frequently than they do with their associated genes (216 interactions). The SDs contain high densities of pluripotency transcription factors, Mediator, and cohesin, together with histone modifications associated with transcriptionally active enhancers and genes (FIG. 3C). It was notable that the majority (82%) of interactions within SDs do not cross the CTCF sites at SD borders (FIG. 3D) and that the majority of Mediator, Pol2, and H3K27ac signal associated with super-enhancers and their associated genes occurs inside of the CTCF sites at SD borders (FIG. 3E).

The cohesin ChIA-PET interaction data and the distribution of the transcription apparatus suggest that the interacting cohesin-occupied CTCF sites tend to restrict the interactions of super-enhancers to those genes within the SD.

Super-Enhancer Domain Function

Because super-enhancers contain an exceptional amount of transcription apparatus and CTCF has been associated with insulator activity (Essafi et al., 2011; Handoko et al., 2011; Ong and Corces, 2014; Phillips and Corces, 2009; Phillips-Cremins and Corces, 2013), we postulated that SD structures might be necessary for proper regulation of genes in the vicinity of these structures. To test this model, we investigated the effect of deleting SD boundary CTCF sites on expression of genes inside and immediately outside of SDs (FIG. 4).

For this purpose, we studied five SDs whose super-enhancer-associated genes play key roles in embryonic stem cell biology (miR-290-295, Nanog, Tdgf1, Pou5f1 [Oct4], and Prdm14). In all cases, we found that deletion of a CTCF site led to altered expression of nearby genes. In four out of five cases, deletion of a CTCF site led to increased expression of genes immediately outside the SDs, and in three of five cases, deletion of a CTCF site caused changes in expression of genes within the SDs. The miR-290-295 locus, which specifies miRNAs with roles in ESC biology, is located within an SD (FIG. 4A). The miR-290-295 SD contains no other annotated gene, and the closest gene that resides outside this SD is Nlrp12, located ~20 kb downstream of miR-290-295. CRISPR-mediated deletion of a boundary CTCF site (C1) at the miR-290-295 locus caused an ~50% reduction in the miR-290-295 pri-miRNA transcript and an 8-fold increase in transcript levels for Nlrp12 (FIG. 4A). The CTCF deletion had no effect on expression of two genes located further away, AU018091 and Myadm (FIG. 4A).

These results indicate that normal expression of the miR-290-295 primiRNA transcript is dependent on the CTCF boundary site and furthermore that genes located immediately outside of this SD can be activated when the SD CTCF boundary site is disrupted. The Nanog gene, which encodes a key pluripotency transcription factor, is located within an SD shown in FIG. 4B. The Nanog SD contains no other annotated gene, and the closest upstream gene that resides outside this SD is Dppa3, which is located ~50 kb upstream of Nanog.

CRISPR-mediated deletion of the boundary CTCF site C1 of the Nanog SD led to a ~40% drop in Nanog transcript levels (FIG. 4B). In this case, there was no significant change in the level of the Dppa3 transcript (FIG. 4B). These results indicate that normal expression of the Nanog transcript is dependent on the C1 CTCF site. The Tdgf1 gene, which encodes an epidermal growth factor essential for embryonic development, is located within an SD (FIG. 4C). In this SD, it is possible that the super-enhancer regulates both the Tdgf1 and Lrrc2 genes and this Tdgf1/Lrrc2 SD also contains the Rtp3 gene. The closest gene that resides outside this SD is Gm590, which is located 30 kb downstream of Tdgf1. CRISPR-mediated deletion of a boundary CTCF site (C1) of the Tdgf1/Lrrc2 SD had little effect on Tdgf1 and Rtp3 transcript levels but had a modest effect on Lrrc2 transcript levels and caused a nearly 10-fold increase in the levels of Gm590 transcripts (FIG. 4C). The Pou5f1 gene, which encodes the pluripotency transcription factor OCT4, is located within an SD (FIG. 4D). The Pou5f1 SD contains no other annotated gene.

We were not able to obtain a bi-allelic CRISPR-mediated deletion of a boundary CTCF site despite multiple attempts, but we did obtain a mono-allelic deletion of the boundary CTCF site C1 (FIG. 4D). This mono-allelic deletion had little effect on the levels of Pou5f1 transcripts but increased the levels of transcripts for H2-Q10, the gene closest to the deleted boundary, by ~2.5-fold (FIG. 4D). Transcription of the gene closest to the uninterrupted boundary of the Pou5f1 SD, Tcf19, was unaffected by the C1 deletion. The Prdm14 gene, which encodes a pluripotency transcription factor, is located within an SD (FIG. 4E). The Prdm14 SD contains no other annotated gene, and the closest downstream gene that resides outside this SD is Slco5a1, which is located 100 kb downstream of Prdm14. The Prdm14 SD has two neighboring cohesin-associated CTCF sites at one boundary; CRISPR-mediated deletion of a single boundary CTCF site (C1) had no effect on expression of Prdm14 or Slco5a1, but deletion of both CTCF sites (C1 and C2) at that boundary caused an ~4.5-fold increase in expression of Slco5a1 (FIG. 4E).

We tested whether the super-enhancers from disrupted SD structures show increased interaction frequencies with the newly activated genes outside the SD by using 3C. At two loci where loss of an SD boundary CTCF site led to significant activation of the gene outside the SD (miR-290-295 and Pou5f1), we performed quantitative 3C experiments to measure the contact frequency between the super-enhancers and the genes immediately outside of SDs in wild-type cells and in cells where the SD boundary CTCF site was deleted. In both cases, loss of the CTCF site led to an increase in the contact frequency between the super-enhancers and the genes immediately outside of SDs that were newly activated (Figures S4A and S4B).

We investigated whether altered SD boundaries that affect cell identity genes cause ESCs to express markers consistent with an altered cell state. Indeed, we found that ESCs lacking the miR-290-295 boundary CTCF site C1 exhibit increased expression of the ectodermal marker Pax6 and decreased expression of the endodermal lineage markers Gata6 and Sox17, suggesting that loss of the SD structure is sufficient to affect cell identity (Figure S4C). Previous studies have shown that miR-290-295 null ESCs show an increased propensity to differentiate into ectodermal lineages at the expense of endoderm (Kaspi et al., 2013). In summary, the loss of CTCF sites at the boundaries of SDs can cause a change in the level of transcripts for superenhancer-associated genes within the SD and frequently leads to activation of genes near these CTCF sites. These results indicate that the integrity of SDs is important for normal expression of genes located in the vicinity of the SD, which can include genes that are key to control of cell identity.

Polycomb Domains

Maintenance of the pluripotent ESC state requires that genes encoding lineage-specifying developmental regulators are repressed, and these repressed lineage-specifying genes are occupied by nucleosomal histones that carry the polycomb-associated mark H3K27me3 (Margueron and Reinberg, 2011; Young, 2011). The mechanisms responsible for maintaining the H3K27me3 mark across short spans of regulatory regions and promoters of repressed genes are not well understood, although CTCF sites have been implicated (Cuddapah et al., 2009; Schwartz et al., 2012; Van Bortle et al., 2012).

Analysis of the H3K27me3-marked genes revealed that they, like the super enhancer-associated genes, are typically located within a loop between two interacting CTCF sites co-occupied by cohesin (FIGS. 5A, 5B, and S5A-S5J and Table S5A). These polycomb domain (PD) structures share many features with the super enhancer domains. The majority (70%) (380/546) of polycomb-associated genes occur in PD structures. PDs average 112 kb and generally contain one or two genes (Table S5B). The PDs contain exceptionally high densities of the polycomb proteins EZH2 and SUZ12 and the associated histone modification H3K27me3 (FIG. 5C).

The majority (78%) of cohesin ChIAPET interactions originating in PDs occur within the PD boundaries (FIG. 5D). Furthermore, the polycomb mark H3K27me3 tends to be retained within the PD (FIG. 5E).

We postulated that the CTCF boundaries that form PD structures might be important for repression of the polycomb-marked genes within the PD and investigated the effect of deleting boundary CTCF sites on a PD containing Tcfap2e to test this idea (FIG. 5F). CRISPR-mediated deletion of one of the boundary CTCF sites (C1) of the Tcfap2e PD caused a 1.7-fold increase in transcript levels for Tcfap2e ($p<0.05$) and no significant change in transcript levels for nearby genes within or outside of the PD.

CRISPR-mediated deletion of the other boundary CTCF site (C2) caused a 4-fold increase in the expression of Tcfap2e ($p<0.001$) and had little effect on adjacent genes. These results suggest that the integrity of the CTCF boundaries of PDs is important for full repression of H3K27me3-occupied genes.

Insulated Neighborhoods in Multiple Cell Types

A previous study suggested that DNA loops mediated by cohesin and CTCF tend to be larger and more shared among multiple cell types than DNA loops associated with cohesin and Mediator, which represent enhancer-promoter interactions that may be cell type specific (Phillips-Cremins et al., 2013). This led us to postulate that: (1) the interacting CTCF structures of SDs and PDs may be common to multiple cell types and (2) the acquisition of super-enhancers and polycomb binding within these common domain structures will vary based on the gene expression program of the cell type (FIG. 6A).

To test this model, we compared the SDs identified in ESCs to comparable regions in neural precursor cells (NPCs) for which 5C interaction data was available for specific loci (Phillips-Cremins et al., 2013).

We found, for example, that the Nanog locus SD observed in ESCs with ChIA-PET data was also detected by 5C data in NPCs (FIG. 6B). In NPCs, the Nanog gene is not expressed, and no super-enhancers are formed at this locus (FIG. 6B). Similarly, there is evidence for a common structure involving CTCF sites bounding the Olig1/Olig2 locus in both ESCs and NPCs (FIG. 6B).

In this domain, the Olig1/Olig2 genes are not active and no super-enhancers are formed in ESCs, whereas there are three super-enhancers in NPCs, where these genes are highly expressed (FIGS. 6B and S6).

For regions where 5C interaction data in NPCs and ChIA-PET interaction data in ESCs could be compared, a total of 11 out of 32 interactions between CTCF sites identified in NPCs were supported by interaction data in ESCs (Table S3B), which is impressive given the sparsity of interaction data.

This supports the view that the interacting CTCF structures of ESC SDs may be common to multiple cell types. If the CTCF boundaries of ESC SDs and PDs are common to many cell types, we would expect that the binding of CTCF to the SD and PD boundary sites observed in ESCs will be conserved across multiple cell types.

To test this notion, we examined CTCF ChIP-seq peaks from 18 mouse cell types and determined how frequently CTCF binding occurred across these cell types (FIG. 6C). When all ESC CTCF ChIP-seq peaks were included in the analysis, we found that there was fairly even distribution of the data into bins representing one or more cell types (FIG. 6C). In contrast, CTCF peaks co-bound by cohesin, which included those at SD and PD borders, were observed more frequently in bins representing a larger fraction of the cell types (FIG. 6C). These results indicate that the CTCF boundary sites of ESC SDs and PDs are frequently occupied by CTCF in multiple cell types and, together with the analysis of interaction data for NPCs described above, support the idea that CTCFCTCF interaction structures may often be shared by ESCs and more differentiated cell types.

TABLES

The following Tables are referenced throughout the specification.

The following Tables are referenced throughout the specification.

TABLE S1A

| ChIA-PET linker sequences and mapping statistics | |
|---|---|
| Name | Sequence |
| Linker A | 3'-GAC GAC AGG CTA T(biotin) AG CGC CGG-5'<br>5'-CTG CTG TCC GAT ATC GC-3' |
| Linker B | 3'-GAC GAC AGT ATA T(biotin) AG CGC CGG-5'<br>5'-CTG CTG TCA TAT ATC GC-3' |

TABLE S1A-continued

| ChIA-PET linker sequences and mapping statistics | | | | |
|---|---|---|---|---|
| mESC Smc1 ChIA-PET | Biological replicate 1 | | Biological replicate 2 | |
| Total reads | | 221,653,525 | | 176,705,499 |
| chimeric | 16,137,370 | 7% | 10,348,925 | 6% |
| non_chimeric | 49,993,038 | 23% | 58,657,541 | 33% |
| too short (<27 nt after trimming) | 81,501,625 | 37% | 80,181,174 | 45% |
| ambiguous | 74,021,492 | 33% | 27,517,859 | 16% |
| | PET1 | PET2 | PET1 | PET2 |
| Trimmed | 49,993,038 | 49,993,038 | 58,657,541 | 58,657,541 |
| Total aligned | 36,439,501 | 36,149,180 | 42,213,793 | 41,932,150 |
| Joined Mate Pairs | | 28,988,477 | | 32,284,454 |
| Unique Intra-chromosomal Mate Pairs | | 7,025,799 | | 3,418,723 |
| Unique Inter-chromosomal Mate Pairs | | 4,349,407 | | 4,648,962 |
| Ligations | | | | |
| Intra-chromosomal (>4 kb) | | 1,239,023 | | 980,462 |
| Interactions | | | | |
| Interactions (PET2, FDR <0.01) | | 22,025 | | 17,540 |
| Intra-chromosomal Interactions | | 21,630 | | 17,086 |
| Inter-chromosomal Interactions | | 395 | | 454 |
| chimeric | | | | |
| _ Trimmed | 16,137,370 | 16,137,370 | 10,348,925 | 10,348,925 |
| Total aligned | 11,597,024 | 11,438,519 | 7,443,723 | 7,380,674 |
| Joined Mate Pairs | | 8,322,581 | | 5,309,975 |
| Unique Intra-chromosomal Mate Pairs | | 188,501 | | 70,398 |
| Unique Inter-chromosomal Mate Pairs | | 2,901,591 | | 1,167,445 |

TABLE S1B

| Frequencies of PETs and interactions at various thresholds | | | |
|---|---|---|---|
| | Unique intra-chromosomal PETs | Low Confidence Intra- and inter-chromosomal Interactions (>4 kb) | High Confidence Intra-chromosomal Interactions (>4 kb, 3 PET, FDR 0.01) |
| Total | 10,444,522 | 1,234,006 | 23,739 |
| Enhancer-Promoter | 147,270 | 148,080 | 2,921 |
| Enhancer-Enhancer | 2,252,066 | 104,394 | 2,700 |
| CTCF-CTCF | 2,306,128 | 262,149 | 7,841 |

| | Inter-chromosomal | Intra-chromosomal | Inter:Intra Ratio |
|---|---|---|---|
| 1 PETs | 1,006,202 | 227,804 | 4:1 |
| 3+ PETs | 96 | 23,739 | 1:247 |

| Overlap with SMC1 ChIP-seq peaks (1e−05) | High Confidence Interactions (>4 kb, 3 PET, FDR 0.01) | % of High confidence Interactions |
|---|---|---|
| Both End | 21195 | 89.3% |
| 1 End | 2456 | 10.3% |
| None | 88 | 0.4% |

TABLE S2B

Super-enhancer to gene assignments

| Chr | Start | End | SE_ID | SE_rank | Proximal active genes (SE within 4 kb of TSS) | Interacting genes (SMC1 PET interactions) | Nearest active genes |
|---|---|---|---|---|---|---|---|
| chr1 | 36070190 | 36074608 | INT_STITCHED_100 | 215 | . | Hs6st1 | Hs6st1 |
| chr1 | 36111164 | 36118698 | INT_STITCHED_101 | 152 | . | Hs6st1 | Hs6st1 |
| chr1 | 72260528 | 72261272 | INT_STITCHED_230 | 189 | Mreg | . | Mreg |
| chr1 | 72839563 | 72858199 | INT_STITCHED_237 | 99 | . | Igfbp2 | Igfbp2 |
| chr1 | 91766947 | 91773527 | INT_STITCHED_315 | 231 | . | Gbx2 | Gbx2 |
| chr1 | 120538712 | 120545414 | INT_STITCHED_368 | 96 | . | Tcfcp2l1 | Tcfcp2l1 |
| chr1 | 120971968 | 120973737 | INT_STITCHED_372 | 73 | . | Gli2 | Gli2 |
| chr1 | 121201424 | 121202481 | INT_STITCHED_374 | 170 | . | Inhbb | Inhbb |
| chr1 | 121295085 | 121296031 | INT_STITCHED_376 | 137 | . | Inhbb | Inhbb |
| chr1 | 138841643 | 138850970 | INT_STITCHED_466 | 156 | Nr5a2 | Nr5a2 | Nr5a2 |
| chr1 | 168054897 | 168073079 | INT_STITCHED_556 | 97 | Dusp27, Gpa33 | . | Dusp27 |
| chr1 | 169201106 | 169220423 | INT_STITCHED_559 | 190 | Uck2 | . | Uck2 |
| chr1 | 182818684 | 182819554 | INT_STITCHED_610 | 59 | Lefty2 | . | Lefty2 |
| chr1 | 182854521 | 182864307 | INT_STITCHED_611 | 54 | Lefty1 | Lefty2, Tmem63a, Lefty1 | Lefty1 |
| chr1 | 183948212 | 183961841 | INT_STITCHED_615 | 123 | Enah | . | Enah |
| chr2 | 20574602 | 20591747 | INT_STITCHED_746 | 25 | . | Etl4 | Etl4 |
| chr2 | 32008891 | 32030736 | INT_STITCHED_812 | 31 | Bat2l | . | Bat2l |
| chr2 | 33282029 | 33300860 | INT_STITCHED_817 | 56 | Zbtb34 | Zbtb34 | Zbtb34 |
| chr2 | 71488013 | 71494617 | INT_STITCHED_928 | 115 | . | Gm1631 | Gm1631 |
| chr2 | 152552277 | 152563676 | INT_STITCHED_1198 | 178 | Id1 | Id1 | Id1 |
| chr2 | 162877048 | 162893236 | INT_STITCHED_1257 | 18 | Mybl2 | . | Mybl2 |
| chr2 | 165981373 | 165983444 | INT_STITCHED_1279 | 121 | Sulf2 | . | Sulf2 |
| chr2 | 168589688 | 168617170 | INT_STITCHED_1300 | 95 | Sall4 | . | Sall4 |
| chr3 | 34544904 | 34553511 | INT_STITCHED_1480 | 34 | Sox2 | Mir1897 | Sox2 |
| chr3 | 34633687 | 34660705 | INT_STITCHED_1482 | 2 | . | Mir1897, Sox2 | Sox2 |
| chr3 | 88375442 | 88380083 | INT_STITCHED_1607 | 193 | Ssr2 | . | Ssr2 |
| chr3 | 95455034 | 95468269 | INT_STITCHED_1626 | 9 | Mcl1 | . | Mcl1 |
| chr3 | 96380383 | 96382115 | INT_STITCHED_1629 | 69 | . | Txnip, Ankrd34a, Polr3gl | Txnip |
| chr3 | 96479158 | 96484864 | INT_STITCHED_1630 | 116 | Ankrd35 | Ankrd35, Nudt17 | Ankrd35 |
| chr3 | 129247012 | 129261362 | INT_STITCHED_1732 | 112 | . | Elovl6 | Elovl6 |
| chr4 | 118743867 | 118745786 | INT_STITCHED_2152 | 23 | . | Slc2a1 | Slc2a1 |
| chr4 | 125211671 | 125223450 | INT_STITCHED_2192 | 143 | . | Grik3 | Grik3 |
| chr4 | 137329436 | 137357766 | INT_STITCHED_2268 | 108 | Alpl | Alpl | Alpl |
| chr4 | 138000554 | 138006368 | INT_STITCHED_2273 | 228 | Camk2n1 | Camk2n1 | Camk2n1 |

TABLE S2B-continued

| Super-enhancer to gene assignments | | | | | | | |
|---|---|---|---|---|---|---|---|
| Chr | Start | End | SE_ID | SE_rank | Proximal active genes (SE within 4 kb of TSS) | Interacting genes (SMC1 PET interactions) | Nearest active genes |
| chr4 | 141120768 | 141126477 | INT_STITCHED_2292 | 39 | . | Gm694, B330016D10Rik, Fblim1, Tmem82, AI507597 | B330016D10Rik |
| chr4 | 147459254 | 147463850 | INT_STITCHED_2317 | 196 | Agtrap | . | Agtrap |
| chr5 | 53933177 | 53947327 | INT_STITCHED_2510 | 71 | Rbpj | . | Rbpj |
| chr5 | 65255735 | 65256794 | INT_STITCHED_2535 | 84 | . | Klf3 | Klf3 |
| chr5 | 113758941 | 113775389 | INT_STITCHED_2712 | 64 | Mir469 | Mir469 | Mir469 |
| chr5 | 116845764 | 116860853 | INT_STITCHED_2736 | 153 | . | Hspb8, 2410137F16Rik | Hspb8 |
| chr5 | 118884660 | 118896412 | INT_STITCHED_2745 | 35 | . | Med13l | Med13l |
| chr5 | 123584659 | 123590728 | INT_STITCHED_2770 | 41 | Rhof | Rhof | Rhof |
| chr5 | 135417523 | 135421698 | INT_STITCHED_2830 | 142 | Cldn4 | . | Cldn4 |
| chr6 | 39370384 | 39371286 | INT_STITCHED_3044 | 225 | Mkrn1 | . | Mkrn1 |
| chr6 | 91640161 | 91661247 | INT_STITCHED_3217 | 124 | Slc6a6 | Slc6a6 | Slc6a6 |
| chr6 | 122290093 | 122293017 | INT_STITCHED_3342 | 13 | Phc1 | . | Phc1 |
| chr6 | 122640118 | 122657871 | INT_STITCHED_3348 | 32 | Nanog, Nanogpd | Nanog, Nanogpd | Nanog |
| chr6 | 122714316 | 122720862 | INT_STITCHED_3349 | 40 | . | Slc2a3 | Slc2a3 |
| chr6 | 142458188 | 142461905 | INT_STITCHED_3429 | 222 | Ldhb | . | Ldhb |
| chr6 | 143047309 | 143065758 | INT_STITCHED_3437 | 98 | 5730419I09Rik | . | 5730419I09Rik |
| chr6 | 145223385 | 145225674 | INT_STITCHED_3450 | 230 | . | Kras | Kras |
| chr7 | 3193004 | 3218183 | INT_STITCHED_3467 | 1 | LOC100303645, Mir291b, Mir293, Mir290, Mir291a, Mir292, Mir294, Mir295 | LOC100303645, Mir291b, Mir293, Mir290, Mir291a, Mir292, Mir294, Mir295 | LOC100303645 |
| chr7 | 13599334 | 13600325 | INT_STITCHED_3481 | 172 | Zbtb45 | Zbtb45, Trim28 | Zbtb45 |
| chr7 | 30982397 | 30983339 | INT_STITCHED_3523 | 154 | Capns1 | Cox7a1 | Capns1 |
| chr7 | 31248315 | 31250619 | INT_STITCHED_3525 | 87 | Nphs1 | Aplp1, Nphs1, Kirrel2 | Nphs1 |
| chr7 | 52806853 | 52814768 | INT_STITCHED_3568 | 201 | . | Bcat2 | Bcat2 |
| chr7 | 71092246 | 71102481 | INT_STITCHED_3601 | 102 | . | Klf13 | Klf13 |
| chr7 | 87159908 | 87169963 | INT_STITCHED_3658 | 176 | Zfp710 | . | Zfp710 |
| chr7 | 87274999 | 87276022 | INT_STITCHED_3661 | 65 | . | Idh2 | Idh2 |
| chr7 | 87333420 | 87345334 | INT_STITCHED_3662 | 209 | Sema4b | Sema4b | Sema4b |
| chr7 | 91027196 | 91051830 | INT_STITCHED_3685 | 199 | Mesdc1, Mesdc2 | . | Mesdc1 |
| chr7 | 119831735 | 119835688 | INT_STITCHED_3765 | 166 | . | Tead1 | Tead1 |
| chr7 | 140304156 | 140307245 | INT_STITCHED_3856 | 51 | . | Ctbp2 | Ctbp2 |
| chr8 | 12499468 | 12504771 | INT_STITCHED_3947 | 125 | . | Sox1 | Sox1 |
| chr8 | 35023426 | 35027483 | INT_STITCHED_4014 | 173 | . | Rbpms | Rbpms |
| chr8 | 37602064 | 37613850 | INT_STITCHED_4033 | 6 | . | Dlc1 | Dlc1 |
| chr8 | 37642521 | 37671979 | INT_STITCHED_4034 | 36 | . | Dlc1 | Dlc1 |
| chr8 | 44405736 | 44406755 | INT_STITCHED_4046 | 161 | . | Zfp42 | Zfp42 |
| chr8 | 87174072 | 87174643 | INT_STITCHED_4163 | 79 | . | Ier2 | Ier2 |
| chr8 | 91514813 | 91540176 | INT_STITCHED_4179 | 15 | . | Sall1 | Sall1 |
| chr8 | 93351924 | 93355292 | INT_STITCHED_4190 | 131 | Chd9 | . | Chd9 |
| chr9 | 78207143 | 78223442 | INT_STITCHED_4657 | 14 | Ooep, Dppa5a | Dppa5a, Ooep | Dppa5a |
| chr9 | 110849422 | 110863371 | INT_STITCHED_4748 | 4 | Lrrc2 | Tdgf1, Lrrc2 | Lrrc2 |
| chr9 | 114458126 | 114474355 | INT_STITCHED_4766 | 113 | Trim71 | Trim71 | Trim71 |
| chr10 | 21546502 | 21549691 | INT_STITCHED_4891 | 135 | . | Sgk1 | Sgk1 |
| chr10 | 21700576 | 21708946 | INT_STITCHED_4893 | 68 | Sgk1 | Sgk1 | Sgk1 |
| chr10 | 39977900 | 39978752 | INT_STITCHED_4495 | 60 | Gtf3c6 | . | Gtf3c6 |
| chr10 | 59420365 | 59437537 | INT_STITCHED_5021 | 181 | Ddit4 | Ddit4 | Ddit4 |
| chr10 | 62346394 | 62361563 | INT_STITCHED_5044 | 5 | Tet1 | . | Tet1 |
| chr10 | 66380351 | 66383761 | INT_STITCHED_5054 | 164 | . | Reep3 | Reep3 |
| chr10 | 66546199 | 66564235 | INT_STITCHED_5059 | 134 | Reep3 | Reep3 | Reep3 |
| chr10 | 75400370 | 75401358 | INT_STITCHED_5092 | 183 | Mmpl1, Chchd10 | Mmpl1, Chchd10, Vpreb3, Gm5134 | Chchd10 |
| chr10 | 76655655 | 76662360 | INT_STITCHED_5100 | 187 | . | Col18a1 | Col18a1 |
| chr10 | 79508474 | 79515168 | INT_STITCHED_5111 | 55 | Polr2e, Gpx4 | Gpx4 | Gpx4 |
| chr11 | 52173182 | 52184686 | INT_STITCHED_5484 | 218 | Vdac1 | Vdac1 | Vdac1 |
| chr11 | 66824791 | 66838230 | INT_STITCHED_5555 | 74 | Tmem220 | Pirt, Tmem220, Myh3 | Tmem220 |
| chr11 | 77697704 | 77718786 | INT_STITCHED_5597 | 58 | Pipox | Pipox | Pipox |

TABLE S2B-continued

Super-enhancer to gene assignments

| Chr | Start | End | SE_ID | SE_rank | Proximal active genes (SE within 4 kb of TSS) | Interacting genes (SMC1 PET interactions) | Nearest active genes |
|---|---|---|---|---|---|---|---|
| chr11 | 97517673 | 97524159 | INT_STITCHED_5711 | 24 | . | Pcgf2, Mllt6, Cisd3 | Cisd3 |
| chr11 | 98823511 | 98826466 | INT_STITCHED_5719 | 194 | Rara | Rara | Rara |
| chr11 | 116943025 | 116953583 | INT_STITCHED_5819 | 57 | 2810008D09Rik | Sec14l1 | 2810008D09Rik |
| chr12 | 12790432 | 12795881 | INT_STITCHED_5875 | 38 | . | Mycn | Mycn |
| chr12 | 12810177 | 12811020 | INT_STITCHED_5876 | 185 | . | Mycn | Mycn |
| chr12 | 12933791 | 12950936 | INT_STITCHED_5880 | 45 | Mycn | Mycn | Mycn |
| chr12 | 56587347 | 56607146 | INT_STITCHED_6000 | 165 | Nfkbia | Nfkbia | Nfkbia |
| chr12 | 88239069 | 88245155 | INT_STITCHED_6118 | 90 | . | 6430527G18Rik, 2310044G17Rik | 2310044G17Rik |
| chr12 | 103940487 | 103953004 | INT_STITCHED_6151 | 197 | Itpk1 | . | Itpk1 |
| chr12 | 111725920 | 111743677 | INT_STITCHED_6188 | 117 | Ppp2r5c | . | Ppp2r5c |
| chr13 | 98052562 | 98062842 | INT_STITCHED_6557 | 217 | . | Enc1 | Enc1 |
| chr13 | 98202400 | 98225162 | INT_STITCHED_6559 | 182 | . | Enc1 | Enc1 |
| chr14 | 55704349 | 55705463 | INT_STITCHED_6815 | 145 | Zfhx2 | Jph4, Zfhx2, Thtpa | Zfhx2 |
| chr14 | 64118817 | 64131901 | INT_STITCHED_6859 | 62 | Tdh | Tdh | Tdh |
| chr14 | 65251303 | 65269514 | INT_STITCHED_6864 | 219 | Kif13b | Kif13b | Kif13b |
| chr14 | 71022659 | 71035930 | INT_STITCHED_6887 | 66 | Fgf17 | Fgf17 | Fgf17 |
| chr14 | 76894682 | 76915946 | INT_STITCHED_6904 | 27 | Tsc22d1 | Tsc22d1 | Tsc22d1 |
| chr14 | 106250319 | 106260753 | INT_STITCHED_6981 | 140 | . | Spry2 | Spry2 |
| chr14 | 106296486 | 106304433 | INT_STITCHED_6982 | 110 | Spry2 | . | Spry2 |
| chr16 | 23099373 | 23103471 | INT_STITCHED_7434 | 101 | Eif4a2, Snord2 | . | Eif4a2 |
| chr16 | 84769173 | 84780686 | INT_STITCHED_7597 | 53 | Jam2 | Mrp139, Jam2 | Jam2 |
| chr17 | 10549089 | 10570838 | INT_STITCHED_7680 | 114 | . | Qk | Qk |
| chr17 | 26631721 | 26648689 | INT_STITCHED_7728 | 139 | Dusp1 | Dusp1 | Dusp1 |
| chr17 | 29209618 | 29218426 | INT_STITCHED_7747 | 200 | . | Cdkn1a | Cdkn1a |
| chr17 | 29587776 | 29588942 | INT_STITCHED_7752 | 157 | . | Pim1 | Pim1 |
| chr17 | 31939569 | 31956756 | INT_STITCHED_7767 | 29 | . | Sik1 | Sik1 |
| chr17 | 35639211 | 35642435 | INT_STITCHED_7784 | 186 | Pou5f1 | Tcf19, Cchcr1 | Pou5f1 |
| chr17 | 37110202 | 37134996 | INT_STITCHED_7792 | 12 | 2410137M14Rik, Zfp57, H2-M5 | Znrd1, Znrd1as, 2410137M14Rik, Trim40, Gabbr1, H2-M5, Zfp57, Olfr90 | 2410137M14Rik |
| chr17 | 45593477 | 45596503 | INT_STITCHED_7812 | 37 | . | Spats1 | Spats1 |
| chr17 | 47640414 | 47649043 | INT_STITCHED_7822 | 141 | Ccnd3, Taf8 | Ccnd3, Bysl, Med20 | Ccnd3 |
| chr17 | 71213804 | 71222433 | INT_STITCHED_7887 | 42 | . | Tgif1 | Tgif1 |
| chr17 | 71241991 | 71250610 | INT_STITCHED_7888 | 203 | . | Tgif1 | Tgif1 |
| chr18 | 75504155 | 75505202 | INT_STITCHED_8260 | 198 | . | Smad7 | Smad7 |
| chr18 | 75520332 | 75527277 | INT_STITCHED_8261 | 91 | Smad7 | Smad7 | Smad7 |
| chr19 | 5835881 | 5847014 | INT_STITCHED_8324 | 16 | Neat1 | Malat1, Slc25a45, Frmd8 | Neat1 |
| chr19 | 21858770 | 21866770 | INT_STITCHED_8378 | 103 | Tmem2 | Tmem2 | Tmem2 |
| chr19 | 23207455 | 23208806 | INT_STITCHED_8386 | 82 | . | Klf9,Mir1192 | Klf9 |
| chrX | 50098631 | 50114110 | INT_STITCHED_8629 | 150 | Mir18b, Mir19b-2, Kis2, Mir20b, Mir92-2, Mir106a, Mir363 | . | Kis2 |

TABLE S2C

Typical enhancer to gene assignment

| chr | start | end | TE_ID | TE_rank | proximal active genes (TE within 4 kb of TSS) | interacting active genes (SMC1 PET interactions) | nearest genes |
|---|---|---|---|---|---|---|---|
| chr1 | 4845264 | 4846195 | INT_STITCHED_4 | 4358 | Tcea1 | . | Tcea1 |
| chr1 | 9691815 | 9692699 | INT_STITCHED_22 | 2543 | Mybl1 | . | Mybl1 |
| chr1 | 10021675 | 10022274 | INT_STITCHED_25 | 4284 | Csppl, Cops5 | . | Cops5 |
| chr1 | 12681792 | 12682608 | INT_STITCHED_40 | 2368 | Sulf1 | . | Sulf1 |
| chr1 | 12734270 | 12735431 | INT_STITCHED_41 | 521 | . | Sulf1 | Sulf1 |

TABLE S2C-continued

| Typical enhancer to gene assignment | | | | | | | |
|---|---|---|---|---|---|---|---|
| chr | start | end | TE_ID | TE_rank | proximal active genes (TE within 4 kb of TSS) | interacting active genes (SMC1 PET interactions) | nearest genes |
| chr1 | 13650476 | 13651156 | INT_STITCHED_48 | 726 | Lactb2 | . | Lactb2 |
| chr1 | 14302611 | 14303160 | INT_STITCHED_54 | 5331 | Eya1 | . | Eya1 |
| chr1 | 20944720 | 20945563 | INT_STITCHED_66 | 3579 | Efhc1 | . | Efhc1 |
| chr1 | 34063557 | 34064527 | INT_STITCHED_87 | 1218 | Dst | . | Dst |
| chr1 | 36296870 | 36297624 | INT_STITCHED_102 | 4246 | Uggt1 | . | Uggt1 |
| chr1 | 38960832 | 38961217 | INT_STITCHED_122 | 5874 | Chst10 | . | Chst10 |
| chr1 | 39959153 | 39960298 | INT_STITCHED_127 | 3253 | Map4k4 | . | Map4k4 |
| chr1 | 52065557 | 52066452 | INT_STITCHED_153 | 3287 | Stat4 | . | Stat4 |
| chr1 | 53009978 | 53010966 | INT_STITCHED_156 | 499 | 1700019D03Rik | . | 1700019D03Rik |
| chr1 | 55188460 | 55189193 | INT_STITCHED_165 | 3945 | Mobkl3 | . | Mobkl3 |
| chr1 | 58045669 | 58046468 | INT_STITCHED_177 | 7085 | Sgol2 | . | Sgol2 |
| chr1 | 59543982 | 59544804 | INT_STITCHED_185 | 1108 | Fzd7 | . | Fzd7 |
| chr1 | 63256644 | 63260998 | INT_STITCHED_199 | 729 | Gpr1 | . | Gpr1 |
| chr1 | 63488535 | 63489242 | INT_STITCHED_201 | 2410 | Adam23 | . | Adam23 |
| chr1 | 66746373 | 66747073 | INT_STITCHED_217 | 2899 | Rpe | . | Rpe |
| chr1 | 71692414 | 71697825 | INT_STITCHED_227 | 505 | Fn1 | Fn1 | Fn1 |
| chr1 | 71719790 | 71720485 | INT_STITCHED_228 | 1904 | . | Fn1 | Fn1 |
| chr1 | 72359403 | 72360070 | INT_STITCHED_234 | 1813 | Xrcc5 | . | Xrcc5 |
| chr1 | 72873970 | 72875037 | INT_STITCHED_238 | 905 | Igfbp2 | . | Igfbp2 |
| chr1 | 74354703 | 74355378 | INT_STITCHED_245 | 5971 | Tmbim1 | . | Tmbim1 |
| chr1 | 75477134 | 75477769 | INT_STITCHED_250 | 5588 | Chpf, Tmem198 | . | Chpf |
| chr1 | 75508284 | 75508949 | INT_STITCHED_251 | 1914 | Obsl1, Inha | . | Inha |
| chr1 | 82816971 | 82817766 | INT_STITCHED_274 | 2678 | . | Agfg1 | Agfg1 |
| chr1 | 87920884 | 87921540 | INT_STITCHED_284 | 3696 | Spata3 | . | Spata3 |
| chr1 | 87959141 | 87959957 | INT_STITCHED_285 | 4733 | Psmd1 | . | Psmd1 |
| chr1 | 88204615 | 88208596 | INT_STITCHED_290 | 250 | B3gnt7 | B3gnt7 | B3gnt7 |
| chr1 | 88245025 | 88246107 | INT_STITCHED_291 | 2122 | Snora75 | . | Snora75 |
| chr1 | 90565168 | 90566043 | INT_STITCHED_305 | 2089 | . | Arl4c | Arl4c |
| chr1 | 91819328 | 91831892 | INT_STITCHED_316 | 497 | Gbx2 | Gbx2 | Gbx2 |
| chr1 | 92098794 | 92106028 | INT_STITCHED_318 | 688 | Cxcr7 | . | Cxcr7 |
| chr1 | 95376908 | 95377612 | INT_STITCHED_332 | 6388 | Hdlbp, Sept2 | . | Hdlbp |
| chr1 | 98771158 | 98773296 | INT_STITCHED_339 | 2005 | Slco4c1 | . | Slco4c1 |
| chr1 | 99983100 | 99989373 | INT_STITCHED_342 | 3966 | Pam | . | Pam |
| chr1 | 108073359 | 108073939 | INT_STITCHED_358 | 8767 | Phlpp1 | . | Phlppl |
| chr1 | 120521806 | 120522612 | INT_STITCHED_367 | 2301 | Tcfcp2l1 | . | Tcfcp2l1 |
| chr1 | 120945487 | 120946330 | INT_STITCHED_371 | 1302 | Gli2 | . | Gli2 |
| chr1 | 121974196 | 121974786 | INT_STITCHED_381 | 3822 | Tmem37 | . | Tmem37 |
| chr1 | 133035565 | 133036620 | INT_STITCHED_412 | 1146 | Dyrk3 | . | Dyrk3 |
| chr1 | 133808795 | 133809368 | INT_STITCHED_417 | 5138 | Nucks1 | . | Nucks1 |
| chr1 | 134094126 | 134098050 | INT_STITCHED_418 | 325 | Mir135b, Lemd1 | . | Mir135b |
| chr1 | 134219166 | 134219919 | INT_STITCHED_422 | 1727 | Nuak2 | . | Nuak2 |
| chr1 | 134367243 | 134368398 | INT_STITCHED_423 | 926 | Rbbp5 | . | Rbbp5 |
| chr1 | 134632637 | 134633301 | INT_STITCHED_424 | 7437 | Nfasc | . | Nfasc |
| chr1 | 134908975 | 134916403 | INT_STITCHED_428 | 576 | Mdm4 | . | Mdm4 |
| chr1 | 135025718 | 135027101 | INT_STITCHED_430 | 1307 | Ppp1r15b | . | Ppp1r15b |
| chr1 | 135293890 | 135294788 | INT_STITCHED_433 | 1273 | . | Sox13 | Sox13 |
| chr1 | 135388767 | 135401699 | INT_STITCHED_434 | 543 | . | Sox13 | Sox13 |
| chr1 | 135563926 | 135569034 | INT_STITCHED_435 | 358 | Zc3h11a, Zbed6 | . | Zc3h11a |
| chr1 | 135590624 | 135593014 | INT_STITCHED_436 | 560 | Lax1 | . | Lax1 |
| chr1 | 136397332 | 136398015 | INT_STITCHED_443 | 4773 | Rabif | . | Rabif |
| chr1 | 136431225 | 136432331 | INT_STITCHED_444 | 2150 | . | Kdm5b | Kdm5b |
| chr1 | 137113999 | 137114858 | INT_STITCHED_450 | 706 | . | Elf3 | Elf3 |
| chr1 | 137620382 | 137621364 | INT_STITCHED_456 | 2681 | Csrp1 | . | Csrp1 |
| chr1 | 145580899 | 145581539 | INT_STITCHED_484 | 4234 | Glrx2 | . | Glrx2 |
| chr1 | 153273953 | 153274850 | INT_STITCHED_494 | 8758 | 1200016B10Rik, 1190005F20Rik | . | 1200016B10Rik |
| chr1 | 154747403 | 154748240 | INT_STITCHED_504 | 3069 | Smg7 | . | Smg7 |
| chr1 | 155038686 | 155047086 | INT_STITCHED_509 | 1743 | Lamc2 | . | Lamc2 |
| chr1 | 155587804 | 155588362 | INT_STITCHED_515 | 8754 | Rgs16 | . | Rgs16 |
| chr1 | 158404784 | 158405439 | INT_STITCHED_524 | 5448 | Soat1 | . | Soat1 |
| chr1 | 158598688 | 158600322 | INT_STITCHED_526 | 564 | Tor3a | Tor3a | Tor3a |
| chr1 | 159347974 | 159348711 | INT_STITCHED_530 | 5728 | Rasal2, 2810025M15Rik | . | Rasal2 |
| chr1 | 162139563 | 162148759 | INT_STITCHED_536 | 836 | Cacybp | Mrps14 | Cacybp |
| chr1 | 163177529 | 163178269 | INT_STITCHED_540 | 5753 | Prdx6 | . | Prdx6 |
| chr1 | 166391111 | 166401507 | INT_STITCHED_550 | 1257 | Atp1b1 | . | Atp1b1 |
| chr1 | 166420037 | 166434276 | INT_STITCHED_551 | 257 | . | Atp1b1 | Atp1b1 |
| chr1 | 167932859 | 167934026 | INT_STITCHED_555 | 955 | Pou2f1 | . | Pou2f1 |
| chr1 | 170356969 | 170357484 | INT_STITCHED_564 | 6866 | Pbx1 | . | Pb1 |

TABLE S2C-continued

| Typical enhancer to gene assignment | | | | | | | |
|---|---|---|---|---|---|---|---|
| chr | start | end | TE_ID | TE_rank | proximal active genes (TE within 4 kb of TSS) | interacting active genes (SMC1 PET interactions) | nearest genes |
| chr1 | 172801604 | 172802054 | INT_STITCHED_569 | 2160 | Atf6 | . | Atf6 |
| chr1 | 173151620 | 173152144 | INT_STITCHED_573 | 1593 | Apoa2, Tomm401 | 1700009P17Rik | Tomm401 |
| chr1 | 173954295 | 173954872 | INT_STITCHED_575 | 7014 | Vangl2 | . | Vangl2 |
| chr1 | 174253188 | 174253931 | INT_STITCHED_577 | 8046 | Kcnj9 | . | Kcnj9 |
| chr1 | 180267618 | 180268830 | INT_STITCHED_593 | 731 | Hnrnpu | . | Hnrnpu |
| chr1 | 180336631 | 180337473 | INT_STITCHED_594 | 2688 | Efcab2 | . | Efcab2 |
| chr1 | 182500935 | 182501845 | INT_STITCHED_609 | 1729 | Parp1 | . | Parp1 |
| chr1 | 187032263 | 187033005 | INT_STITCHED_625 | 4425 | Rab3gap2 | . | Rab3gap2 |
| chr1 | 187934331 | 187934769 | INT_STITCHED_630 | 7896 | Lyplal1 | . | Lyplal1 |
| chr1 | 190822409 | 190837835 | INT_STITCHED_646 | 676 | Kctd3 | . | Kctd3 |
| chr1 | 191740124 | 191740887 | INT_STITCHED_650 | 1458 | Smyd2 | . | Smyd2 |
| chr1 | 192888978 | 192894651 | INT_STITCHED_655 | 2500 | Tatdn3, Nsl1 | . | Tatdn3 |
| chr1 | 193647966 | 193643573 | INT_STITCHED_660 | 6749 | Nek7 | . | Nek2 |
| chr1 | 194590595 | 194591390 | INT_STITCHED_664 | 6035 | Hhat | . | Hhat |
| chr1 | 195330571 | 1953334 | INT_STITCHED_670 | 2128 | Mir205 | . | Mir205 |
| chr1 | 196442242 | 196442858 | INT_STITCHED_676 | 7610 | Plxna2 | . | Plxna2 |
| chr2 | 17854471 | 17865277 | INT_STITCHED_732 | 482 | . | LOC100034739 | LOC100034739 |
| chr2 | 17895135 | 17911418 | INT_STITCHED_733 | 361 | . | LOC100034739 | LOC100034739 |
| chr2 | 22747132 | 22756399 | INT_STITCHED_756 | 797 | Pdss1 | . | Pdss1 |
| chr2 | 26198387 | 26199182 | INT_STITCHED_766 | 5022 | . | Dnlz | Dnlz |
| chr2 | 26298047 | 26304190 | INT_STITCHED_767 | 2561 | Sec16a | Notch1 | Sec16a |
| chr2 | 26356857 | 26358299 | INT_STITCHED_768 | 1708 | Notch1 | . | Notch1 |
| chr2 | 28361728 | 28365199 | INT_STITCHED_775 | 3084 | Ralgds | . | Ralgds |
| chr2 | 28391046 | 28391512 | INT_STITCHED_776 | 6931 | Ralgds | . | Ralgds |
| chr2 | 28976424 | 28976978 | INT_STITCHED_783 | 3537 | Setx | . | Setx |
| chr2 | 29100520 | 29101142 | INT_STITCHED_785 | 2171 | Ntng2 | . | Ntng2 |
| chr2 | 29484671 | 79487572 | INT_STITCHED_790 | 375 | . | Rapgef1 | Rapgef1 |
| chr2 | 29675439 | 29676619 | INT_STITCHED_793 | 1058 | Urm1 | . | Urm1 |
| chr2 | 29917303 | 29917729 | INT_STITCHED_796 | 1358 | Set | . | Set |
| chr2 | 29990414 | 29991153 | INT_STITCHED_797 | 2134 | Tbcld13 | . | Tbcld13 |
| chr2 | 31427293 | 31428087 | INT_STITCHED_808 | 635 | Fubp3 | Prdm12 | Fubp3 |
| chr2 | 31736153 | 31736754 | INT_STITCHED_810 | 5015 | Lamc3 | . | Lamc3 |
| chr2 | 33738008 | 33739000 | INT_STITCHED_823 | 4826 | Fam125b | . | Fam125b |
| chr2 | 38780488 | 38781118 | INT_STITCHED_839 | 3934 | Olfml2a, Nr6a1 | Wdr38 | Nr6a1 |
| chr2 | 44959885 | 44960550 | INT_STITCHED_849 | 4033 | Gm13476 | . | Gm13476 |
| chr2 | 49304139 | 49305084 | INT_STITCHED_856 | 7363 | Epc2 | . | Epc2 |
| chr2 | 50894125 | 50905941 | INT_STITCHED_861 | 897 | . | Rnd3 | Rnd3 |
| chr2 | 51926608 | 51928267 | INT_STITCHED_865 | 280 | Rif1 | . | Rif1 |
| chr2 | 60213132 | 60223107 | INT_STITCHED_884 | 419 | Ly75 | . | Ly75 |
| chr2 | 62246033 | 62246887 | INT_STITCHED_895 | 3985 | Dpp4 | . | Dpp4 |
| chr2 | 65679605 | 65687302 | INT_STITCHED_900 | 745 | Csmp3 | . | Csrnp3 |
| chr2 | 71556963 | 71557704 | INT_STITCHED_930 | 400 | Gm1631 | . | Gm1631 |
| chr2 | 71704256 | 71705255 | INT_STITCHED_932 | 380 | Pdk1 | Pdk1 | Pdk1 |
| chr2 | 72823322 | 72824095 | INT_STITCHED_936 | 3178 | Sp3 | . | Sp3 |
| chr2 | 75544463 | 75545103 | INT_STITCHED_951 | 2667 | Nfe2l2 | . | Nfe2l2 |
| chr2 | 76238133 | 76238918 | INT_STITCHED_958 | 3707 | Osbp16 | . | Osbp16 |
| chr2 | 79269600 | 79270299 | INT_STITCHED_973 | 2411 | Cerkl | Neurod1 | Cerkl |
| chr2 | 83550377 | 83559168 | INT_STITCHED_980 | 1203 | Itgav | . | Itgav |
| chr2 | 84677181 | 84679035 | INT_STITCHED_986 | 860 | Slc43a1 | . | Slc43a1 |
| chr2 | 91544344 | 91548597 | INT_STITCHED_993 | 3127 | Atg13, Harbi1 | . | Atg13 |
| chr2 | 91772530 | 91773198 | INT_STITCHED_994 | 1226 | Mdk | Chrm4 | Mdk |
| chr2 | 94103254 | 94103817 | INT_STITCHED_1002 | 2880 | Mir670 | . | Mir670 |
| chr2 | 102023859 | 102024282 | INT_STITCHED_1013 | 6628 | Ldlrad3 | . | Ldlrad3 |
| chr2 | 102243909 | 102243994 | INT_STITCHED_1014 | 8718 | Trim44 | . | Trim44 |
| chr2 | 103632070 | 103632867 | INT_STITCHED_1022 | 3964 | Caprin1 | . | Caprin1 |
| chr2 | 103938892 | 103939697 | INT_STITCHED_1024 | 4914 | Cd59a | . | Cd59a |
| chr2 | 104428555 | 104429275 | INT_STITCHED_1026 | 6129 | Cstf3 | . | Cstf3 |
| chr2 | 104657804 | 104666793 | INT_STITCHED_1028 | 1623 | Qser1 | . | Qser1 |
| chr2 | 104695622 | 104696627 | INT_STITCHED_1029 | 3340 | Prrg4 | . | Prrg4 |
| chr2 | 105237758 | 105249007 | INT_STITCHED_1031 | 1507 | Rcn1 | . | Rcn1 |
| chr2 | 109753059 | 109753825 | INT_STITCHED_1048 | 2198 | Gm13939, Lgr4 | . | Gm13939 |
| chr2 | 114003762 | 114004516 | INT_STITCHED_1054 | 2091 | Aqr | . | Aqr |
| chr2 | 115885482 | 115886413 | INT_STITCHED_1061 | 3063 | Meis2 | 3110099E03Rik, 2810405F15Rik | Meis2 |
| chr2 | 116945256 | 116946216 | INT_STITCHED_1066 | 1301 | Spred1 | . | Spred1 |
| chr2 | 119615493 | 119616460 | INT_STITCHED_1079 | 1269 | Rpap1 | Tyro3 | Rpap1 |
| chr2 | 120069560 | 120070347 | INT_STITCHED_1081 | 4738 | Pla2g4e | . | Pla2g4e |
| chr2 | 121095895 | 121096949 | INT_STITCHED_1083 | 5489 | Trp53bp1 | . | Trp53bp1 |
| chr2 | 121303040 | 121303595 | INT_STITCHED_1084 | 4080 | Mfap1b | . | Mfap1b |

TABLE S2C-continued

Typical enhancer to gene assignment

| chr | start | end | TE_ID | TE_rank | proximal active genes (TE within 4 kb of TSS) | interacting active genes (SMC1 PET interactions) | nearest genes |
|---|---|---|---|---|---|---|---|
| chr2 | 121628647 | 121629289 | INT_STITCHED_1086 | 6300 | Frmd5 | . | Frmd5 |
| chr2 | 122195660 | 122196747 | INT_STITCHED_1091 | 1739 | Shf | . | Shf |
| chr2 | 125973476 | 125973812 | INT_STITCHED_1098 | 7151 | Dtwdl | . | Dtwdl |
| chr2 | 127664828 | 127665772 | INT_STITCHED_1105 | 2730 | . | Bub1 | Bub1 |
| chr2 | 128638582 | 128639150 | INT_STITCHED_1111 | 3886 | Tmem87b | . | Tmem87b |
| chr2 | 128887217 | 128888053 | INT_STITCHED_1113 | 6432 | Ttl | . | Ttl |
| chr2 | 129412877 | 129414126 | INT_STITCHED_1117 | 2016 | Sirpa | . | Sirpa |
| chr2 | 129521285 | 129528427 | INT_STITCHED_1118 | 967 | Pdyn | . | Pdyn |
| chr2 | 129623870 | 129626180 | INT_STITCHED_1119 | 1155 | Stk35, 4932416H05Rik | . | Stk35 |
| chr2 | 131058146 | 131070063 | INT_STITCHED_1125 | 1091 | Mays | . | Mays |
| chr2 | 140502439 | 140503025 | INT_STITCHED_1155 | 3559 | Flrt3 | . | Flrt3 |
| chr2 | 145614651 | 145615227 | INT_STITCHED_1167 | 5472 | Rin2 | . | Rin2 |
| chr2 | 146837021 | 146837769 | INT_STITCHED_1177 | 2634 | Xrn2 | . | Xrn2 |
| chr2 | 148700392 | 148701063 | INT_STITCHED_1185 | 1716 | Cst3 | 9230104L09Rik | Cst3 |
| chr2 | 150482907 | 150491844 | INT_STITCHED_1190 | 744 | Acss1 | . | Acss1 |
| chr2 | 150863293 | 150863974 | INT_STITCHED_1193 | 7212 | Nanp | . | Nanp |
| chr2 | 152048814 | 152049781 | INT_STITCHED_1197 | 4239 | Csnk2a1 | . | Csnk2a1 |
| chr2 | 152932871 | 152933554 | INT_STITCHED_1200 | 1971 | Hck | . | Hck |
| chr2 | 153172351 | 153173278 | INT_STITCHED_1202 | 2564 | Asxl1 | . | Asxl1 |
| chr2 | 153467302 | 153469325 | INT_STITCHED_1208 | 3527 | Dnmt3b | . | Dnmt3b |
| chr2 | 154905247 | 154906205 | INT_STITCHED_1212 | 5226 | Ahcy | . | Ahcy |
| chr2 | 156251118 | 156251931 | INT_STITCHED_1218 | 1519 | Epb4.1l1 | . | Epb4.1l1 |
| chr2 | 156667667 | 156668409 | INT_STITCHED_1223 | 1808 | Tgif2 | . | Tgif2 |
| chr2 | 157243952 | 157244973 | INT_STITCHED_1229 | 337 | Src | Ghrh, Src | Src |
| chr2 | 157978463 | 157980974 | INT_STITCHED_1233 | 239 | Tgm2 | . | Tgm2 |
| chr2 | 158614658 | 158615457 | INT_STITCHED_1238 | 4450 | Dhx35 | . | Dhx35 |
| chr2 | 162753625 | 162754468 | INT_STITCHED_1255 | 7920 | Srsf6 | . | Srsf6 |
| chr2 | 163890381 | 163891019 | INT_STITCHED_1261 | 6983 | Tomm34 | . | Tomm34 |
| chr2 | 164277250 | 164277825 | INT_STITCHED_1263 | 4381 | . | Sdc4 | Sdc4 |
| chr2 | 164649260 | 164649880 | INT_STITCHED_1265 | 1164 | Zswim1, 1700020007Rik | . | Zswim1 |
| chr2 | 164680558 | 164681078 | INT_STITCHED_1266 | 5540 | Pltp | . | Pltp |
| chr2 | 165682802 | 165683641 | INT_STITCHED_1273 | 1421 | . | Zmynd8 | Zmynd8 |
| chr2 | 165700123 | 165704304 | INT_STITCHED_1274 | 2229 | Zmynd8 | . | Zmynd8 |
| chr2 | 165719928 | 165725066 | INT_STITCHED_1275 | 557 | . | Zmynd8 | Zmynd8 |
| chr2 | 166019666 | 166020678 | INT_STITCHED_1280 | 431 | . | Sulf2 | Sulf2 |
| chr2 | 166884075 | 166898489 | INT_STITCHED_1288 | 240 | Snord12, 1500012E01Rik, Znfx1 | Kcnb1 | Snord12 |
| chr2 | 167248382 | 167249300 | INT_STITCHED_1294 | 2679 | Slc9a8 | . | Slc9a8 |
| chr2 | 167355489 | 167366175 | INT_STITCHED_1295 | 652 | Snai1 | . | Snai1 |
| chr2 | 167979755 | 167980437 | INT_STITCHED_1297 | 1110 | . | Adnp | Adnp |
| chr2 | 168039253 | 168040134 | INT_STITCHED_1299 | 6482 | . | Adnp | Adnp |
| chr2 | 168664093 | 168667592 | INT_STITCHED_1301 | 675 | . | Atp9a, Sall4 | Sall4 |
| chr2 | 168784552 | 168785568 | INT_STITCHED_1302 | 1060 | Zfp64 | . | Zfp64 |
| chr2 | 174082837 | 174087567 | INT_STITCHED_1339 | 943 | Mir296 | . | Mir296 |
| chr2 | 174113130 | 174113943 | INT_STITCHED_1340 | 2341 | Gnas | . | Gnas |
| chr2 | 180443435 | 180445072 | INT_STITCHED_1358 | 534 | Dido1, 2310003C93Rik | Slc17a9 | Dido1 |
| chr2 | 180462024 | 180475727 | INT_STITCHED_1359 | 329 | Slc17a9 | Slc17a9, Dido1 | Slc17a9 |
| chr2 | 180687447 | 180688955 | INT_STITCHED_1362 | 2111 | Nkain4 | Birc7, Arfgap1 | Nkain4 |
| chr2 | 180947699 | 180948243 | INT_STITCHED_1364 | 3425 | BC051628 | Ppdpf | BC051628 |
| chr2 | 180979223 | 180980098 | INT_STITCHED_1365 | 7507 | BC006779 | . | BC006779 |
| chr2 | 181056733 | 181067845 | INT_STITCHED_1366 | 1346 | Rtel1 | . | Rtel1 |
| chr3 | 7366490 | 7367336 | INT_STITCHED_1376 | 8686 | Pkia | . | Pkia |
| chr3 | 8509668 | 8511844 | INT_STITCHED_1381 | 318 | Stmn2 | . | Stmn2 |
| chr3 | 8963969 | 8965013 | INT_STITCHED_1382 | 3662 | Tpd52 | . | Tpd52 |
| chr3 | 9008384 | 9009250 | INT_STITCHED_1384 | 1165 | Tpd52 | . | Tpd52 |
| chr3 | 9243943 | 9244611 | INT_STITCHED_1386 | 4596 | Zbtb10 | . | Zbtb10 |
| chr3 | 9610853 | 9611748 | INT_STITCHED_1391 | 1939 | Zfp704 | C030034L19Rik | Zfp704 |
| chr3 | 10353887 | 10354547 | INT_STITCHED_1395 | 5545 | Zfand1 | . | Zfand1 |
| chr3 | 14863038 | 14863599 | INT_STITCHED_1406 | 1714 | Car3 | . | Car3 |
| chr3 | 18523768 | 18524685 | INT_STITCHED_1418 | 1649 | . | Cyp7b1 | Cyp7b1 |
| chr3 | 19797116 | 19797596 | INT_STITCHED_1423 | 7359 | 4632415L05Rik | . | 4632415L05Rik |
| chr3 | 19957995 | 19958715 | INT_STITCHED_1425 | 3002 | Hltf | . | Hltf |
| chr3 | 21834336 | 21835378 | INT_STITCHED_1430 | 708 | . | Tbl1xr1 | Tbl1xr1 |
| chr3 | 21964172 | 21975748 | INT_STITCHED_1433 | 312 | Tbl1xr1 | . | Tbl1xr1 |
| chr3 | 27602172 | 27603039 | INT_STITCHED_1447 | 1051 | Fndc3b | . | Fndc3b |
| chr3 | 27834469 | 27836247 | INT_STITCHED_1449 | 2019 | Pld1 | . | Pd1 |
| chr3 | 30545417 | 30547747 | INT_STITCHED_1462 | 694 | Lrriq4 | . | Lrriq4 |
| chr3 | 30899964 | 30917089 | INT_STITCHED_1468 | 432 | Prkci | . | Pkci |

TABLE S2C-continued

| Typical enhancer to gene assignment | | | | | | | |
|---|---|---|---|---|---|---|---|
| chr | start | end | TE_ID | TE_rank | proximal active genes (TE within 4 kb of TSS) | interacting active genes (SMC1 PET interactions) | nearest genes |
| chr3 | 30988014 | 30988781 | INT_STITCHED_1469 | 1571 | Skil | . | Skil |
| chr3 | 53261382 | 53262179 | INT_STITCHED_1518 | 2450 | 2810046L04Rik, Nhlrc3 | . | Nhlrc3 |
| chr3 | 53453757 | 53454852 | INT_STITCHED_1521 | 1227 | Frem2 | Frem2 | Frem2 |
| chr3 | 53672950 | 53673878 | INT_STITCHED_1522 | 3451 | Ufm1 | . | Ufm1 |
| chr3 | 57536429 | 57536949 | INT_STITCHED_1530 | 4492 | Rnf13 | . | Rnf13 |
| chr3 | 62145578 | 62146250 | INT_STITCHED_1539 | 5028 | 4631416L12Rik | . | 4631416L12Rik |
| chr3 | 63098862 | 63099542 | INT_STITCHED_1541 | 2296 | Mme | . | Mme |
| chr3 | 65339039 | 65339696 | INT_STITCHED_1548 | 7074 | 4931440P22Rik | . | 4931440P22Rik |
| chr3 | 67307480 | 67318756 | INT_STITCHED_1552 | 1308 | Rarres1 | . | Rarres1 |
| chr3 | 68368482 | 68369877 | INT_STITCHED_1558 | 1231 | Schip1 | . | Schip1 |
| chr3 | 79375842 | 79376337 | INT_STITCHED_1573 | 6825 | Fnip2 | . | Fnip2 |
| chr3 | 80838336 | 80839401 | INT_STITCHED_1575 | 1948 | Pdgfc | . | Pdgfc |
| chr3 | 83824381 | 83838289 | INT_STITCHED_1586 | 957 | D930015E06Rik | . | D930015E06Rik |
| chr3 | 83985389 | 84010994 | INT_STITCHED_1587 | 439 | . | Gm6525, Trim2 | Gm6525 |
| chr3 | 84624646 | 84625298 | INT_STITCHED_1589 | 7481 | Fbxw7 | . | Fbxw7 |
| chr3 | 85952913 | 85953587 | INT_STITCHED_1596 | 4519 | Rps3a | . | Rps3a |
| chr3 | 86940621 | 86941199 | INT_STITCHED_1600 | 3865 | . | Kirrel | Kirrel |
| chr3 | 87777956 | 87778942 | INT_STITCHED_1603 | 1687 | Nes | . | Nes |
| chr3 | 89258497 | 89259386 | INT_STITCHED_1609 | 2576 | Pmvk | . | Pmvk |
| chr3 | 89626047 | 89631123 | INT_STITCHED_1611 | 1463 | She | . | She |
| chr3 | 94110855 | 94111307 | INT_STITCHED_1620 | 5187 | Them4 | . | Them4 |
| chr3 | 94965812 | 94966422 | INT_STITCHED_1623 | 3377 | Sema6c | . | Sema6c |
| chr3 | 95237742 | 95238552 | INT_STITCHED_1625 | 1341 | Gm4349, Arnt | . | Arnt |
| chr3 | 95505802 | 95506443 | INT_STITCHED_1627 | 539 | . | Adamtsl4 | Adamtsl4 |
| chr3 | 95694960 | 95695228 | INT_STITCHED_1628 | 3845 | BC028528, Aph1a | Car14 | BC028528 |
| chr3 | 96963138 | 96963961 | INT_STITCHED_1632 | 713 | Acp6 | . | Acp6 |
| chr3 | 100914800 | 100915619 | INT_STITCHED_1639 | 2609 | Ptgfrn | . | Ptgfrn |
| chr3 | 100957135 | 100967876 | INT_STITCHED_1640 | 260 | . | Ptgfrn | Ptgfrn |
| chr3 | 101993816 | 102007402 | INT_STITCHED_1651 | 608 | Vangl1 | Casq2 | Vangl1 |
| chr3 | 102930941 | 102931790 | INT_STITCHED_1656 | 1207 | Dennd2c | Bcas2 | Dennd2c |
| chr3 | 102949003 | 102950801 | INT_STITCHED_1657 | 267 | . | Dennd2c | Dennd2c |
| chr3 | 104618028 | 104623683 | INT_STITCHED_1662 | 584 | Mov10 | . | Mov10 |
| chr3 | 106351238 | 106351736 | INT_STITCHED_1664 | 4051 | Cept1, Dram2 | . | Cept1 |
| chr3 | 108391181 | 108391923 | INT_STITCHED_1672 | 4003 | Wdr47 | . | Wdr47 |
| chr3 | 116358806 | 116359743 | INT_STITCHED_1685 | 7347 | Hiat1 | . | Hiatl |
| chr3 | 116563049 | 116563725 | INT_STITCHED_1687 | 2868 | Frrs1 | . | Frrs1 |
| chr3 | 121121824 | 121122736 | INT_STITCHED_1701 | 355 | . | Cnn3 | Cnn3 |
| chr3 | 121513631 | 121513714 | INT_STITCHED_1706 | 8004 | Abcd3 | . | Abcd3 |
| chr3 | 122136782 | 122137600 | INT_STITCHED_1711 | 971 | . | Bcar3 | Bcar3 |
| chr3 | 127155894 | 127167528 | INT_STITCHED_1724 | 453 | . | 4930422G04Rik, Larp7, Mir302c, Mir302a, Mir302b, Mir302d, Mir367 | Larp7 |
| chr3 | 129767261 | 129768048 | INT_STITCHED_1735 | 6486 | Sec24b | . | Sec24b |
| chr3 | 130973460 | 130973878 | INT_STITCHED_1739 | 7393 | Hadh | . | Hadh |
| chr3 | 135099287 | 135099829 | INT_STITCHED_1747 | 8660 | 4930539J05Rik, Ube2d3 | . | 4930539J05Rik |
| chr3 | 137284970 | 137285636 | INT_STITCHED_1754 | 3413 | Ddit4l | . | Ddit4l |
| chr3 | 142423276 | 142423843 | INT_STITCHED_1775 | 6964 | Gtf2b | . | Gtf2b |
| chr3 | 157584207 | 157595548 | INT_STITCHED_1814 | 885 | Cth | . | Cth |
| chr3 | 157694803 | 157695284 | INT_STITCHED_1815 | 3887 | Srsfl1, Lrrc40 | . | Srsfl1 |
| chr4 | 5575140 | 5577164 | INT_STITCHED_1821 | 1933 | Fam110b | . | Fam110b |
| chr4 | 6380266 | 6383720 | INT_STITCHED_1823 | 6789 | Nsmaf | . | Nsmaf |
| chr4 | 8614996 | 8616011 | INT_STITCHED_1833 | 2101 | Chd7 | . | Chd7 |
| chr4 | 10940912 | 10941926 | INT_STITCHED_1839 | 1366 | Plekhf2 | . | Plekhf2 |
| chr4 | 11005337 | 11005975 | INT_STITCHED_1841 | 4993 | 2310030N02Rik | . | 2310030N02Rik |
| chr4 | 13677114 | 13679150 | INT_STITCHED_1855 | 1395 | Runxlt1 | Runxlt1 | Runxlt1 |
| chr4 | 13700476 | 13708564 | INT_STITCHED_1856 | 1357 | . | Runxlt1 | Runxlt1 |
| chr4 | i9630174 | 19631009 | INT_STITCHED_1868 | 3658 | Wwp1 | . | Wwp1 |
| chr4 | 20704454 | 20704779 | INT_STITCHED_1870 | 8650 | Nkain3 | . | Nkain3 |
| chr4 | 21650023 | 21650732 | INT_STITCHED_1871 | 2045 | Ccnc | . | Ccnc |
| chr4 | 25722977 | 25726500 | INT_STITCHED_1881 | 1530 | Fut9 | . | Fut9 |
| chr4 | 32046934 | 32047476 | INT_STITCHED_1891 | 8647 | Map3k7 | . | Map3k7 |
| chr4 | 33035412 | 33043970 | INT_STITCHED_1897 | 2592 | Ankrd6 | Ankrd6 | Ankrd6 |
| chr4 | 33071439 | 33072448 | INT_STITCHED_1898 | 5608 | Rragd | . | Rragd |
| chr4 | 34501938 | 34506322 | INT_STITCHED_1903 | 1658 | Akirin2 | . | Akirin2 |

TABLE S2C-continued

Typical enhancer to gene assignment

| chr | start | end | TE_ID | TE_rank | proximal active genes (TE within 4 kb of TSS) | interacting active genes (SMC1 PET interactions) | nearest genes |
|---|---|---|---|---|---|---|---|
| chr4 | 34832744 | 34833418 | INT_STITCHED_1905 | 7860 | Zfp292 | . | Zfp292 |
| chr4 | 40180008 | 40186010 | INT_STITCHED_1913 | 1659 | Ddx58 | . | Ddx58 |
| chr4 | 40803541 | 40803952 | INT_STITCHED_1915 | 4554 | B4galt1 | . | B4galt1 |
| chr4 | 41047848 | 41048517 | INT_STITCHED_1917 | 1551 | Aqp3 | . | Aqp3 |
| chr4 | 43661458 | 43661812 | INT_STITCHED_1923 | 6119 | Spag8 | . | Spag8 |
| chr4 | 45121483 | 45121498 | INT_STITCHED_1932 | 8010 | Tomm5 | . | Tomm5 |
| chr4 | 45215967 | 45216757 | INT_STITCHED_1933 | 3974 | . | Frmpd1 | Frmpd1 |
| chr4 | 45420433 | 45421075 | INT_STITCHED_1935 | 3596 | Mcart1 | . | Mcart1 |
| chr4 | 48592304 | 48592977 | INT_STITCHED_1947 | 4785 | Tmeff1 | . | Tmeff1 |
| chr4 | 53646937 | 53647675 | INT_STITCHED_1962 | 7225 | Fsd1l | . | Fsd1l |
| chr4 | 57932572 | 57933991 | INT_STITCHED_1986 | 814 | D630039A03Rik | . | D630039A03Rik |
| chr4 | 59198444 | 59199036 | INT_STITCHED_1991 | 4924 | Ugcg | . | Ugcg |
| chr4 | 59593068 | 59593702 | INT_STITCHED_1994 | 4509 | Hsdl2 | . | Hsdl2 |
| chr4 | 73903676 | 73905912 | INT_STITCHED_2018 | 1260 | Kdm4c | . | Kdm4c |
| chr4 | 80520013 | 80520803 | INT_STITCHED_2024 | 3576 | . | D4Bwg0951e | D4Bwg0951e |
| chr4 | 80557651 | 80558330 | INT_STITCHED_2025 | 1850 | D4Bwg0951e | . | D4Bwg0951e |
| chr4 | 82047159 | 82047945 | INT_STITCHED_2033 | 1456 | . | Nfib | Nfib |
| chr4 | 82153147 | 82158518 | INT_STITCHED_2036 | 558 | Nfib | Nfib | Nfib |
| chr4 | 82180557 | 82189832 | INT_STITCHED_2037 | 7204 | . | Nfib | Nfib |
| chr4 | 82973975 | 82976812 | INT_STITCHED_2041 | 343 | Ttc39b | . | Ttc39b |
| chr4 | 83059982 | 83060620 | INT_STITCHED_2042 | 2352 | Snapc3 | . | Snapc3 |
| chr4 | 83164867 | 83165620 | INT_STITCHED_2044 | 2906 | 4930473A06Rik | . | 4930473A06Rik |
| chr4 | 84854207 | 84855065 | INT_STITCHED_2051 | 2922 | Sh3gl2 | . | Sh3gl2 |
| chr4 | 91065881 | 91066800 | INT_STITCHED_2065 | 4904 | Elavl2 | . | Elavl2 |
| chr4 | 98394367 | 98395329 | INT_STITCHED_2073 | 336 | L1td1 | . | L1td1 |
| chr4 | 99769780 | 99770611 | INT_STITCHED_2084 | 6051 | Ror1 | . | Ror1 |
| chr4 | 100451625 | 100452191 | INT_STITCHED_2085 | 5943 | Cachd1 | . | Cachd1 |
| chr4 | 101223833 | 101224306 | INT_STITCHED_2087 | 6107 | Dnajc6 | . | Dnajc6 |
| chr4 | 104831497 | 104842867 | INT_STITCHED_2096 | 535 | Ppap2b | Ppap2b | Ppap2b |
| chr4 | 104868425 | 104869271 | INT_STITCHED_2097 | 947 | . | Ppap2b | Ppap2b |
| chr4 | 104896507 | 104898349 | INT_STITCHED_2098 | 235 | . | Ppap2b | Ppap2b |
| chr4 | 107035327 | 107035897 | INT_STITCHED_2106 | 3847 | Tmem48 | . | Tmem48 |
| chr4 | 107550428 | 107550830 | INT_STITCHED_2107 | 8621 | Magoh | . | Magoh |
| chr4 | 107974909 | 107975592 | INT_STITCHED_2112 | 7080 | Zyg11b | . | Zyg11b |
| chr4 | 108515672 | 108516321 | INT_STITCHED_2117 | 5600 | Kti12 | . | Kti12 |
| chr4 | 110069602 | 110070245 | INT_STITCHED_2124 | 5744 | Agbl4 | . | Agbl4 |
| chr4 | 115743638 | 115744295 | INT_STITCHED_2133 | 4916 | Uqcrh, Lrrc41 | . | Uqcrh |
| chr4 | 116397804 | 116398474 | INT_STITCHED_2134 | 5503 | Tesk2 | . | Tesk2 |
| chr4 | 116825141 | 116825878 | INT_STITCHED_2138 | 599 | Snord38a, Rps8, Snord55 | . | Snord38a |
| chr4 | 116924570 | 116925269 | INT_STITCHED_2140 | 7045 | Gm1661, Tmem53 | . | Gm1661 |
| chr4 | 117085700 | 117088622 | INT_STITCHED_2143 | 815 | . | Rnf220 | Rnf220 |
| chr4 | 118212353 | 118213114 | INT_STITCHED_2147 | 6341 | Tmem125 | . | Tmem125 |
| chr4 | 118359572 | 118360154 | INT_STITCHED_2148 | 2902 | Olfr1342 | . | Olfr1342 |
| chr4 | 118910530 | 118911287 | INT_STITCHED_2154 | 4305 | Lepre1, AU022252 | . | Lepre1 |
| chr4 | 118964429 | 118965089 | INT_STITCHED_2155 | 7516 | Ybx1 | . | Ybx1 |
| chr4 | 119076007 | 119084885 | INT_STITCHED_2156 | 4562 | Ccdc30 | . | Ccdc30 |
| chr4 | 119170858 | 119171363 | INT_STITCHED_2157 | 4607 | Rimkla | . | Rimkla |
| chr4 | 119487998 | 119488754 | INT_STITCHED_2160 | 1604 | Hivep3 | . | Hivep3 |
| chr4 | 119831385 | 119832062 | INT_STITCHED_2161 | 3892 | Edn2 | . | Edn2 |
| chr4 | 122514588 | 122515039 | INT_STITCHED_2172 | 5193 | Ppt1 | . | Ppt1 |
| chr4 | 122676422 | 122676991 | INT_STITCHED_2173 | 7715 | Mycl1 | . | Mycl1 |
| chr4 | 124811451 | 124811907 | INT_STITCHED_2185 | 641 | Zc3h12a | . | Zc3h12a |
| chr4 | 125779943 | 125780736 | INT_STITCHED_2196 | 2275 | Lsm10, Stk40 | . | Stk40 |
| chr4 | 126142985 | 126143622 | INT_STITCHED_2198 | 1019 | Eif2c1 | . | Eif2c1 |
| chr4 | 126741328 | 126741791 | INT_STITCHED_2202 | 4312 | Zmym1 | . | Zmym1 |
| chr4 | 126801236 | 126802125 | INT_STITCHED_2203 | 2032 | Gm12942 | . | Gm12942 |
| chr4 | 127021763 | 127022891 | INT_STITCHED_2208 | 690 | . | Gjb3, Gjb5 | Gjb5 |
| chr4 | 128334780 | 128335398 | INT_STITCHED_2211 | 5180 | Phc2 | . | Phc2 |
| chr4 | 128405346 | 128406067 | INT_STITCHED_2212 | 8615 | Phc2 | . | Phc2 |
| chr4 | 128556315 | 128556889 | INT_STITCHED_2213 | 2454 | Trim62 | . | Trim62 |
| chr4 | 129050358 | 129052712 | INT_STITCHED_2218 | 255 | Zbtb8a | . | Zbtb8a |
| chr4 | 129221212 | 129221953 | INT_STITCHED_2219 | 5426 | Hdac1 | . | Hdac1 |
| chr4 | 129779132 | 129780024 | INT_STITCHED_2222 | 1812 | Pef1 | Tinagl1 | Pef1 |
| chr4 | 130213352 | 130214031 | INT_STITCHED_2225 | 2627 | Pum1 | . | Pum1 |
| chr4 | 132061470 | 132062305 | INT_STITCHED_2233 | 2028 | Sesn2 | . | Sesn2 |
| chr4 | 133371377 | 133372545 | INT_STITCHED_2245 | 436 | . | Arid1a, Pigv | Arid1a, |
| chr4 | 133567462 | 133568053 | INT_STITCHED_2248 | 2013 | . | Lin28a | Lin28a |
| chr4 | 134406960 | 134407757 | INT_STITCHED_2251 | 7098 | Tmem57 | . | Tmem57 |
| chr4 | 135137211 | 135138212 | INT_STITCHED_2256 | 1300 | . | Grhl3 | Grhl3 |
| chr4 | 135702424 | 135703370 | INT_STITCHED_2258 | 1210 | Id3 | . | Id3 |

TABLE S2C-continued

Typical enhancer to gene assignment

| chr | start | end | TE_ID | TE_rank | proximal active genes (TE within 4 kb of TSS) | interacting active genes (SMC1 PET interactions) | nearest genes |
|---|---|---|---|---|---|---|---|
| ch14 | 135847102 | 135847490 | INT_STITCHED_2260 | 5446 | Zfp46 | . | Zf4J46 |
| chr4 | 135873252 | 135874283 | INT_STITCHED_2261 | 3874 | Hnrnpr | . | Hnrnpr |
| chr4 | 136016956 | 136019978 | INT_STITCHED_2262 | 655 | Luzp1 | . | Luzp1 |
| chr4 | 137025750 | 137026764 | INT_STITCHED_2264 | 587 | Hspg2 | . | Hspg2 |
| chr4 | 137879059 | 137879857 | INT_STITCHED_2271 | 4511 | Pink1 | . | Pink1 |
| chr4 | 139520165 | 139520892 | INT_STITCHED_2282 | 3096 | Klhdc7a | . | Klhdc7a |
| chr4 | 140200327 | 140201030 | INT_STITCHED_2286 | 3387 | Arhgef101 | . | Arhgef101 |
| chr4 | 140249934 | 140251467 | INT_STITCHED_2287 | 1738 | Rcc2 | . | Rcc2 |
| chr4 | 140515660 | 140516266 | INT_STITCHED_2288 | 3301 | Sdhb | . | Sdhb |
| chr4 | 141154043 | 141155058 | INT_STITCHED_2293 | 509 | Fblim1 | . | Fblim1 |
| chr4 | 141784495 | 141791290 | INT_STITCHED_2298 | 1170 | 9030409G11Rik | . | 9030409G11Rik |
| chr4 | 142891686 | 142896659 | INT_STITCHED_2306 | 555 | Pdpn | . | Pdpn |
| chr4 | 147407829 | 147408586 | INT_STITCHED_2316 | 2518 | Clcn6, Mthfr | . | Clcn6 |
| chr4 | 149604905 | 149605684 | INT_STITCHED_2326 | 1574 | Eno1, Gm5506 | . | Eno1 |
| chr4 | 150415590 | 150416311 | INT_STITCHED_2333 | 7184 | Per3 | . | Per3 |
| chr4 | 151373388 | 151381390 | INT_STITCHED_2335 | 1548 | Klhl21,Phf13 | . | Klhl21 |
| chr4 | 151417116 | 151417695 | INT_STITCHED_2336 | 4939 | Nol9, Tas1r1 | . | Nol9 |
| chr4 | 151559144 | 151559677 | INT_STITCHED_2337 | 3681 | Acot7 | Acot7 | Acot7 |
| chr4 | 151664406 | 151665150 | INT_STITCHED_2338 | 3943 | Icmt | . | Icmt |
| chr4 | 153469755 | 153470645 | INT_STITCHED_2346 | 2164 | Trp73 | . | Trp73 |
| chr4 | 155043894 | 155044798 | INT_STITCHED_2356 | 991 | Mib2 | . | Mib2 |
| chr4 | 155562905 | 155563924 | INT_STITCHED_2358 | 1143 | Agrn | . | Agrn |
| chr5 | 5698769 | 5699506 | INT_STITCHED_2369 | 3137 | Steap2 | . | Steap2 |
| chr5 | 8423915 | 8424874 | INT_STITCHED_2372 | 1629 | Slc25a40, Dbf4 | . | Slc25a40 |
| chr5 | 20389584 | 20390410 | INT_STITCHED_2405 | 3630 | Phtf2, Tmem60 | . | Phtf2 |
| chr5 | 21144388 | 21144924 | INT_STITCHED_2410 | 7716 | Fbxl13 | . | Fbxl13 |
| chr5 | 21157440 | 21158426 | INT_STITCHED_2411 | 5853 | Fbxl13, Armc10 | . | Armc10 |
| chr5 | 21237845 | 21238483 | INT_STITCHED_2412 | 7016 | Pmpcb | . | Pmpcb |
| chr5 | 24190157 | 24190688 | INT_STITCHED_2425 | 4368 | Nub1 | . | Nub1 |
| chr5 | 24515415 | 24516073 | INT_STITCHED_2426 | 2110 | . | Prkag2 | Prkag2 |
| chr5 | 25038744 | 25042771 | INT_STITCHED_2428 | 863 | 1700096K18Rik | Mll3, 4831440E17Rik | 1700096K18Rik |
| chr5 | 25266891 | 25267570 | INT_STITCHED_2431 | 3382 | Actr3b | . | Actr3b |
| chr5 | 27368835 | 27369369 | INT_STITCHED_2438 | 8605 | Dpp6 | . | Dpp6 |
| chr5 | 29525401 | 29526304 | INT_STITCHED_2446 | 2338 | Rnf32 | . | Rnf32 |
| chr5 | 30063886 | 30064743 | INT_STITCHED_2450 | 3241 | Dnajb6, Gm5129 | . | Dnajb6 |
| chr5 | 31791484 | 31795140 | INT_STITCHED_2453 | 1536 | 4930548H24Rik, Gpn1 | . | Gpn1 |
| chr5 | 32918629 | 32919653 | INT_STITCHED_2458 | 8602 | Yes1 | . | Yes1 |
| chr5 | 33444956 | 33450141 | INT_STITCHED_2461 | 2733 | Slc5a1 | . | Slc5a1 |
| chr5 | 35447171 | 35447793 | INT_STITCHED_2473 | 2708 | Lrpap1 | . | Lrpap1 |
| chr5 | 37188271 | 37189788 | INT_STITCHED_2477 | 1412 | Mrfap1 | . | Mrfap1 |
| chr5 | 44251617 | 44261048 | INT_STITCHED_2494 | 503 | Cd38 | . | Cd38 |
| chr5 | 45886696 | 45887517 | INT_STITCHED_2497 | 2501 | Lap3 | . | Lap3 |
| chr5 | 45906343 | 45906785 | INT_STITCHED_2498 | 5778 | Med28 | . | Med28 |
| chr5 | 53857769 | 53859125 | INT_STITCHED_2508 | 1228 | . | Rbpj | Rbpj |
| chr5 | 53983387 | 53983835 | INT_STITCHED_2512 | 4655 | Rbpj | . | Rbpj |
| chr5 | 64362131 | 64362846 | INT_STITCHED_2524 | 8593 | Rell1 | . | Rell1 |
| chr5 | 64486701 | 64494650 | INT_STITCHED_2526 | 3034 | Pgm1 | . | Pgm1 |
| chr5 | 64891420 | 64892157 | INT_STITCHED_2531 | 506 | . | Klf3 | Klf3 |
| chr5 | 64970809 | 64971754 | INT_STITCHED_2532 | 2035 | . | Klf3 | Klf3 |
| chr5 | 65038454 | 65039558 | INT_STITCHED_2533 | 747 | . | Klf3 | Klf3 |
| chr5 | 65203049 | 65203823 | INT_STITCHED_2534 | 605 | . | Klf3 | Klf3 |
| chr5 | 65521902 | 65522600 | INT_STITCHED_2537 | 3759 | Klhl5 | . | Klhl5 |
| chr5 | 65832295 | 65833237 | INT_STITCHED_2539 | 4448 | Ugdh | . | Ugdh |
| chr5 | 66091258 | 66091720 | INT_STITCHED_2541 | 5666 | Pds5a | . | Pds5a |
| chr5 | 66153811 | 66154536 | INT_STITCHED_2543 | 8591 | N4bp2 | . | N4bp2 |
| chr5 | 66542614 | 66545335 | INT_STITCHED_2544 | 1354 | Rbm47 | . | Rbm47 |
| chr5 | 68240570 | 68241089 | INT_STITCHED_2556 | 4241 | Atp8a1 | . | Atp8a1 |
| chr5 | 75972506 | 75973498 | INT_STITCHED_2583 | 2620 | Kit | . | Kit |
| chr5 | 76798260 | 76799006 | INT_STITCHED_2588 | 2195 | Nmu | . | Nmu |
| chr5 | 77339613 | 77340383 | INT_STITCHED_2590 | 8032 | Aasdh | . | Aasdh |
| ch15 | 77683194 | 77694467 | INT_STITCHED_2593 | 238 | Rest | . | Rest |
| chr5 | 89108097 | 89114909 | INT_STITCHED_2614 | 1675 | Grsf1 | . | Grsf1 |
| chr5 | 92926941 | 92933665 | INT_STITCHED_2621 | 904 | Scarb2 | . | Scarb2 |
| chr5 | 93112043 | 93112714 | INT_STITCHED_2624 | 5586 | Shroom3 | . | Shroom3 |
| chr5 | 93322548 | 93323285 | INT_STITCHED_2626 | 3484 | Shroom3 | . | Shroom3 |
| chr5 | 100472593 | 100473735 | INT_STITCHED_2652 | 2432 | Enoph1, Hnrpdl | . | Enoph1 |
| chr5 | 101101211 | 101101831 | INT_STITCHED_2655 | 2682 | Coq2 | . | Coq2 |
| chr5 | 103847896 | 103848433 | INT_STITCHED_2669 | 5025 | Ptpn13 | . | Ptpn13 |

TABLE S2C-continued

Typical enhancer to gene assignment

| chr | start | end | TE_ID | TE_rank | proximal active genes (TE within 4 kb of TSS) | interacting active genes (SMC1 PET interactions) | nearest genes |
|---|---|---|---|---|---|---|---|
| chr5 | 104862866 | 104872330 | INT_STITCHED_2676 | 320 | Spp1 | . | Spp1 |
| chr5 | 109097366 | 109098181 | INT_STITCHED_2691 | 2714 | Idua, Slc26a1 | . | Idua |
| chr5 | 110527885 | 110528617 | INT_STITCHED_2695 | 2800 | Plcxd1 | . | Plcxd1 |
| chr5 | 110656201 | 110658296 | INT_STITCHED_2696 | 2455 | Ankle2 | . | Ankle2 |
| chr5 | 110897904 | 110899242 | INT_STITCHED_2700 | 292 | . | Fbrsl1 | Fbrsl1 |
| chr5 | 111232926 | 111236161 | INT_STITCHED_2702 | 276 | Ulk1 | Ulk1 | Ulk1 |
| chr5 | 111306460 | 111307534 | INT_STITCHED_2703 | 4183 | Ttc28 | . | Ttc28 |
| chr5 | 113915656 | 113916217 | INT_STITCHED_2715 | 5417 | Wscd2 | . | Wscd2 |
| chr5 | 114725389 | 114725938 | INT_STITCHED_2720 | 3071 | Foxn4 | . | Foxn4 |
| chr5 | 115021009 | 115022171 | INT_STITCHED_2724 | 1268 | BC057022 | . | BC057022 |
| chr5 | 115721625 | 115722390 | INT_STITCHED_2727 | 1373 | Rnf10 | . | Rnf10 |
| chr5 | 115750818 | 115751483 | INT_STITCHED_2728 | 1977 | Dynll1 | . | Dynll1 |
| chr5 | 115886385 | 115894671 | INT_STITCHED_2732 | 368 | . | Msi1 | Msi1 |
| chr5 | 115929383 | 115929949 | INT_STITCHED_2733 | 390 | Sirt4 | . | Sirt4 |
| chr5 | 116739839 | 116740353 | INT_STITCHED_2735 | 4769 | Ccdc60 | . | Ccdc60 |
| chr5 | 117764474 | 117765420 | INT_STITCHED_2741 | 2391 | Vsig10 | Wsb2 | Vsig10 |
| chr5 | 121986673 | 121990552 | INT_STITCHED_2757 | 2098 | Mapkapk5 | . | Mapkapk5 |
| chr5 | 123607764 | 123608595 | INT_STITCHED_2771 | 1902 | . | Rhof | Rhof |
| chr5 | 123840532 | 123840817 | INT_STITCHED_2773 | 7999 | Mlxip | . | Mlxip |
| chr5 | 128103516 | 128103953 | INT_STITCHED_2789 | 8575 | Slc15a4 | . | Slc15a4 |
| chr5 | 129105766 | 129110009 | INT_STITCHED_2794 | 828 | 5930412G12Rik, Fzd10 | . | 5930412G12Rik |
| chr5 | 129459327 | 129459946 | INT_STITCHED_2795 | 4878 | Rimbp2 | . | Rimbp2 |
| chr5 | 130216498 | 130217009 | INT_STITCHED_2801 | 4380 | Mrps17 | . | Mrps17 |
| chr5 | 130234026 | 130234832 | INT_STITCHED_2802 | 4152 | Gbas | . | Gbas |
| chr5 | 130363609 | 130364562 | INT_STITCHED_2803 | 8574 | Chchd2 | . | Chchd2 |
| chr5 | 134654188 | 134654880 | INT_STITCHED_2825 | 1841 | Wbscr16, Gtf2ird2 | . | Wbscr16 |
| chr5 | 135402290 | 135403027 | INT_STITCHED_2829 | 1370 | Wbscr27 | . | Wbscr27 |
| chr5 | 135476827 | 135477544 | INT_STITCHED_2832 | 1445 | Wbscr25 | Abhd11 | Wbscr25 |
| chr5 | 136105127 | 136105914 | INT_STITCHED_2834 | 3937 | Rhbdd2 | . | Rhbdd2 |
| chr5 | 136410740 | 136412181 | INT_STITCHED_2838 | 736 | Ywhag | . | Ywhag |
| chr5 | 137747012 | 137747785 | INT_STITCHED_2845 | 2219 | Srrt | . | Srrt |
| chr5 | 137778171 | 137778873 | INT_STITCHED_2846 | 2182 | Slc12a9 | . | Slc12a9 |
| chr5 | 137792787 | 137793553 | INT_STITCHED_2847 | 3627 | Ephb4 | . | Ephb4 |
| chr5 | 138531655 | 138532586 | INT_STITCHED_2849 | 4057 | Zkscan1 | . | Zkscan1 |
| chr5 | 139675717 | 139676582 | INT_STITCHED_2854 | 1584 | Sun1 | . | Sun1 |
| chr5 | 139734064 | 139734931 | INT_STITCHED_2855 | 4824 | Get4 | . | Get4 |
| chr5 | 141087076 | 141088486 | INT_STITCHED_2864 | 1220 | Lfng | . | Lfrig |
| chr5 | 143022054 | 143037530 | INT_STITCHED_2874 | 494 | Radi1 | . | Radi1 |
| chr5 | 143543892 | 143544993 | INT_STITCHED_2876 | 2397 | . | Tnrc18 | Tnrc18 |
| chr5 | 143560794 | 143579912 | INT_STITCHED_2877 | 946 | Tnrc18 | Tnrc18 | Tnrc18 |
| chr5 | 141718476 | 143719226 | INT_STITCHED_2878 | 3909 | Fscn1 | . | Fscn1 |
| chr5 | 149350152 | 149362682 | INT_STITCHED_2907 | 864 | Ubl3 | . | Ubl3 |
| chr5 | 149556262 | 149556865 | INT_STITCHED_2910 | 3402 | 2210417A02Rik | . | 2210417A02Rik |
| chr6 | 7644080 | 7663321 | INT_STITCHED_2939 | 847 | Asns | . | Asns |
| chr6 | 15664027 | 15664459 | INT_STITCHED_2958 | 5388 | Mdfic | . | Mdfic |
| chr6 | 30109355 | 30110097 | INT_STITCHED_2995 | 772 | Mir182 | Mir183, Mir96 | Mir182 |
| chr6 | 37384202 | 37386490 | INT_STITCHED_3028 | 3134 | Creb3l2 | . | Creb3l2 |
| chr6 | 38242963 | 38243836 | INT_STITCHED_3037 | 5549 | Zc3hav1l | . | Zc3hav1l |
| chr6 | 42205849 | 42206459 | INT_STITCHED_3058 | 7001 | Tmem139 | . | Tmem139 |
| chr6 | 50066065 | 50074818 | INT_STITCHED_3072 | 1637 | Mpp6 | . | Mpp6 |
| chr6 | 50209997 | 50210610 | INT_STITCHED_3073 | 6221 | Dfna5 | . | Dfna5 |
| chr6 | 51483276 | 51494780 | INT_STITCHED_3078 | 826 | Snx10 | . | Snx10 |
| chr6 | 51956055 | 51963851 | INT_STITCHED_3081 | 577 | Skap2 | . | Skap2 |
| chr6 | 52103875 | 52104482 | INT_STITCHED_3084 | 5045 | Hoxa1 | . | Hoxa1 |
| chr6 | 54914440 | 54915345 | INT_STITCHED_3101 | 1628 | Nod1 | . | Nod1 |
| chr6 | 66980137 | 66981045 | INT_STITCHED_3129 | 2263 | Gadd45a | Gadd45a | Gadd45a |
| chr6 | 71575730 | 71576551 | INT_STITCHED_3144 | 3531 | Kdm3a | . | Kdm3a |
| chr6 | 72502671 | 72503229 | INT_STITCHED_3147 | 2910 | Capg | . | Capg |
| chr6 | 72703827 | 72708966 | INT_STITCHED_3150 | 1561 | . | Tcf7l1 | Tcf7l1 |
| chr6 | 72736980 | 72745613 | INT_STITCHED_3151 | 634 | Tcf7l1 | Tcf7l1 | Tcf7l1 |
| chr6 | 72848028 | 72848774 | INT_STITCHED_3153 | 5856 | Kcmf1 | . | Kcmf1 |
| chr6 | 82710614 | 82711291 | INT_STITCHED_3177 | 2460 | . | Hk2 | Hk2 |
| chr6 | 84012527 | 84015422 | INT_STITCHED_3186 | 1066 | . | Zfml, Dysf | Dysf |
| chr6 | 85024817 | 85025619 | INT_STITCHED_3191 | 5735 | Exoc6b | . | Exoc6b |
| chr6 | 87863162 | 87864161 | INT_STITCHED_3199 | 1880 | 8430410A17Rik | . | 8430410A17Rik |
| chr6 | 92196225 | 92198121 | INT_STITCHED_3219 | 1001 | Trh | . | Trh |
| chr6 | 97051422 | 97052960 | INT_STITCHED_3248 | 492 | . | Fam19a4 | Fam19a4 |
| chr6 | 98979333 | 98980035 | INT_STITCHED_3262 | 2081 | Foxp1 | . | Foxp1 |
| chr6 | 100235278 | 10023657 | INT_STITCHED_3276 | 4629 | Rybp | . | Rybp |
| chr6 | 100369906 | 100372686 | INT_STITCHED_3279 | 988 | . | Rybp | Rybp |

TABLE S2C-continued

Typical enhancer to gene assignment

| chr | start | end | TE_ID | TE_rank | proximal active genes (TE within 4 kb of TSS) | interacting active genes (SMC1 PET interactions) | nearest genes |
|---|---|---|---|---|---|---|---|
| chr6 | 108020709 | 108021593 | INT_STITCHED_3290 | 2984 | Setmar | . | Setmar |
| chr6 | 112899075 | 112900921 | INT_STITCHED_3305 | 1751 | Srgap3 | . | Srgap3 |
| chr6 | 113452636 | 113453205 | INT_STITCHED_3310 | 4977 | Prrt3 | . | Prrt3 |
| chr6 | 113566995 | 113567675 | INT_STITCFIED_3311 | 7573 | Vhl | . | Vhl |
| chr6 | 115633121 | 115635841 | INT_STITCHED_3320 | 1845 | Raf1 | . | Raf1 |
| chr6 | 116148172 | 116148826 | INT_STITCHED_3324 | 4749 | Tmcc1 | . | Tmcc1 |
| chr6 | 119274532 | 119275309 | INT_STITCHED_3331 | 2012 | Lrtm2 | . | Lrtm2 |
| chr6 | 119364465 | 119369724 | INT_STITCHED_3332 | 869 | Adipor2 | . | Adipor2 |
| chr6 | 120241456 | 120242188 | INT_STITCHED_3335 | 2421 | B4galnt3 | . | B4galnt3 |
| chr6 | 122316022 | 122317010 | INT_STITCHED_3343 | 278 | . | Phc1 | Phc1 |
| chr6 | 122558176 | 122559103 | INT_STITCHED_3345 | 907 | Gdf3, Apobec1 | . | Gdf3 |
| chr6 | 122574257 | 122575075 | INT_STITCHED_3346 | 1790 | Dppa3 | . | Dppa3 |
| chr6 | 124754367 | 124755031 | INT_STITCHED_3353 | 6468 | Spsb2 | . | Spsb2 |
| chr6 | 124781521 | 124782304 | INT_STITCHED_3354 | 3019 | Cdca3, Usp5 | . | Cdca3 |
| chr6 | 125146126 | 125147005 | INT_STITCHED_3357 | 2986 | Mrpl51, Ncapd2 | . | Mrpl51 |
| chr6 | 127053459 | 127054097 | INT_STITCHED_3369 | 3276 | 9630033F20Rik | . | 9630033F20Rik |
| chr6 | 128092062 | 128092947 | INT_STITCHED_3375 | 2085 | Tspan9 | . | Tspan9 |
| chr6 | 128395390 | 128396444 | INT_STITCHED_3380 | 1491 | . | Gm10069, Fkbp4 | Gm10069 |
| chr6 | 134839572 | 134840045 | INT_STITCHED_3399 | 7135 | Gpr19 | . | Gpr19 |
| chr6 | 135016609 | 135017490 | INT_STITCHED_3402 | 2909 | Gprc5a | . | Gprc5a |
| chr6 | 135143600 | 135144185 | INT_STITCHED_3403 | 7525 | 8430419L09Rik | . | 8430419L09Rik |
| chr6 | 137118500 | 137119078 | INT_STITCHED_3414 | 4375 | Rerg | . | Rerg |
| chr6 | 142910352 | 142911545 | INT_STITCHED_3433 | 1851 | St8sia1 | . | St8sia1 |
| chr6 | 142969103 | 142969851 | INT_STITCHED_3435 | 1647 | . | St8sia1, 5730419I09Rik | St8sia1 |
| chr6 | 143119001 | 143119729 | INT_STITCHED_3439 | 5592 | Etnk1 | . | Etnk1 |
| chr6 | 144997218 | 145010452 | INT_STITCHED_3446 | 738 | Bcat1 | . | Bcat1 |
| chr6 | 146668166 | 146674748 | INT_STITCHED_3453 | 2469 | Stk381 | . | Stk381 |
| chr6 | 148894789 | 148906259 | INT_STITCHED_3463 | 362 | Fam60a | . | Fam60a |
| chr6 | 149260435 | 149261383 | INT_STITCHED_3466 | 2613 | 2810474O19Rik | . | 2810474O19Rik |
| chr7 | 4076531 | 4077316 | INT_STITCHED_3470 | 1222 | 9430041J12Rik, Ttyh1 | Leng9 | 9430041J12Rik |
| chr7 | 4487732 | 4488465 | INT_STITCHED_3473 | 7092 | 6030429G01Rik | . | 6030429G01Rik |
| chr7 | 4703001 | 4704500 | INT_STITCHED_3474 | 696 | Cox6b2 | . | Cox6b2 |
| chr7 | 7085385 | 7086148 | INT_STITCHED_3480 | 2995 | Zfp773 | . | Zfp773 |
| chr7 | 20045717 | 20046525 | INT_STITCHED_3486 | 3637 | Mark4 | . | Mark4 |
| chr7 | 20093826 | 20094324 | INT_STITCHED_3487 | 7263 | Bloc1s3, Trappc6a | . | Bloc1s3 |
| chr7 | 20157934 | 20161677 | INT_STITCHED_3488 | 357 | Gemin7 | Gemin7, Zfp296 | Gemin7 |
| chr7 | 20326833 | 20328288 | INT_STITCHED_3489 | 579 | . | Pvrl2 | Pvrl2 |
| chr7 | 20400342 | 20402067 | INT_STITCHED_3490 | 649 | Bcl3 | Bcl3 | Bcl3 |
| chr7 | 74877697 | 94873996 | INT_STITCHFD_3492 | 4012 | Zfp180 | . | Zfp180 |
| chr7 | 25289770 | 25302672 | INT_STITCHED_3493 | 236 | Zfp428 | Zfp428 | Zfp428 |
| chr7 | 25664201 | 25665192 | INT_STITCHED_3495 | 3298 | Rps19 | . | Rps19 |
| chr7 | 25998956 | 25999482 | INT_STITCHED_3498 | 4323 | Dedd2 | . | Dedd2 |
| chr7 | 26048760 | 26049461 | INT_STITCHED_3499 | 530 | . | Erf | Erf |
| chr7 | 27965321 | 27966083 | INT_STITCHED_3504 | 2673 | Rab4b, Mia1 | . | Rab4b |
| chr7 | 27983767 | 27984476 | INT_STITCHED_3505 | 3541 | Snrpa | . | Snrpa |
| chr7 | 28043302 | 28043716 | INT_STITCHED_3506 | 2757 | Numbl | . | Numbl |
| chr7 | 28518631 | 28521086 | INT_STITCHED_3510 | 1758 | Zfp60 | . | Zfp60 |
| chr7 | 28624916 | 28625830 | INT_STITCHED_3511 | 1744 | Zfp59 | . | Zfp59 |
| chr7 | 29363488 | 29364974 | INT_STITCHED_3513 | 845 | . | Pak4 | Pak4 |
| chr7 | 29420248 | 29420834 | INT_STITCHED_3514 | 4991 | C330005M16Rik | . | C330005M16Rik |
| chr7 | 29477392 | 29478200 | INT_STITCHED_3515 | 1927 | Fbxo27 | . | Fbxo27 |
| chr7 | 30078547 | 30079377 | INT_STITCHED_3517 | 1761 | Ppp1r14a | Ppp1r14a | Ppp1r14a |
| chr7 | 30757305 | 30768472 | INT_STITCHED_3520 | 612 | Zfp568 | Zfp74 | Zfp568 |
| chr7 | 30872494 | 30873179 | INT_STITCHED_3522 | 7178 | Zfp566 | . | Zfp566 |
| chr7 | 31372373 | 31372940 | INT_STITCHED_3526 | 4996 | Zbtb32, Wbp7 | . | Wbp7 |
| chr7 | 31392634 | 31393353 | INT_STITCHED_3527 | 1582 | Upkla | Wbp7, Prodh2 | Upkla |
| chr7 | 31937273 | 31938066 | INT_STITCHED_3530 | 4926 | Gramd1a | . | Gramd1a |
| chr7 | 34949720 | 34950749 | INT_STITCHED_3531 | 8526 | Uba2 | . | Uba2 |
| chr7 | 35437649 | 35438290 | INT_STITCHED_3532 | 2994 | Kctd15 | . | Kctd15 |
| chr7 | 36107701 | 36120798 | INT_STITCHED_3535 | 610 | Gpatch1, Rhpn2 | . | Rhpn2 |
| chr7 | 38338600 | 38339282 | INT_STITCHED_3547 | 2440 | . | Zfp536 | Zfp536 |
| chr7 | 50862978 | 50863932 | INT_STITCHED_3560 | 1804 | Zfp819 | . | Zfp819 |
| chr7 | 51630296 | 51631278 | INT_STITCHED_3562 | 1315 | 1700008O03Rik | Syt3 | 1700008O03Rik |
| chr7 | 51954357 | 51964325 | INT_STITCHED_3565 | 582 | Izumo2 | . | Izumo2 |
| chr7 | 52878661 | 52879259 | INT_STITCHED_3569 | 6738 | Izumo1, | . | Izumo1 |

TABLE S2C-continued

Typical enhancer to gene assignment

| chr | start | end | TE_ID | TE_rank | proximal active genes (TE within 4 kb of TSS) | interacting active genes (SMC1 PET interactions) | nearest genes |
|---|---|---|---|---|---|---|---|
| | | | | | Rasip1, Fut1 | | |
| chr7 | 54053865 | 54054483 | INT_STITCHED_3571 | 5445 | Gtf2h1, Hps5 | . | Gtf2h1 |
| chr7 | 57029746 | 57030493 | INT_STITCHED_3581 | 4420 | Prmt3 | . | Prmt3 |
| chr7 | 70585007 | 70585674 | INT_STITCHED_3600 | 7567 | Otud7a | . | Otud7a |
| chr7 | 72302006 | 72302711 | INT_STITCHED_3608 | 4605 | Fam189a1 | . | Fam189a1 |
| chr7 | 75418913 | 75421020 | INT_STITCHED_3619 | 2227 | Fam169b | . | Fam169b |
| chr7 | 80286018 | 80286585 | INT_STITCHED_3632 | 4127 | . | Rgma | Rgma |
| chr7 | 80531416 | 80545623 | INT_STITCHED_3636 | 1261 | . | Rgma | Rgma |
| chr7 | 80679726 | 80684471 | INT_STITCHED_3637 | 512 | Chd2 | . | Chd2 |
| chr7 | 86284126 | 86284802 | INT_STITCHED_3651 | 4132 | . | Hapin3 | Hapin3 |
| chr7 | 86423381 | 86424010 | INT_STITCHED_3653 | 4382 | Abhd2 | . | Abhd2 |
| chr7 | 86799396 | 86806853 | INT_STITCHED_3657 | 741 | 5730590G19Rik | . | 5730590G19Rik |
| chr7 | 87253990 | 87254677 | INT_STITCHED_3660 | 8111 | Idh2 | . | Idh2 |
| chr7 | 87954066 | 87954752 | INT_STITCHED_3666 | 4847 | Iqgap1 | . | Iqgap1 |
| chr7 | 88208035 | 88208759 | INT_STITCHED_3671 | 2017 | A1pk3 | . | A1pk3 |
| chr7 | 95578089 | 95578712 | INT_STITCHED_3691 | 5604 | Rab38 | . | Rab38 |
| chr7 | 96490332 | 96490891 | INT_STITCHED_3692 | 4627 | Tmem135 | . | Tmem135 |
| chr7 | 97123764 | 97124610 | INT_STITCHED_3695 | 2094 | Eed | . | Eed |
| chr7 | 97410448 | 97410819 | INT_STITCHED_3698 | 6727 | Ccdc83 | . | Ccdc83 |
| chr7 | 103353190 | 103354078 | INT_STITCHED_3713 | 1669 | Odz4 | . | Odz4 |
| chr7 | 107377250 | 107377769 | INT_STITCHED_3734 | 7819 | Pgm2l1 | . | Pgm2l1 |
| chr7 | 107436366 | 107436962 | INT_STITCHED_3735 | 7651 | P4ha3 | . | P4ha3 |
| chr7 | 107848144 | 107849130 | INT_STITCHED_3738 | 1234 | Fam168a | . | Fam168a |
| chr7 | 109248288 | 109249058 | INT_STITCHED_3741 | 1466 | Artl1,Art5 | . | Art1 |
| chr7 | 111392319 | 111392670 | INT_STITCHED_3744 | 5692 | Trim34 | . | Trim34 |
| chr7 | 112551030 | 112551509 | INT_STITCHED_3746 | 7631 | Fam160a2 | . | Fam160a2 |
| chr7 | 114351139 | 114351754 | INT_STITCHED_3748 | 3262 | Rbmxl2 | . | Rbmxl2 |
| chr7 | 121782144 | 121782733 | INT_STITCHED_3780 | 2434 | Calca | . | Calca |
| chr7 | 121883989 | 121884609 | INT_STITCHED_3781 | 2465 | Tnsc | . | Insc |
| chr7 | 125723349 | 125724114 | INT_STITCHED_3793 | 5085 | Tmc7 | . | Tmc7 |
| chr7 | 127040059 | 127042484 | INT_STITCHED_3801 | 448 | Dcun1d3, Lyrm1 | . | Dcun1d3 |
| chr7 | 130354891 | 130355503 | INT_STITCHED_3820 | 2662 | Slc5a11 | . | Slc5a11 |
| chr7 | 133520840 | 133521647 | INT_STITCHED_3830 | 1910 | Spns1 | . | Spns1 |
| chr7 | 133535744 | 133536602 | INT_STITCHED_3831 | 4899 | Nfatc2ip | . | Nfatc2ip |
| chr7 | 134367327 | 134369311 | INT_STITCHED_3833 | 282 | Sept1 | Mylpf, Sept1 | 1-Sep |
| chr7 | 134659607 | 134660269 | INT_STITCHED_3834 | 5484 | 1700008J07Rik | . | 1700008J07Rik |
| chr7 | 134912208 | 134912952 | INT_STITCHED_3835 | 1928 | Orai3 | . | Orai3 |
| chr7 | 137395511 | 137408698 | INT_STITCHED_3841 | 529 | Fgfr2 | Fgfr2 | Fgfr2 |
| chr7 | 138004134 | 138005002 | INT_STITCHED_3845 | 2881 | Plekha1 | . | Plekha1 |
| chr7 | 139807718 | 139808551 | INT_STITCHED_3853 | 1520 | Lhpp | . | Lhpp |
| chr7 | 140000477 | 140001636 | INT_STITCHED_3854 | 2558 | Fam53b | . | Fam53b |
| chr7 | 146041339 | 146048877 | INT_STITCHED_3884 | 388 | Ppp2r2d, Mapk1ip1 | . | Ppp2r2d |
| chr7 | 148026799 | 148027562 | INT_STITCHED_3894 | 2582 | 1190003J15Rik | . | 1190003J15Rik |
| chr7 | 148124539 | 148125460 | INT_STITCHED_3895 | 6228 | Athl1 | BC024386 | Athl1 |
| chr7 | 148144326 | 148149350 | INT_STITCHED_3896 | 269 | Ifitm1, Ifitm2 | BC024386, Ifitm3 | Ifitm2 |
| chr7 | 148210613 | 148212675 | INT_STITCHED_3898 | 1559 | . | Ifitm3 | Ifitm3 |
| chr7 | 149767035 | 149767709 | INT_STITCHED_3903 | 8496 | H19 | . | H19 |
| chr8 | 3394398 | 3401126 | INT_STITCHED_3919 | 466 | Arhgef18 | . | Arhgef18 |
| chr8 | 4341931 | 4370480 | INT_STITCHED_3923 | 630 | Ccl25 | . | Ccl25 |
| chr8 | 8655610 | 8656423 | INT_STITCHED_3932 | 8493 | Efnb2 | . | Efnb2 |
| chr8 | 10924754 | 10925468 | INT_STITCHED_3939 | 2611 | 3930402G23Rik | . | 3930402G23Rik |
| chr8 | 11640471 | 11650624 | INT_STITCHED_3941 | 1100 | Ankrd10 | Ankrd10 | Ankrd10 |
| chr8 | 12481728 | 12482441 | INT_STITCHED_3946 | 1518 | . | Sox1 | Sox1 |
| chr8 | 12759924 | 12760464 | INT_STITCHED_3951 | 3049 | Atp11a | . | Atp11a |
| chr8 | 12928814 | 12929349 | INT_STITCHED_3953 | 2295 | . | Mcf2l | Mcf2l |
| chr8 | 23526226 | 23527098 | INT_STITCHED_3973 | 2380 | Mrps31 | . | Mrps31 |
| chr8 | 23913976 | 23914613 | INT_STITCHED_3975 | 4178 | Ap3m2 | . | Ap3m2 |
| chr8 | 24360828 | 24361492 | INT_STITCHED_3979 | 1685 | Golga7 | . | Golga7 |
| chr8 | 24470989 | 24471980 | INT_STITCHED_3980 | 3038 | . | Sfrp1 | Sfrp1 |
| chr8 | 24509604 | 24521644 | INT_STITCHED_3981 | 472 | Sfrp1 | Sfrp1 | Sfrp1 |
| chr8 | 25555859 | 25556317 | INT_STITCHED_3986 | 6273 | 1810011O10Rik | . | 1810011O10Rik |
| chr8 | 26623789 | 26624247 | INT_STITCHED_3990 | 2962 | Fgfr1 | . | Fgfr1 |
| chr8 | 26863847 | 26864429 | INT_STITCHED_3992 | 4336 | Ddhd2 | . | Ddhd2 |
| chr8 | 32280929 | 32281569 | INT_STITCHED_4004 | 4366 | Mak16 | . | Mak16 |
| chr8 | 41720049 | 41720645 | INT_STITCHED_4039 | 2047 | Mtmr7 | . | Mtmr7 |
| chr8 | 42048148 | 42048839 | INT_STITCHED_4041 | 1897 | . | Pdgfrl, Frg1, Mtus1 | Pdgfrl |

TABLE S2C-continued

Typical enhancer to gene assignment

| chr | start | end | TE_ID | TE_rank | proximal active genes (TE within 4 kb of TSS) | interacting active genes (SMC1 PET interactions) | nearest genes |
|---|---|---|---|---|---|---|---|
| chr8 | 42217833 | 42218697 | INT_STITCHED_4043 | 2284 | Mtus1 | . | Mtus1 |
| chr8 | 44265400 | 44266109 | INT_STITCHED_4044 | 408 | Triml2 | . | Triml2 |
| chr8 | 44392194 | 44392898 | INT_STITCHED_4045 | 289 | Zfp42 | . | Zfp42 |
| chr8 | 47299342 | 47299968 | INT_STITCHED_4051 | 7463 | Slc25a4 | . | Slc25a4 |
| chr8 | 47704015 | 47704883 | INT_STITCHED_4054 | 4022 | Casp3, Ccdc111 | . | Casp3 |
| chr8 | 48424007 | 48424844 | INT_STITCHED_4059 | 1569 | . | Stox2 | Stox2 |
| chr8 | 55161375 | 55162311 | INT_STITCHED_4071 | 913 | Vegfc | . | Vegfc |
| chr8 | 59968722 | 59969274 | INT_STITCHED_4078 | 2709 | Sap30 | . | Sap30 |
| chr8 | 67475993 | 67476480 | INT_STITCHED_4094 | 5721 | Tmem192 | . | Tmem192 |
| chr8 | 70794823 | 70795320 | INT_STITCHED_4105 | 4825 | Sh2d4a | . | Sh2d4a |
| chr8 | 72797791 | 72798792 | INT_STITCHED_4113 | 1697 | . | Homer3 | Homer3 |
| chr8 | 75076675 | 75085391 | INT_STITCHED_4119 | 501 | Med26 | Med26 | Med26 |
| chr8 | 82579447 | 82580481 | INT_STITCHED_4146 | 4901 | Hhip | . | Hhip |
| chr8 | 85678936 | 85684999 | INT_STITCHED_4154 | 1067 | Tbc1d9 | Tbc1d9 | Tbc1d9 |
| chr8 | 86114380 | 86114994 | INT_STITCHED_4156 | 4890 | Tecr | . | Tecr |
| chr8 | 86701216 | 86703034 | INT_STITCHED_4158 | 1364 | Mir181d, Mir181c | . | Mir181d |
| chr8 | 86718129 | 86718656 | INT_STITCHED_4159 | 832 | . | Nanos3, Mir181d, Mir181c, Mir24-2, Mir27a, Mir23a | Mir23a |
| chr8 | 87438974 | 87439767 | INT_STITCHED_4165 | 915 | Dnase2a | . | Dnase2a |
| chr8 | 88022293 | 88023151 | INT_STITCHED_4168 | 2230 | Gpt2 | . | Gpt2 |
| chr8 | 89411697 | 89412634 | INT_STITCHED_4172 | 1024 | N4bp1 | . | N4bp1 |
| chr8 | 91569015 | 91569562 | INT_STITCHED_4180 | 1801 | Sall1 | . | Sall1 |
| chr8 | 91795502 | 91796285 | INT_STITCHED_4183 | 1473 | . | Sall1 | Sall1 |
| chr8 | 93375315 | 93376069 | INT_STITCHED_4191 | 2318 | . | Chd9 | Chd9 |
| chr8 | 93405177 | 93406102 | INT_STITCHED_4192 | 2533 | . | Chd9 | Chd9 |
| chr8 | 93427969 | 93428698 | INT_STITCHED_4193 | 1106 | . | Chd9 | Chd9 |
| chr8 | 96557414 | 96558124 | INT_STITCHED_4213 | 5469 | Ogfod1, Nudt21 | . | Nudt21 |
| chr8 | 97446210 | 97446860 | INT_STITCHED_4216 | 1878 | Ccdc102a | . | Ccdc102a |
| chr8 | 97667312 | 97668037 | INT_STITCHED_4217 | 1672 | Kifc3 | . | Kifc3 |
| chr8 | 98052059 | 98056627 | INT_STITCHED_4218 | 956 | Ccdc113 | . | Ccdc113 |
| chr8 | 98220746 | 98221252 | INT_STITCHED_4219 | 6116 | Ndrg4 | . | Ndrg4 |
| chr8 | 107751860 | 107757896 | INT_STITCHED_4233 | 914 | D230025D16Rik | D230025D16Rik | D230025D16Rik |
| chr8 | 108495132 | 108495876 | INT_STITCHED_4235 | 3388 | Slc12a4 | Slc12a4 | Slc12a4 |
| chr8 | 109811081 | 109811921 | INT_STITCHED_4244 | 2689 | Nfat5 | . | Nfat5 |
| chr8 | 110118419 | 110119429 | INT_STITCHED_4245 | 1265 | Psmd7 | . | Psmd7 |
| chr8 | 111246518 | 111254244 | INT_STITCHED_4251 | 508 | . | Zfhx3 | Zfhx3 |
| chr8 | 112216041 | 112217027 | INT_STITCHED_4256 | 1943 | 2400003C14Rik | . | 2400003C14Rik |
| chr8 | 112397963 | 112409627 | INT_STITCHED_4257 | 3668 | Phlpp2 | . | Phlpp2 |
| chr8 | 114064905 | 114065322 | INT_STITCHED_4260 | 4168 | Znrf1 | . | Znrf1 |
| chr8 | 114136803 | 114146846 | INT_STITCHED_4262 | 2102 | . | Znrf1, Ldhd | Ldhd |
| chr8 | 114172500 | 114175132 | INT_STITCHED_4263 | 823 | Zfp1 | Ldhd | Zfp1 |
| chr8 | 119498759 | 119499379 | INT_STITCHED_4282 | 2905 | 1700030J22Rik | . | 1700030J22Rik |
| chr8 | 119683409 | 119683904 | INT_STITCHED_4284 | 6290 | Gan | . | Gan |
| chr8 | 120017171 | 120028015 | INT_STITCHED_4287 | 1135 | Plcg2 | Plcg2 | Plcg2 |
| chr8 | 120809727 | 120810433 | INT_STITCHED_4290 | 8471 | Cdh13 | . | Cdh13 |
| chr8 | 123033008 | 123033772 | INT_STITCHED_4299 | 1429 | . | Gse1 | Gse1 |
| chr8 | 123056306 | 123057280 | INT_STITCHED_4300 | 631 | . | Gse1 | Gse1 |
| chr8 | 123195397 | 123196271 | INT_STITCHED_4301 | 3438 | Cox4nb, Cox4i1 | . | Cox4i1 |
| chr8 | 125857754 | 125858952 | INT_STITCHED_4304 | 2207 | Spire2 | . | Spire2 |
| chr8 | 125899749 | 125900605 | INT_STITCHED_4305 | 8468 | Tcf25 | Tubb3 | Tcf25 |
| chr8 | 126330309 | 126331154 | INT_STITCHED_4309 | 2390 | Rab4a | . | Rab4a |
| chr8 | 126535550 | 126538752 | INT_STITCHED_4311 | 2203 | Taf5l | . | Taf5l |
| chr8 | 128189605 | 128190453 | INT_STITCHED_4323 | 2510 | 4933403G14Rik | . | 4933403G14Rik |
| chr9 | 15081242 | 15081878 | INT_STITCHED_4375 | 6833 | Med17 | . | Med17 |
| chr9 | 20257900 | 20258612 | INT_STITCHED_4389 | 4697 | Zfp26 | . | Zfp26 |
| chr9 | 20782392 | 20784089 | INT_STITCHED_4391 | 266 | S1pr2 | . | S1pr2 |
| chr9 | 21222272 | 21222788 | INT_STITCHED_4392 | 3282 | Qtrt1 | . | Qtrt1 |
| chr9 | 21566312 | 21573527 | INT_STITCHED_4395 | 309 | Spc24 | Spc24 | Spc24 |
| chr9 | 21652171 | 21652836 | INT_STITCHED_4397 | 2144 | Dock6 | . | Dock6 |
| chr9 | 21941572 | 21942182 | INT_STITCHED_4398 | 1823 | Acp5 | . | Acp5 |
| chr9 | 26965221 | 26965892 | INT_STITCHED_4409 | 6637 | Jam3 | . | Jam3 |
| chr9 | 30840106 | 30840580 | INT_STITCHED_4423 | 5243 | Zbtb44 | . | Zbtb44 |
| chr9 | 34919369 | 34920459 | INT_STITCHED_4441 | 1254 | St3gal4, 4930581E22Rik | St3gal4, 4930581F22Rik | 4930581F22Rik |

TABLE S2C-continued

| chr | start | end | TE_ID | TE_rank | proximal active genes (TE within 4 kb of TSS) | interacting active genes (SMC1 PET interactions) | nearest genes |
|---|---|---|---|---|---|---|---|
| Typical enhancer to gene assignment | | | | | | | |
| chr9 | 36601807 | 36611238 | INT_STITCHED_4443 | 929 | Ei24 | . | Ei24 |
| chr9 | 37056042 | 37056855 | INT_STITCHED_4448 | 5381 | Slc37a2 | . | Slc37a2 |
| chr9 | 37292583 | 37293531 | INT_STITCHED_4449 | 1633 | BC024479 | . | BC024479 |
| chr9 | 43537646 | 43538191 | INT_STITCHED_4476 | 1993 | . | Pvrl1 | Pvrl1 |
| chr9 | 44119256 | 4420060 | INT_STITCHED_4481 | 4619 | Hinfp | . | Hinfp |
| chr9 | 44141293 | 44142111 | INT_STITCHED_4482 | 302 | Dpagt1, H2afx | . | H2afx |
| chr9 | 45649159 | 45649717 | INT_STITCHED_4488 | 8454 | Bace1 | . | Bace1 |
| chr9 | 47341278 | 47342102 | INT_STITCHED_4500 | 5543 | Cadm1 | . | Cadm1 |
| chr9 | 48647618 | 48648098 | INT_STITCHED_4507 | 6925 | Zbtb16 | . | Zbtb16 |
| chr9 | 48799482 | 48800362 | INT_STITCHED_4509 | 1285 | Usp28 | . | Usp28 |
| chr9 | 48862028 | 48862859 | INT_STITCHED_4511 | 5295 | Zw10 | . | Zw10 |
| chr9 | 49559299 | 49560181 | INT_STITCHED_4519 | 1413 | . | Ncam1 | Ncam1 |
| chr9 | 49604426 | 49604976 | INT_STITCHED_4520 | 2399 | Ncam1 | . | Ncam1 |
| chr9 | 49743610 | 49744745 | INT_STITCHED_4521 | 1765 | . | Ncam1 | Ncam1 |
| chr9 | 51854804 | 51855366 | INT_STITCHED_4527 | 8453 | Rdx, Gm6981 | . | Rdx |
| chr9 | 53618496 | 53619776 | INT_STITCHED_4531 | 781 | Slc35f2 | . | Slc35f2 |
| chr9 | 54703743 | 54705821 | INT_STITCHED_4539 | 1908 | Ireb2 | . | Ireb2 |
| chr9 | 55063210 | 55073663 | INT_STITCHED_4542 | 285 | Fbxo22 | . | Fbxo22 |
| chr9 | 57010741 | 57014562 | INT_STITCHED_4548 | 2444 | Commd4 | . | Commd4 |
| chr9 | 57358103 | 57371993 | INT_STITCHED_4549 | 395 | Cox5a | . | Cox5a |
| chr9 | 57677536 | 57678655 | INT_STITCHED_4550 | 2513 | Arid3b | . | Arid3b |
| chr9 | 60635345 | 60636054 | INT_STITCHED_4568 | 2794 | Uaca | . | Uaca |
| chr9 | 61208965 | 61209654 | INT_STITCHED_4575 | 1542 | . | Tle3 | Tle3 |
| chr9 | 61233897 | 61234814 | INT_STITCHED_4576 | 4412 | . | Tle3 | Tle3 |
| chr9 | 62185724 | 62186999 | INT_STITCHED_4582 | 2018 | Anp32a | . | Anp32a |
| chr9 | 62383015 | 62383432 | INT_STITCHED_4585 | 7274 | Coro2b | . | Coro2b |
| chr9 | 64988516 | 64989016 | INT_STITCHED_4595 | 8450 | Igdcc3 | . | Igdcc3 |
| chr9 | 65186892 | 65195417 | INT_STITCHED_4598 | 1055 | Pdcd7 | . | Pdcd7 |
| chr9 | 65441290 | 65442044 | INT_STITCHED_4599 | 1266 | Pif1 | . | Pif1 |
| chr9 | 67056190 | 67062471 | INT_STITCHED_4607 | 611 | . | Tpm1 | Tpm1 |
| chr9 | 70067253 | 70071655 | INT_STITCHED_4620 | 3207 | . | Myo1e | Myo1e |
| chr9 | 72505560 | 72506130 | INT_STITCHED_4635 | 4790 | Nedd4 | . | Nedd4 |
| chr9 | 72627390 | 72628209 | INT_STITCHED_4636 | 2084 | . | Prtg | Prtg |
| chr9 | 72660060 | 72660935 | INT_STITCHED_4637 | 1839 | Prtg | . | Prtg |
| chr9 | 72918450 | 72919308 | INT_STITCHED_4639 | 2373 | . | Rab27a | Rab27a |
| chr9 | 75412496 | 75413425 | INT_STITCHED_4648 | 2748 | Tmod3 | . | Tmod3 |
| chr9 | 77606686 | 77607650 | INT_STITCHED_4652 | 2346 | Gclc | . | Gclc |
| chr9 | 77951768 | 77952528 | INT_STITCHED_4654 | 8446 | Ick, Fbxo9 | . | Fbxo9 |
| chr9 | 78038277 | 78039230 | INT_STITCHED_4656 | 1191 | Gsta4 | . | Gsta4 |
| chr9 | 88227178 | 88228053 | INT_STITCHED_4678 | 2664 | Nt5e | . | Nt5e |
| chr9 | 88377528 | 88378586 | INT_STITCHED_4680 | 2087 | Syncrip | . | Syncrip |
| chr9 | 97013591 | 97015267 | INT_STITCHED_4696 | 251 | Slc25a36 | . | Slc25a36 |
| chr9 | 100540961 | 100541608 | INT_STITCHED_4706 | 5773 | Stag1 | Nck1 | Stag1 |
| chr9 | 100934315 | 100942688 | INT_STITCHED_4708 | 795 | Pccb | . | Pccb |
| chr9 | 102592120 | 102593562 | INT_STITCHED_4714 | 366 | . | Amotl2 | Amotl2 |
| chr9 | 106069546 | 106074893 | INT_STITCHED_4726 | 870 | Wdr82 | . | Wdr82 |
| chr9 | 107477688 | 107478518 | INT_STITCHED_4729 | 1235 | Hyal2, Nat6, Hyal3, Hyal1 | . | Hyal1 |
| chr9 | 107496491 | 107497240 | INT_STITCHED_4730 | 3614 | Ifrd2, BY080835 | . | BY080835 |
| chr9 | 107529104 | 107533461 | INT_STITCHED_4731 | 483 | Gnai2 | BY080835, Sema3b, Gnai2 | Gnai2 |
| chr9 | 107579734 | 107580327 | INT_STITCHED_4732 | 8441 | . | BY080835, Sema3b, Slc38a3 | Slc38a3 |
| chr9 | 108198631 | 108208673 | INT_STITCHED_4735 | 642 | Nicn1, Tcta, Rhoa, Amt | . | Tcta |
| chr9 | 108424057 | 108425078 | INT_STITCHED_4736 | 6827 | Qrich1 | . | Qrich1 |
| chr9 | 108469174 | 108470010 | INT_STITCHED_4737 | 746 | Ndufaf3, Dalrd3, Mir425, Mir191, Impdh2 | . | Ndufaf3 |
| chr9 | 108556747 | 108557725 | INT_STITCHED_4738 | 910 | Arih2 | . | Arih2 |
| chr9 | 109774888 | 109775365 | INT_STITCHED_4742 | 6978 | Cdc25a | . | Cde25a |
| chr9 | 110562502 | 110563156 | INT_STITCHED_4745 | 5313 | Nbeal2,C cdc12 | . | Ccdc12 |

TABLE S2C-continued

Typical enhancer to gene assignment

| chr | start | end | TE_ID | TE_rank | proximal active genes (TE within 4 kb of TSS) | interacting active genes (SMC1 PET interactions) | nearest genes |
|---|---|---|---|---|---|---|---|
| chr9 | 110647812 | 110648457 | INT_STITCHED_4746 | 4458 | Pth1r | . | Pth1r |
| chr9 | 110757426 | 110757966 | INT_STITCHED_4747 | 4546 | Prss50 | . | Prss50 |
| chr9 | 114493073 | 114494132 | INT_STITCFIED_4767 | 342 | . | Trim71, Ccr4, Cnot10 | Trim71 |
| chr9 | 114549100 | 114549959 | INT_STITCHED_4769 | 1830 | Cnot10 | . | Cnot10 |
| chr9 | 121898518 | 121899106 | INT_STITCHED_4805 | 5244 | C85492 | . | C85492 |
| chr10 | 4521315 | 4524373 | INT_STITCHED_4811 | 2104 | Mtrfl1 | . | Mtrfl1 |
| chr10 | 6056028 | 6057101 | INT_STITCHED_4818 | 761 | . | Akap12 | Akap12 |
| chr10 | 6080029 | 6080762 | INT_STITCHED_4819 | 917 | Akap12 | . | Akap12 |
| chr10 | 6096866 | 6104516 | INT_STITCHED_4820 | 441 | . | Akap12 | Akap12 |
| chr10 | 8605895 | 8609821 | INT_STITCHED_4831 | 1322 | Sashl | . | Sashl |
| chr10 | 12733586 | 12734303 | INT_STITCHED_4846 | 5442 | Sf3b5 | . | Sc3b5 |
| chr10 | 14423031 | 14423523 | INT_STITCHED_4852 | 7521 | Vta1 | . | Vta1 |
| chr10 | 18188738 | 18189638 | INT_STITCHED_4868 | 3221 | Nhsl1 | . | Nhsl1 |
| chr10 | 19428463 | 19429212 | INT_STITCHED_4875 | 6208 | Il20ra | . | Il20ra |
| chr10 | 19658492 | 19658963 | INT_STITCHED_4878 | 7066 | Map3k5 | . | Map3k5 |
| chr10 | 21018761 | 21019274 | INT_STITCHED_4887 | 8431 | Hbsl1 | . | Hbsl1 |
| chr10 | 21421393 | 21422103 | INT_STITCHED_4889 | 1253 | . | Sgk1 | Sgk1 |
| chr10 | 21565286 | 21568461 | INT_STITCHED_4892 | 286 | . | Sgk1 | Sgk1 |
| chr10 | 24310265 | 24311057 | INT_STITCHED_4897 | 2376 | Ctgf | . | Ctgf |
| chr10 | 24545811 | 24555200 | INT_STITCHED_4901 | 526 | Enpp3 | . | Enpp3 |
| chr10 | 24582734 | 24583438 | INT_STITCHED_4902 | 5640 | Med23 | . | Med23 |
| chr10 | 33950012 | 33957066 | INT_STITCHED_4929 | 283 | . | Dse, Bet31 | Dse |
| chr10 | 39338030 | 39338814 | INT_STITCHED_4948 | 1945 | Traf3ip2 | . | Traf3ip2 |
| chr10 | 39455931 | 39456518 | INT_STITCHED_4951 | 3274 | Rev3l | . | Rev3l |
| chr10 | 41186875 | 41187821 | INT_STITCHED_4960 | 960 | . | Mical1 | Mical1 |
| chr10 | 41346832 | 41347467 | INT_STITCHED_4962 | 5177 | . | Cd164 | Cd164 |
| chr10 | 43196881 | 43198135 | INT_STITCHED_4973 | 840 | Bend3 | . | Bend3 |
| chr10 | 44792055 | 44792644 | INT_STITCHED_4991 | 4429 | Prep | . | Prep |
| chr10 | 56093669 | 56096370 | INT_STITCHED_5009 | 954 | Gja1 | . | Gja1 |
| chr10 | 57211848 | 57212434 | INT_STITCHED_5011 | 4297 | Hsf2 | . | Hsf2 |
| chr10 | 60837711 | 60845392 | INT_STITCHED_5034 | 833 | X99384 | Nodal | X99384 |
| chr10 | 60878292 | 60880002 | INT_STITCHED_5035 | 307 | . | X99384 | X99384 |
| chr10 | 61695639 | 61705502 | INT_STITCHED_5041 | 1103 | Tspan15 | . | Tspan15 |
| chr10 | 61976766 | 61977458 | INT_STITCHED_5043 | 4198 | Srgn | . | Srgn |
| chr10 | 62699664 | 62700521 | INT_STITCHED_5046 | 2504 | Herc4 | . | Herc4 |
| chr10 | 66465837 | 66467256 | INT_STITCHED_5056 | 264 | . | Reep3 | Reep3 |
| chr10 | 69388191 | 69389259 | INT_STITCHED_5073 | 2588 | Ank3 | . | Ank3 |
| chr10 | 69557563 | 69558392 | INT_STITCHED_5074 | 1760 | Ccdc6 | . | Ccdc6 |
| chr10 | 69895948 | 69896630 | INT_STITCHED_5079 | 5291 | . | Fam13c | Fam13c |
| chr10 | 70808586 | 70809333 | INT_STITCHED_5083 | 4254 | Cisd1, Ipmk | . | Cisd1 |
| chr10 | 75491765 | 75492542 | INT_STITCHED_5094 | 1070 | Zfp280b | . | Zfp280b |
| chr10 | 75902165 | 75902804 | INT_STITCHED_5096 | 1995 | Pcnt | . | Pcnt |
| chr10 | 77065603 | 77066355 | INT_STITCHED_5102 | 2639 | Sumo3 | . | Sumo3 |
| chr10 | 77500956 | 77501452 | INT_STITCHED_5103 | 1526 | Aire, Dnmt3l | . | Dnmt3l |
| chr10 | 79135588 | 79136419 | INT_STITCHED_5110 | 572 | Gm16517 | . | Gm16517 |
| chr10 | 80692540 | 80693324 | INT_STITCHED_5115 | 2022 | Zfr2, Atcay | . | Atcay |
| chr10 | 82323925 | 82324687 | INT_STITCHED_5120 | 3996 | Txnrdl | . | Txnrdl |
| chr10 | 82806815 | 82809352 | INT_STITCHED_5121 | 1327 | Slc41a2 | . | Slc41a2 |
| chr10 | 84218273 | 84221859 | INT_STITCHED_5131 | 1622 | Rfx4 | . | Rfx4 |
| chr10 | 84373188 | 84374377 | INT_STITCHED_5135 | 1465 | Ric8b | Rfx4 | Ric8b |
| chr10 | 86247737 | 86248402 | INT_STITCHED_5145 | 3820 | Nt5dc3 | . | Nt5dc3 |
| chr10 | 87323661 | 87324242 | INT_STITCHED_5151 | 8413 | Igfl | . | Igfl |
| chr10 | 91625760 | 91626428 | INT_STITCHED_5166 | 4875 | Rmst | . | Rmst |
| chr10 | 92628272 | 92629369 | INT_STITCHED_5170 | 6413 | Cdk17, Mir1931 | . | Mir1931 |
| chr10 | 94877813 | 94878427 | INT_STITCHED_5186 | 1768 | Socs2 | . | Socs2 |
| chr10 | 99484471 | 99485189 | INT_STITCHED_5204 | 4932 | Kitl | . | Kitl |
| chr10 | 102831472 | 102832261 | INT_STITCHED_5212 | 2315 | Slc6a15 | . | Slc6a15 |
| chr10 | 114819854 | 114820700 | INT_STITCHED_5234 | 8036 | Zfc3h1, Thap2 | . | Zfc3h1 |
| che10 | 116589007 | 116589893 | INT_STITCHED_5241 | 2171 | Frs2 | . | Frs2 |
| chr10 | 117140641 | 117141390 | INT_STITCHED_5243 | 8406 | Mdm2 | . | Mdm2 |
| chr10 | 117285236 | 117286671 | INT_STITCHED_5245 | 5005 | Rap1b | . | Rap1b |
| chr10 | 121179350 | 121180065 | INT_STITCHED_5263 | 3080 | BC048403 | . | BC048403 |
| chr10 | 125407173 | 125407844 | INT_STITCHED_5274 | 4971 | Lrig3 | . | Lrig3 |
| chr10 | 126707459 | 126707875 | INT_STITCHED_5278 | 5620 | Dctn2 | . | Dctn2 |
| chr10 | 127027476 | 127027943 | INT_STITCHED_5279 | 1610 | . | Lrp1 | Lrp1 |
| chr10 | 127531580 | 127532717 | INT_STITCHED_5281 | 1409 | Baz2a | . | Baz2a |
| chr10 | 127806805 | 127807509 | INT_STITCHED_5284 | 2080 | Coq10a | . | Coq10a |
| chr10 | 128068373 | 128069108 | INT_STITCHED_5286 | 2913 | Rps26 | . | Rps26 |
| chr11 | 3189708 | 3193686 | INT_STITCHED_5290 | 502 | Patz1 | Drg1 | Patz1 |
| chr11 | 4543384 | 4544389 | INT_STITCHED_5303 | 4817 | Ascc2 | . | Ascc2 |

TABLE S2C-continued

| chr | start | end | TE_ID | TE_rank | proximal active genes (TE within 4 kb of TSS) | interacting active genes (SMC1 PET interactions) | nearest genes |
|---|---|---|---|---|---|---|---|
| Typical enhancer to gene assignment | | | | | | | |
| chr11 | 4605024 | 4605900 | INT_STITCHED_5305 | 5202 | Zmat5, Uqcr10 | . | Zmat5 |
| chr11 | 5602509 | 5603082 | INT_STITCHED_5311 | 4735 | Mrps24 | . | Mrps24 |
| chr11 | 5640939 | 5641684 | INT_STITCHED_5312 | 1772 | Urgcp | . | Urgcp |
| chr11 | 18925903 | 18926553 | INT_STITCHED_5359 | 8097 | . | Meis1 | Meis1 |
| chr11 | 19817749 | 19818637 | INT_STITCHED_5365 | 2246 | Spred2 | . | Spred2 |
| chr11 | 20094772 | 20095341 | INT_STITCHED_5371 | 5514 | Rab1 | . | Rab1 |
| chr11 | 29922145 | 29922784 | INT_STITCHED_5413 | 6619 | Eml6 | . | Eml6 |
| chr11 | 34215057 | 34215897 | INT_STITCHED_5430 | 3638 | Fam196b | . | Fam196b |
| chr11 | 40550744 | 40551400 | INT_STITCHED_5447 | 4727 | Nudcd2, Hmmr | . | Nudcd2 |
| chr11 | 43338652 | 43339165 | INT_STITCHED_5452 | 6258 | Ccnjl | . | Ccnjl |
| chr11 | 43399014 | 43399833 | INT_STITCHED_5453 | 3868 | . | Ccnjl | Ccnjl |
| chr11 | 45869858 | 45873818 | INT_STITCHED_5465 | 1130 | Adam19 | . | Adam19 |
| chr11 | 51451223 | 51451993 | INT_STITCHED_5482 | 848 | Rmnd5b | D930048N14Rik, N4bp3 | Rmnd5b |
| chr11 | 54672906 | 54673698 | INT_STITCHED_5498 | 3249 | Hint1, Lyrm7 | . | Lyrm7 |
| chr11 | 59324891 | 59325529 | INT_STITCHED_5512 | 5165 | Zkscan17, 4933439C10Rik | . | Zkscan17 |
| chr11 | 59627660 | 59635535 | INT_STITCHED_5513 | 2071 | Flcn | . | Flcn |
| chr11 | 60236311 | 60237216 | INT_STITCHED_5515 | 6543 | Atpaf2, 4933439F18Rik | . | 4933439F18Rik |
| chr11 | 60590721 | 60591349 | INT_STITCHED_5516 | 3272 | Top3a, Smcr8 | . | Top3a |
| chr11 | 60650172 | 60651011 | INT_STITCHED_5517 | 3776 | Dhrs7b | . | Dhrs7b |
| chr11 | 60736253 | 60737190 | INT_STITCHED_5519 | 1008 | . | Map2k3, Gm16516 | Gm16516 |
| chr11 | 60994880 | 60995724 | INT_STITCHED_5521 | 3196 | Usp22 | . | Usp22 |
| chr11 | 61391409 | 61392089 | INT_STITCHED_5527 | 7849 | Epn2 | . | Epn2 |
| chr11 | 62351245 | 62352154 | INT_STITCHED_5534 | 2339 | Cenpv | . | Cenpv |
| chr11 | 62686433 | 62687279 | INT_STITCHED_5535 | 1997 | Fam18b | . | Fam18b |
| chr11 | 62950261 | 62950815 | INT_STITCHED_5538 | 7452 | Pmp22 | . | Pmp22 |
| chr11 | 69377638 | 69378461 | INT_STITCHED_5563 | 3113 | Efnb3 | . | Efnb3 |
| chr11 | 69394651 | 69396118 | INT_STITCHED_5564 | 602 | Trp53, Wrap53 | Dnahc2, Atp1b2 | Trp53 |
| chr11 | 74534022 | 74534794 | INT_STITCHED_5581 | 3606 | Pafah1b1 | . | Pafah1b1 |
| chr11 | 77486774 | 77494239 | INT_STITCHED_5595 | 593 | Nufip2 | . | Nufip2 |
| chr11 | 78060890 | 78061883 | INT_STITCHED_5601 | 2175 | Supt6h, Sdf2 | . | Supt6h |
| chr11 | 79066770 | 79067524 | INT_STITCHED_5610 | 3716 | Wsb1 | . | Wsb1 |
| chr11 | 79945260 | 79951952 | INT_STITCHED_5618 | 259 | 1110002N22Rik | . | 1110002N22Rik |
| chr11 | 79990875 | 79991582 | INT_STITCHED_5619 | 1000 | Rnf135 | . | Rnf135 |
| chr11 | 80942931 | 80947956 | INT_STITCHED_5623 | 1654 | . | Accn1 | Accn1 |
| chr11 | 82648830 | 82649486 | INT_STITCHED_5636 | 8383 | Rffl | . | Rffl |
| chr11 | 85052297 | 85054262 | INT_STITCHED_5646 | 4478 | Appbp2, D630032N06Rik | . | D630032N06Rik |
| chr11 | 86809492 | 86810234 | INT_STITCHED_5657 | 8055 | Ypel2 | . | Ypel2 |
| chr11 | 87983937 | 87984484 | INT_STITCHED_5660 | 5125 | Cuedc1 | . | Cuedc1 |
| chr11 | 88006524 | 88016104 | INT_STITCHED_5661 | 1190 | Mrps23 | Vezf1 | Mrps23 |
| chr11 | 88718915 | 88724318 | INT_STITCHED_5670 | 1418 | Akap1 | . | Akap1 |
| chr11 | 88829276 | 88830722 | INT_STITCHED_5672 | 515 | Coil, 2210409E12Rik | Coil, 2210409E12Rik | 2210409E12Rik |
| chr11 | 89103298 | 89103997 | INT_STITCFIED_5678 | 2377 | . | Nog | Nog |
| chr11 | 89857107 | 89857767 | INT_STITCHED_5681 | 6616 | Pctp | . | Pctp |
| chr11 | 93749460 | 93750030 | INT_STITCHED_5687 | 8380 | Mbtd1, Utp18 | . | Mbtd1 |
| chr11 | 95172573 | 95174382 | INT_STITCHED_5689 | 796 | Myst2 | . | Myst2 |
| chr11 | 95841647 | 95842789 | INT_STITCHED_5696 | 698 | . | Igf2bp1 | Igf2bp1 |
| chr11 | 95878892 | 95879756 | INT_STITCHED_5697 | 1471 | . | Igf2bp1 | Igf2bp1 |
| chr11 | 95975203 | 95975967 | INT_STITCHED_5698 | 5002 | Calcoco2 | , | Calcoco2 |
| chr11 | 96641262 | 96642250 | INT_STITCHED_5703 | 4098 | Snx11 | . | Snx11 |
| chr11 | 96712000 | 96712739 | INT_STITCHED_5705 | 2650 | Copz2, Mir152 | . | Copz2 |
| chr11 | 97053223 | 97053840 | INT_STITCHED_5706 | 5798 | Kpnb1 | . | Kpnb1 |
| chr11 | 97428279 | 97440933 | INT_STITCHED_5709 | 449 | Srcin1 | Srcin1 | Srcin1 |
| chr11 | 97486767 | 97487595 | INT_STITCHED_5710 | 8378 | E130012A19Rik | . | E130012A19Rik |
| chr11 | 97638286 | 97638942 | INT_STITCHED_5713 | 2574 | Snora21, Rp123, 1700001P01Rik | . | 1700001P01Rik |
| chr11 | 98062871 | 98063570 | INT_STITCHED_5715 | 2004 | Cdk12 | . | Cdk12 |
| chr11 | 98653131 | 98654005 | INT_STITCHED_5717 | 1984 | Msl1 | . | Msl1 |
| chr11 | 98787666 | 98788235 | INT_STITCHED_5718 | 1642 | . | Rara | Rara |

TABLE S2C-continued

Typical enhancer to gene assignment

| chr | start | end | TE_ID | TE_rank | proximal active genes (TE within 4 kb of TSS) | interacting active genes (SMC1 PET interactions) | nearest genes |
|---|---|---|---|---|---|---|---|
| chr11 | 99105144 | 99105721 | INT_STITCHED_5723 | 5192 | Krt222 | . | Krt222 |
| chr11 | 100394982 | 100396447 | INT_STITCHED_5727 | 3839 | Acly | . | Acly |
| chr11 | 100477440 | 100478074 | INT_STITCHED_5728 | 4810 | Dnajc7, Nkiras2 | . | Dnajc7 |
| chr11 | 101168796 | 101169594 | INT_STITCHED_5732 | 5395 | Becn1 | . | Becn1 |
| chr11 | 101188000 | 101188651 | INT_STITCHED_5733 | 5601 | Aoc2 | . | Aoc2 |
| chr11 | 101409700 | 101410324 | INT_STITCHED_5735 | 3018 | Nbr1, Brca1 | . | Brca1 |
| chr11 | 101442692 | 101443650 | INT_STITCHED_5736 | 1150 | Tmem106a | . | Tmem106a |
| chr11 | 102464622 | 102465176 | INT_STITCHED_5744 | 3982 | Fzd2 | . | Fzd2 |
| chr11 | 102680774 | 102688178 | INT_STITCHED_5745 | 573 | Gjc1 | . | Gjc1 |
| chr11 | 102973458 | 102974493 | INT_STITCHED_5747 | 3140 | Hexim1 | . | Hexim1 |
| chr11 | 104461680 | 104462667 | INT_STITCHED_5754 | 3299 | . | Itgb3 | Itgb3 |
| chr11 | 106130335 | 106130757 | INT_STITCHED_5756 | 4137 | Smarcd2 | . | Smarcd2 |
| chr11 | 107372036 | 107379089 | INT_STITCHED_5769 | 1159 | . | Helz | Helz |
| chr11 | 108285157 | 108286105 | INT_STITCHED_5772 | 3390 | Ccdc46 | . | Ccdc46 |
| chr11 | 109212771 | 109222498 | INT_STITCHED_5778 | 498 | Gna13 | . | Gna13 |
| chr11 | 109337038 | 109341696 | INT_STITCHED_5779 | 2659 | Slc16a6, Arsg | . | Slcl6a6 |
| chr11 | 110904378 | 110905140 | INT_STITCHED_5784 | 4199 | . | Kcnj2 | Kcnj2 |
| chr11 | 113570971 | 113572300 | INT_STITCHED_5798 | 646 | Cpsf41 | . | Cpsf41 |
| chr11 | 116272666 | 116273421 | INT_STITCHED_5813 | 3629 | Rnf157 | . | Rnf157 |
| chr11 | 116286146 | 116291508 | INT_STITCHED_5814 | 242 | Fam100b, Gm7367 | Fam100b, Gm7367 | Fam100b |
| chr11 | 116447490 | 116448378 | INT_STITCHED_5815 | 1674 | Ube2o | Rhbdf2, Aanat | Ube2o |
| chr11 | 117180985 | 117182314 | INT_STITCHED_5821 | 683 | . | Sept9 | 9-Sep |
| chr11 | 117736789 | 117737509 | INT_STITCHED_5830 | 985 | Tha1 | Gm125 81, Socs3 | Tha1 |
| chr11 | 118335167 | 118335821 | INT_STITCHED_5833 | 3791 | Engase | . | Engase |
| chr11 | 119256568 | 119257332 | INT_STITCHED_5838 | 3429 | Mir1932 | . | Mir1932 |
| chr11 | 119798926 | 119799586 | INT_STITCHED_5842 | 2594 | Baiap2 | . | Baiap2 |
| chr11 | 120009574 | 120010144 | INT_STITCHED_5843 | 5089 | Slc38a10 | . | Slc38a10 |
| chr11 | 120092762 | 120093212 | INT_STITCHED_5845 | 1725 | Bahcc1 | . | Bahcc1 |
| chr11 | 120638338 | 120641722 | INT_STITCHED_5848 | 8042 | Rfng, Gps1 | Dcxr, Rac3, Lrrc45, Stra13, Cd7 | Rfng |
| chr11 | 120687588 | 120688365 | INT_STITCHED_5850 | 2331 | Fasn | . | Fasn |
| chr12 | 3889637 | 3890588 | INT_STITCHED_5856 | 1043 | Dnmt3a | . | Dnmt3a |
| chr12 | 8504710 | 8505271 | INT_STITCHED_5867 | 3636 | Rhob | . | Rhob |
| chr12 | 8947875 | 8949112 | INT_STITCHED_5868 | 1831 | Matn3 | . | Matn3 |
| chr12 | 12826439 | 12835796 | INT_STITCHED_5877 | 291 | . | Mycn | Mycn |
| chr12 | 12882069 | 12897292 | INT_STITCHED_5878 | 704 | . | Mycn | Mycn |
| chr12 | 12916267 | 12917170 | INT_STITCHED_5879 | 619 | . | Mycn | Mycn |
| chr12 | 15821175 | 15834231 | INT_STITCHED_5886 | 3248 | Trib2 | . | Trib2 |
| chr12 | 21424419 | 21425048 | INT_STITCHED_5899 | 1820 | Ywhaq | . | Ywhaq |
| chr12 | 30624985 | 30625635 | INT_STITCHED_5920 | 7091 | Pxdn | . | Pxdn |
| chr12 | 33509420 | 33509920 | INT_STITCHED_5930 | 7423 | Nampt | . | Nampt |
| chr12 | 34111976 | 34112967 | INT_STITCHED_5937 | 1469 | Twistnb | . | Twistnb |
| chr12 | 35730495 | 35731263 | INT_STITCHED_5940 | 6653 | Snx13 | . | Snx13 |
| chr12 | 39505938 | 39511410 | INT_STITCHED_5946 | 1065 | Etv1 | . | Etv1 |
| chr12 | 40724179 | 40725294 | INT_STITCHED_5951 | 685 | . | Arl4a | Arl4a |
| chr12 | 53192336 | 53192990 | INT_STITCHED_5981 | 4952 | Nubpl | . | Nubpl |
| chr12 | 56574184 | 56574829 | INT_STITCHED_5999 | 1512 | . | Nfkbia | Nfkbia |
| chr12 | 57621203 | 57622656 | INT_STITCHED_6005 | 3963 | . | Nkx2-9, Nkx2-1 | Nkx2-9 |
| chr12 | 70265691 | 70266182 | INT_STITCHED_6029 | 4819 | Rps29, Ppil5 | . | Ppil5 |
| chr12 | 70831225 | 70831963 | INT_STITCHED_6030 | 6534 | L2hgdh, Atp5s | . | Atp5s |
| chr12 | 73766180 | 73766775 | INT_STITCHED_6045 | 4739 | Dhrs7 | . | Dhs7 |
| chr12 | 74186448 | 74187579 | INT_STITCHED_6050 | 440 | . | Six4 | Stx4 |
| chr12 | 76765083 | 76765824 | INT_STITCHED_6059 | 4579 | Wdr89 | . | Wdr89 |
| chr12 | 78065948 | 78066766 | INT_STITCHED_6068 | 1575 | Max | . | Max |
| chr12 | 80129129 | 80136928 | INT_STITCHED_6073 | 1017 | Plekhh1 | . | Plekhh1 |
| chr12 | 81212072 | 81218304 | INT_STITCHED_6080 | 510 | Zfp36l1 | 2310015A10Rik | Zfp36l1 |
| chr12 | 82022144 | 82022886 | INT_STITCHED_6087 | 1355 | 1700052122Rik | . | 1700052122Rik |
| chr12 | 85349930 | 85350505 | INT_STITCHED_6099 | 3435 | Acot1 | . | Acot1 |
| chr12 | 85395735 | 85396391 | INT_STITCHED_6101 | 7236 | Acot3 | . | Acot3 |
| chr12 | 85542980 | 85552631 | INT_STITCHED_6102 | 547 | . | C130039016Rik | C130039016Rik |
| chr12 | 85959743 | 85966609 | INT_STITCHED_6104 | 2233 | Abcd4 | . | Abcd4 |
| chr12 | 85981457 | 85981955 | INT_STITCHED_6105 | 3978 | 7420416P09Rik | . | 7420416P09Rik |
| chr12 | 86961855 | 86962511 | INT_STITCHED_6108 | 1400 | . | Jdp2 | Jdp2 |
| chr12 | 88272118 | 88274195 | INT_STITCHED_6119 | 243 | . | 2310044G17Rik | 2310044G17Rik |
| chr12 | 92821598 | 92822554 | INT_STITCHED_6125 | 6873 | Gtf2a1 | . | Gtf2a1 |

TABLE S2C-continued

Typical enhancer to gene assignment

| chr | start | end | TE_ID | TE_rank | proximal active genes (TE within 4 kb of TSS) | interacting active genes (SMC1 PET interactions) | nearest genes |
|---|---|---|---|---|---|---|---|
| chr12 | 101575664 | 101576434 | INT_STITCHED_6140 | 2502 | . | Calm1 | Calm1 |
| chr12 | 101958877 | 101959439 | INT_STITCHED_6144 | 8355 | Rps6ka5 | . | Rps6ka5 |
| chr12 | 102234372 | 102235188 | INT_STITCHED_6147 | 1248 | . | Ccdc88c, Mir1190 | Ccdc88c |
| chr12 | 102256843 | 102257522 | INT_STITCHED_6148 | 4400 | . | Ccdc88c | Ccdc88c |
| chr12 | 103997082 | 103997697 | INT_STITCHED_6153 | 1726 | LOC100233175, Ubr7 | . | LOC100233175 |
| chr12 | 106462467 | 106463587 | INT_STITCHED_6165 | 1527 | Tcl1 | . | Tcl1 |
| chr12 | 107250243 | 107250762 | INT_STITCHED_6169 | 6539 | Vrk1 | . | Vrk1 |
| chr12 | 111940531 | 111941453 | INT_STITCHED_6190 | 295 | Hsp90aa1 | . | Hsp90aa1 |
| chr12 | 112075298 | 112076240 | INT_STITCHED_6192 | 273 | Stk30 | . | Stk30 |
| chr12 | 112908378 | 112914863 | INT_STITCHED_6195 | 705 | Ckb, Trmt61a | . | Ckb |
| chr12 | 117645942 | 117646660 | INT_STITCHED_6200 | 8345 | Ncapg2, D430020J02Rik | . | Ncapg2 |
| chr12 | 120476393 | 120476813 | INT_STITCHED_6215 | 7174 | Itgb8 | . | Itgb8 |
| chr13 | 17791823 | 17792717 | INT_STITCHED_6256 | 6230 | 5033411D12Rik, 2810021B07Rik | . | 2810021B07Rik |
| chr13 | 19720204 | 19721138 | INT_STITCHED_6261 | 3029 | Sfrp4 | . | Sfrp4 |
| chr13 | 20132694 | 20133451 | INT_STITCHED_6264 | 3726 | . | Elmo1 | Elmo1 |
| chr13 | 20275154 | 20275936 | INT_STITCHED_6267 | 1192 | Elmo1 | Txndc3 | Elmo1 |
| chr13 | 21819716 | 21820326 | INT_STITCHED_6274 | 3648 | Hist1h2bm | . | Hist1h2bm |
| chr13 | 21840858 | 21841391 | INT_STITCHED_6275 | 4915 | Hist1h2bn, Hist1h2ak, Hist1h4k | . | Hist1h4k |
| chr13 | 21877978 | 21883093 | INT_STITCHED_6276 | 351 | Hist1h2bp, Hist1h2an, Hist1h3i, Hist1h1b | . | Hist1h2kbp |
| chr13 | 23583742 | 23584526 | INT_STITCHED_6279 | 3060 | Btn2a2 | . | Btn2a2 |
| chr13 | 23678018 | 23687970 | INT_STITCHED_6280 | 344 | Hist1h4d | . | Hist1h4d |
| chr13 | 23833718 | 23834547 | INT_STITCHED_6281 | 391 | Hist1h1c, Hist1h3c, Hist1h2bb | . | Hist1h3c |
| chr13 | 24929573 | 24930214 | INT_STITCHED_6284 | 6023 | Tdp2, Acot13 | . | Tdp2 |
| chr13 | 25366681 | 25367257 | INT_STITCHED_6287 | 3396 | Nrsn1 | . | Nrsn1 |
| chr13 | 34130311 | 34131047 | INT_STITCHED_6307 | 6483 | Bph1 | . | Bph1 |
| chr13 | 34201201 | 34202268 | INT_STITCHED_6308 | 434 | . | Tubb2b | Tubb2b |
| chr13 | 34222647 | 34226305 | INT_STITCHED_6309 | 622 | Tubb2b | Tubb2a | Tubb2b |
| chr13 | 35829899 | 35831775 | INT_STITCHED_6317 | 1240 | Cdyl | . | Cdyl |
| chr13 | 40959133 | 40964971 | INT_STITCHED_6339 | 319 | Gcnt2 | . | Gcnt2 |
| chr13 | 41012552 | 41013182 | INT_STITCHED_6340 | 1683 | Gcnt2 | . | Gcnt2 |
| chr13 | 43709828 | 43710545 | INT_STITCHED_6355 | 5257 | Rnf182 | . | Rnf182 |
| chr13 | 44800270 | 44801323 | INT_STITCHED_6366 | 461 | . | Jarid2 | Jarid2 |
| chr13 | 44817274 | 44824484 | INT_STITCHED_6367 | 581 | Jarid2 | . | Jarid2 |
| chr13 | 49276801 | 49277722 | INT_STITCHED_6386 | 2201 | Ninj1 | . | Ninj1 |
| chr13 | 51940931 | 51942277 | INT_STITCHED_6396 | 523 | Gadd45g | . | Gadd45g |
| chr13 | 52015693 | 52016983 | INT_STITCHED_6398 | 674 | . | Gadd45g | Gadd45g |
| chr13 | 52347463 | 52348186 | INT_STITCHED_6401 | 2330 | . | Gadd45g, Diras2 | Diras2 |
| chr13 | 53329991 | 53330847 | INT_STITCHED_6409 | 1992 | . | Ror2 | Ror2 |
| chr13 | 54162877 | 54163531 | INT_STITCHED_6412 | 6319 | Sfxn1 | . | Sfxn1 |
| chr13 | 54884318 | 54885163 | INT_STITCHED_6417 | 3296 | Tspan17 | . | Tspan17 |
| chr13 | 56244196 | 56245355 | INT_STITCHED_6422 | 854 | . | H2afy | H2afy |
| chr13 | 56713179 | 56714077 | INT_STITCHED_6427 | 2610 | Tgfbi | . | Tgfbi |
| chr13 | 59690911 | 59691486 | INT_STITCHED_6440 | 7090 | Naa35 | . | Naa35 |
| chr13 | 60272270 | 60272721 | INT_STITCHED_6442 | 5894 | Gas1 | . | Gas1 |
| chr13 | 60728970 | 60729626 | INT_STITCHED_6443 | 2400 | . | Dapk1 | Dapk1 |
| chr13 | 63629801 | 63643443 | INT_STITCHED_6456 | 406 | . | Ptch1 | Ptch1 |
| chr13 | 63670190 | 63671046 | INT_STITCHED_6457 | 2439 | Ptch1 | . | Ptch1 |
| chr13 | 67945216 | 67959075 | INT_STITCHED_6469 | 465 | BC048507 | BC048507 | BC048507 |
| chr13 | 73919814 | 73920680 | INT_STITCHED_6489 | 2743 | . | Slc12a7 | Slc12a7 |
| chr13 | 81025875 | 81025976 | INT_STITCHED_6503 | 7815 | Arrdc3 | . | Arrdc3 |
| chr13 | 81795260 | 81796035 | INT_STITCHED_6504 | 5336 | Lysmd3 | . | Lysmd3 |
| chr13 | 91064620 | 91065354 | INT_STITCHED_6526 | 3284 | Rps23, Gm15450 | . | Rps23 |
| chr13 | 93381777 | 93382383 | INT_STITCHED_6530 | 7201 | Serinc5 | . | Serinc5 |
| chr13 | 95135009 | 95135833 | INT_STITCHED_6533 | 2985 | Ap3b1 | . | Ap3b1 |
| chr13 | 97443596 | 97446190 | INT_STITCHED_6552 | 2544 | Hmgcr | . | Hmgcr |
| chr13 | 97836707 | 97837573 | INT_STITCHED_6553 | 1068 | Fam169a | . | Fam169a |
| chr13 | 97966165 | 97977878 | INT_STITCHED_6555 | 616 | Hexb | Hexb | Hexb |
| chr13 | 98014519 | 98015236 | INT_STITCHED_6556 | 3643 | Enc1 | . | Enc1 |

TABLE S2C-continued

| Typical enhancer to gene assignment | | | | | | | |
|---|---|---|---|---|---|---|---|
| chr | start | end | TE_ID | TE_rank | proximal active genes (TE within 4 kb of TSS) | interacting active genes (SMC1 PET interactions) | nearest genes |
| chr13 | 98087481 | 98090981 | INT_STITCHED_6558 | 1579 | . | Enc1 | Enc1 |
| chr13 | 98264472 | 98265266 | INT_STITCHED_6560 | 2674 | . | Enc1 | Enc1 |
| chr13 | 98357754 | 98358697 | INT_STITCHED_6562 | 669 | . | Enc1 | Enc1 |
| chr13 | 100284416 | 100285117 | INT_STITCHED_6580 | 4686 | Mtap1b | . | Mtap1b |
| chr13 | 110565130 | 110569253 | INT_STITCHED_6617 | 879 | . | Mir1904 | Mir1904 |
| chr13 | 113230066 | 113231347 | INT_STITCHED_6629 | 1467 | . | Il6st | Il6st |
| chr13 | 113252258 | 113253581 | INT_STITCHED_6630 | 1221 | Il6st | . | Il6st |
| chr13 | 114397781 | 114409794 | INT_STITCHED_6636 | 433 | Snx18 | Snx18 | Snx18 |
| chr13 | 115890657 | 115891471 | INT_STITCHED_6647 | 5940 | Itga1 | . | Itga1 |
| chr13 | 118004296 | 118004900 | INT_STITCHED_6650 | 3770 | Emb | . | Emb |
| chr14 | 9051276 | 9051941 | INT_STITCHED_6658 | 4216 | Kctd6 | . | Kctd6 |
| chr14 | 19159762 | 19160472 | INT_STITCHED_6696 | 3410 | Ube2e1 | . | Ube2e1 |
| chr14 | 21296378 | 21296820 | INT_STITCHED_6706 | 5511 | Anxa7 | . | Anxa7 |
| chr14 | 26137169 | 26138011 | INT_STITCHED_6720 | 1523 | . | Zmiz1 | Zmiz1 |
| chr14 | 26410307 | 26411097 | INT_STITCHED_6722 | 496 | 4931406H21Rik | . | 4931406H21Rik |
| chr14 | 31470534 | 31471189 | INT_STITCHED_6747 | 5925 | Rft1 | . | Rft1 |
| chr14 | 33667117 | 33667576 | INT_STITCHED_6755 | 5182 | E130203B14Rik | . | E130203B14Rik |
| chr14 | 35125619 | 35137157 | INT_STITCHED_6757 | 918 | Glud1, Fam35a | . | Glud1 |
| chr14 | 37908776 | 37909202 | INT_STITCHED_6767 | 5315 | Cdhr1 | . | Cdhr1 |
| chr14 | 48192256 | 48193061 | INT_STITCHED_6783 | 724 | Atg14 | . | Atg14 |
| chr14 | 51402468 | 51403045 | INT_STITCHED_6800 | 5810 | Ttc5 | . | Ttc5 |
| chr14 | 51558001 | 51558879 | INT_STITCHED_6802 | 3169 | Pnp | . | Pnp |
| chr14 | 52505644 | 52512650 | INT_STITCHED_6806 | 2589 | Mett11d1 | . | Mett11d1 |
| chr14 | 52685699 | 52686443 | INT_STITCHED_6807 | 1423 | Snord58b | . | Snord58b |
| chr14 | 52903759 | 52904402 | INT_STITCHED_6808 | 6169 | Rab2b, Tox4 | . | Rab2b |
| chr14 | 55034351 | 55034932 | INT_STITCHED_6813 | 1230 | Slc7a7 | . | Slc7a7 |
| chr14 | 56453893 | 56454720 | INT_STITCHED_6820 | 1918 | . | Nfatc4 | Nfatc4 |
| chr14 | 58148750 | 58156587 | INT_STITCHED_6825 | 353 | Il17d | . | Il17d |
| chr14 | 58351276 | 58352213 | INT_STITCHED_6826 | 4644 | . | Lats2 | Lats2 |
| chr14 | 61274229 | 61274887 | INT_STITCHED_6840 | 3553 | . | Spata13 | Spata13 |
| chr14 | 61752861 | 61757994 | INT_STITCHED_6847 | 1431 | Sacs | . | Sacs |
| chr14 | 62221688 | 62222494 | INT_STITCHED_6848 | 2608 | Trim13 | . | Trim13 |
| chr14 | 62950025 | 62953666 | INT_STITCHED_6853 | 597 | Rnaseh2b | Gucy1b2 | Rnaseh2b |
| chr14 | 66422334 | 66422947 | INT_STITCHED_6868 | 7006 | Pbk | . | Pbk |
| chr14 | 66741005 | 66742036 | INT_STITCHED_6870 | 2212 | Ephx2 | . | Ephx2 |
| chr14 | 66902737 | 66903245 | INT_STITCHED_6871 | 7981 | Ptk2b | . | Ptk2b |
| chr14 | 68506004 | 68512434 | INT_STITCHED_6878 | 770 | . | Dock5 | Dock5 |
| chr14 | 68554515 | 68560104 | INT_STITCHED_6879 | 1749 | Dock5 | . | Dock5 |
| chr14 | 70751362 | 70752223 | INT_STITCHED_6886 | 1690 | Slc39a14 | . | Slc39a14 |
| chr14 | 73637897 | 73638790 | INT_STITCHED_6892 | 2422 | Lpar6 | . | Lpar6 |
| chr14 | 76958882 | 76959494 | INT_STITCHED_6905 | 4979 | Serp2 | . | Serp2 |
| chr14 | 78937419 | 78938329 | INT_STITCHED_6918 | 3162 | Akap11 | . | Akap11 |
| chr14 | 79121670 | 79134144 | INT_STITCHED_6920 | 751 | Dgkh | . | Dgkh |
| chr14 | 79964561 | 79965081 | INT_STITCHED_6925 | 3530 | . | Sugt1 | Sugt1 |
| chr14 | 79983072 | 79983942 | INT_STITCHED_6926 | 3473 | Sugt1 | . | Sugt1 |
| chr14 | 99438364 | 99439107 | INT_STITCHED_6951 | 2329 | Mzt1, 6720463M24Rik | . | Mzt1 |
| chr14 | 103474469 | 103477990 | INT_STITCHED_6969 | 6686 | Cln5 | . | Cln5 |
| chr14 | 105572867 | 105573451 | INT_STITCHED_6977 | 7790 | Rbm26 | . | Rbm26 |
| chr14 | 106319658 | 106320994 | INT_STITCHED_6983 | 663 | . | Spry2 | Spry2 |
| chr14 | 117326693 | 117327070 | INT_STITCHED_6995 | 6044 | Gpc6 | . | Gpc6 |
| chr14 | 118629366 | 118630181 | INT_STITCHED_6999 | 5217 | Sox21 | . | Sox21 |
| chr14 | 119332449 | 119333029 | INT_STITCHED_7007 | 4788 | Dnajc3 | . | Dnajc3 |
| chr14 | 120883645 | 120884276 | INT_STITCHED_7011 | 8270 | Rap2a | . | Rap2a |
| chr14 | 121905233 | 121906137 | INT_STITCHED_7018 | 716 | Slc15a1 | . | Slc15a1 |
| chr15 | 7065153 | 7068694 | INT_STITCHED_7046 | 435 | . | Lifr | Lifr |
| chr15 | 9064661 | 9065183 | INT_STITCHED_7054 | 1757 | Skp2, Tmbrd2 | . | Skp2 |
| chr15 | 10615155 | 10617848 | INT_STITCHED_7060 | 687 | . | Rai14 | Rai14 |
| chr15 | 10640824 | 10653875 | INT_STITCHED_7061 | 331 | Rai14 | Rai14 | Rai14 |
| chr15 | 10906708 | 10907428 | INT_STITCHED_7063 | 6029 | Amacr | . | Amacr |
| chr15 | 12045435 | 12046215 | INT_STITCHED_7072 | 2830 | Zfr | . | Zfr |
| chr15 | 12133202 | 12134066 | INT_STITCHED_7073 | 1153 | Mtmr12 | . | Mtmr12 |
| chr15 | 12243117 | 12252382 | INT_STITCHED_7075 | 4108 | Golph3 | . | Golph3 |
| chr15 | 18748130 | 18748646 | INT_STITCHED_7092 | 3781 | Cdh10 | . | Cdh10 |
| chr15 | 28000620 | 28001311 | INT_STITCHED_7111 | 2701 | . | Trio | Trio |
| chr15 | 36941214 | 36941629 | INT_STITCHED_7133 | 3228 | Zfp706 | . | Zfp706 |
| chr15 | 37989429 | 38008159 | INT_STITCHED_7140 | 718 | Ubr5 | Ubr5 | Ubr5 |
| chr15 | 53173777 | 53175470 | INT_STITCHED_7170 | 2943 | Ext1 | . | Ext1 |
| chr15 | 54746572 | 54747189 | INT_STITCHED_7173 | 7556 | Enpp2 | . | Enpp2 |

TABLE S2C-continued

| Typical enhancer to gene assignment | | | | | | | |
|---|---|---|---|---|---|---|---|
| chr | start | end | TE_ID | TE_rank | proximal active genes (TE within 4 kb of TSS) | interacting active genes (SMC1 PET interactions) | nearest genes |
| chr15 | 55095920 | 55100307 | INT_STITCHED_7175 | 571 | . | Depdc6 | Depdc6 |
| chr15 | 56573900 | 56575358 | INT_STITCHED_7180 | 1521 | . | Has2as, Has2 | Has2 |
| chr15 | 58052823 | 58053270 | INT_STITCHED_7184 | 4922 | Fbxo32 | . | Fbxo32 |
| chr15 | 58244484 | 58245397 | INT_STITCHED_7186 | 2649 | D15Ertd621e | . | D15Ertd621e |
| chr15 | 58901790 | 58915123 | INT_STITCHED_7187 | 323 | Mtss1 | . | Mtss1 |
| chr15 | 61810188 | 61811058 | INT_STITCHED_7200 | 3145 | Myc | . | Myc |
| chr15 | 61841217 | 61844889 | INT_STITCHED_7201 | 648 | . | Myc | Myc |
| chr15 | 68752023 | 68752528 | INT_STITCHED_7219 | 7222 | Khdrbs3 | . | Khdrbs3 |
| chr15 | 73013516 | 73014184 | INT_STITCHED_7224 | 1136 | Eif2c2 | Kcnk9 | Eif2c2 |
| chr15 | 75708006 | 75732455 | INT_STITCHED_7240 | 354 | Naprt1 | Ze3h3, Pycrl | Naprt1 |
| chr15 | 76909283 | 76909985 | INT_STITCHED_7245 | 7260 | . | Rbm9 | Rbm9 |
| chr15 | 77678011 | 77678785 | INT_STITCHED_7249 | 2418 | Myh9 | . | Myh9 |
| chr15 | 78726841 | 78727700 | INT_STITCHED_7252 | 6124 | Sh3bp1 | . | Sh3bp1 |
| chr15 | 79278426 | 79279059 | INT_STITCHED_7254 | 5952 | Csnk1e | . | Csnk1e |
| chr15 | 81530381 | 81531523 | INT_STITCHED_7267 | 1732 | Chadl | . | Chadl |
| chr15 | 81560234 | 81560989 | INT_STITCHED_7268 | 1988 | Rangap1 | . | Rangap1 |
| chr15 | 82050108 | 82060103 | INT_STITCHED_7269 | 965 | Tnfrsf13c | . | Tnfrsf13c |
| chr15 | 84016374 | 84020249 | INT_STITCHED_7275 | 763 | Samm50 | . | Samm50 |
| chr15 | 85668308 | 85668848 | INT_STITCHED_7280 | 8064 | Ttc38 | . | Ttc38 |
| chr15 | 85696253 | 85696964 | INT_STITCHED_7281 | 1767 | Gtse1 | . | Gtse1 |
| chr15 | 89308072 | 89308194 | INT_STITCHED_7289 | 3434 | Arsa | . | Arsa |
| chr15 | 90886302 | 90887037 | INT_STITCHED_7294 | 2964 | Kif21aa | . | Kif21a |
| chr15 | 93227987 | 93228712 | INT_STITCHED_7300 | 3529 | Pphln1, Zcrb1 | . | Pphln1 |
| chr15 | 95618532 | 95618978 | INT_STITCHED_7305 | 8246 | Ano6 | . | Ano6 |
| chr15 | 96009647 | 96010368 | INT_STITCHED_7308 | 3414 | Gm4371 | . | Gm4371 |
| chr15 | 96532896 | 96533663 | INT_STITCHED_7314 | 2240 | Slc38a2 | . | Slc38a2 |
| chr15 | 97659779 | 97660356 | INT_STITCHED_7319 | 1887 | Hdac7 | . | Hdac7 |
| chr15 | 99702760 | 99705639 | INT_STITCHED_7327 | 425 | Lima1 | . | Lima1 |
| chr15 | 99871865 | 99872478 | INT_STITCHED_7329 | 5280 | Dip2b | . | Dip2b |
| chr15 | 100304382 | 100305176 | INT_STITCHED_7332 | 1241 | Letmd1 | . | Letmd1 |
| chr15 | 101107344 | 101108241 | INT_STITCHED_7336 | 865 | 9430023L20Rik | 9430023L20Rik | 9430023L20Rik |
| chr15 | 102044350 | 102045008 | INT_STITCHED_7337 | 1330 | Zfp740 | . | Zfp740 |
| chr15 | 102073324 | 102074272 | INT_STITCHED_7338 | 421 | Rarg | Itgb7, Mfsd5, Rarg | Rarg |
| chr16 | 3849599 | 3850539 | INT_STITCHED_7344 | 4390 | Zfp174 | . | Zfp174 |
| chr16 | 5252339 | 5252888 | INT_STITCHED_7349 | 4879 | Fam86 | . | Fam86 |
| chr16 | 11260700 | 11261095 | INT_STITCHED_7374 | 5533 | Gspt1, Mir1945 | . | Mir1945 |
| chr16 | 13785839 | 13786611 | INT_STITCHED_7389 | 2293 | Rrn3 | . | Rrn3 |
| chr16 | 15587600 | 15588338 | INT_STITCHED_7394 | 5959 | Ube2v2 | . | Ube2v2 |
| chr16 | 16302093 | 16302827 | INT_STITCHED_7399 | 3684 | Yars2 | . | Yars2 |
| chr16 | 16825494 | 16826238 | INT_STITCHED_7401 | 4532 | Spag6 | . | Spag6 |
| chr16 | 17928738 | 17929621 | INT_STITCHED_7404 | 2773 | Slc25a1 | Dgcr14, Gsc2 | Sle25a1 |
| chr16 | 18242932 | 18243570 | INT_STITCHED_7405 | 4927 | Ranbp1, Trmt2a | . | Ranbp1 |
| chr16 | 21995128 | 21996129 | INT_ST1TCHED_7422 | 1389 | Liph | . | Liph |
| chr16 | 22015572 | 22016286 | INT_STITCHED_7423 | 3870 | Senp2 | . | Senp2 |
| chr16 | 22139712 | 22161378 | INT_STITCHED_7425 | 750 | Igf2bp2 | . | Igf2bp2 |
| chr16 | 22441980 | 22442886 | INT_STITCHED_7428 | 4560 | Etv5 | . | Etv5 |
| chr16 | 24443296 | 24444024 | INT_STITCHED_7439 | 4206 | Lpp | . | Lpp |
| chr16 | 30062920 | 30063517 | INT_STITCHED_7457 | 379 | Hes1 | 4632428C04Rik | Hes1 |
| chr16 | 30280722 | 30286306 | INT_STITCHED_7459 | 799 | Lrrc15 | . | Lrrc15 |
| chr16 | 33178393 | 33179116 | INT_STITCHED_7474 | 2437 | Osbpl11 | . | Osbpl11 |
| chr16 | 33246666 | 33247168 | INT_STITCHED_7475 | 3771 | Snx4 | . | Snx4 |
| chr16 | 33379458 | 33380156 | INT_STITCHED_7476 | 2939 | Zfp148 | . | Zfp148 |
| chr16 | 34692943 | 34693565 | INT_STITCHED_7487 | 7029 | Ccdc14 | . | Ccdc14 |
| chr16 | 35966441 | 35966967 | INT_STITCHED_7498 | 4502 | . | Parp9, Dtx31 | Dtx31 |
| chr16 | 36069406 | 36070168 | INT_STITCHED_7499 | 4226 | Fam162a, Ccdc58 | . | Fam162a |
| chr16 | 36821606 | 36822164 | INT_STITCHED_7504 | 5866 | Iqcb1, Eaf2 | . | Eaf2 |
| chr16 | 38558387 | 38558980 | INT_STITCHED_7510 | 553 | Tmem39a | . | Tmem39a |
| chr16 | 45726028 | 45726467 | INT_STITCHED_7533 | 5076 | Tagln3 | . | Tagln3 |
| chr16 | 46500728 | 46501425 | INT_STITCHED_7535 | 2532 | Pvrl3 | . | Pvrl3 |
| chr16 | 48283498 | 4828425 | INT_STITCHED_7537 | 4304 | Dppa4 | . | Dppa4 |
| chr16 | 48303474 | 48311051 | INT_STITCHED_7538 | 424 | Dppa2 | . | Dppa2 |
| chr16 | 49861220 | 49862107 | INT_STITCHED_7545 | 6187 | Cd47 | . | Cd47 |
| chr16 | 59643496 | 59644072 | INT_STITCHED_7559 | 6185 | Arl6 | . | Arl6 |
| chr16 | 64766788 | 64767304 | INT_STITCHED_7563 | 3850 | 4930453N24Rik | . | 4930453N24Rik |
| chr16 | 78573987 | 78574492 | INT_STITCHED_7592 | 6130 | D16Ertd472e | . | D16Ertd472e |
| chr16 | 84825000 | 84825796 | INT_STITCHED_7598 | 6321 | LOC654426 | . | LOC654426 |

TABLE S2C-continued

| Typical enhancer to gene assignment | | | | | | | |
|---|---|---|---|---|---|---|---|
| chr | start | end | TE_ID | TE_rank | proximal active genes (TE within 4 kb of TSS) | interacting active genes (SMC1 PET interactions) | nearest genes |
| chr16 | 90283267 | 90283824 | INT_STITCHED_7605 | 4518 | Srsf15 | . | Srsf15 |
| chr16 | 91379084 | 91379709 | INT_STITCHED_7614 | 5871 | Ifnar2 | . | Ifnar2 |
| chr16 | 91480485 | 91481228 | INT_STITCHED_7616 | 3701 | Ifna1 | . | Ifnar1 |
| chr16 | 93826367 | 93827291 | INT_STITCHED_7625 | 1443 | Morc3 | . | Morc3 |
| chr16 | 96304699 | 96305588 | INT_STITCFIED_7631 | 500 | Brwd1 | . | Brwd1 |
| chr17 | 3551086 | 3551760 | INT_STITCHED_7642 | 6038 | Tfb1m | . | Tfb1m |
| chr17 | 5407856 | 5417145 | INT_STITCHED_7655 | 1717 | Ldhal6b | . | Ldhal6b |
| chr17 | 5490301 | 5490994 | INT_STITCHED_7656 | 6367 | Zdhhc14 | . | Zdhhc14 |
| chr17 | 8568963 | 8569332 | INT_STITCHED_7669 | 7541 | T2 | . | T2 |
| chr17 | 10527703 | 10528580 | INT_STITCHED_7679 | 1195 | . | Qk | Qk |
| chr17 | 10693553 | 10694165 | INT_STITCIIED_7683 | 2446 | . | Qk | Qk |
| chr17 | 14336522 | 14337258 | INT_STITCHED_7693 | 3352 | Dact2 | . | Dact2 |
| chr17 | 14829950 | 14831243 | INT_STITCHED_7696 | 2466 | Thbs2 | . | Thbs2 |
| chr17 | 15326610 | 15327365 | INT_STITCHED_7697 | 2593 | . | Dll1 | Dll1 |
| chr17 | 15384508 | 15385475 | INT_STITCHED_7699 | 733 | . | Dll1 | Dll1 |
| chr17 | 15513799 | 15519743 | INT_STITCHED_7700 | 994 | Dll1 | Dll1 | Dll1 |
| chr17 | 17749211 | 17749858 | INT_STITCHED_7709 | 5200 | . | Lnpep | Lnpep |
| chr17 | 23739864 | 23740605 | INT_STITCHED_7716 | 2010 | Zfp13, Zscan10 | . | Zscan10 |
| chr17 | 23780427 | 23780792 | INT_STITCHED_7718 | 6220 | Mmp25 | . | Mmp25 |
| chr17 | 23864226 | 23864239 | INT_STITCHED_7720 | 8089 | Pkmyt1 | . | Pkmyt1 |
| chr17 | 23926672 | 23927280 | INT_STITCHED_7721 | 3044 | Flywch2 | . | Flywch2 |
| chr17 | 24270829 | 24277012 | INT_STITCHED_7722 | 3300 | Pdpk1 | . | Pdpk1 |
| chr17 | 24339885 | 24340488 | INT_STITCHED_7723 | 2003 | Ntn3 | . | Ntn3 |
| chr17 | 25891931 | 25892657 | INT_STITCHED_7727 | 8210 | . | Narfl | Narfl |
| chr17 | 27638391 | 27639320 | INT_STITCHED_7735 | 2037 | Grm4 | . | Grm4 |
| chr17 | 28317168 | 28317281 | INT_STITCHED_7740 | 8206 | Zfp523 | . | Zfp523 |
| chr17 | 29144582 | 29145786 | INT_STITCHED_7744 | 843 | Stk38 | . | Stk38 |
| chr17 | 29631024 | 29631722 | INT_STITCHED_7754 | 2521 | Pim1 | . | Pim1 |
| chr17 | 31433655 | 31445349 | INT_STITCHED_7763 | 393 | Slc37a1 | Slc37a1 | Slc37a1 |
| chr17 | 32330938 | 32331519 | INT_STITCHED_7769 | 6586 | Ephx3 | . | Ephx3 |
| chr17 | 33493774 | 33494196 | INT_STITCHED_7774 | 7483 | Zfp81 | . | Zfp81 |
| chr17 | 34029161 | 34029875 | INT_STITCHED_7777 | 2571 | Kifc1 | . | Kifc1 |
| chr17 | 35029917 | 35030731 | INT_STITCHED_7781 | 4836 | Ehmt2, Zbtb12 | . | Zbtb12 |
| chr17 | 35087242 | 35087957 | INT_STITCHED_7782 | 3133 | Snord52, 1110038B12Rik | . | Snord52 |
| chr17 | 35201745 | 35214088 | INT_STITCHED_7783 | 489 | Ly6g6c, AU023871, G6b, Ddah2, Ly6g6e, Ly6g6d | G6b, Ddah2, Ly6g6c, AU023871, Ly6g6e, Ly6g6d | Ly6g6c |
| chr17 | 36969445 | 36981968 | INT_STITCHED_7790 | 811 | Trim26 | . | Trim26 |
| chr17 | 43010751 | 43011486 | INT_STITCHED_7803 | 7133 | Cd2ap | . | Cd2ap |
| chr17 | 45743747 | 45744742 | INT_STITCHED_7814 | 249 | Gm7325 | Gm7325, Slc29a1 | Gm7325 |
| chr17 | 45743747 | 45767400 | INT_STITCHED_7815 | | . | Gm7325 | Gm7325 |
| chr17 | 46134937 | 46135825 | INT_STITCHED_7817 | 2549 | . | Vegfa | Vegfa |
| chr17 | 46929748 | 46930535 | INT_STITCHED_7819 | 1600 | . | Rpl7l1 | Rpl7l1 |
| chr17 | 47702974 | 47709143 | INT_STITCHED_7823 | 233 | . | Ccnd3 | Ccnd3 |
| chr17 | 47876080 | 47877026 | INT_STITCHED_7825 | 668 | . | Frs3 | Frs3 |
| chr17 | 47925179 | 47925764 | INT_STITCHED_7826 | 3923 | Tcfeb | . | Taal |
| chr17 | 48013535 | 48035748 | INT_STITCHED_7828 | 415 | . | Foxp4 | Foxp4 |
| chr17 | 48112639 | 48113467 | INT_STITCHED_7830 | 1618 | . | Foxp4 | Foxp4 |
| chr17 | 53690666 | 53701713 | INT_STITCHED_7849 | 516 | Kat2b | . | Kat2b |
| chr17 | 56437658 | 56438221 | INT_STITCHED_7852 | 8198 | Arrdc5, Uhrf1 | . | Arrdc5 |
| chr17 | 56972466 | 56973551 | INT_STITCHED_7853 | 1996 | Rfx2 | . | Rfx2 |
| chr17 | 57008637 | 57009589 | INT_STITCHED_7854 | 1483 | 1700061G19Rik | | 1700061G19Rik |
| chr17 | 66305463 | 66305913 | INT_STITCHED_7870 | 4767 | Twsg1 | . | Twsg1 |
| chr17 | 66453333 | 66453853 | INT_STITCHED_7871 | 4415 | Ndufv2 | . | Ndufv2 |
| chr17 | 68041107 | 68061143 | INT_STITCHED_7877 | 468 | Lama1 | . | Lama1 |
| chr17 | 68353194 | 68354191 | INT_STITCHED_7878 | 2835 | Arhgap28 | . | Arhgap28 |
| chr17 | 74927087 | 74927097 | INT_STITCHED_7897 | 8063 | Birc6 | . | Birc6 |
| chr17 | 75956321 | 75956983 | INT_STITCHED_7905 | 5048 | Fam98a | . | Fam98a |
| chr17 | 79313190 | 79313799 | INT_STITCHED_7912 | 1560 | 1110001A16Rik | . | 1110001A16Rik |
| chr17 | 81128692 | 81129358 | INT_STITCHED_7931 | 6152 | Map4k3 | . | Map4k3 |
| chr17 | 84582744 | 84583323 | INT_STITCHED_7948 | 1781 | Zfp36l2 | Zfp36l2 | Zfp36l2 |
| chr17 | 86535700 | 86548495 | INT_STITCHED_7964 | 2602 | Srbd1 | . | Srbd1 |
| chr17 | 87930591 | 87931316 | INT_STITCHED_7969 | 1832 | . | Calm2 | Calm2 |
| chr17 | 88076955 | 88077637 | INT_STITCHED_7971 | 5992 | Msh2 | . | Msh2 |
| chr17 | 88372701 | 88373685 | INT_STITCHED_7972 | 900 | Msh6 | . | Msh6 |
| chr18 | 3385402 | 3385870 | INT_STITCHED_7995 | 5889 | Cul2 | . | Cul2 |

TABLE S2C-continued

Typical enhancer to gene assignment

| chr | start | end | TE_ID | TE_rank | proximal active genes (TE within 4 kb of TSS) | interacting active genes (SMC1 PET interactions) | nearest genes |
|---|---|---|---|---|---|---|---|
| chr18 | 5163169 | 5163726 | INT_STITCHED_8001 | 1733 | . | Zfp438 | Zfp438 |
| chr18 | 6516515 | 6517140 | INT_STITCHED_8006 | 5074 | Epc1 | . | Epc1 |
| chr18 | 9214813 | 9216976 | INT_STITCHED_8012 | 8186 | Fzd8 | . | Fzd8 |
| chr18 | 12002313 | 12002823 | INT_STITCHED_8021 | 6352 | Cables1, Mir1901 | . | Mir1901 |
| chr18 | 12397312 | 12398585 | INT_STITCHED_8024 | 2342 | Npc1 | . | Npc1 |
| chr18 | 12797614 | 12797946 | INT_STITCHED_8029 | 7046 | Ttc39c | . | Ttc39c |
| chr18 | 14832586 | 14835577 | INT_STITCHED_8038 | 2705 | Ss18 | . | 5s18 |
| chr18 | 20899101 | 20900111 | INT_STITCHED_8051 | 1742 | B4galt6 | . | B4galt6 |
| chr18 | 21101897 | 21102870 | INT_STITCHED_8053 | 899 | Rnf125 | . | Rnf125 |
| chr18 | 24151920 | 24152681 | INT_STITCHED_8065 | 3525 | Zfp35 | . | Zfp35 |
| chr18 | 33621690 | 33622128 | INT_STITCHED_8099 | 7581 | D0H4S114 | . | D0H4S114 |
| chr18 | 34109932 | 34110743 | INT_STITCHED_8104 | 1197 | . | Epb4.1l4a | Epb4.1l4a |
| chr18 | 34157592 | 34158493 | INT_STITCHED_8106 | 1702 | . | Epb4.1l4a | Epb4.1l4a |
| chr18 | 34701440 | 34715289 | INT_STITCHED_8109 | 1027 | Wnt8a | Wnt8a | Wnt8a |
| chr18 | 34884236 | 34884615 | INT_STITCHED_8111 | 4424 | Gfra3 | . | Gfra3 |
| chr18 | 34937293 | 34938906 | INT_STITCHED_8112 | 1343 | Kdm3b | . | Kdm3b |
| chr18 | 35982138 | 35983371 | INT_STITCHED_8122 | 717 | Cxxc5 | Cxxc5 | Cxxc5 |
| chr18 | 36924103 | 36924650 | INT_STITCHED_8127 | 4027 | Wdr55, Dnd1 | . | Dnd1 |
| chr18 | 37892904 | 37893442 | INT_STITCHED_8128 | 5966 | Pcdhgb5, Pcdhga9 | . | Pcdhgb5 |
| chr18 | 37911821 | 37912317 | INT_STITCHED_8129 | 7509 | Pcdhga11 | . | Pcdhga11 |
| chr18 | 37931149 | 37931649 | INT_STITCHED_8130 | 2988 | Pcdhga12 | Pcdhgc3 | Pcdhga12 |
| chr18 | 38000290 | 38000857 | INT_STITCHED_8131 | 3762 | . | Pcdhgc3, Pcdhgc5, Pcdhga12, Pcdhgb8 | Pcdhgc5 |
| chr18 | 38092039 | 38092926 | INT_STITCHED_8132 | 1852 | Diap1 | . | Diap1 |
| chr18 | 42432273 | 42432907 | INT_STITCHED_8152 | 8174 | Rbm27, Gm4013 | . | Rbm27 |
| chr18 | 44538369 | 44547262 | INT_STITCHED_8160 | 8173 | Dcp2 | . | Dcp2 |
| chr18 | 47518017 | 47518632 | INT_STITCHED_8170 | 3236 | . | Sema6a | Sema6a |
| chr18 | 47652330 | 47656137 | INT_STITCHED_8172 | 1172 | . | Sema6a | Sema6a |
| chr18 | 49992787 | 49993420 | INT_STITCHED_8179 | 8172 | Dmxl1 | . | Dmxl1 |
| chr18 | 53570940 | 53571612 | INT_STITCHED_8184 | 4918 | Ppic | . | Ppic |
| chr18 | 58016521 | 58042474 | INT_STITCHED_8201 | 1921 | Slc12q2 | . | Slc12q2 |
| chr18 | 61194178 | 61196405 | INT_STITCHED_8207 | 1611 | . | Slc6a7 | Slc6a7 |
| chr18 | 65575946 | 65587598 | INT_STITCHED_8222 | 1816 | Malt1 | . | Malt1 |
| chr18 | 65737262 | 65738119 | INT_STITCHED_8223 | 2710 | Zfp532 | . | Zfp532 |
| chr18 | 66620651 | 66621456 | INT_STITCHED_8233 | 2103 | Pmaip1 | . | Pmaip1 |
| chr18 | 74223279 | 74224086 | INT_STITCHED_8255 | 2698 | Mapk4 | . | Mapk4 |
| chr18 | 77799062 | 77800652 | INT_STITCHED_8272 | 446 | Rnf165 | . | Rnf165 |
| chr18 | 77947287 | 77947954 | INT_STITCHED_8273 | 4453 | 8030462N17Rik, 4930465K10Rik | . | 8030462N17Rik |
| chr18 | 79302745 | 79303389 | INT_STITCHED_8281 | 2887 | Setbp1 | . | Setbp1 |
| chr18 | 80345132 | 80345668 | INT_STITCHED_8285 | 4859 | Adnp2 | . | Adnp2 |
| chr18 | 83085081 | 83085678 | INT_STITCHED_8304 | 5214 | Zfp516, 4930592I03Rik | . | Zfp516 |
| chr18 | 85101655 | 85104293 | INT_STITCHED_8309 | 369 | Fbxo15 | . | Fbxo15 |
| chr19 | 3578494 | 3579148 | INT_STITCHED_8314 | 5749 | Ppp6r3 | . | Ppp6r3 |
| chr19 | 4809961 | 4810938 | INT_STITCHED_8317 | 1591 | Rbm14 | Rbm4b | Rbm14 |
| chr19 | 4849752 | 4850334 | INT_STITCHED_8318 | 2176 | Ctsf | . | Ctsf |
| chr19 | 5362176 | 5362769 | INT_STITCHED_8321 | 5559 | Eiflad, Banf1 | . | Banf1 |
| chr19 | 5806301 | 5807102 | INT_STITCHED_8323 | 567 | Malat1 | Neat1 | Malat1 |
| chr19 | 6008924 | 6009669 | INT_STITCHED_8325 | 2365 | Capn1 | . | Capnl |
| chr19 | 7556157 | 7556974 | INT_STITCHED_8330 | 7656 | Rtn3 | . | Rtn3 |
| chr19 | 10750948 | 10751863 | INT_STITCHED_8339 | 5044 | Pga5 | . | Pga5 |
| chr19 | 10909944 | 10910853 | INT_STITCHED_8342 | 3107 | Slc15a3 | . | Slc15a3 |
| chr19 | 11897650 | 11898585 | INT_STITCHED_8348 | 4958 | Stx3 | . | Stx3 |
| chr19 | 23226190 | 23228627 | INT_STITCHED_8387 | 340 | Mir1192 | Klf9 | Mir1192 |
| chr19 | 24625504 | 24626811 | INT_STITCHED_8395 | 5338 | Pip5k1b | . | Pip5k1b |
| chr19 | 30019855 | 30020504 | INT_STITCHED_8420 | 4142 | Il33 | . | Il33 |
| chr19 | 30103198 | 30104145 | INT_STITCHED_8422 | 8079 | Uhrf2 | . | Uhrf2 |
| chr19 | 34270171 | 34270617 | INT_STITCHED_8437 | 4678 | Stambpl1 | . | Stambpl1 |
| chr19 | 38110109 | 38124425 | INT_STITCHED_8451 | 1141 | Myof, Cep55 | . | Myof |
| chr19 | 40335693 | 40347774 | INT_STITCHED_8457 | 575 | Pdlim1 | . | Pdlim1 |
| chr19 | 41340652 | 41341549 | INT_STITCHED_8462 | 2243 | Tm9sf3 | . | Tm9sf3 |
| chr19 | 41924877 | 41928541 | INT_STITCHED_8467 | 4990 | Frat2 | . | Frat2 |
| chr19 | 42210160 | 42211146 | INT_STITCHED_8468 | 381 | . | Avpi1 | Avpi1 |
| chr19 | 44336251 | 44340919 | INT_STITCHED_8482 | 397 | . | Scd2 | Scd2 |

TABLE S2C-continued

| Typical enhancer to gene assignment | | | | | | | |
|---|---|---|---|---|---|---|---|
| chr | start | end | TE_ID | TE_rank | proximal active genes (TE within 4 kb of TSS) | interacting active genes (SMC1 PET interactions) | nearest genes |
| chr19 | 45431191 | 45431778 | INT_STITCHED_8492 | 4657 | Btrc | . | Btrc |
| chr19 | 46111427 | 46112378 | INT_STITCHED_8495 | 1345 | Ldb1 | Ldb1, Nolc1 | Ldb1 |
| chr19 | 46147545 | 46148245 | INT_STITCHED_8496 | 2738 | Nolc1 | . | Nolc1 |
| chr19 | 46571486 | 46579213 | INT_STITCHED_8497 | 398 | Trim8 | . | Trim8 |
| chr19 | 47062698 | 47063420 | INT_STITCHED_8499 | 2624 | . | Cnnm2, Nt5c2, Ina | Nt5c2 |
| chr19 | 47524932 | 47525874 | INT_STITCHED_8502 | 923 | . | Sh3pxd2a | Sh3pxd2a |
| chr19 | 55810476 | 55811196 | INT_STITCHED_8528 | 5265 | Tcf7l2 | Tcf7l2 | Tcf7l2 |
| chr19 | 57440147 | 57441699 | INT_STITCHED_8534 | 1163 | Fam160b1 | . | Fam160b1 |
| chrX | 7341901 | 7342556 | INT_STITCHED_8551 | 1800 | Tcfe3 | . | Tcfe3 |
| chrX | 7504022 | 7504775 | INT_STITCHED_8553 | 2401 | Eras | . | Eras |
| chrX | 7783981 | 7797322 | INT_STITCHED_8558 | 902 | Porcn | . | Porcn |
| chrX | 11585060 | 11585603 | INT_STITCHED_8566 | 6900 | . | Bcor | Bcor |
| chrX | 11650689 | 11656529 | INT_STITCHED_8568 | 2596 | Bcor | . | Bcor |
| chrX | 12336063 | 12336542 | INT_STITCHED_8571 | 8138 | Med14 | . | Med14 |
| chrX | 12623919 | 12624670 | INT_STITCHED_8574 | 1251 | . | Usp9x | Usp9x |
| chrX | 17148568 | 17149028 | INT_STITCHED_8579 | 2968 | Fundc1 | . | Fundc1 |
| chrX | 20450222 | 20452884 | INT_STITCHED_8589 | 1414 | Timp1 | . | Timp1 |
| chrX | 20639136 | 20640111 | INT_STITCHED_8591 | 4023 | Zfp182 | . | Zfp182 |
| chrX | 34345348 | 34357788 | INT_STITCHED_8599 | 417 | . | Slc25a5 | Slc25a5 |
| chrX | 45948994 | 45949828 | INT_STITCHED_8615 | 5413 | Zfp280c | . | Zfp280c |
| chrX | 49037620 | 49038464 | INT_STITCHED_8621 | 4650 | Hs6st2 | . | Hs6st2 |
| chrX | 49516745 | 49521331 | INT_STITCHED_8623 | 1198 | Gpc4 | . | Gpc4 |
| chrX | 49542203 | 49542936 | INT_STITCHED_8624 | 1909 | . | Gpc4 | Gpc4 |
| chrX | 68472013 | 68472518 | INT_STITCHED_8648 | 6076 | Mtm1 | . | Mtm1 |
| chrX | 68812416 | 68812867 | INT_STITCHED_8650 | 6998 | Hmgb3 | . | Hmgb3 |
| chrX | 71062069 | 71066856 | INT_STITCHED_8654 | 1325 | Pdzd4 | . | Pdzd4 |
| chrX | 74758128 | 74771144 | INT_STITCHED_8657 | 2215 | Tbl1x | . | Tbl1x |
| chrX | 83432509 | 83439416 | INT_STITCHED_8673 | 699 | Nr0b1 | . | Nr0b1 |
| chrX | 90909066 | 90918687 | INT_STITCHED_8678 | 2200 | Pcyt1b | . | Pcyt1b |
| chrX | 98279269 | 98280110 | INT_STITCHED_8695 | 2327 | Slc7a3 | . | Slc7a3 |
| chrX | 98832291 | 98835492 | INT_STITCFIED_8698 | 888 | Ogt | . | Ogt |
| chrX | 100521875 | 100522311 | INT_STITCHED_8704 | 8132 | Cdx4 | . | Cdx4 |
| chrX | 100633203 | 100633921 | INT_STITCHED_8705 | 545 | Tsix | . | Tsix |
| chrX | 101176973 | 101183244 | INT_STITCHED_8708 | 520 | Rlim | . | Rlim |
| chrX | 101391779 | 101392412 | INT_STITCHED_8709 | 4316 | C77370 | . | C77370 |
| chrX | 103119917 | 103120479 | INT_STITCHED_8713 | 7677 | Atrx | . | Atrx |
| chrX | 103207250 | 103207835 | INT_STITCHED_8714 | 3325 | Cox7b, Magt1 | . | Magt1 |
| chrX | 106210257 | 106210674 | INT_STITCHED_8718 | 6403 | Hmgn5 | . | Hmgn5 |
| chrX | 131251894 | 131252554 | INT_STITCHED_8736 | 2782 | Armcx1 | . | Armcx1 |
| chrX | 133571771 | 133572514 | INT_STITCHED_8739 | 4136 | Mcart6 | . | Mcart6 |
| chrX | 136317111 | 136317651 | INT_STITCHED_8742 | 2358 | Ripply1 | . | Ripply1 |
| chrX | 136990746 | 136995388 | INT_STITCHED_8745 | 2167 | Prps1 | . | Prps1 |
| chrX | 146912148 | 146912772 | INT_STITCHED_8754 | 1199 | . | Tmem29 | Tmem29 |
| chrX | 147484225 | 147485001 | INT_STITCHED_8756 | 2685 | Fgd1 | . | Fgd1 |
| chrX | 150159561 | 150160090 | INT_STITCHED_8766 | 6795 | 2210013O21Rik | . | 2210013O21Rik |
| chrX | 151776277 | 151776643 | INT_STITCHED_8767 | 7880 | Prdx4 | . | Prdx4 |
| chrX | 153930097 | 153930709 | INT_STITCHED_8769 | 4541 | Sms | . | Sms |
| chrX | 154034237 | 154039879 | INT_STITCHED_8771 | 1270 | Mbtps2 | . | Mbtps2 |
| chrX | 154253329 | 154253706 | INT_STITCHED_8773 | 7680 | Klh134 | . | Klh134 |
| chrX | 159193849 | 159194432 | INT_STITCHED_8781 | 2630 | Rbbp7 | . | Rbbp7 |
| chrX | 159269864 | 159270795 | INT_STITCHED_8782 | 1741 | Txlng | . | Txlng |

TABLE S3A

| Overlap with previously defined domain structures or interactions | | | | | |
|---|---|---|---|---|---|
| Sets of SMC1 high-confidence interactions (X) | Testing Query (Y) | Metric | Overlap (at least 80% reciprocal) (counts) | Out of # interactions | Overlap (at least 80% reciprocal) (percentage) |
| all intrachromosomal interactions | SMC1 ChIA-PET DeMare et al., (limb bud) | Reciprocal overlap | 1251 | 23739 | 5% |

TABLE S3A-continued

| Overlap with previously defined domain structures or interactions | | | | | |
|---|---|---|---|---|---|
| CTCF-CTCF Interactions | CTCF ChIA-PET PETs Handoko et al. | Reciprocal overlap | 6770 | 20080 | 34% |
| SD boundary interactions | CTCF ChIA-PET PETs Handoko et al. | Reciprocal overlap | 65 | 197 | 33% |
| SD boundary interactions | TD/TAD Dixon et al. | Reciprocal overlap | 5 | 197 | 3% |
| SD boundary interactions | TD/TAD Filippova et al. | Reciprocal overlap | 16 | 197 | 8% |
| SD boundary interactions | SMC1 ChIA-PET DeMare et al., (limb bud) | Reciprocal overlap | 16 | 197 | 8% |
| PD boundary interactions | CTCF ChIA-PET PETs Handoko et al. | Reciprocal overlap | 115 | 349 | 33% |
| PD boundary interactions | TD/TAD Dixon et al. | Reciprocal overlap | 13 | 349 | 4% |
| PD boundary interactions | TD/TAD Filippova et al. | Reciprocal overlap | 30 | 349 | 9% |
| PD boundary interactions | SMC1 ChIA-PET DeMare et al., (limb bud) | Reciprocal overlap | 29 | 349 | 8% |
| Enhancer-Promoter interactions | PolII ChIA-PET interactions Kieffer-Kwon et al. | Reciprocal overlap | 873 | 2921 | 30% |
| Enhancer-Promoter interactions | PolII ChIA-PET PETs Kieffer-Kwon et al. | Reciprocal overlap | 2402 | 2921 | 82% |
| Enhancer-Enhancer interactions | PolII ChIA-PET interactions Kieffer-Kwon et al. | Reciprocal overlap | 511 | 2700 | 19% |
| Enhancer-Enhancer interactions | PolII ChIA-PET PETs Kieffer-Kwon et al. | Reciprocal overlap | 1969 | 2700 | 73% |
| Promoter-Promoter interactions | PolII ChIA-PET interactions Kieffer-Kwon et al. | Reciprocal overlap | 264 | 818 | 32% |
| Promoter-Promoter interactions | PolII ChIA-PET PETs Kieffer-Kwon et al. | Reciprocal overlap | 649 | 818 | 79% |

| Sets of SMC1 high-confidence interactions (X) | Testing Query (Y) | Metric | Interactions Crossing Y (counts) | Out of # interactions | Interactions Crossing Y (percentage) |
|---|---|---|---|---|---|
| all intrachromosomal interactions | TD/TAD boundaries Dixon et al. | % X spanning Y | 1,354 | 23,739 | 6% |
| all intrachromosomal interactions | LAD boundaries Meuleman et al. | % X spanning Y | 1,180 | 23,739 | 5% |
| all intrachromosomal interactions | LOCK boundaries Wen et al. | % X spanning Y | 1,053 | 23,739 | 4% |

TABLE S3B

NPC 5C interactions that are overlapped with SMC1 interactions

| Chr | Start | End | ID | Score | Strand | Thick Start | Thick End | Item Rgb | Block Count | Block Sizes | Block Starts |
|---|---|---|---|---|---|---|---|---|---|---|---|
| chr17 | 35876754 | 36004126 | chr17: 35876754-36004126 | 999 | + | 35876754 | 36004126 | 0, 0, 0 | 2 | 1213, 7320 | 0, 120052 |
| chr16 | 91081692 | 91315585 | chr16: 91081692-91315585 | 999 | + | 91081692 | 91315585 | 0, 0, 0 | 2 | 8121, 6123 | 0, 227770 |
| chr6 | 122605776 | 122670401 | chr6: 122605776-122670401 | 999 | + | 122605776 | 122670401 | 0, 0, 0 | 2 | 8322, 3902 | 0, 60723 |

TABLE S3B-continued

| NPC 5C interactions that are overlapped with SMC1 interactions | | | | | | | | | | | |
|---|---|---|---|---|---|---|---|---|---|---|---|
| Chr | Start | End | ID | Score | Strand | Thick Start | Thick End | Item Rgb | Block Count | Block Sizes | Block Starts |
| chr16 | 91079632 | 91353041 | chr16: 91079632-91353041 | 999 | + | 91079632 | 91353041 | 0, 0, 0 | 2 | 2059, 2468 | 0, 270941 |
| chr17 | 35309283 | 35369792 | chr17: 35309283-35369792 | 999 | + | 35309283 | 35369792 | 0, 0, 0 | 2 | 12375, 17869 | 0, 42640 |
| chr17 | 35300042 | 35369792 | chr17: 35300042-35369792 | 999 | + | 35300042 | 35369792 | 0, 0, 0 | 2 | 7232, 17869 | 0, 51881 |
| chr17 | 35712435 | 35863083 | chr17 35712435-35863083 | 999 | + | 35712435 | 35863083 | 0, 0, 0 | 2 | 3047, 2345 | 0, 148303 |
| chr17 | 35770148 | 35873306 | chr17: 35770148-35873306 | 999 | + | 35770148 | 35873306 | 0, 0, 0 | 2 | 3903, 9716 | 0, 93442 |
| chr16 | 91079632 | 91365059 | chr16: 91079632-91365059 | 999 | + | 91079632 | 91365059 | 0, 0, 0 | 2 | 2059, 7174 | 0, 278253 |
| chr17 | 35782938 | 35876753 | chr17: 35782938-35876753 | 999 | + | 35782938 | 35876753 | 0, 0, 0 | 2 | 5265, 2748 | 0, 91067 |
| chr16 | 91159407 | 91315585 | chr16: 91159407-91315585 | 999 | + | 91159407 | 91315585 | 0, 0, 0 | 2 | 2410, 6123 | 0, 150055 |

TABLE S4A

| Super-enhancer Domains | | |
|---|---|---|
| Chr | Start | End |
| chr4 | 137282987 | 137358228 |
| chr4 | 141062149 | 141133641 |
| chr9 | 121156481 | 121284570 |
| chr3 | 34536922 | 34661110 |
| chr12 | 111691772 | 111830585 |
| chr19 | 5817540 | 5852134 |
| chr12 | 111691772 | 111729264 |
| chr7 | 30965803 | 30984969 |
| chr1 | 169150382 | 169237365 |
| chr1 | 137067918 | 137266493 |
| chr4 | 154502843 | 154625262 |
| chr1 | 36960319 | 37190152 |
| chr13 | 98004422 | 98291871 |
| chr14 | 64117842 | 64155310 |
| chr6 | 142425554 | 142468451 |
| chr1 | 72810841 | 72902355 |
| chr19 | 5792497 | 5886724 |
| chr7 | 87300923 | 87362292 |
| chr2 | 71454171 | 71655886 |
| chr1 | 34061676 | 34222447 |
| chr12 | 57342031 | 57506908 |
| chr1 | 120460689 | 120657075 |
| chr2 | 154237288 | 154366317 |
| chr15 | 97065222 | 97329663 |
| chr5 | 116814343 | 116927034 |
| chr7 | 86283831 | 86495624 |
| chr18 | 40414663 | 42171491 |
| chr11 | 66718693 | 66799394 |
| chr6 | 91615554 | 91692012 |
| chr10 | 66463947 | 66597903 |
| chr6 | 145190466 | 145291289 |
| chr4 | 141560318 | 141655254 |
| chr1 | 72212313 | 72267390 |
| chr7 | 38784232 | 38860117 |
| chr3 | 132992046 | 133215781 |
| chr14 | 71017056 | 71047830 |
| chr1 | 121241277 | 121341353 |
| chr7 | 152031593 | 152075769 |
| chr11 | 97517094 | 97528498 |
| chr17 | 35620607 | 35672311 |
| chr15 | 103312356 | 103379385 |

TABLE S4A-continued

| Super-enhancer Domains | | |
|---|---|---|
| Chr | Start | End |
| chr10 | 76592621 | 76716478 |
| chr12 | 56533123 | 56600970 |
| chr8 | 34878299 | 35059244 |
| chr11 | 97505763 | 97552130 |
| chr9 | 58094359 | 58130191 |
| chr10 | 84916886 | 85088671 |
| chr12 | 111654141 | 112084206 |
| chr6 | 125371654 | 125449180 |
| chr8 | 12388966 | 12513419 |
| chr11 | 117730560 | 117880702 |
| chr18 | 75423941 | 75656017 |
| chr17 | 35620607 | 35647314 |
| chr2 | 30879347 | 31008384 |
| chr7 | 4507929 | 4892642 |
| chr19 | 5792497 | 5852134 |
| chr13 | 110403658 | 110714021 |
| chr1 | 35895775 | 36192303 |
| chr14 | 76877794 | 77141159 |
| chr16 | 23087368 | 23136382 |
| chr8 | 44336405 | 44414870 |
| chr10 | 21320132 | 21716683 |
| chr1 | 138461016 | 138635417 |
| chr6 | 83829249 | 84014273 |
| chr8 | 74794083 | 74890930 |
| chr18 | 38531148 | 38620561 |
| chr3 | 9397733 | 9706079 |
| chr6 | 39365369 | 39397187 |
| chr2 | 152529858 | 152569327 |
| chr9 | 78205346 | 78234729 |
| chr12 | 12629041 | 13017241 |
| chr10 | 79495253 | 79527506 |
| chr2 | 162823799 | 162916341 |
| chr6 | 122257932 | 122343761 |
| chr9 | 110824885 | 110900571 |
| chr3 | 96354611 | 96386636 |
| chr17 | 37050504 | 37341488 |
| chr12 | 111654141 | 111913505 |
| chr1 | 183851391 | 184046719 |
| chr5 | 53745413 | 53986500 |
| chr4 | 98405832 | 98554929 |
| chr7 | 147116120 | 147156352 |

TABLE S4A-continued

| Super-enhancer Domains | | |
|---|---|---|
| Chr | Start | End |
| chr10 | 75359462 | 75415411 |
| chr10 | 75329011 | 75415411 |
| chr3 | 96470813 | 96497406 |
| chr7 | 13594061 | 13617283 |
| chr19 | 23089343 | 23229072 |
| chr11 | 77648017 | 77759107 |
| chr2 | 31988954 | 32048213 |
| chr19 | 21808238 | 22379774 |
| chr18 | 36287108 | 36489385 |
| chr10 | 66375750 | 66564168 |
| chr8 | 37594982 | 37753361 |
| chr6 | 66911889 | 67093167 |
| chr2 | 151937066 | 152023854 |
| chr1 | 168052731 | 168085769 |
| chr8 | 93337017 | 93461643 |
| chr10 | 20753144 | 20909870 |
| chr1 | 182803710 | 182905559 |
| chr3 | 34048462 | 35382238 |
| chr2 | 168565336 | 168670183 |
| chr5 | 64977526 | 65258932 |
| chr11 | 116942064 | 117039648 |
| chr1 | 91755202 | 91840923 |
| chr6 | 122689212 | 122737156 |
| chr19 | 25549889 | 25621172 |
| chr11 | 8465819 | 8761806 |
| chr4 | 118687950 | 118815868 |
| chr5 | 135407901 | 135444028 |
| chr4 | 138002737 | 138021762 |
| chr9 | 114434686 | 114494861 |
| chr17 | 31865371 | 32163212 |
| chr18 | 35180089 | 35693422 |
| chr5 | 123571740 | 123606315 |
| chr13 | 96159680 | 96721858 |
| chr11 | 11925186 | 12441361 |
| chr11 | 117823113 | 117880702 |
| chr1 | 182849231 | 182905559 |
| chr11 | 54692478 | 54798550 |
| chr11 | 52163912 | 52188686 |
| chr7 | 70896448 | 71205797 |
| chr6 | 64923531 | 65029967 |
| chr8 | 91467275 | 91572066 |
| chr14 | 55642580 | 55796912 |
| chr11 | 33236011 | 33455087 |
| chr11 | 88365951 | 88591129 |
| chr11 | 102169637 | 102201539 |
| chr4 | 141717621 | 141806679 |
| chr3 | 96350545 | 96443947 |
| chr16 | 84734897 | 84880243 |
| chr11 | 66718693 | 66899782 |
| chr4 | 140985352 | 141133641 |
| chr7 | 3198402 | 3222975 |
| chr19 | 5792497 | 5878810 |
| chr9 | 56261740 | 56401717 |
| chr3 | 135071737 | 135395232 |
| chr2 | 20335900 | 20595748 |
| chr17 | 26603012 | 26776615 |
| chr2 | 33256274 | 33352075 |
| chr17 | 71086210 | 71216894 |

TABLE S4A-continued

| Super-enhancer Domains | | |
|---|---|---|
| Chr | Start | End |
| chr15 | 77055148 | 77199664 |
| chr12 | 87742959 | 87956056 |
| chr17 | 71195618 | 71250889 |
| chr17 | 47609255 | 47735975 |
| chr14 | 55695067 | 55717888 |
| chr11 | 107243228 | 107335537 |
| chr14 | 105796075 | 106303003 |
| chr10 | 59356750 | 59468872 |
| chr12 | 55300475 | 55591628 |
| chr8 | 87984083 | 88051875 |
| chr17 | 29556459 | 29652227 |
| chr4 | 125162485 | 125485934 |
| chr14 | 49201179 | 49509716 |
| chr3 | 88348083 | 88408550 |
| chr7 | 52792902 | 52845517 |
| chr12 | 103939956 | 103958858 |
| chr17 | 29181193 | 29233320 |
| chr9 | 57885470 | 58130191 |
| chr14 | 21955683 | 22561917 |
| chr19 | 53493838 | 53654456 |
| chr11 | 66718693 | 66839583 |
| chr2 | 165910064 | 165985682 |
| chr17 | 66674595 | 66840188 |
| chr2 | 71492827 | 71652869 |
| chr7 | 31224743 | 31258292 |
| chr1 | 182803710 | 182832479 |
| chr3 | 129222980 | 129325895 |
| chr6 | 122618790 | 122670811 |
| chr1 | 120667669 | 120981204 |
| chr16 | 8685741 | 8795721 |
| chr11 | 69467645 | 69529968 |
| chr7 | 119787192 | 119837366 |
| chr4 | 126832402 | 126893727 |
| chr11 | 116932982 | 117039648 |
| chr14 | 65244350 | 65372358 |
| chr11 | 69494914 | 69529968 |
| chr18 | 61707865 | 61826914 |
| chr17 | 10086176 | 10938877 |
| chr5 | 120021125 | 120139928 |
| chr4 | 147451592 | 147468949 |
| chr3 | 95436247 | 95482321 |
| chr11 | 97505763 | 97601227 |
| chr9 | 58048791 | 58130191 |
| chr2 | 162873366 | 162916341 |
| chr11 | 98813654 | 98828524 |
| chr10 | 44047591 | 44482037 |
| chr1 | 13041583 | 13125339 |
| chr12 | 88134365 | 88316531 |
| chr8 | 87162269 | 87234127 |
| chr1 | 120989689 | 121341353 |
| chr7 | 140223741 | 140326676 |
| chr4 | 140812787 | 140920032 |
| chr12 | 88211553 | 88248387 |
| chr17 | 37130666 | 37222465 |
| chr11 | 8887662 | 9037343 |
| chr1 | 138669873 | 138901249 |
| chr5 | 118882848 | 119045654 |

TABLE S4B

| Super-enhancers and their associated Super-enhancer Domains | | | | | |
|---|---|---|---|---|---|
| Chr | Start | End | SE | Rank | in SDs |
| chr7 | 3193004 | 3218183 | INT_STITCHED_3467 | 1 | TRUE |
| chr3 | 34633687 | 34660705 | INT_STITCHED_1482 | 2 | TRUE |
| chr12 | 87839385 | 87846192 | INT_STITCHED_6113 | 3 | TRUE |
| chr9 | 110849422 | 110863371 | INT_STITCHED_4748 | 4 | TRUE |
| chr8 | 37602064 | 37613850 | INT_STITCHED_4033 | 6 | TRUE |
| chr4 | 140826072 | 140840922 | INT_STITCHED_2291 | 8 | TRUE |
| chr3 | 95455034 | 95468269 | INT_STITCHED_1626 | 9 | TRUE |
| chr2 | 154242651 | 154254374 | INT_STITCHED_1210 | 10 | TRUE |
| chr17 | 37110202 | 37134996 | INT_STITCHED_7792 | 12 | TRUE |

TABLE S4B-continued

Super-enhancers and their associated Super-enhancer Domains

| Chr | Start | End | SE | Rank | in SDs |
|---|---|---|---|---|---|
| chr6 | 122290093 | 122293017 | INT_STITCHED_3342 | 13 | TRUE |
| chr9 | 78207143 | 78223442 | INT_STITCHED_4657 | 14 | TRUE |
| chr8 | 91514813 | 91540176 | INT_STITCHED_4179 | 15 | TRUE |
| chr19 | 5835881 | 5847014 | INT_STITCHED_8324 | 16 | TRUE |
| chr17 | 66818723 | 66836409 | INT_STITCHED_7876 | 17 | TRUE |
| chr2 | 162877048 | 162893236 | INT_STITCHED_1257 | 18 | TRUE |
| chr9 | 58119837 | 58128504 | INT_STITCHED_4555 | 19 | TRUE |
| chr6 | 64961359 | 64985161 | INT_STITCHED_3120 | 20 | TRUE |
| chr7 | 152036872 | 152050716 | INT_STITCHED_3914 | 21 | TRUE |
| chr12 | 87807046 | 87820319 | INT_STITCHED_6112 | 22 | TRUE |
| chr4 | 118743867 | 118745786 | INT_STITCHED_2152 | 23 | TRUE |
| chr11 | 97517673 | 97524159 | INT_STITCHED_5711 | 24 | TRUE |
| chr2 | 20574602 | 20591747 | INT_STITCHED_746 | 25 | TRUE |
| chr17 | 71177302 | 71179956 | INT_STITCHED_7886 | 26 | TRUE |
| chr14 | 76894682 | 76915946 | INT_STITCHED_6904 | 27 | TRUE |
| chr17 | 31939569 | 31956756 | INT_STITCHED_7767 | 29 | TRUE |
| chr1 | 13049615 | 13094765 | INT_STITCHED_45 | 30 | TRUE |
| chr2 | 32008891 | 32030736 | INT_STITCHED_812 | 31 | TRUE |
| chr6 | 122640118 | 122657871 | INT_STITCHED_3348 | 32 | TRUE |
| chr3 | 34544904 | 34553511 | INT_STITCHED_1480 | 34 | TRUE |
| chr5 | 118884660 | 118896412 | INT_STITCHED_2745 | 35 | TRUE |
| chr8 | 37642521 | 37671979 | INT_STITCHED_4034 | 36 | TRUE |
| chr12 | 12790432 | 12795881 | INT_STITCHED_5875 | 38 | TRUE |
| chr4 | 141120768 | 141126477 | INT_STITCHED_2292 | 39 | TRUE |
| chr6 | 122714316 | 122720862 | INT_STITCHED_3349 | 40 | TRUE |
| chr5 | 123584659 | 123590728 | INT_STITCHED_2770 | 41 | TRUE |
| chr17 | 71213804 | 71222433 | INT_STITCHED_7887 | 42 | TRUE |
| chr19 | 23139991 | 23170189 | INT_STITCHED_8385 | 43 | TRUE |
| chr3 | 135208956 | 135210744 | INT_STITCHED_1749 | 44 | TRUE |
| chr12 | 12933791 | 12950936 | INT_STITCHED_5880 | 45 | TRUE |
| chr17 | 71096763 | 71100905 | INT_STITCHED_7884 | 46 | TRUE |
| chr11 | 117833701 | 117838253 | INT_STITCHED_5831 | 47 | TRUE |
| chr11 | 33427175 | 33451476 | INT_STITCHED_5427 | 48 | TRUE |
| chr1 | 37039139 | 37045411 | INT_STITCHED_108 | 49 | TRUE |
| chr7 | 140304156 | 140307245 | INT_STITCHED_3856 | 51 | TRUE |
| chr4 | 141616653 | 141627603 | INT_STITCHED_2295 | 52 | TRUE |
| chr16 | 84769173 | 84780686 | INT_STITCHED_7597 | 53 | TRUE |
| chr1 | 182854521 | 182864307 | INT_STITCHED_611 | 54 | TRUE |
| chr10 | 79508474 | 79515168 | INT_STITCHED_5111 | 55 | TRUE |
| chr2 | 33282029 | 33300860 | INT_STITCHED_817 | 56 | TRUE |
| chr11 | 116943025 | 116953583 | INT_STITCHED_5819 | 57 | TRUE |
| chr11 | 77697704 | 77718786 | INT_STITCHED_5597 | 58 | TRUE |
| chr1 | 182818684 | 182819554 | INT_STITCHED_610 | 59 | TRUE |
| chr11 | 8466451 | 8486876 | INT_STITCHED_5325 | 61 | TRUE |
| chr14 | 64118817 | 64131901 | INT_STITCHED_6859 | 62 | TRUE |
| chr14 | 77015215 | 77030315 | INT_STITCHED_6906 | 63 | TRUE |
| chr14 | 71022659 | 71035930 | INT_STITCHED_6887 | 66 | TRUE |
| chr11 | 12357626 | 12370205 | INT_STITCHED_5340 | 67 | TRUE |
| chr10 | 21700576 | 21708946 | INT_STITCHED_4893 | 68 | TRUE |
| chr3 | 96380383 | 96382115 | INT_STITCHED_1629 | 69 | TRUE |
| chr11 | 69517060 | 69522803 | INT_STITCHED_5565 | 70 | TRUE |
| chr5 | 53933177 | 53947327 | INT_STITCHED_2510 | 71 | TRUE |
| chr7 | 147131117 | 147136231 | INT_STITCHED_3890 | 72 | TRUE |
| chr1 | 120971968 | 120973737 | INT_STITCHED_372 | 73 | TRUE |
| chr11 | 66824791 | 66838230 | INT_STITCHED_5555 | 74 | TRUE |
| chr3 | 133181431 | 133197648 | INT_STITCHED_1744 | 75 | TRUE |
| chr19 | 25553498 | 25564092 | INT_STITCHED_8399 | 77 | TRUE |
| chr18 | 61787544 | 61788400 | INT_STITCHED_8209 | 78 | TRUE |
| chr8 | 87174072 | 87174643 | INT_STITCHED_4163 | 79 | TRUE |
| chr17 | 37209046 | 37217726 | INT_STITCHED_7794 | 80 | TRUE |
| chr13 | 96295094 | 96306119 | INT_STITCHED_6544 | 81 | TRUE |
| chr19 | 23207455 | 23208806 | INT_STITCHED_8386 | 82 | TRUE |
| chr18 | 40467587 | 40468140 | INT_STITCHED_8148 | 83 | TRUE |
| chr5 | 65255735 | 65256794 | INT_STITCHED_2535 | 84 | TRUE |
| chr15 | 77168852 | 77187251 | INT_STITCHED_7248 | 85 | TRUE |
| chr11 | 88481360 | 88491812 | INT_STITCHED_5666 | 86 | TRUE |
| chr7 | 31248315 | 31250619 | INT_STITCHED_3525 | 87 | TRUE |
| chr12 | 55407498 | 55415046 | INT_STITCHED_5995 | 89 | TRUE |
| chr12 | 88239069 | 88245155 | INT_STITCHED_6118 | 90 | TRUE |
| chr18 | 75520332 | 75527277 | INT_STITCHED_8261 | 91 | TRUE |
| chr11 | 9015537 | 9017663 | INT_STITCHED_5331 | 92 | TRUE |
| chr1 | 137071028 | 137096284 | INT_STITCHED_449 | 93 | TRUE |
| chr6 | 39395571 | 39396779 | INT_STITCHED_3045 | 94 | TRUE |
| chr2 | 168589688 | 168617170 | INT_STITCHED_1300 | 95 | TRUE |
| chr1 | 120538712 | 120545414 | INT_STITCHED_368 | 96 | TRUE |
| chr1 | 168054897 | 168073079 | INT_STITCHED_556 | 97 | TRUE |

TABLE S4B-continued

Super-enhancers and their associated Super-enhancer Domains

| Chr | Start | End | SE | Rank | in SDs |
|---|---|---|---|---|---|
| chr1 | 72839563 | 72858199 | INT_STITCHED_237 | 99 | TRUE |
| chr4 | 98507649 | 98514709 | INT_STITCHED_2076 | 100 | TRUE |
| chr16 | 23099373 | 23103471 | INT_STITCHED_7434 | 101 | TRUE |
| chr7 | 71092246 | 71102481 | INT_STITCHED_3601 | 102 | TRUE |
| chr19 | 21858770 | 21866770 | INT_STITCHED_8378 | 103 | TRUE |
| chr2 | 152002668 | 152003777 | INT_STITCHED_1196 | 104 | TRUE |
| chr4 | 137329436 | 137357766 | INT_STITCHED_2268 | 108 | TRUE |
| chr5 | 120029649 | 120037063 | INT_STITCHED_2752 | 109 | TRUE |
| chr14 | 106296486 | 106304433 | INT_STITCHED_6982 | 110 | TRUE |
| chr4 | 141721916 | 141726166 | INT_STITCHED_2297 | 111 | TRUE |
| chr3 | 129247012 | 129261362 | INT_STITCHED_1732 | 112 | TRUE |
| chr9 | 114458126 | 114474355 | INT_STITCHED_4766 | 113 | TRUE |
| chr17 | 10549089 | 10570838 | INT_STITCHED_7680 | 114 | TRUE |
| chr2 | 71488013 | 71494617 | INT_STITCHED_928 | 115 | TRUE |
| chr3 | 96479158 | 96484864 | INT_STITCHED_1630 | 116 | TRUE |
| chr12 | 111725920 | 111743677 | INT_STITCHED_6188 | 117 | TRUE |
| chr14 | 22293688 | 22308989 | INT_STITCHED_6709 | 118 | TRUE |
| chr6 | 125383335 | 125398024 | INT_STITCHED_3360 | 119 | TRUE |
| chr2 | 165981373 | 165983444 | INT_STITCHED_1279 | 121 | TRUE |
| chr1 | 183948212 | 183961841 | INT_STITCHED_615 | 123 | TRUE |
| chr6 | 91640161 | 91661247 | INT_STITCHED_3217 | 124 | TRUE |
| chr8 | 12499468 | 12504771 | INT_STITCHED_3947 | 125 | TRUE |
| chr11 | 102190649 | 102193692 | INT_STITCHED_5741 | 126 | TRUE |
| chr6 | 67061148 | 67064202 | INT_STITCHED_3130 | 127 | TRUE |
| chr10 | 85002060 | 85006553 | INT_STITCHED_5140 | 129 | TRUE |
| chr8 | 87996475 | 87997654 | INT_STITCHED_4167 | 130 | TRUE |
| chr8 | 93351924 | 93355292 | INT_STITCHED_4190 | 131 | TRUE |
| chr10 | 75335464 | 75345568 | INT_STITCHED_5091 | 132 | TRUE |
| chr12 | 111709296 | 111710794 | INT_STITCHED_6187 | 133 | TRUE |
| chr10 | 66546199 | 66564235 | INT_STITCHED_5059 | 134 | TRUE |
| chr10 | 21546502 | 21549691 | INT_STITCHED_4891 | 135 | TRUE |
| chr7 | 38812914 | 38816123 | INT_STITCHED_3550 | 136 | TRUE |
| chr1 | 121295085 | 121296031 | INT_STITCHED_376 | 137 | TRUE |
| chr7 | 86355826 | 86368339 | INT_STITCHED_3652 | 138 | TRUE |
| chr17 | 26631721 | 26648689 | INT_STITCHED_7728 | 139 | TRUE |
| chr14 | 106250319 | 106260753 | INT_STITCHED_6981 | 140 | TRUE |
| chr17 | 47640414 | 47649043 | INT_STITCHED_7822 | 141 | TRUE |
| chr5 | 135417523 | 135421698 | INT_STITCHED_2830 | 142 | TRUE |
| chr4 | 125211671 | 125223450 | INT_STITCHED_2192 | 143 | TRUE |
| chr11 | 107296669 | 107310982 | INT_STITCHED_5768 | 144 | TRUE |
| chr14 | 55704349 | 55705463 | INT_STITCHED_6815 | 145 | TRUE |
| chr2 | 162856904 | 162860933 | INT_STITCHED_1256 | 146 | TRUE |
| chr8 | 74834685 | 74840663 | INT_STITCHED_4116 | 147 | TRUE |
| chr15 | 97198605 | 97227633 | INT_STITCHED_7317 | 148 | TRUE |
| chr18 | 36412873 | 36414154 | INT_STITCHED_8124 | 149 | TRUE |
| chr9 | 56382386 | 56395769 | INT_STITCHED_4546 | 151 | TRUE |
| chr1 | 36111164 | 36118698 | INT_STITCHED_101 | 152 | TRUE |
| chr5 | 116845764 | 116860853 | INT_STITCHED_2736 | 153 | TRUE |
| chr7 | 30982397 | 30983339 | INT_STITCHED_3523 | 154 | TRUE |
| chr1 | 138841643 | 138850970 | INT_STITCHED_466 | 156 | TRUE |
| chr17 | 29587776 | 29588942 | INT_STITCHED_7752 | 157 | TRUE |
| chr1 | 138586629 | 138593131 | INT_STITCHED_464 | 158 | TRUE |
| chr19 | 53523440 | 53535319 | INT_STITCHED_8519 | 159 | TRUE |
| chr8 | 44405736 | 44406755 | INT_STITCHED_4046 | 161 | TRUE |
| chr7 | 4772296 | 4777612 | INT_STITCHED_3475 | 162 | TRUE |
| chr6 | 83839914 | 83844315 | INT_STITCHED_3184 | 163 | TRUE |
| chr10 | 66380351 | 66383761 | INT_STITCHED_5054 | 164 | TRUE |
| chr12 | 56587347 | 56607146 | INT_STITCHED_6000 | 165 | TRUE |
| chr7 | 119831735 | 119835688 | INT_STITCHED_3765 | 166 | TRUE |
| chr18 | 35202713 | 35203454 | INT_STITCHED_8114 | 169 | TRUE |
| chr1 | 121201424 | 121202481 | INT_STITCHED_374 | 170 | TRUE |
| chr5 | 118951444 | 118960269 | INT_STITCHED_2746 | 171 | TRUE |
| chr7 | 13599334 | 13600325 | INT_STITCHED_3481 | 172 | TRUE |
| chr8 | 35023426 | 35027483 | INT_STITCHED_4014 | 173 | TRUE |
| chr3 | 9641461 | 9655131 | INT_STITCHED_1392 | 174 | TRUE |
| chr11 | 66733372 | 66746990 | INT_STITCHED_5553 | 177 | TRUE |
| chr2 | 152552277 | 152563676 | INT_STITCHED_1198 | 178 | TRUE |
| chr1 | 34130107 | 34134640 | INT_STITCHED_88 | 179 | TRUE |
| chr10 | 59420365 | 59437537 | INT_STITCHED_5021 | 181 | TRUE |
| chr13 | 98202400 | 98225162 | INT_STITCHED_6559 | 182 | TRUE |
| chr10 | 75400370 | 75401358 | INT_STITCHED_5092 | 183 | TRUE |
| chr11 | 54767341 | 54785832 | INT_STITCHED_5499 | 184 | TRUE |
| chr12 | 12810177 | 12811020 | INT_STITCHED_5876 | 185 | TRUE |
| chr17 | 35639211 | 35642435 | INT_STITCHED_7784 | 186 | TRUE |
| chr10 | 76655655 | 76662360 | INT_STITCHED_5100 | 187 | TRUE |
| chr10 | 44110139 | 44112766 | INT_STITCHED_4981 | 188 | TRUE |

TABLE S4B-continued

Super-enhancers and their associated Super-enhancer Domains

| Chr | Start | End | SE | Rank | in SDs |
|---|---|---|---|---|---|
| chr1 | 72260528 | 72261272 | INT_STITCHED_230 | 189 | TRUE |
| chr1 | 169201106 | 169220423 | INT_STITCHED_559 | 190 | TRUE |
| chr14 | 49273113 | 49283200 | INT_STITCHED_6789 | 191 | TRUE |
| chr4 | 126875757 | 126879027 | INT_STITCHED_2205 | 192 | TRUE |
| chr3 | 88375442 | 88380083 | INT_STITCHED_1607 | 193 | TRUE |
| chr11 | 98823511 | 98826466 | INT_STITCHED_5719 | 194 | TRUE |
| chr4 | 147459254 | 147463850 | INT_STITCHED_2317 | 196 | TRUE |
| chr12 | 103940487 | 103953004 | INT_STITCHED_6151 | 197 | TRUE |
| chr18 | 75504155 | 75505202 | INT_STITCHED_8260 | 198 | TRUE |
| chr17 | 29209618 | 29218426 | INT_STITCHED_7747 | 200 | TRUE |
| chr7 | 52806853 | 52814768 | INT_STITCHED_3568 | 201 | TRUE |
| chr17 | 71241991 | 71250610 | INT_STITCHED_7888 | 203 | TRUE |
| chr16 | 8758173 | 8779472 | INT_STITCHED_7359 | 204 | TRUE |
| chr13 | 110418702 | 110442750 | INT_STITCHED_6615 | 206 | TRUE |
| chr10 | 20802131 | 20830236 | INT_STITCHED_4885 | 207 | TRUE |
| chr18 | 38538325 | 38551037 | INT_STITCHED_8136 | 208 | TRUE |
| chr7 | 87333420 | 87345334 | INT_STITCHED_3662 | 209 | TRUE |
| chr4 | 154563584 | 154564383 | INT_STITCHED_2355 | 210 | TRUE |
| chr9 | 121244501 | 121254102 | INT_STITCHED_4802 | 213 | TRUE |
| chr1 | 36070190 | 36074608 | INT_STITCHED_100 | 215 | TRUE |
| chr2 | 30913257 | 30925299 | INT_STITCHED_803 | 216 | TRUE |
| chr13 | 98052562 | 98062842 | INT_STITCHED_6557 | 217 | TRUE |
| chr11 | 52173182 | 52184686 | INT_STITCHED_5484 | 218 | TRUE |
| chr14 | 65251303 | 65269514 | INT_STITCHED_6864 | 219 | TRUE |
| chr4 | 154537213 | 154538078 | INT_STITCHED_2354 | 220 | TRUE |
| chr12 | 111655417 | 111656705 | INT_STITCHED_6186 | 221 | TRUE |
| chr6 | 142458188 | 142461905 | INT_STITCHED_3429 | 222 | TRUE |
| chr2 | 71575856 | 71583914 | INT_STITCHED_931 | 223 | TRUE |
| chr6 | 39370384 | 39371286 | INT_STITCHED_3044 | 225 | TRUE |
| chr12 | 57385208 | 57400114 | INT_STITCHED_6004 | 226 | TRUE |
| chr15 | 103349226 | 103353500 | INT_STITCHED_7343 | 227 | TRUE |
| chr4 | 138000554 | 138006368 | INT_STITCHED_2273 | 228 | TRUE |
| chr6 | 145223385 | 145225674 | INT_STITCHED_3450 | 230 | TRUE |
| chr1 | 91766947 | 91773527 | INT_STITCHED_315 | 231 | TRUE |

TABLE S4C

Super-enhancer associated genes in SDs

| Chr | Start | End | Gene_ID | Strand | RefSeq_ID | Symbol |
|---|---|---|---|---|---|---|
| chr1 | 13103508 | 13117244 | NM_001081209:Prdm14 | − | NM_001081209 | Prdm14 |
| chr1 | 34068669 | 34365497 | NM_133833:Dst | + | NM_133833 | Dst |
| chr1 | 34068669 | 34365497 | NM_134448:Dst | + | NM_134448 | Dst |
| chr1 | 36849033 | 36996372 | NM_018872:Tmem131 | − | NM_018872 | Tmem131 |
| chr1 | 72205806 | 72258881 | NM_001005423:Mreg | − | NM_001005423 | Mreg |
| chr1 | 72871076 | 72899045 | NM_008342:Igfbp2 | + | NM_008342 | Igfbp2 |
| chr1 | 120730637 | 120950196 | NM_001081125:Gli2 | − | NM_001081125 | Gli2 |
| chr1 | 138740160 | 138850207 | NM_001159769:Nr5a2 | − | NM_001159769 | Nr5a2 |
| chr1 | 168028278 | 168058029 | NM_001160049:Dusp27 | − | NM_001160049 | Dusp27 |
| chr1 | 169156216 | 169215258 | NM_030724:Uck2 | − | NM_030724 | Uck2 |
| chr1 | 183834575 | 183950111 | NM_010135:Enah | − | NM_010135 | Enah |
| chr1 | 183834575 | 183950111 | NM_001083121:Enah | − | NM_001083121 | Enah |
| chr1 | 183834575 | 183950111 | NM_001083120:Enah | − | NM_001083120 | Enah |
| chr1 | 36125244 | 36163291 | NM_015818:Hs6st1 | + | NM_015818 | Hs6st1 |
| chr1 | 91824536 | 91827751 | NM_010262:Gbx2 | − | NM_010262 | Gbx2 |
| chr1 | 120524521 | 120581745 | NM_023755:Tcfcp2l1 | + | NM_023755 | Tcfcp2l1 |
| chr1 | 121312041 | 121318825 | NM_008381:Inhbb | − | NM_008381 | Inhbb |
| chr1 | 137150150 | 137155049 | NM_007921:Elf3 | − | NM_007921 | Elf3 |
| chr1 | 138521477 | 138526968 | NM_001160251:Zfp281 | + | NM_001160251 | Zfp281 |
| chr1 | 138521477 | 138526968 | NM_177643:Zfp281 | + | NM_177643 | Zfp281 |
| chr1 | 168060590 | 168096641 | NM_021610:Gpa33 | + | NM_021610 | Gpa33 |
| chr1 | 182823249 | 182829233 | NM_177099:Lefty2 | + | NM_177099 | Lefty2 |
| chr1 | 182872648 | 182905235 | NM_144794:Tmem63a | + | NM_144794 | Tmem63a |
| chr1 | 182865169 | 182868532 | NM_010094:Lefty1 | + | NM_010094 | Lefty1 |
| chr2 | 20431673 | 20732162 | NM_178059:Etl4 | + | NM_178059 | Etl4 |
| chr2 | 20431673 | 20732162 | NM_029895:Etl4 | + | NM_029895 | Etl4 |
| chr2 | 30881725 | 30997528 | NM_001177648:Fnbp1 | − | NM_001177648 | Fnbp1 |
| chr2 | 71557473 | 71569023 | NM_201366:Gm1631 | + | NM_201366 | Gm1631 |
| chr2 | 154262219 | 154365092 | NM_009823:Cbfa2t2 | + | NM_009823 | Cbfa2t2 |
| chr2 | 165898588 | 165981156 | NM_028072:Sulf2 | − | NM_028072 | Sulf2 |
| chr2 | 32006667 | 32090057 | NM_001159634:Bat2l | + | NM_001159634 | Bat2l |
| chr2 | 33261627 | 33286844 | NM_001085507:Zbtb34 | − | NM_001085507 | Zbtb34 |

TABLE S4C-continued

| Super-enhancer associated genes in SDs | | | | | | |
|---|---|---|---|---|---|---|
| Chr | Start | End | Gene_ID | Strand | RefSeq_ID | Symbol |
| chr2 | 151969344 | 151974832 | NM_009328:Tcf15 | + | NM_009328 | Tcf15 |
| chr2 | 152562009 | 152563146 | NM_010495:Id1 | + | NM_010495 | Id1 |
| chr2 | 162880370 | 162910423 | NM_008652:Mybl2 | + | NM_008652 | Mybl2 |
| chr2 | 162843207 | 162871871 | NM_172150:Ift52 | + | NM_172150 | Ift52 |
| chr2 | 168573831 | 168592701 | NM_201395:Sall4 | − | NM_201395 | Sall4 |
| chr2 | 168573831 | 168592701 | NM_175303:Sall4 | − | NM_175303 | Sall4 |
| chr2 | 168573831 | 168592701 | NM_201396:Sall4 | − | NM_201396 | Sall4 |
| chr3 | 9427009 | 9610085 | NM_133218:Zfp704 | − | NM_133218 | Zfp704 |
| chr3 | 133126640 | 133207354 | NM_001040400:Tet2 | − | NM_001040400 | Tet2 |
| chr3 | 129235303 | 129341411 | NM_130450:Elovl6 | + | NM_130450 | Elovl6 |
| chr3 | 34537385 | 34537464 | NR_035433:Mir1897 | + | NR_035433 | Mir1897 |
| chr3 | 34548926 | 34551382 | NM_011443:Sox2 | + | NM_011443 | Sox2 |
| chr3 | 88383592 | 88392335 | NM_025448:Ssr2 | + | NM_025448 | Ssr2 |
| chr3 | 95462642 | 95467101 | NM_008562:Mcl1 | + | NM_008562 | Mcl1 |
| chr3 | 96361879 | 96365780 | NM_023719:Txnip | + | NM_023719 | Txnip |
| chr3 | 96400558 | 96403701 | NM_001024851:Ankrd34a | + | NM_001024851 | Ankrd34a |
| chr3 | 96381796 | 96398081 | NM_027241:Polr3gl | − | NM_027241 | Polr3gl |
| chr3 | 96474053 | 96494957 | NM_001081139:Ankrd35 | + | NM_001081139 | Ankrd35 |
| chr3 | 135148574 | 135234367 | NM_027288:Manba | + | NM_027288 | Manba |
| chr4 | 126846514 | 126914266 | NM_198618:Dlgap3 | + | NM_198618 | Dlgap3 |
| chr4 | 98421582 | 98484228 | NM_172872:Kank4 | − | NM_172872 | Kank4 |
| chr4 | 125168074 | 125391417 | NM_001081097:Grik3 | + | NM_001081097 | Grik3 |
| chr4 | 147451169 | 147462173 | NM_009642:Agtrap | − | NM_009642 | Agtrap |
| chr4 | 154528183 | 154596644 | NM_011385:Ski | − | NM_011385 | Ski |
| chr4 | 118781349 | 118809934 | NM_011400:Slc2a1 | + | NM_011400 | Slc2a1 |
| chr4 | 137297646 | 137352292 | NM_007431:Alpl | − | NM_007431 | Alpl |
| chr4 | 138011062 | 138016041 | NM_025451:Camk2n1 | + | NM_025451 | Camk2n1 |
| chr4 | 140857154 | 140885293 | NM_010139:Epha2 | + | NM_010139 | Epha2 |
| chr4 | 140988817 | 140992020 | NM_001033374:Gm694 | − | NM_001033374 | Gm694 |
| chr4 | 141102076 | 141104228 | NR_030695:B330016D10Rik | + | NR_030695 | B330016D10Rik |
| chr4 | 141640212 | 141644016 | NR_027137:Gm10565 | + | NR_027137 | Gm10565 |
| chr4 | 141695154 | 141795316 | NM_001109685:9030409G11Rik | − | NM_001109685 | 9030409G11Rik |
| chr5 | 53947017 | 54048684 | NM_001080928:Rbpj | + | NM_001080928 | Rbpj |
| chr5 | 119010727 | 119215446 | NM_172424:Med131 | + | NM_172424 | Med131 |
| chr5 | 65194761 | 65221368 | NM_008453:Klf3 | + | NM_008453 | Klf3 |
| chr5 | 116858503 | 116872873 | NM_030704:Hspb8 | − | NM_030704 | Hspb8 |
| chr5 | 116888730 | 116915496 | NR_015595:2410137F16Rik | + | NR_015595 | 2410137F16Rik |
| chr5 | 120120677 | 120134610 | NM_011535:Tbx3 | + | NM_011535 | Tbx3 |
| chr5 | 120120677 | 120134610 | NM_198052:Tbx3 | + | NM_198052 | Tbx3 |
| chr5 | 123568188 | 123582638 | NM_175092:Rhof | − | NM_175092 | Rhof |
| chr5 | 135420992 | 135422804 | NM_009903:Cldn4 | − | NM_009903 | Cldn4 |
| chr6 | 83864346 | 83936865 | NM_001166371:Zfml | + | NM_001166371 | Zfml |
| chr6 | 83864346 | 83936865 | NM_008717:Zfml | + | NM_008717 | Zfml |
| chr6 | 64992660 | 65066043 | NM_007958:Smarcad1 | + | NM_007958 | Smarcad1 |
| chr6 | 122677826 | 122692763 | NM_011401:Slc2a3 | − | NM_011401 | Slc2a3 |
| chr6 | 125410283 | 125444773 | NM_007657:Cd9 | − | NM_007657 | Cd9 |
| chr6 | 39347819 | 39370368 | NM_018810:Mkrn1 | − | NM_018810 | Mkrn1 |
| chr6 | 66985089 | 66987401 | NM_007836:Gadd45a | − | NM_007836 | Gadd45a |
| chr6 | 91634060 | 91709057 | NM_009320:Slc6a6 | + | NM_009320 | Slc6a6 |
| chr6 | 122267748 | 122287033 | NM_007905:Phc1 | − | NM_007905 | Phc1 |
| chr6 | 122657585 | 122663796 | NM_028016:Nanog | + | NM_028016 | Nanog |
| chr6 | 122657800 | 122663573 | NM_001080945:Nanogpd | + | NM_001080945 | Nanogpd |
| chr6 | 142438768 | 142456463 | NM_008492:Ldhb | − | NM_008492 | Ldhb |
| chr6 | 145165218 | 145198751 | NM_021284:Kras | − | NM_021284 | Kras |
| chr7 | 38745010 | 38804571 | NM_011274:C80913 | − | NM_011274 | C80913 |
| chr7 | 71031236 | 71083801 | NM_021366:Klf13 | − | NM_021366 | Klf13 |
| chr7 | 119822833 | 120050319 | NM_001166584:Tead1 | + | NM_001166584 | Tead1 |
| chr7 | 140178693 | 140315166 | NM_009980:Ctbp2 | − | NM_009980 | Ctbp2 |
| chr7 | 3218784 | 3221016 | NR_028425:LOC100303645 | + | NR_028425 | LOC100303645 |
| chr7 | 3219482 | 3219561 | NR_030276:Mir291b | + | NR_030276 | Mir291b |
| chr7 | 3220343 | 3220423 | NR_029643:Mir293 | + | NR_029643 | Mir293 |
| chr7 | 3218626 | 3218709 | NR_029640:Mir290 | + | NR_029640 | Mir290 |
| chr7 | 3218919 | 3219001 | NR_029641:Mir291a | + | NR_029641 | Mir291a |
| chr7 | 3219189 | 3219271 | NR_029642:Mir292 | + | NR_029642 | Mir292 |
| chr7 | 4759615 | 4763942 | NM_133777:Ube2s | − | NM_133777 | Ube2s |
| chr7 | 13609500 | 13616381 | NM_011588:Trim28 | + | NM_011588 | Trim28 |
| chr7 | 30971960 | 30980067 | NM_009795:Capns1 | − | NM_009795 | Capns1 |
| chr7 | 30969189 | 30971049 | NM_009944:Cox7a1 | + | NM_009944 | Cox7a1 |
| chr7 | 31220000 | 31230580 | NM_007467:Aplp1 | − | NM_007467 | Aplp1 |
| chr7 | 31245076 | 31273628 | NM_019459:Nphs1 | + | NM_019459 | Nphs1 |
| chr7 | 31232784 | 31242534 | NM_172898:Kirrel2 | − | NM_172898 | Kirrel2 |
| chr7 | 52825732 | 52845078 | NM_009737:Bcat2 | + | NM_009737 | Bcat2 |
| chr7 | 86418151 | 86506487 | NM_018811:Abhd2 | + | NM_018811 | Abhd2 |
| chr7 | 87331726 | 87371410 | NM_013659:Sema4b | + | NM_013659 | Sema4b |
| chr7 | 147129754 | 147131011 | NM_009482:Utf1 | + | NM_009482 | Utf1 |
| chr7 | 152047290 | 152051148 | NM_010202:Fgf4 | + | NM_010202 | Fgf4 |

TABLE S4C-continued

| Super-enhancer associated genes in SDs | | | | | | |
|---|---|---|---|---|---|---|
| Chr | Start | End | Gene_ID | Strand | RefSeq_ID | Symbol |
| chr8 | 34893115 | 35040313 | NM_019733:Rbpms | − | NM_019733 | Rbpms |
| chr8 | 93352733 | 93578407 | NM_177224:Chd9 | + | NM_177224 | Chd9 |
| chr8 | 12395518 | 12399555 | NM_009233:Sox1 | + | NM_009233 | Sox1 |
| chr8 | 37630792 | 37676997 | NM_015802:Dlc1 | − | NM_015802 | Dlc1 |
| chr8 | 44380420 | 44392363 | NM_009556:Zfp42 | − | NM_009556 | Zfp42 |
| chr8 | 74842960 | 74845553 | NM_008452:Klf2 | + | NM_008452 | Klf2 |
| chr8 | 87185229 | 87186751 | NM_010499:Ier2 | − | NM_010499 | Ier2 |
| chr8 | 88016515 | 88051457 | NM_173866:Gpt2 | + | NM_173866 | Gpt2 |
| chr8 | 91551142 | 91568061 | NM_021390:Sall1 | − | NM_021390 | Sall1 |
| chr9 | 114420390 | 114473487 | NM_001042503:Trim71 | − | NM_001042503 | Trim71 |
| chr9 | 120873571 | 121186290 | NM_177589:Ulk4 | − | NM_177589 | Ulk4 |
| chr9 | 56266652 | 56344743 | NM_025812:Hmg20a | + | NM_025812 | Hmg20a |
| chr9 | 58050703 | 58056615 | NR_033522:1600029O15Rik | + | NR_033522 | 1600029O15Rik |
| chr9 | 58044103 | 58052126 | NM_001161541:Islr2 | − | NM_001161541 | Islr2 |
| chr9 | 58064986 | 58097593 | NM_008884:Pml | − | NM_008884 | Pml |
| chr9 | 78224709 | 78226395 | NM_026480:Ooep | − | NM_026480 | Ooep |
| chr9 | 78214860 | 78216006 | NM_025274:Dppa5a | − | NM_025274 | Dppa5a |
| chr9 | 110854048 | 110886568 | NM_028838:Lrrc2 | + | NM_028838 | Lrrc2 |
| chr9 | 110842111 | 110848662 | NM_011562:Tdgf1 | − | NM_011562 | Tdgf1 |
| chr10 | 76514923 | 76629275 | NM_009929:Col18a1 | − | NM_009929 | Col18a1 |
| chr10 | 44156980 | 44178493 | NM_007548:Prdm1 | − | NM_007548 | Prdm1 |
| chr10 | 85061155 | 85123037 | NM_001017525:Btbd11 | + | NM_001017525 | Btbd11 |
| chr10 | 20844735 | 20880790 | NM_010848:Myb | − | NM_010848 | Myb |
| chr10 | 21698477 | 21719708 | NM_001161847:Sgk1 | + | NM_001161847 | Sgk1 |
| chr10 | 21712028 | 21719708 | NM_001161849:Sgk1 | + | NM_001161849 | Sgk1 |
| chr10 | 59412422 | 59414518 | NM_029083:Ddit4 | − | NM_029083 | Ddit4 |
| chr10 | 66474255 | 66559605 | NM_178606:Reep3 | − | NM_178606 | Reep3 |
| chr10 | 75385968 | 75395208 | NM_008606:Mmp11 | − | NM_008606 | Mmp11 |
| chr10 | 75398317 | 75400479 | NM_175329:Chchd10 | + | NM_175329 | Chchd10 |
| chr10 | 75411056 | 75412391 | NM_009514:Vpreb3 | + | NM_009514 | Vpreb3 |
| chr10 | 79498697 | 79502404 | NM_025554:Polr2e | − | NM_025554 | Polr2e |
| chr10 | 79516254 | 79519184 | NM_008162:Gpx4 | + | NM_008162 | Gpx4 |
| chr11 | 8331654 | 8564538 | NM_001083587:Tns3 | − | NM_001083587 | Tns3 |
| chr11 | 11830501 | 11927974 | NM_001177629:Grb10 | − | NM_001177629 | Grb10 |
| chr11 | 33111793 | 33413746 | NM_023146:Ranbp17 | − | NM_023146 | Ranbp17 |
| chr11 | 66838655 | 66848292 | NM_177392:Tmem220 | + | NM_177392 | Tmem220 |
| chr11 | 88152883 | 88579543 | NM_054043:Msi2 | − | NM_054043 | Msi2 |
| chr11 | 98821784 | 98836256 | NM_001176528:Rara | + | NM_001176528 | Rara |
| chr11 | 107069205 | 107332034 | NM_145823:Pitpnc1 | − | NM_145823 | Pitpnc1 |
| chr11 | 8893144 | 8911140 | NM_008316:Hus1 | − | NM_008316 | Hus1 |
| chr11 | 52174616 | 52202898 | NM_011694:Vdac1 | + | NM_011694 | Vdac1 |
| chr11 | 54716427 | 54723889 | NM_008161:Gpx3 | + | NM_008161 | Gpx3 |
| chr11 | 66725492 | 66742202 | NM_178656:Pirt | + | NM_178656 | Pirt |
| chr11 | 66891801 | 66915793 | NM_001099635:Myh3 | + | NM_001099635 | Myh3 |
| chr11 | 69496078 | 69499056 | NM_001159505:Tnfsf13 | − | NM_001159505 | Tnfsf13 |
| chr11 | 69486611 | 69495472 | NM_030702:Senp3 | − | NM_030702 | Senp3 |
| chr11 | 77694116 | 77707374 | NM_008952:Pipox | − | NM_008952 | Pipox |
| chr11 | 97547265 | 97549939 | NM_001085500:Cisd3 | + | NM_001085500 | Cisd3 |
| chr11 | 97550136 | 97560698 | NM_001163307:Pcgf2 | − | NM_001163307 | Pcgf2 |
| chr11 | 97524725 | 97546772 | NM_139311:Mllt6 | + | NM_139311 | Mllt6 |
| chr11 | 102165873 | 102180410 | NM_011551:Ubtf | − | NM_011551 | Ubtf |
| chr11 | 116976485 | 117020582 | NM_001166507:Sec14l1 | + | NM_001166507 | Sec14l1 |
| chr11 | 116976485 | 116990077 | NR_029459:Sec14l1 | + | NR_029459 | Sec14l1 |
| chr11 | 116976485 | 117020582 | NM_028777:Sec14l1 | + | NM_028777 | Sec14l1 |
| chr11 | 116938096 | 116940269 | NR_027059:2810008D09Rik | + | NR_027059 | 2810008D09Rik |
| chr11 | 117729262 | 117734840 | NM_027919:Tha1 | − | NM_027919 | Tha1 |
| chr11 | 117827400 | 117830680 | NM_007707:Socs3 | − | NM_007707 | Socs3 |
| chr12 | 103806792 | 103943079 | NM_172584:Itpk1 | − | NM_172584 | Itpk1 |
| chr12 | 87762593 | 87862578 | NM_011934:Esrrb | + | NM_011934 | Esrrb |
| chr12 | 111723948 | 111821271 | NM_012023:Ppp2r5c | + | NM_012023 | Ppp2r5c |
| chr12 | 111723948 | 111821271 | NM_001081457:Ppp2r5c | + | NM_001081457 | Ppp2r5c |
| chr12 | 112046007 | 112079149 | NM_011973:Stk30 | − | NM_011973 | Stk30 |
| chr12 | 12942898 | 12948642 | NM_008709:Mycn | − | NM_008709 | Mycn |
| chr12 | 55279967 | 55304861 | NM_028133:Egln3 | − | NM_028133 | Egln3 |
| chr12 | 56590395 | 56593634 | NM_010907:Nfkbia | − | NM_010907 | Nfkbia |
| chr12 | 57429293 | 57446881 | NM_145442:Mbip | − | NM_145442 | Mbip |
| chr12 | 88288292 | 88306314 | NM_173735:2310044G17Rik | + | NM_173735 | 2310044G17Rik |
| chr12 | 88221652 | 88225764 | NM_145836:6430527G18Rik | − | NM_145836 | 6430527G18Rik |
| chr12 | 111839604 | 111905154 | NM_030238:Dync1h1 | + | NM_030238 | Dync1h1 |
| chr13 | 96281683 | 96295195 | NM_007974:F2rl1 | − | NM_007974 | F2rl1 |
| chr13 | 98011059 | 98022995 | NM_007930:Enc1 | + | NM_007930 | Enc1 |
| chr13 | 110694016 | 110694096 | NR_035442:Mir1904 | + | NR_035442 | Mir1904 |
| chr14 | 22319075 | 22491355 | NM_017479:Myst4 | + | NM_017479 | Myst4 |
| chr14 | 55680495 | 55710885 | NM_001039198:Zfhx2 | − | NM_001039198 | Zfhx2 |
| chr14 | 65271367 | 65425133 | NM_001081177:Kif13b | + | NM_001081177 | Kif13b |
| chr14 | 71036011 | 71042075 | NM_008004:Fgf17 | − | NM_008004 | Fgf17 |

TABLE S4C-continued

| Super-enhancer associated genes in SDs | | | | | | |
|---|---|---|---|---|---|---|
| Chr | Start | End | Gene_ID | Strand | RefSeq_ID | Symbol |
| chr14 | 49277858 | 49282547 | NM_144841:Otx2 | − | NM_144841 | Otx2 |
| chr14 | 49288962 | 49413023 | NR_029384:Otx2os1 | + | NR_029384 | Otx2os1 |
| chr14 | 55725662 | 55735115 | NM_177049:Jph4 | − | NM_177049 | Jph4 |
| chr14 | 55713620 | 55717832 | NM_153083:Thtpa | + | NM_153083 | Thtpa |
| chr14 | 64111183 | 64127929 | NM_021480:Tdh | − | NM_021480 | Tdh |
| chr14 | 76904316 | 76907573 | NM_009366:Tsc22d1 | + | NM_009366 | Tsc22d1 |
| chr14 | 106291163 | 106296036 | NM_011897:Spry2 | − | NM_011897 | Spry2 |
| chr15 | 76909419 | 77137483 | NM_001110827:Rbm9 | − | NM_001110827 | Rbm9 |
| chr15 | 76909419 | 77137483 | NM_053104:Rbm9 | − | NM_053104 | Rbm9 |
| chr15 | 76909419 | 77137483 | NM_175387:Rbm9 | − | NM_175387 | Rbm9 |
| chr15 | 97074504 | 97077718 | NM_178114:Amigo2 | − | NM_178114 | Amigo2 |
| chr15 | 97074504 | 97077718 | NM_001164602:Amigo2 | − | NM_001164602 | Amigo2 |
| chr15 | 97074504 | 97077718 | NM_001164563:Amigo2 | − | NM_001164563 | Amigo2 |
| chr15 | 103360709 | 103368423 | NM_021391:Ppp1r1a | − | NM_021391 | Ppp1r1a |
| chr16 | 84774367 | 84823129 | NM_023844:Jam2 | + | NM_023844 | Jam2 |
| chr16 | 8688814 | 8738435 | NM_001003918:Usp7 | − | NM_001003918 | Usp7 |
| chr16 | 23107551 | 23114205 | NM_013506:Eif4a2 | + | NM_013506 | Eif4a2 |
| chr16 | 23107551 | 23114205 | NM_001123038:Eif4a2 | + | NM_001123038 | Eif4a2 |
| chr16 | 23107551 | 23114205 | NM_001123037:Eif4a2 | + | NM_001123037 | Eif4a2 |
| chr16 | 23109025 | 23109093 | NR_030705:Snord2 | + | NR_030705 | Snord2 |
| chr17 | 10399335 | 10512226 | NM_001159517:Qk | − | NM_001159517 | Qk |
| chr17 | 10403044 | 10512226 | NM_021881:Qk | − | NM_021881 | Qk |
| chr17 | 10403044 | 10512226 | NM_001159516:Qk | − | NM_001159516 | Qk |
| chr17 | 35649679 | 35653769 | NM_001163764:Tcf19 | − | NM_001163764 | Tcf19 |
| chr17 | 35649679 | 35653769 | NM_025674:Tcf19 | − | NM_025674 | Tcf19 |
| chr17 | 35649679 | 35653769 | NM_001163763:Tcf19 | − | NM_001163763 | Tcf19 |
| chr17 | 29227930 | 29237667 | NM_001111099:Cdkn1a | + | NM_001111099 | Cdkn1a |
| chr17 | 31981194 | 31992737 | NM_010831:Sik1 | − | NM_010831 | Sik1 |
| chr17 | 37091302 | 37095373 | NM_023162:Znrd1 | − | NM_023162 | Znrd1 |
| chr17 | 66686321 | 66799090 | NM_172963:1110012J17Rik | − | NM_172963 | 1110012J17Rik |
| chr17 | 66686321 | 66799090 | NM_001114098:1110012J17Rik | − | NM_001114098 | 1110012J17Rik |
| chr17 | 26642535 | 26645417 | NM_013642:Dusp1 | − | NM_013642 | Dusp1 |
| chr17 | 29627989 | 29632404 | NM_008842:Pim1 | + | NM_008842 | Pim1 |
| chr17 | 35642983 | 35647722 | NM_013633:Pou5f1 | + | NM_013633 | Pou5f1 |
| chr17 | 35654060 | 35667960 | NM_146248:Cchcr1 | + | NM_146248 | Cchcr1 |
| chr17 | 37114645 | 37118182 | NM_029747:2410137M14Rik | − | NM_029747 | 2410137M14Rik |
| chr17 | 37138107 | 37147674 | NM_001168502:Zfp57 | + | NM_001168502 | Zfp57 |
| chr17 | 37095536 | 37102568 | NM_029602:Znrd1as | + | NM_029602 | Znrd1as |
| chr17 | 37182910 | 37211250 | NM_019439:Gabbr1 | + | NM_019439 | Gabbr1 |
| chr17 | 37123799 | 37126449 | NM_001115075:H2-M5 | − | NM_001115075 | H2-M5 |
| chr17 | 37222135 | 37223181 | NM_146477:Olfr90 | − | NM_146477 | Olfr90 |
| chr17 | 47624998 | 47639236 | NM_022015:Taf8 | − | NM_022015 | Taf8 |
| chr17 | 47730415 | 47736637 | NM_007632:Ccnd3 | + | NM_007632 | Ccnd3 |
| chr17 | 71193544 | 71201074 | NM_001164075:Tgif1 | − | NM_001164075 | Tgif1 |
| chr17 | 71193544 | 71196117 | NM_001164077:Tgif1 | − | NM_001164077 | Tgif1 |
| chr18 | 35278565 | 35414429 | NM_009818:Ctnna1 | + | NM_009818 | Ctnna1 |
| chr18 | 36177311 | 36356814 | NM_001167891:Nrg2 | − | NM_001167891 | Nrg2 |
| chr18 | 40418014 | 40690838 | NM_026135:Kctd16 | + | NM_026135 | Kctd16 |
| chr18 | 38578628 | 38624060 | NM_022996:Ndfip1 | + | NM_022996 | Ndfip1 |
| chr18 | 61807478 | 61807548 | NR_029557:Mir145 | − | NR_029557 | Mir145 |
| chr18 | 75527018 | 75555588 | NM_001042660:Smad7 | + | NM_001042660 | Smad7 |
| chr19 | 21852831 | 21932817 | NM_001033759:Tmem2 | + | NM_001033759 | Tmem2 |
| chr19 | 21852831 | 21932817 | NM_031997:Tmem2 | + | NM_031997 | Tmem2 |
| chr19 | 5878465 | 5885768 | NM_134154:Slc25a45 | + | NM_134154 | Slc25a45 |
| chr19 | 5850973 | 5875208 | NM_026169:Frmd8 | − | NM_026169 | Frmd8 |
| chr19 | 5795689 | 5802671 | NR_002847:Malat1 | − | NR_002847 | Malat1 |
| chr19 | 5842301 | 5845478 | NR_003513:Neat1 | − | NR_003513 | Neat1 |
| chr19 | 23215715 | 23241401 | NM_010638:Klf9 | + | NM_010638 | Klf9 |
| chr19 | 23223920 | 23224041 | NR_035423:Mir1192 | + | NR_035423 | Mir1192 |
| chr19 | 25580195 | 25678818 | NM_015826:Dmrt1 | + | NM_015826 | Dmrt1 |
| chr19 | 53515701 | 53539286 | NR_028427:5830416P10Rik | − | NR_028427 | 5830416P10Rik |

TABLE S5A

| Polycomb Domains | | |
|---|---|---|
| Chr | Start | End |
| chr15 | 78453437 | 78575580 |
| chr10 | 61589218 | 61647017 |
| chr8 | 80799571 | 80992709 |
| chr1 | 39066910 | 39268483 |
| chr3 | 87994703 | 88039854 |

TABLE S5A-continued

| Polycomb Domains | | |
|---|---|---|
| Chr | Start | End |
| chr13 | 99120951 | 99232262 |
| chr9 | 111191818 | 111217605 |
| chr3 | 38782628 | 39605373 |
| chr15 | 74344113 | 74369524 |
| chr14 | 69762825 | 69854746 |

TABLE S5A-continued

| Polycomb Domains | | |
|---|---|---|
| Chr | Start | End |
| chr18 | 42502366 | 42628138 |
| chr1 | 74941139 | 74963127 |
| chr12 | 56618442 | 56822149 |
| chr18 | 67288025 | 67431503 |
| chr6 | 83645094 | 83677967 |
| chr2 | 146783872 | 147005727 |
| chr2 | 37780790 | 38232361 |
| chr4 | 140760096 | 140824721 |
| chr4 | 139345249 | 139415427 |
| chr19 | 25653445 | 25698186 |
| chr11 | 23948726 | 23983139 |
| chr3 | 87572271 | 87621437 |
| chr11 | 33076054 | 33455087 |
| chr2 | 74552598 | 74804510 |
| chr13 | 40712815 | 40845489 |
| chr10 | 86588382 | 86967665 |
| chr18 | 22832286 | 23286887 |
| chr12 | 112666820 | 112698672 |
| chr14 | 30949584 | 31274059 |
| chr5 | 120264806 | 120539422 |
| chr15 | 75557525 | 75579942 |
| chr9 | 40644350 | 40791552 |
| chr5 | 98595699 | 98759186 |
| chr7 | 139767015 | 139850634 |
| chr7 | 53647930 | 53863753 |
| chr15 | 11682493 | 11840486 |
| chr15 | 31244932 | 31349476 |
| chr7 | 149795933 | 149858881 |
| chr19 | 59184016 | 59271634 |
| chr18 | 81176251 | 81423397 |
| chr5 | 148036975 | 148106542 |
| chr4 | 139735055 | 139809270 |
| chr15 | 99389024 | 99428304 |
| chr8 | 123636646 | 123738210 |
| chr3 | 105253211 | 105478450 |
| chr5 | 120730927 | 120891521 |
| chr1 | 77974835 | 78416978 |
| chr11 | 103500171 | 103620942 |
| chr11 | 94977809 | 95022857 |
| chr1 | 74834000 | 74856527 |
| chr8 | 123493766 | 123617406 |
| chr1 | 157421785 | 157632809 |
| chr13 | 31299149 | 31713020 |
| chr11 | 107490351 | 107715175 |
| chr10 | 79802236 | 79813916 |
| chr3 | 93210295 | 93298739 |
| chr4 | 114589269 | 114620822 |
| chr2 | 147002703 | 147083205 |
| chr11 | 96059282 | 96208742 |
| chr18 | 74590407 | 74732341 |
| chr2 | 181393443 | 181414355 |
| chr3 | 87790216 | 87876709 |
| chr16 | 94075259 | 94481179 |
| chr8 | 47326713 | 47392786 |
| chr4 | 114710430 | 114758788 |
| chr11 | 85677002 | 85786772 |
| chr15 | 72346773 | 72854302 |
| chr6 | 126103930 | 126118687 |
| chr1 | 186315551 | 186562611 |
| chr5 | 140313918 | 140402553 |
| chr2 | 105362765 | 105522705 |
| chr2 | 143662464 | 144279180 |
| chr1 | 121241277 | 121341353 |
| chr11 | 98125902 | 98204996 |
| chr6 | 115850549 | 115958682 |
| chr11 | 116087328 | 116156661 |
| chr8 | 127140592 | 127352171 |
| chr2 | 107808286 | 109535988 |
| chr13 | 73388336 | 73448824 |
| chr5 | 38207655 | 38343863 |
| chr1 | 129396087 | 129577246 |
| chr6 | 82946180 | 83216057 |
| chr6 | 85129186 | 85190029 |
| chr1 | 19195103 | 20504651 |
| chr18 | 37248918 | 37379159 |
| chr11 | 120376481 | 120474857 |

TABLE S5A-continued

| Polycomb Domains | | |
|---|---|---|
| Chr | Start | End |
| chr2 | 118463167 | 118522728 |
| chr11 | 101780380 | 101831001 |
| chr11 | 96006370 | 96085858 |
| chr4 | 153981410 | 154050097 |
| chr9 | 57899009 | 58053538 |
| chr17 | 8580889 | 8655235 |
| chr2 | 133375372 | 133856190 |
| chr7 | 148091905 | 148125698 |
| chr7 | 56870962 | 57009360 |
| chr3 | 82680738 | 82800141 |
| chr2 | 103973933 | 104263430 |
| chr2 | 73004649 | 73120657 |
| chr4 | 136484379 | 136527669 |
| chr10 | 66780210 | 67192868 |
| chr5 | 148527856 | 148628871 |
| chr3 | 106896401 | 106991995 |
| chr9 | 74377669 | 74719719 |
| chr14 | 63825457 | 63977777 |
| chr2 | 127187661 | 127261670 |
| chr19 | 45655337 | 45822802 |
| chr9 | 78635225 | 79569738 |
| chr7 | 26410442 | 26486618 |
| chr3 | 17949132 | 18059258 |
| chr19 | 46209175 | 46329575 |
| chr11 | 71865741 | 71959460 |
| chr1 | 74930650 | 74940957 |
| chr3 | 55323975 | 55805071 |
| chr3 | 66214095 | 67149358 |
| chr1 | 122490637 | 123077811 |
| chr2 | 90706201 | 90902061 |
| chr2 | 61505881 | 62124926 |
| chr17 | 93557330 | 93932696 |
| chr8 | 87282578 | 87337839 |
| chr13 | 22065408 | 22121612 |
| chr8 | 124241314 | 124276189 |
| chr11 | 95751315 | 95802340 |
| chr5 | 37553758 | 37681406 |
| chr3 | 86131864 | 86566496 |
| chr10 | 126761070 | 126780074 |
| chr12 | 57781525 | 58087936 |
| chr4 | 136719874 | 136844703 |
| chr14 | 67009269 | 67404617 |
| chr2 | 147672633 | 147936683 |
| chr12 | 105696987 | 105785432 |
| chr1 | 72911922 | 72926795 |
| chr5 | 147976190 | 148040071 |
| chr6 | 52255415 | 52528135 |
| chr11 | 96143184 | 96166703 |
| chr11 | 120519625 | 120541935 |
| chr1 | 18349577 | 19169874 |
| chr3 | 118128160 | 118695479 |
| chr11 | 69576597 | 69620280 |
| chr9 | 49094744 | 49295473 |
| chr5 | 35704009 | 35818634 |
| chr4 | 88790816 | 88957518 |
| chr16 | 17743009 | 17813058 |
| chr7 | 89104078 | 89265473 |
| chr14 | 33122592 | 33287052 |
| chr6 | 53744181 | 53909484 |
| chr12 | 57342031 | 57642931 |
| chr4 | 46701340 | 47034439 |
| chr13 | 31892385 | 32049355 |
| chr15 | 99425402 | 99509823 |
| chr2 | 35864545 | 35998232 |
| chr2 | 93317161 | 93499982 |
| chr12 | 10810937 | 11186443 |
| chr10 | 61379340 | 61444236 |
| chr14 | 67830035 | 67869190 |
| chr5 | 37251936 | 37312176 |
| chr16 | 35539620 | 35597647 |
| chr9 | 20956721 | 20974128 |
| chr4 | 12167572 | 14363530 |
| chr7 | 31781201 | 31863978 |
| chr7 | 147154506 | 147249861 |
| chr2 | 170301302 | 170335132 |
| chr1 | 140731509 | 141053781 |

TABLE S5A-continued

| Polycomb Domains | | |
|---|---|---|
| Chr | Start | End |
| chr6 | 22071418 | 22397674 |
| chr18 | 80802693 | 80926892 |
| chr14 | 13151609 | 13364431 |
| chr7 | 137916138 | 138126964 |
| chr7 | 107136814 | 107178717 |
| chr11 | 116361766 | 116396593 |
| chr6 | 5955031 | 6835966 |
| chr15 | 98409888 | 98630657 |
| chr13 | 113775570 | 113827017 |
| chr14 | 70948562 | 71038375 |
| chr6 | 8885196 | 9185688 |
| chr8 | 87460671 | 87471691 |
| chr6 | 49468491 | 49870322 |
| chr1 | 88994744 | 89073481 |
| chr9 | 31366495 | 31734459 |
| chr9 | 99746742 | 100202840 |
| chr10 | 79908131 | 79970767 |
| chr11 | 85519669 | 85659081 |
| chr13 | 56321977 | 56362699 |
| chr16 | 11980485 | 12202145 |
| chr4 | 97417187 | 97911485 |
| chr10 | 29252035 | 29524795 |
| chr15 | 73663090 | 74369524 |
| chr11 | 103992553 | 104033788 |
| chr18 | 66093628 | 66125656 |
| chr8 | 125633945 | 125715446 |
| chr4 | 138477307 | 138635320 |
| chr2 | 147146382 | 147205592 |
| chr3 | 90215853 | 90271243 |
| chr16 | 18470420 | 18618580 |
| chr10 | 126612870 | 126621738 |
| chr14 | 57711442 | 57982545 |
| chr5 | 118451662 | 118520213 |
| chr8 | 73964776 | 74234839 |
| chr4 | 151587708 | 151753870 |
| chr11 | 57637946 | 57732427 |
| chr9 | 121385947 | 121581248 |
| chr4 | 142913865 | 142971364 |
| chr9 | 119466739 | 119490709 |
| chr15 | 10850327 | 10969260 |
| chr1 | 74972911 | 75064325 |
| chr15 | 64748903 | 65157656 |
| chr2 | 70116066 | 70402381 |
| chr2 | 118525313 | 118586356 |
| chr5 | 121129209 | 121165287 |
| chr2 | 119125322 | 119338875 |
| chr4 | 137937707 | 137983525 |
| chr17 | 46402394 | 46436363 |
| chr15 | 99044494 | 99097095 |
| chr5 | 148036975 | 148132108 |
| chr5 | 28777131 | 28797336 |
| chr17 | 14369226 | 14426045 |
| chr9 | 95440367 | 95574006 |
| chr2 | 84710105 | 84730933 |
| chr2 | 19352305 | 19442249 |
| chr13 | 113783396 | 113827017 |
| chr18 | 66392485 | 66564986 |
| chr2 | 121895058 | 122129431 |
| chr9 | 101083779 | 102257926 |
| chr16 | 17910946 | 17939895 |
| chr19 | 16876605 | 17060283 |
| chr9 | 37236402 | 37271442 |
| chr2 | 24264226 | 24425121 |
| chr3 | 153980376 | 154236535 |
| chr2 | 26037592 | 26084274 |
| chr9 | 87602547 | 87636359 |
| chr16 | 20508899 | 20643120 |
| chr2 | 93710179 | 93843387 |
| chr11 | 103624481 | 103773502 |
| chr19 | 43645038 | 43699410 |
| chr12 | 9576159 | 10445632 |
| chr15 | 100442477 | 100469933 |
| chr8 | 72938972 | 73031283 |
| chr6 | 88138316 | 88193555 |
| chr9 | 32212249 | 32398591 |
| chr15 | 75378540 | 75491511 |

TABLE S5A-continued

| Polycomb Domains | | |
|---|---|---|
| Chr | Start | End |
| chr10 | 19016883 | 19212199 |
| chr7 | 132926269 | 133234081 |
| chr17 | 46594272 | 46648931 |
| chr5 | 126008996 | 126060338 |
| chr3 | 99037342 | 99092954 |
| chr8 | 11468672 | 11486938 |
| chr13 | 13608409 | 13960951 |
| chr2 | 28610521 | 28833163 |
| chr4 | 114319862 | 114620822 |
| chr10 | 79812609 | 79837658 |
| chr10 | 22500836 | 22801962 |
| chr12 | 58926308 | 60049180 |
| chr4 | 21524834 | 21624000 |
| chr1 | 122234083 | 122366310 |
| chr7 | 151983330 | 152038090 |
| chr13 | 48750476 | 48775414 |
| chr6 | 52206381 | 52789571 |
| chr10 | 42027361 | 42322178 |
| chr4 | 124660720 | 124737193 |
| chr11 | 115130964 | 115216487 |
| chr12 | 87742959 | 87956056 |
| chr1 | 56809694 | 57035831 |
| chr6 | 29466717 | 29600672 |
| chr9 | 89721374 | 89869235 |
| chr2 | 180479038 | 180515035 |
| chr11 | 95258699 | 95383898 |
| chr9 | 118300480 | 118399774 |
| chr8 | 17166802 | 17538331 |
| chr5 | 67438839 | 67493882 |
| chr7 | 150280034 | 150325582 |
| chr16 | 35109416 | 35273269 |
| chr5 | 67971103 | 68119849 |
| chr2 | 71289578 | 71386963 |
| chr4 | 125954539 | 125987917 |
| chr11 | 118942545 | 118953732 |
| chr2 | 38546606 | 38595794 |
| chr1 | 5904967 | 6125995 |
| chr17 | 26939804 | 27024045 |
| chr1 | 74927030 | 74940957 |
| chr2 | 21839013 | 22578236 |
| chr5 | 35519528 | 35692272 |
| chr5 | 75356242 | 75540215 |
| chr12 | 8065982 | 8314120 |
| chr12 | 85886346 | 85931538 |
| chr12 | 103291998 | 103420889 |
| chr4 | 126344059 | 126419635 |
| chr7 | 57041827 | 57179746 |
| chr18 | 82202955 | 82739205 |
| chr8 | 86533322 | 86546421 |
| chr17 | 88171992 | 88278103 |
| chr11 | 76810383 | 76907780 |
| chr1 | 74809202 | 74831880 |
| chr19 | 45294566 | 45319625 |
| chr7 | 105891216 | 105990913 |
| chr2 | 31679069 | 31704211 |
| chr4 | 115574868 | 115626304 |
| chr2 | 158375206 | 158455993 |
| chr8 | 107787790 | 107808029 |
| chr19 | 45190897 | 45236347 |
| chr10 | 19427631 | 19614663 |
| chr17 | 85588047 | 86033886 |
| chr19 | 43101550 | 43471702 |
| chr16 | 44299003 | 44363083 |
| chr6 | 23707772 | 23837273 |
| chr14 | 58652944 | 59130521 |
| chr17 | 80098100 | 80241035 |
| chr17 | 23796716 | 23884186 |
| chr11 | 59051979 | 59107993 |
| chr19 | 5528726 | 5569646 |
| chr18 | 53580157 | 53832492 |
| chr5 | 75514435 | 75553930 |
| chr6 | 117116125 | 117127164 |
| chr2 | 31347377 | 31511670 |
| chr11 | 100927557 | 101039225 |
| chr14 | 65175865 | 65243974 |
| chr14 | 70473679 | 70497000 |

TABLE S5A-continued

| Polycomb Domains | | |
|---|---|---|
| Chr | Start | End |
| chr13 | 95329322 | 95712368 |
| chr13 | 51512928 | 51714192 |
| chr7 | 138682999 | 138739170 |
| chr17 | 57386369 | 57417093 |
| chr4 | 125162485 | 125173714 |
| chr15 | 85353258 | 85414686 |
| chr18 | 76537526 | 77130094 |
| chr19 | 44814055 | 44963095 |
| chr13 | 116020184 | 117504475 |
| chr2 | 91760879 | 91774433 |
| chr3 | 104591025 | 104771906 |
| chr5 | 113002319 | 113073418 |
| chr17 | 56641571 | 56688134 |
| chr17 | 86063603 | 86463636 |
| chr10 | 126947405 | 126975889 |
| chr17 | 8832553 | 9001147 |
| chr1 | 89142254 | 89190277 |
| chr1 | 13041583 | 13125339 |

TABLE S5A-continued

| Polycomb Domains | | |
|---|---|---|
| Chr | Start | End |
| chr12 | 73948167 | 74064551 |
| chr11 | 75594932 | 75717981 |
| chr15 | 98721260 | 98736004 |
| chr3 | 107158587 | 107266031 |
| chr4 | 128907441 | 128950835 |
| chr15 | 98409888 | 98488576 |
| chr1 | 133103585 | 133143809 |
| chr6 | 126513425 | 126653016 |
| chr6 | 23129575 | 23413638 |
| chr8 | 72397734 | 72415735 |
| chr19 | 54118289 | 54324013 |
| chr6 | 112356746 | 112651673 |
| chr9 | 30747116 | 30890857 |
| chr4 | 109249104 | 109693768 |
| chr3 | 104582317 | 104592928 |
| chr8 | 12191468 | 12565334 |
| chr6 | 145778132 | 145918769 |

TABLE S5B

| Polycomb target genes in PDs | | | | | | |
|---|---|---|---|---|---|---|
| Chr | Start | End | Gene_ID | Strand | RefSeq_ID | Symbol |
| chr1 | 13103508 | 13117244 | NM_001081209:Prdm14 | − | NM_001081209 | Prdm14 |
| chr1 | 19093102 | 19156413 | NM_153154:Tcfap2d | + | NM_153154 | Tcfap2d |
| chr1 | 39251116 | 39420085 | NM_008719:Npas2 | + | NM_008719 | Npas2 |
| chr1 | 56850824 | 57028178 | NM_139146:Satb2 | − | NM_139146 | Satb2 |
| chr1 | 74838592 | 74850749 | NM_009518:Wnt10a | + | NM_009518 | Wnt10a |
| chr1 | 78097841 | 78193711 | NM_008781:Pax3 | − | NM_008781 | Pax3 |
| chr1 | 78097841 | 78193711 | NM_001159520:Pax3 | − | NM_001159520 | Pax3 |
| chr1 | 129386918 | 129574598 | NM_028135:Tmem163 | − | NM_028135 | Tmem163 |
| chr1 | 5903787 | 5907479 | NM_010342:Npbwr1 | − | NM_010342 | Npbwr1 |
| chr1 | 19198994 | 19228815 | NM_009334:Tcfap2b | + | NM_009334 | Tcfap2b |
| chr1 | 19202134 | 19228815 | NM_001025305:Tcfap2b | + | NM_001025305 | Tcfap2b |
| chr1 | 57028312 | 57032040 | NR_024326:9130024F11Rik | + | NR_024326 | 9130024F11Rik |
| chr1 | 57028312 | 57032040 | NR_024325:9130024F11Rik | + | NR_024325 | 9130024F11Rik |
| chr1 | 72904638 | 72921439 | NM_010518:Igfbp5 | − | NM_010518 | Igfbp5 |
| chr1 | 74818465 | 74831893 | NM_009526:Wnt6 | + | NM_009526 | Wnt6 |
| chr1 | 74928082 | 74931982 | NM_153111:Fev | − | NM_153111 | Fev |
| chr1 | 74947231 | 74947295 | NR_029876:Mir375 | − | NR_029876 | Mir375 |
| chr1 | 74936517 | 74939709 | NM_021541:Cryba2 | − | NM_021541 | Cryba2 |
| chr1 | 74991891 | 74998225 | NM_010544:Ihh | − | NM_010544 | Ihh |
| chr1 | 89044229 | 89051602 | NM_021306:Ecel1 | − | NM_021306 | Ecel1 |
| chr1 | 89160938 | 89207366 | NM_028889:Efhd1 | + | NM_028889 | Efhd1 |
| chr1 | 121312041 | 121318825 | NM_008381:Inhbb | − | NM_008381 | Inhbb |
| chr1 | 122237158 | 122239751 | NM_207233:C1ql2 | + | NM_207233 | C1ql2 |
| chr1 | 122499063 | 122504568 | NM_010133:En1 | + | NM_010133 | En1 |
| chr1 | 133072986 | 133141755 | NM_018750:Rassf5 | − | NM_018750 | Rassf5 |
| chr1 | 140721762 | 140744156 | NM_010714:Lhx9 | − | NM_010714 | Lhx9 |
| chr1 | 140727523 | 140739021 | NM_001042577:Lhx9 | − | NM_001042577 | Lhx9 |
| chr1 | 140721762 | 140739021 | NM_001025565:Lhx9 | − | NM_001025565 | Lhx9 |
| chr1 | 157548823 | 157589157 | NM_010712:Lhx4 | − | NM_010712 | Lhx4 |
| chr1 | 186551023 | 186556372 | NM_008250:Hlx | − | NM_008250 | Hlx |
| chr2 | 22477846 | 22549397 | NM_008078:Gad2 | + | NM_008078 | Gad2 |
| chr2 | 103983231 | 104250491 | NM_001033347:D430041D05Rik | − | NM_001033347 | D430041D05Rik |
| chr2 | 105376236 | 105510487 | NR_002867:Pax6os1 | − | NR_002867 | Pax6os1 |
| chr2 | 147009818 | 147157417 | NR_030769:Nkx2-2as | + | NR_030769 | Nkx2-2as |
| chr2 | 147190729 | 147200784 | NM_008780:Pax1 | + | NM_008780 | Pax1 |
| chr2 | 19367289 | 19369128 | NM_018809:Ptf1a | + | NM_018809 | Ptf1a |
| chr2 | 24276079 | 24331086 | NM_011040:Pax8 | − | NM_011040 | Pax8 |
| chr2 | 26055731 | 26062076 | NM_001039653:Lhx3 | − | NM_001039653 | Lhx3 |
| chr2 | 28763199 | 28771960 | NM_001164186:Barhl1 | − | NM_001164186 | Barhl1 |
| chr2 | 28763199 | 28771941 | NM_019446:Barhl1 | − | NM_019446 | Barhl1 |
| chr2 | 31495556 | 31511315 | NM_001123362:Prdm12 | + | NM_001123362 | Prdm12 |
| chr2 | 31668809 | 31701525 | NM_178887:Fibcd1 | − | NM_178887 | Fibcd1 |
| chr2 | 35937472 | 35959580 | NM_001083127:Lhx6 | − | NM_001083127 | Lhx6 |
| chr2 | 35937472 | 35959580 | NM_001083126:Lhx6 | − | NM_001083126 | Lhx6 |
| chr2 | 35937472 | 35960928 | NM_008500:Lhx6 | − | NM_008500 | Lhx6 |
| chr2 | 35937472 | 35960928 | NM_001083125:Lhx6 | − | NM_001083125 | Lhx6 |
| chr2 | 38206827 | 38225248 | NM_010710:Lhx2 | + | NM_010710 | Lhx2 |
| chr2 | 38548179 | 38570062 | NM_139051:Nr5a1 | − | NM_139051 | Nr5a1 |
| chr2 | 61642509 | 61652170 | NM_009322:Tbr1 | + | NM_009322 | Tbr1 |

TABLE S5B-continued

Polycomb target genes in PDs

| Chr | Start | End | Gene_ID | Strand | RefSeq_ID | Symbol |
|---|---|---|---|---|---|---|
| chr2 | 70312979 | 70315783 | NM_022435:Sp5 | + | NM_022435 | Sp5 |
| chr2 | 71368694 | 71375948 | NR_002854:Dlx1as | − | NR_002854 | Dlx1as |
| chr2 | 71381464 | 71384811 | NM_010054:Dlx2 | − | NM_010054 | Dlx2 |
| chr2 | 73109982 | 73113828 | NM_001005343:Sp9 | + | NM_001005343 | Sp9 |
| chr2 | 74601036 | 74603199 | NM_010467:Hoxd1 | + | NM_010467 | Hoxd1 |
| chr2 | 84712102 | 84726849 | NM_199223:Rtn4rl2 | − | NM_199223 | Rtn4r12 |
| chr2 | 90725942 | 90730683 | NM_026161:C1qtnf4 | + | NM_026161 | C1qtnf4 |
| chr2 | 91762345 | 91769986 | NM_007699:Chrm4 | + | NM_007699 | Chrm4 |
| chr2 | 93482590 | 93521496 | NM_007442:Alx4 | + | NM_007442 | Alx4 |
| chr2 | 93795966 | 93797257 | NM_001145034:Gm13889 | − | NM_001145034 | Gm13889 |
| chr2 | 109514856 | 109567200 | NM_007540:Bdnf | + | NM_007540 | Bdnf |
| chr2 | 118502981 | 118523756 | NM_001145854:Pak6 | + | NM_001145854 | Pak6 |
| chr2 | 118524838 | 118529699 | NM_001081971:Gm1337 | − | NM_001081971 | Gm1337 |
| chr2 | 119151519 | 119161402 | NM_019454:Dll4 | + | NM_019454 | Dll4 |
| chr2 | 119146934 | 119151933 | NR_030683:Gm14207 | − | NR_030683 | Gm14207 |
| chr2 | 122124635 | 122128621 | NM_025777:Duoxa2 | + | NM_025777 | Duoxa2 |
| chr2 | 122106172 | 122123901 | NM_177610:Duox2 | − | NM_177610 | Duox2 |
| chr2 | 127189021 | 127192957 | NM_009633:Adra2b | + | NM_009633 | Adra2b |
| chr2 | 133378934 | 133388621 | NM_007553:Bmp2 | + | NM_007553 | Bmp2 |
| chr2 | 144130911 | 144157816 | NM_026924:Ovol2 | − | NM_026924 | Ovol2 |
| chr2 | 144130911 | 144157098 | NM_152947:Ovol2 | − | NM_152947 | Ovol2 |
| chr2 | 146909611 | 146911081 | NM_023504:Nkx2-4 | − | NM_023504 | Nkx2-4 |
| chr2 | 147008887 | 147012138 | NM_010919:Nkx2-2 | − | NM_010919 | Nkx2-2 |
| chr2 | 147003281 | 147012138 | NM_001077632:Nkx2-2 | − | NM_001077632 | Nkx2-2 |
| chr2 | 147868613 | 147872705 | NM_010446:Foxa2 | − | NM_010446 | Foxa2 |
| chr2 | 158436493 | 158441483 | NM_009508:Slc32a1 | + | NM_009508 | Slc32a1 |
| chr2 | 170308464 | 170322638 | NM_009996:Cyp24a1 | − | NM_009996 | Cyp24a1 |
| chr2 | 170321927 | 170344567 | NM_001013369:Pfdn4 | + | NM_001013369 | Pfdn4 |
| chr2 | 180509085 | 180511605 | NM_080641:Bhlhe23 | − | NM_080641 | Bhlhe23 |
| chr2 | 181404541 | 181406345 | NM_009236:Sox18 | − | NM_009236 | Sox18 |
| chr3 | 38785861 | 38910905 | NM_183221:Fat4 | + | NM_183221 | Fat4 |
| chr3 | 17954324 | 17957514 | NM_021560:Bhlhe22 | + | NM_021560 | Bhlhe22 |
| chr3 | 82696503 | 82707896 | NM_023624:Lrat | − | NM_023624 | Lrat |
| chr3 | 99057682 | 99158183 | NM_009323:Tbx15 | + | NM_009323 | Tbx15 |
| chr3 | 105255247 | 105476920 | NM_001039347:Kcnd3 | + | NM_001039347 | Kcnd3 |
| chr3 | 55586431 | 55589209 | NM_010750:Mab21l1 | + | NM_010750 | Mab21l1 |
| chr3 | 66777190 | 66785693 | NM_013665:Shox2 | − | NM_013665 | Shox2 |
| chr3 | 86349502 | 86352205 | NM_011839:Mab21l2 | − | NM_011839 | Mab21l2 |
| chr3 | 87600872 | 87620023 | NM_011832:Insrr | + | NM_011832 | Insrr |
| chr3 | 87582165 | 87599084 | NM_001033124:Ntrk1 | − | NM_001033124 | Ntrk1 |
| chr3 | 87796435 | 87804278 | NM_001109758:Bcan | − | NM_001109758 | Bcan |
| chr3 | 87791452 | 87804278 | NM_007529:Bcan | − | NM_007529 | Bcan |
| chr3 | 88019519 | 88019608 | NR_029817:Mir9-1 | + | NR_029817 | Mir9-1 |
| chr3 | 90254513 | 90269788 | NM_008727:Npr1 | − | NM_008727 | Npr1 |
| chr3 | 93246251 | 93252999 | NM_001163098:Tchh | + | NM_001163098 | Tchh |
| chr3 | 104570323 | 104580465 | NM_183224:Fam19a3 | − | NM_183224 | Fam19a3 |
| chr3 | 104747722 | 104764627 | NM_009520:Wnt2b | − | NM_009520 | Wnt2b |
| chr3 | 106904484 | 106909797 | NM_008417:Kcna2 | + | NM_008417 | Kcna2 |
| chr3 | 107241220 | 107261816 | NM_145922:Kcnc4 | − | NM_145922 | Kcnc4 |
| chr3 | 118136774 | 118136847 | NR_029551:Mir137 | + | NR_029551 | Mir137 |
| chr3 | 153969257 | 153993524 | NM_010713:Lhx8 | − | NM_010713 | Lhx8 |
| chr4 | 97444316 | 97785567 | NM_010905:Nfia | + | NM_010905 | Nfia |
| chr4 | 97444316 | 97785567 | NM_001122953:Nfia | + | NM_001122953 | Nfia |
| chr4 | 13670448 | 13820790 | NM_001111026:Runx1t1 | + | NM_001111026 | Runx1t1 |
| chr4 | 46676769 | 47004586 | NM_001081141:Gabbr2 | − | NM_001081141 | Gabbr2 |
| chr4 | 115587723 | 115612531 | NM_130865:Dmbx1 | − | NM_130865 | Dmbx1 |
| chr4 | 115587723 | 115612531 | NM_001025567:Dmbx1 | − | NM_001025567 | Dmbx1 |
| chr4 | 125168074 | 125391417 | NM_001081097:Grik3 | + | NM_001081097 | Grik3 |
| chr4 | 136833549 | 136852694 | NM_009523:Wnt4 | + | NM_009523 | Wnt4 |
| chr4 | 139293995 | 139388883 | NM_011039:Pax7 | − | NM_011039 | Pax7 |
| chr4 | 139582766 | 139802726 | NM_198610:Igsf21 | − | NM_198610 | Igsf21 |
| chr4 | 153690233 | 154010982 | NM_027504:Prdm16 | − | NM_027504 | Prdm16 |
| chr4 | 153690233 | 154010982 | NM_001177995:Prdm16 | − | NM_001177995 | Prdm16 |
| chr4 | 21604626 | 21613110 | NM_001080771:Prdm13 | − | NM_001080771 | Prdm13 |
| chr4 | 88920376 | 88928096 | NM_001040654:Cdkn2a | − | NM_001040654 | Cdkn2a |
| chr4 | 109650629 | 109656289 | NM_172296:Dmrta2 | + | NM_172296 | Dmrta2 |
| chr4 | 114597751 | 114598618 | NM_015758:Foxe3 | − | NM_015758 | Foxe3 |
| chr4 | 114578884 | 114581503 | NM_008593:Foxd2 | − | NM_008593 | Foxd2 |
| chr4 | 114581893 | 114593723 | NR_030721:9130206I24Rik | + | NR_030721 | 9130206I24Rik |
| chr4 | 114732131 | 114744360 | NM_011527:Tal1 | + | NM_011527 | Tal1 |
| chr4 | 124663673 | 124686343 | NM_138683:Rspo1 | + | NM_138683 | Rspo1 |
| chr4 | 125964037 | 125991574 | NM_199473:Col8a2 | + | NM_199473 | Col8a2 |
| chr4 | 126393246 | 126413513 | NM_198960:Tcfap2e | − | NM_198960 | Tcfap2e |
| chr4 | 128896821 | 128925687 | NM_001033189:C77080 | − | NM_001033189 | C77080 |
| chr4 | 136485333 | 136512731 | NM_007939:Epha8 | − | NM_007939 | Epha8 |
| chr4 | 137950006 | 137952373 | NM_001081672:Fam43b | − | NM_001081672 | Fam43b |

TABLE S5B-continued

| Polycomb target genes in PDs | | | | | | |
|---|---|---|---|---|---|---|
| Chr | Start | End | Gene_ID | Strand | RefSeq_ID | Symbol |
| chr4 | 138617323 | 138630704 | NM_021358:Htr6 | − | NM_021358 | Htr6 |
| chr4 | 140798798 | 140813477 | NM_172520:Arhgef19 | + | NM_172520 | Arhgef19 |
| chr4 | 142939652 | 142960931 | NM_001162983:Lrrc38 | + | NM_001162983 | Lrrc38 |
| chr4 | 151660080 | 151665771 | NM_008237:Hes3 | − | NM_008237 | Hes3 |
| chr4 | 151681131 | 151692734 | NM_001033489:Rnf207 | − | NM_001033489 | Rnf207 |
| chr5 | 118477832 | 118511879 | NM_021344:Tesc | + | NM_021344 | Tesc |
| chr5 | 28793523 | 29045749 | NR_015562:9530036O11Rik | + | NR_015562 | 9530036O11Rik |
| chr5 | 98683202 | 98706049 | NM_010203:Fgf5 | + | NM_010203 | Fgf5 |
| chr5 | 112848177 | 113006205 | NM_019982:Sez6l | − | NM_019982 | Sez6l |
| chr5 | 120284671 | 120335227 | NM_011537:Tbx5 | + | NM_011537 | Tbx5 |
| chr5 | 126012787 | 126272953 | NM_001190352:Tmem132b | + | NM_001190352 | Tmem132b |
| chr5 | 148373771 | 148537564 | NM_010228:Flt1 | − | NM_010228 | Flt1 |
| chr5 | 28783379 | 28793641 | NM_009170:Shh | − | NM_009170 | Shh |
| chr5 | 35621214 | 35624412 | NM_007418:Adra2c | + | NM_007418 | Adra2c |
| chr5 | 35731765 | 35735521 | NM_010445:Hmx1 | + | NM_010445 | Hmx1 |
| chr5 | 37259808 | 37346317 | NM_172994:Ppp2r2c | + | NM_172994 | Ppp2r2c |
| chr5 | 37633318 | 37683370 | NM_001136058:Crmp1 | + | NM_001136058 | Crmp1 |
| chr5 | 38211802 | 38213990 | NR_027920:Msx1as | + | NR_027920 | Msx1as |
| chr5 | 67485635 | 67490365 | NM_008888:Phox2b | − | NM_008888 | Phox2b |
| chr5 | 67999121 | 68003511 | NM_001033415:Shisa3 | + | NM_001033415 | Shisa3 |
| chr5 | 75471625 | 75473918 | NM_133256:Gsx2 | + | NM_133256 | Gsx2 |
| chr5 | 75548315 | 75594229 | NM_011058:Pdgfra | + | NM_011058 | Pdgfra |
| chr5 | 75552190 | 75594229 | NM_001083316:Pdgfra | + | NM_001083316 | Pdgfra |
| chr5 | 98609887 | 98616467 | NM_029947:Prdm8 | + | NM_029947 | Prdm8 |
| chr5 | 120881894 | 120891466 | NM_008499:Lhx5 | + | NM_008499 | Lhx5 |
| chr5 | 121130272 | 121161678 | NM_008052:Dtx1 | − | NM_008052 | Dtx1 |
| chr5 | 140383896 | 140450678 | NM_175522:Elfn1 | + | NM_175522 | Elfn1 |
| chr5 | 148000271 | 148002522 | NM_008178:Gsx1 | + | NM_008178 | Gsx1 |
| chr5 | 148081706 | 148086725 | NM_008814:Pdx1 | + | NM_008814 | Pdx1 |
| chr5 | 148112475 | 148118825 | NM_007673:Cdx2 | − | NM_007673 | Cdx2 |
| chr6 | 6813333 | 6817970 | NM_010057:Dlx6 | + | NM_010057 | Dlx6 |
| chr6 | 6770545 | 6819533 | NR_015388:Dlx6os1 | − | NR_015388 | Dlx6os1 |
| chr6 | 8900018 | 9198578 | NM_008751:Nxph1 | + | NM_008751 | Nxph1 |
| chr6 | 23212837 | 23789300 | NM_153163:Cadps2 | − | NM_153163 | Cadps2 |
| chr6 | 126051429 | 126116762 | NM_001164034:Ntf3 | − | NM_001164034 | Ntf3 |
| chr6 | 126051429 | 126116762 | NM_008742:Ntf3 | − | NM_008742 | Ntf3 |
| chr6 | 126051429 | 126114978 | NM_001164035:Ntf3 | − | NM_001164035 | Ntf3 |
| chr6 | 6813796 | 6815150 | NR_002839:Dlx6as | − | NR_002839 | Dlx6as |
| chr6 | 6827804 | 6832068 | NM_198854:Dlx5 | − | NM_198854 | Dlx5 |
| chr6 | 6827804 | 6832068 | NM_010056:Dlx5 | − | NM_010056 | Dlx5 |
| chr6 | 22238226 | 22248522 | NM_053116:Wnt16 | + | NM_053116 | Wnt16 |
| chr6 | 23195046 | 23198264 | NM_028462:Fezf1 | − | NM_028462 | Fezf1 |
| chr6 | 29476732 | 29487319 | NM_012057:Irf5 | + | NM_012057 | Irf5 |
| chr6 | 49772727 | 49779504 | NM_023456:Npy | + | NM_023456 | Npy |
| chr6 | 52263491 | 52268372 | NM_007966:Evx1 | + | NM_007966 | Evx1 |
| chr6 | 52208851 | 52210874 | NM_008264:Hoxa13 | − | NM_008264 | Hoxa13 |
| chr6 | 53765461 | 53770819 | NM_025817:1200009O22Rik | − | NM_025817 | 1200009O22Rik |
| chr6 | 83018318 | 83020219 | NM_009392:Tlx2 | − | NM_009392 | Tlx2 |
| chr6 | 83661257 | 83688298 | NM_011912:Vax2 | + | NM_011912 | Vax2 |
| chr6 | 83642799 | 83662195 | NR_002871:Vax2os2 | − | NR_002871 | Vax2os2 |
| chr6 | 83652095 | 83660926 | NR_002873:Vax2os1 | − | NR_002873 | Vax2os1 |
| chr6 | 85137924 | 85154457 | NM_010131:Emx1 | + | NM_010131 | Emx1 |
| chr6 | 88148657 | 88157026 | NM_008090:Gata2 | + | NM_008090 | Gata2 |
| chr6 | 112423677 | 112439802 | NM_001081147:Oxtr | − | NM_001081147 | Oxtr |
| chr6 | 115904828 | 115945023 | NM_026376:Plxnd1 | − | NM_026376 | Plxnd1 |
| chr6 | 117118552 | 117131386 | NM_013655:Cxcl12 | + | NM_013655 | Cxcl12 |
| chr6 | 117118552 | 117125087 | NM_021704:Cxcl12 | + | NM_021704 | Cxcl12 |
| chr6 | 117118552 | 117131386 | NM_001012477:Cxcl12 | + | NM_001012477 | Cxcl12 |
| chr6 | 126586480 | 126595819 | NM_010595:Kcna1 | − | NM_010595 | Kcna1 |
| chr6 | 145811256 | 145813860 | NM_024469:Bhlhe41 | − | NM_024469 | Bhlhe41 |
| chr7 | 89111547 | 89137185 | NM_007562:Bnc1 | − | NM_007562 | Bnc1 |
| chr7 | 133021932 | 133225925 | NM_001101488:Gsg1l | − | NM_001101488 | Gsg1l |
| chr7 | 26472020 | 26490015 | NM_011577:Tgfb1 | + | NM_011577 | Tgfb1 |
| chr7 | 148106800 | 148114439 | NM_001081389:Nlrp6 | + | NM_001081389 | Nlrp6 |
| chr7 | 150293158 | 150612947 | NM_008434:Kcnq1 | + | NM_008434 | Kcnq1 |
| chr7 | 31827533 | 31836473 | NM_022007:Fxyd7 | − | NM_022007 | Fxyd7 |
| chr7 | 31836696 | 31840675 | NM_052992:Fxyd1 | − | NM_052992 | Fxyd1 |
| chr7 | 31836696 | 31840675 | NM_019503:Fxyd1 | − | NM_019503 | Fxyd1 |
| chr7 | 31836696 | 31839872 | NM_194321:Fxyd1 | − | NM_194321 | Fxyd1 |
| chr7 | 31836696 | 31839872 | NM_052991:Fxyd1 | − | NM_052991 | Fxyd1 |
| chr7 | 53651866 | 53694074 | NM_001112739:Kcnc1 | + | NM_001112739 | Kcnc1 |
| chr7 | 53651837 | 53688723 | NM_008421:Kcnc1 | + | NM_008421 | Kcnc1 |
| chr7 | 56886868 | 56892205 | NM_001005232:Dbx1 | − | NM_001005232 | Dbx1 |
| chr7 | 57167069 | 57214863 | NM_148931:Slc6a5 | + | NM_148931 | Slc6a5 |
| chr7 | 57165668 | 57214863 | NM_001146013:Slc6a5 | + | NM_001146013 | Slc6a5 |
| chr7 | 105987354 | 106003257 | NM_009519:Wnt11 | + | NM_009519 | Wnt11 |

TABLE S5B-continued

| Polycomb target genes in PDs | | | | | | |
|---|---|---|---|---|---|---|
| Chr | Start | End | Gene_ID | Strand | RefSeq_ID | Symbol |
| chr7 | 107154913 | 107183236 | NM_133709:Chrdl2 | + | NM_133709 | Chrdl2 |
| chr7 | 138079716 | 138129172 | NM_019564:Htra1 | + | NM_019564 | Htra1 |
| chr7 | 138686476 | 138688445 | NM_008257:Hmx3 | + | NM_008257 | Hmx3 |
| chr7 | 138697575 | 138700096 | NM_145998:Hmx2 | + | NM_145998 | Hmx2 |
| chr7 | 139787921 | 139791320 | NM_009123:Nkx1-2 | − | NM_009123 | Nkx1-2 |
| chr7 | 147232055 | 147234987 | NM_010836:Msx3 | − | NM_010836 | Msx3 |
| chr7 | 149836672 | 149843386 | NM_001122737:Igf2 | − | NM_001122737 | Igf2 |
| chr7 | 149836672 | 149846940 | NM_001122736:Igf2 | − | NM_001122736 | Igf2 |
| chr7 | 149836672 | 149844709 | NM_010514:Igf2 | − | NM_010514 | Igf2 |
| chr7 | 149845597 | 149856261 | NR_002855:Igf2as | + | NR_002855 | Igf2as |
| chr7 | 152024516 | 152029253 | NM_008007:Fgf3 | + | NM_008007 | Fgf3 |
| chr8 | 15892544 | 17535385 | NM_053171:Csmd1 | − | NM_053171 | Csmd1 |
| chr8 | 87231497 | 87298268 | NM_001081981:Nfix | − | NM_001081981 | Nfix |
| chr8 | 87231497 | 87324239 | NM_010906:Nfix | − | NM_010906 | Nfix |
| chr8 | 87231497 | 87324239 | NM_001081982:Nfix | − | NM_001081982 | Nfix |
| chr8 | 124254462 | 124314721 | NM_020605:Jph3 | + | NM_020605 | Jph3 |
| chr8 | 11453976 | 11478499 | NM_011227:Rab20 | − | NM_011227 | Rab20 |
| chr8 | 12385770 | 12436732 | NR_027975:Gm5607 | + | NR_027975 | Gm5607 |
| chr8 | 47377401 | 47380025 | NM_173789:Helt | − | NM_173789 | Helt |
| chr8 | 72404264 | 72411291 | NM_026818:Cilp2 | − | NM_026818 | Cilp2 |
| chr8 | 73017054 | 73027980 | NM_018827:Crlf1 | + | NM_018827 | Crlf1 |
| chr8 | 74213150 | 74214476 | NM_013564:Insl3 | + | NM_013564 | Insl3 |
| chr8 | 80956907 | 80960551 | NM_138944:Pou4f2 | − | NM_138944 | Pou4f2 |
| chr8 | 86535413 | 86535532 | NR_035431:Mir1199 | − | NR_035431 | Mir1199 |
| chr8 | 87470889 | 87480502 | NM_144929:Rtbdn | + | NM_144929 | Rtbdn |
| chr8 | 107793773 | 107799745 | NM_011939:Hsf4 | + | NM_011939 | Hsf4 |
| chr8 | 123651584 | 123654544 | NM_008024:Foxl1 | + | NM_008024 | Foxl1 |
| chr8 | 123640070 | 123642794 | NM_013519:Foxc2 | + | NM_013519 | Foxc2 |
| chr8 | 123608373 | 123610779 | NM_010426:Foxf1a | + | NM_010426 | Foxf1a |
| chr8 | 125641273 | 125659085 | NM_170684:Cpne7 | + | NM_170684 | Cpne7 |
| chr8 | 127316918 | 127358604 | NM_198632:Trim67 | + | NM_198632 | Trim67 |
| chr9 | 20970157 | 21017692 | NM_183408:Pde4a | + | NM_183408 | Pde4a |
| chr9 | 31653628 | 31720870 | NM_013800:Barx2 | − | NM_013800 | Barx2 |
| chr9 | 32229792 | 32348953 | NM_008026:Fli1 | − | NM_008026 | Fli1 |
| chr9 | 37223629 | 37240760 | NM_001164767:Robo3 | − | NM_001164767 | Robo3 |
| chr9 | 49148766 | 49215319 | NM_010077:Drd2 | + | NM_010077 | Drd2 |
| chr9 | 74709727 | 74737454 | NM_008262:Onecut1 | + | NM_008262 | Onecut1 |
| chr9 | 79446797 | 79566485 | NM_007730:Col12a1 | − | NM_007730 | Col12a1 |
| chr9 | 89804612 | 89921817 | NM_011245:Rasgrf1 | + | NM_011245 | Rasgrf1 |
| chr9 | 101824457 | 102257023 | NM_173447:Ephb1 | − | NM_173447 | Ephb1 |
| chr9 | 101824457 | 102257023 | NM_001168296:Ephb1 | − | NM_001168296 | Ephb1 |
| chr9 | 111214242 | 111298279 | NM_001164659:Trank1 | + | NM_001164659 | Trank1 |
| chr9 | 119392528 | 119488134 | NM_021544:Scn5a | − | NM_021544 | Scn5a |
| chr9 | 121486960 | 121550684 | NM_026915:Lyzl4 | − | NM_026915 | Lyzl4 |
| chr9 | 30750147 | 30770443 | NM_013906:Adamts8 | + | NM_013906 | Adamts8 |
| chr9 | 40682209 | 40686055 | NM_178245:Bsx | + | NM_178245 | Bsx |
| chr9 | 58044103 | 58049522 | NM_001161537:Islr2 | − | NM_001161537 | Islr2 |
| chr9 | 58044103 | 58049606 | NM_001161540:Islr2 | − | NM_001161540 | Islr2 |
| chr9 | 58044103 | 58050092 | NM_001161536:Islr2 | − | NM_001161536 | Islr2 |
| chr9 | 58044103 | 58050092 | NM_177193:Islr2 | − | NM_177193 | Islr2 |
| chr9 | 58044103 | 58050341 | NM_001161538:Islr2 | − | NM_001161538 | Islr2 |
| chr9 | 58050703 | 58056615 | NR_033522:1600029O15Rik | + | NR_033522 | 1600029O15Rik |
| chr9 | 58044103 | 58052126 | NM_001161541:Islr2 | − | NM_001161541 | Islr2 |
| chr9 | 58044103 | 58050151 | NM_001161539:Islr2 | − | NM_001161539 | Islr2 |
| chr9 | 58044103 | 58049522 | NM_001161535:Islr2 | − | NM_001161535 | Islr2 |
| chr9 | 87597634 | 87626095 | NM_023814:Tbx18 | − | NM_023814 | Tbx18 |
| chr9 | 89804612 | 89810685 | NM_001039655:Rasgrf1 | + | NM_001039655 | Rasgrf1 |
| chr9 | 95460235 | 95462540 | NM_198414:Paqr9 | + | NM_198414 | Paqr9 |
| chr9 | 99774524 | 99776589 | NM_011440:Sox14 | − | NM_011440 | Sox14 |
| chr9 | 118387306 | 118395250 | NM_001164789:Eomes | + | NM_001164789 | Eomes |
| chr9 | 118387306 | 118395250 | NM_010136:Eomes | + | NM_010136 | Eomes |
| chr9 | 121551833 | 121582072 | NM_011703:Vipr1 | + | NM_011703 | Vipr1 |
| chr10 | 29172912 | 29255673 | NM_028351:Rspo3 | − | NM_028351 | Rspo3 |
| chr10 | 61301245 | 61441856 | NM_007731:Col13a1 | − | NM_007731 | Col13a1 |
| chr10 | 79819203 | 79828234 | NM_183152:Plk5 | + | NM_183152 | Plk5 |
| chr10 | 126609481 | 126617701 | NM_177615:Slc26a10 | − | NM_177615 | Slc26a10 |
| chr10 | 19076344 | 19078410 | NM_053008:Olig3 | + | NM_053008 | Olig3 |
| chr10 | 19567722 | 19571265 | NM_029529:Slc35d3 | − | NM_029529 | Slc35d3 |
| chr10 | 22537078 | 22539934 | NM_011545:Tcf21 | − | NM_011545 | Tcf21 |
| chr10 | 42281776 | 42303394 | NM_152229:Nr2e1 | − | NM_152229 | Nr2e1 |
| chr10 | 61595837 | 61597511 | NM_009719:Neurog3 | + | NM_009719 | Neurog3 |
| chr10 | 67000616 | 67004936 | NM_010118:Egr2 | + | NM_010118 | Egr2 |
| chr10 | 79803460 | 79811191 | NM_001113548:Adamtsl5 | − | NM_001113548 | Adamtsl5 |
| chr10 | 79805483 | 79811157 | NM_025629:Adamtsl5 | − | NM_025629 | Adamtsl5 |
| chr10 | 79957650 | 79980005 | NM_139226:Onecut3 | + | NM_139226 | Onecut3 |
| chr10 | 86953785 | 86956405 | NM_008553:Ascl1 | − | NM_008553 | Ascl1 |

TABLE S5B-continued

Polycomb target genes in PDs

| Chr | Start | End | Gene_ID | Strand | RefSeq_ID | Symbol |
|---|---|---|---|---|---|---|
| chr10 | 126760782 | 126766999 | NM_146011:Arhgap9 | + | NM_146011 | Arhgap9 |
| chr10 | 126962528 | 126971615 | NM_183297:Nxph4 | − | NM_183297 | Nxph4 |
| chr11 | 23978055 | 24073558 | NM_016707:Bcl11a | + | NM_016707 | Bcl11a |
| chr11 | 23980694 | 24073558 | NM_001159290:Bcl11a | + | NM_001159290 | Bcl11a |
| chr11 | 23978055 | 24073558 | NM_001159289:Bcl11a | + | NM_001159289 | Bcl11a |
| chr11 | 85710266 | 85729599 | NM_172798:Tbx4 | + | NM_172798 | Tbx4 |
| chr11 | 85703564 | 85729599 | NM_011536:Tbx4 | + | NM_011536 | Tbx4 |
| chr11 | 103635488 | 103679335 | NM_009521:Wnt3 | + | NM_009521 | Wnt3 |
| chr11 | 107596093 | 107655778 | NM_019431:Cacng4 | − | NM_019431 | Cacng4 |
| chr11 | 33100751 | 33103588 | NM_019916:Tlx3 | − | NM_019916 | Tlx3 |
| chr11 | 57642214 | 57645649 | NM_008213:Hand1 | − | NM_008213 | Hand1 |
| chr11 | 59061543 | 59104253 | NM_009522:Wnt3a | − | NM_009522 | Wnt3a |
| chr11 | 69617096 | 69619126 | NM_001033433:Tmem102 | − | NM_001033433 | Tmem102 |
| chr11 | 71861029 | 71949391 | NM_001081641:Pitpnm3 | − | NM_001081641 | Pitpnm3 |
| chr11 | 71861029 | 71949391 | NM_001024927:Pitpnm3 | − | NM_001024927 | Pitpnm3 |
| chr11 | 75582591 | 75609559 | NM_007873:Doc2b | − | NM_007873 | Doc2b |
| chr11 | 76812098 | 76845845 | NM_010484:Slc6a4 | + | NM_010484 | Slc6a4 |
| chr11 | 85646116 | 85655450 | NM_009324:Tbx2 | + | NM_009324 | Tbx2 |
| chr11 | 94981430 | 94986605 | NM_010055:Dlx3 | + | NM_010055 | Dlx3 |
| chr11 | 95001760 | 95007115 | NM_007867:Dlx4 | − | NM_007867 | Dlx4 |
| chr11 | 95371159 | 95375879 | NM_130858:Nxph3 | − | NM_130858 | Nxph3 |
| chr11 | 95724872 | 95776185 | NM_008081:B4galnt2 | − | NM_008081 | B4galnt2 |
| chr11 | 96055674 | 96057913 | NM_008267:Hoxb13 | + | NM_008267 | Hoxb13 |
| chr11 | 96160484 | 96162883 | NM_008269:Hoxb6 | + | NM_008269 | Hoxb6 |
| chr11 | 96132643 | 96137907 | NM_008270:Hoxb9 | + | NM_008270 | Hoxb9 |
| chr11 | 96126477 | 96126579 | NR_029721:Mir196a-1 | + | NR_029721 | Mir196a-1 |
| chr11 | 96147959 | 96151477 | NM_010460:Hoxb7 | + | NM_010460 | Hoxb7 |
| chr11 | 96143218 | 96146639 | NM_010461:Hoxb8 | + | NM_010461 | Hoxb8 |
| chr11 | 98186730 | 98190959 | NM_010895:Neurod2 | − | NM_010895 | Neurod2 |
| chr11 | 100939724 | 100941819 | NM_010475:Hsd17b1 | + | NM_010475 | Hsd17b1 |
| chr11 | 101823771 | 101828329 | NM_024449:Sost | − | NM_024449 | Sost |
| chr11 | 103588676 | 103611135 | NM_011719:Wnt9b | − | NM_011719 | Wnt9b |
| chr11 | 103994195 | 104036832 | NM_007762:Crhr1 | + | NM_007762 | Crhr1 |
| chr11 | 115176505 | 115183232 | NM_176847:Ush1g | − | NM_176847 | Ush1g |
| chr11 | 116142252 | 116145252 | NM_010254:Galr2 | + | NM_010254 | Galr2 |
| chr11 | 116396053 | 116397989 | NM_011451:Sphk1 | + | NM_011451 | Sphk1 |
| chr11 | 116393757 | 116397989 | NM_001172472:Sphk1 | + | NM_001172472 | Sphk1 |
| chr11 | 116393757 | 116397989 | NM_001172473:Sphk1 | + | NM_001172473 | Sphk1 |
| chr11 | 116393224 | 116397989 | NM_001172475:Sphk1 | + | NM_001172475 | Sphk1 |
| chr11 | 116394551 | 116397989 | NM_025367:Sphk1 | + | NM_025367 | Sphk1 |
| chr11 | 118938884 | 118947551 | NM_007625:Cbx4 | − | NM_007625 | Cbx4 |
| chr11 | 120392040 | 120400298 | NM_008101:Gcgr | + | NM_008101 | Gcgr |
| chr11 | 120515102 | 120522151 | NM_175263:Notum | − | NM_175263 | Notum |
| chr12 | 11097007 | 11157648 | NM_001168564:Kcns3 | − | NM_001168564 | Kcns3 |
| chr12 | 11097007 | 11157179 | NM_173417:Kcns3 | − | NM_173417 | Kcns3 |
| chr12 | 57796625 | 57812217 | NM_011041:Pax9 | + | NM_011041 | Pax9 |
| chr12 | 87762593 | 87862578 | NM_011934:Esrrb | + | NM_011934 | Esrrb |
| chr12 | 103367628 | 103504959 | NM_172152:Slc24a4 | + | NM_172152 | Slc24a4 |
| chr12 | 8304723 | 8308760 | NM_013527:Gdf7 | − | NM_013527 | Gdf7 |
| chr12 | 9581247 | 9588306 | NM_011859:Osr1 | + | NM_011859 | Osr1 |
| chr12 | 56699903 | 56703004 | NM_020287:Insm2 | + | NM_020287 | Insm2 |
| chr12 | 57632923 | 57636093 | NM_001146198:Nkx2-1 | − | NM_001146198 | Nkx2-1 |
| chr12 | 57632923 | 57637895 | NM_009385:Nkx2-1 | − | NM_009385 | Nkx2-1 |
| chr12 | 59312790 | 59317023 | NM_009216:Sstr1 | + | NM_009216 | Sstr1 |
| chr12 | 74040931 | 74045886 | NM_011384:Six6 | + | NM_011384 | Six6 |
| chr12 | 85910801 | 85936407 | NM_007701:Vsx2 | + | NM_007701 | Vsx2 |
| chr12 | 105709418 | 105711446 | NM_010351:Gsc | − | NM_010351 | Gsc |
| chr12 | 112680871 | 112693229 | NM_009396:Tnfaip2 | + | NM_009396 | Tnfaip2 |
| chr13 | 73397944 | 73407068 | NM_018885:Irx4 | + | NM_018885 | Irx4 |
| chr13 | 13876805 | 13920162 | NM_010317:Gng4 | + | NM_010317 | Gng4 |
| chr13 | 48758404 | 48761876 | NM_007526:Barx1 | + | NM_007526 | Barx1 |
| chr13 | 51526410 | 51662453 | NM_009167:Shc3 | − | NM_009167 | Shc3 |
| chr13 | 22094044 | 22101610 | NM_019429:Prss16 | − | NM_019429 | Prss16 |
| chr13 | 31650038 | 31652843 | NM_008239:Foxq1 | + | NM_008239 | Foxq1 |
| chr13 | 31898514 | 31902504 | NM_008592:Foxc1 | + | NM_008592 | Foxc1 |
| chr13 | 40811043 | 40825812 | NM_001122948:Tcfap2a | − | NM_001122948 | Tcfap2a |
| chr13 | 40811043 | 40829192 | NM_011547:Tcfap2a | − | NM_011547 | Tcfap2a |
| chr13 | 56351859 | 56353524 | NM_010896:Neurog1 | − | NM_010896 | Neurog1 |
| chr13 | 95645581 | 95653636 | NM_011021:Otp | + | NM_011021 | Otp |
| chr13 | 99124199 | 99126660 | NM_008242:Foxd1 | + | NM_008242 | Foxd1 |
| chr13 | 113827741 | 113827832 | NR_029961:Mir449a | + | NR_029961 | Mir449a |
| chr13 | 113784075 | 113790602 | NM_001037914:Gm6320 | + | NM_001037914 | Gm6320 |
| chr13 | 113826190 | 113826299 | NR_030452:Mir449c | + | NR_030452 | Mir449c |
| chr13 | 113827626 | 113827706 | NR_030602:Mir449b | + | NR_030602 | Mir449b |
| chr13 | 117088477 | 117099896 | NM_021459:Isl1 | − | NM_021459 | Isl1 |
| chr14 | 58691522 | 58731557 | NM_013518:Fgf9 | + | NM_013518 | Fgf9 |

TABLE S5B-continued

Polycomb target genes in PDs

| Chr | Start | End | Gene_ID | Strand | RefSeq_ID | Symbol |
|---|---|---|---|---|---|---|
| chr14 | 30853124 | 31166672 | NM_001083616:Cacna1d | − | NM_001083616 | Cacna1d |
| chr14 | 63817751 | 63864097 | NM_008092:Gata4 | − | NM_008092 | Gata4 |
| chr14 | 67852128 | 68048604 | NM_010095:Ebf2 | + | NM_010095 | Ebf2 |
| chr14 | 13174405 | 13178379 | NM_080433:Fezf2 | − | NM_080433 | Fezf2 |
| chr14 | 33221388 | 33279095 | NM_009891:Chat | − | NM_009891 | Chat |
| chr14 | 33275622 | 33278036 | NM_021712:Slc18a3 | − | NM_021712 | Slc18a3 |
| chr14 | 57717438 | 57723539 | NM_008125:Gjb2 | − | NM_008125 | Gjb2 |
| chr14 | 65209493 | 65209578 | NR_029813:Mir124a-1 | + | NR_029813 | Mir124a-1 |
| chr14 | 67254094 | 67352166 | NM_013461:Adra1a | + | NM_013461 | Adra1a |
| chr14 | 69790075 | 69793597 | NM_010920:Nkx2-6 | + | NM_010920 | Nkx2-6 |
| chr14 | 70477251 | 70479964 | NM_018781:Egr3 | + | NM_018781 | Egr3 |
| chr14 | 70953862 | 70973349 | NM_021877:Hr | + | NM_021877 | Hr |
| chr15 | 72342548 | 72376709 | NM_001033876:Kcnk9 | − | NM_001033876 | Kcnk9 |
| chr15 | 11769651 | 11835429 | NM_008728:Npr3 | − | NM_008728 | Npr3 |
| chr15 | 11769651 | 11835429 | NM_001039181:Npr3 | − | NM_001039181 | Npr3 |
| chr15 | 64530596 | 64753858 | NM_009623:Adcy8 | − | NM_009623 | Adcy8 |
| chr15 | 73617365 | 73670101 | NM_001033365:Gm628 | − | NM_001033365 | Gm628 |
| chr15 | 78500436 | 78548543 | NM_183141:Elfn2 | − | NM_183141 | Elfn2 |
| chr15 | 10963471 | 10967723 | NM_178717:Rxfp3 | − | NM_178717 | Rxfp3 |
| chr15 | 31221234 | 31297514 | NM_027496:Ankrd33b | − | NM_027496 | Ankrd33b |
| chr15 | 31253709 | 31297514 | NM_026153:Ankrd33b | − | NM_026153 | Ankrd33b |
| chr15 | 31221234 | 31297514 | NM_001164441:Ankrd33b | − | NM_001164441 | Ankrd33b |
| chr15 | 74346625 | 74419894 | NM_174991:Bai1 | + | NM_174991 | Bai1 |
| chr15 | 75395174 | 75397612 | NM_011837:Ly6h | − | NM_011837 | Ly6h |
| chr15 | 75395174 | 75397078 | NM_001135689:Ly6h | − | NM_001135689 | Ly6h |
| chr15 | 75395174 | 75397286 | NM_001135688:Ly6h | − | NM_001135688 | Ly6h |
| chr15 | 75577272 | 75578352 | NM_194350:Mafa | − | NM_194350 | Mafa |
| chr15 | 85365866 | 85411159 | NM_001163633:Wnt7b | − | NM_001163633 | Wnt7b |
| chr15 | 85365866 | 85412251 | NM_009528:Wnt7b | − | NM_009528 | Wnt7b |
| chr15 | 85365866 | 85408500 | NM_001163634:Wnt7b | − | NM_001163634 | Wnt7b |
| chr15 | 98465194 | 98474961 | NM_007581:Cacnb3 | + | NM_007581 | Cacnb3 |
| chr15 | 98462650 | 98474961 | NM_001044741:Cacnb3 | + | NM_001044741 | Cacnb3 |
| chr15 | 98620287 | 98624261 | NM_021279:Wnt1 | + | NM_021279 | Wnt1 |
| chr15 | 98602182 | 98608581 | NM_011718:Wnt10b | − | NM_011718 | Wnt10b |
| chr15 | 98723457 | 98728971 | NM_007857:Dhh | − | NM_007857 | Dhh |
| chr15 | 99055406 | 99073248 | NM_010601:Kcnh3 | + | NM_010601 | Kcnh3 |
| chr15 | 99421458 | 99425260 | NM_009701:Aqp5 | + | NM_009701 | Aqp5 |
| chr15 | 99501148 | 99531559 | NM_009597:Accn2 | + | NM_009597 | Accn2 |
| chr15 | 100451770 | 100467286 | NM_174992:Smagp | − | NM_174992 | Smagp |
| chr15 | 100451770 | 100467296 | NM_001033872:Smagp | − | NM_001033872 | Smagp |
| chr16 | 35541447 | 35664344 | NM_013661:Sema5b | + | NM_013661 | Sema5b |
| chr16 | 11984205 | 12270997 | NM_001174086:Shisa9 | + | NM_001174086 | Shisa9 |
| chr16 | 11984205 | 12270997 | NM_028277:Shisa9 | + | NM_028277 | Shisa9 |
| chr16 | 35155721 | 35304635 | NM_001012765:Adcy5 | + | NM_001012765 | Adcy5 |
| chr16 | 44240292 | 44332951 | NM_001159419:Sidt1 | − | NM_001159419 | Sidt1 |
| chr16 | 44240292 | 44332951 | NM_198034:Sidt1 | − | NM_198034 | Sidt1 |
| chr16 | 94085504 | 94348638 | NM_011377:Sim2 | + | NM_011377 | Sim2 |
| chr16 | 17797374 | 17808380 | NM_153790:Scarf2 | + | NM_153790 | Scarf2 |
| chr16 | 17913646 | 17915152 | NM_029469:Gsc2 | − | NM_029469 | Gsc2 |
| chr16 | 18581805 | 18587062 | NM_011532:Tbx1 | − | NM_011532 | Tbx1 |
| chr16 | 20589654 | 20598540 | NM_182636:Vwa5b2 | + | NM_182636 | Vwa5b2 |
| chr16 | 20589654 | 20605450 | NM_001144953:Vwa5b2 | + | NM_001144953 | Vwa5b2 |
| chr17 | 8994609 | 9179513 | NM_011866:Pde10a | + | NM_011866 | Pde10a |
| chr17 | 14416512 | 14541797 | NM_022315:Smoc2 | + | NM_022315 | Smoc2 |
| chr17 | 8627287 | 8635361 | NM_009309:T | + | NM_009309 | T |
| chr17 | 23878165 | 23882796 | NM_028416:Kremen2 | − | NM_028416 | Kremen2 |
| chr17 | 26975609 | 26978510 | NM_008700:Nkx2-5 | − | NM_008700 | Nkx2-5 |
| chr17 | 46434369 | 46440220 | NM_207666:Dlk2 | + | NM_207666 | Dlk2 |
| chr17 | 46579396 | 46624624 | NM_001162864:Ttbk1 | − | NM_001162864 | Ttbk1 |
| chr17 | 56650670 | 56651906 | NM_011483:Znrf4 | − | NM_011483 | Znrf4 |
| chr17 | 57418522 | 57468659 | NM_001163816:Vav1 | + | NM_001163816 | Vav1 |
| chr17 | 57418522 | 57468659 | NM_011691:Vav1 | + | NM_011691 | Vav1 |
| chr17 | 57418522 | 57468659 | NM_001163815:Vav1 | + | NM_001163815 | Vav1 |
| chr17 | 80106292 | 80114381 | NM_009994:Cyp1b1 | − | NM_009994 | Cyp1b1 |
| chr17 | 86083607 | 86087594 | NM_011380:Six2 | − | NM_011380 | Six2 |
| chr17 | 86006697 | 86017705 | NR_015387:Six3os1 | − | NR_015387 | Six3os1 |
| chr17 | 86010602 | 86017615 | NR_015386:Six3os1 | − | NR_015386 | Six3os1 |
| chr17 | 86014726 | 86018751 | NR_015385:Six3os1 | − | NR_015385 | Six3os1 |
| chr17 | 86020173 | 86025531 | NM_011381:Six3 | + | NM_011381 | Six3 |
| chr17 | 88145160 | 88197334 | NM_199251:Kcnk12 | − | NM_199251 | Kcnk12 |
| chr17 | 93598761 | 93604829 | NM_009625:Adcyap1 | + | NM_009625 | Adcyap1 |
| chr18 | 22851655 | 23197164 | NM_001161483:Nol4 | − | NM_001161483 | Nol4 |
| chr18 | 66216509 | 66451492 | NM_178793:Ccbe1 | − | NM_178793 | Ccbe1 |
| chr18 | 67293479 | 67386445 | NM_010307:Gnal | + | NM_010307 | Gnal |
| chr18 | 74602272 | 74931131 | NM_201600:Myo5b | + | NM_201600 | Myo5b |
| chr18 | 80802943 | 80904912 | NM_001164111:Nfatc1 | − | NM_001164111 | Nfatc1 |

TABLE S5B-continued

| Polycomb target genes in PDs | | | | | | |
|---|---|---|---|---|---|---|
| Chr | Start | End | Gene_ID | Strand | RefSeq_ID | Symbol |
| chr18 | 80802943 | 80904912 | NM_001164112:Nfatc1 | – | NM_001164112 | Nfatc1 |
| chr18 | 80802943 | 80909810 | NM_198429:Nfatc1 | – | NM_198429 | Nfatc1 |
| chr18 | 80802943 | 80909810 | NM_001164110:Nfatc1 | – | NM_001164110 | Nfatc1 |
| chr18 | 80844173 | 80904912 | NM_016791:Nfatc1 | – | NM_016791 | Nfatc1 |
| chr18 | 80844173 | 80909810 | NM_001164109:Nfatc1 | – | NM_001164109 | Nfatc1 |
| chr18 | 82561887 | 82576169 | NM_008082:Galr1 | – | NM_008082 | Galr1 |
| chr18 | 37303622 | 37347311 | NM_001003672:Pcdhac2 | + | NM_001003672 | Pcdhac2 |
| chr18 | 42554250 | 42555747 | NM_138945:Pou4f3 | + | NM_138945 | Pou4f3 |
| chr18 | 53624199 | 53735511 | NM_001033281:Prdm6 | + | NM_001033281 | Prdm6 |
| chr18 | 66094292 | 66098743 | NM_013833:Rax | – | NM_013833 | Rax |
| chr18 | 77095143 | 77139081 | NM_001109743:Skor2 | + | NM_001109743 | Skor2 |
| chr18 | 81163112 | 81183317 | NM_178280:Sall3 | – | NM_178280 | Sall3 |
| chr19 | 42863084 | 43462801 | NM_001081257:Hpse2 | – | NM_001081257 | Hpse2 |
| chr19 | 25685026 | 25698411 | NM_177360:Dmrt3 | + | NM_177360 | Dmrt3 |
| chr19 | 5549136 | 5560575 | NM_019935:Ovol1 | – | NM_019935 | Ovol1 |
| chr19 | 16946805 | 16948320 | NM_008023:Foxb2 | – | NM_008023 | Foxb2 |
| chr19 | 43686814 | 43690382 | NM_008699:Nkx2-3 | + | NM_008699 | Nkx2-3 |
| chr19 | 44831883 | 44910517 | NM_011037:Pax2 | + | NM_011037 | Pax2 |
| chr19 | 45225204 | 45231433 | NM_021901:Tlx1 | + | NM_021901 | Tlx1 |
| chr19 | 45308217 | 45309726 | NM_010691:Lbx1 | – | NM_010691 | Lbx1 |
| chr19 | 45811287 | 45817374 | NM_001166363:Fgf8 | – | NM_001166363 | Fgf8 |
| chr19 | 45811287 | 45817374 | NM_001166361:Fgf8 | – | NM_001166361 | Fgf8 |
| chr19 | 45811287 | 45817374 | NM_010205:Fgf8 | – | NM_010205 | Fgf8 |
| chr19 | 45811287 | 45817374 | NM_001166362:Fgf8 | – | NM_001166362 | Fgf8 |
| chr19 | 46210175 | 46222815 | NM_008852:Pitx3 | – | NM_008852 | Pitx3 |
| chr19 | 54119671 | 54123472 | NM_007417:Adra2a | + | NM_007417 | Adra2a |
| chr19 | 59240676 | 59244519 | NM_009501:Vax1 | – | NM_009501 | Vax1 |

TABLE S6

| Accession numbers of all datasets used in this study | | | | |
|---|---|---|---|---|
| Data Type | Factor | Cell Type | Factor Accession Number | Background Accession Number |
| ChIP-seq | SMC1 | ESC | GSM560341, GSM560342 | GSM1082343 |
| ChIP-seq | CTCF | ESC | GSM747534, GSM747535, GSM747536 | GSM747545, GSM747546 |
| ChIP-seq | Pol2 | ESC | GSM515670, GSM515672 | GSM1082343 |
| ChIP-seq | OCT4 | ESC | GSM1082340 | GSM1082343 |
| ChIP-seq | SOX2 | ESC | GSM1082341 | GSM1082343 |
| ChIP-seq | NANOG | ESC | GSM1082342 | GSM1082343 |
| ChIP-seq | KLF4 | ESC | GSM288354 | GSM1082343 |
| ChIP-seq | ESRRB | ESC | GSM288355 | GSM1082343 |
| ChIP-seq | MED1 | ESC | GSM560348 | GSM1082343 |
| ChIP-seq | MED12 | ESC | GSM560345, GSM560346 | GSM1082343 |
| ChIP-seq | H3K27ac | ESC | GSM594579 | GSM1082343 |
| ChIP-seq | H3K4me3 | ESC | GSM1082344, GSM307149 | GSM1082344 |
| ChIP-seq | H3K36me3 | ESC | GSM307153 | GSM1082345 |
| ChIP-seq | H3K27me3 | ESC | GSM1397343 | GSM1082343 |
| ChIP-seq | SUZ12 | ESC | GSM480162 | GSM480164 |
| ChIP-seq | EZH2 | ESC | GSM480161 | GSM480164 |
| ChIP-seq | SOX2 | NPC | GSM1050288, GSM1050289 | GSM1050290 |

TABLE S6-continued

| Accession numbers of all datasets used in this study | | | | |
|---|---|---|---|---|
| Data Type | Factor | Cell Type | Factor Accession Number | Background Accession Number |
| ChIP-seq | BRN2 | NPC | GSM1050286, GSM1050287 | GSM1050290 |
| ChIP-seq | SMC1 | NPC | GSM883646 | GSM883648 |
| ChIP-seq | CTCF | NPC | GSM883647 | GSM883648 |
| RNA-seq | none | ProB | SRR499680 | none |
| RNA-seq | none | Th1 | SRR557795 | none |
| RNA-seq | none | C2C12 | SRR496442 | none |
| RNA-seq | none | macrophage | SRR836120 | none |
| ChIA-PET | SMC1 | ESC | GSM1397342 | none |
| ChIA-PET | SMC1 | ESC | GSM1480237 | none |

LENGTHY TABLES

The patent application contains a lengthy table section. A copy of the tables are available in electronic form from the USPTO web site. An electronic copy of the tables will also be available from the USPTO upon request and payment of the fee set forth in 37 CFR 1.19(b)(3).

The Tables referenced herein were previously submitted in U.S. Provisional Application No. 62/234,770, and are hereby incorporated by reference in their entirety.

We claim:

1. A method of decreasing expression of a murine Nanog gene, the method comprising contacting a murine embryonic stem cell with a gene modulatory composition , wherein the Nanog gene is located in an insulated neighborhood (IN) formed by looping of two CTCF interaction sites occupied by cohesin on a chromosome in the cell, and the gene modulatory composition is a CRISPR/Cas9 system comprising Cas9 and a first guide RNA complementary to SEQ ID NO: 8 and a second guide RNA complementary to SEQ ID NO: 9, wherein the gene modulatory composition deletes the sequence of one of the CTCF interaction sites and disrupts binding of CTCF protein, and wherein expression of the Nanog gene is decreased by about 40%.

2. The method of claim 1, wherein the insulated neighborhood is contained within a topologically active domain (TAD).

3. The method of claim 1, wherein the IN comprises a super-enhancer domain (SD).

4. The method of claim 3, wherein the SD is chr6: 122640118 -122657871.

5. A method of decreasing expression of a Nanog gene in a murine embryonic stem cell in cell culture, the method comprising deleting a DNA sequence comprising one of two CTCF interaction sites that flank the Nanog gene on a chromosome in the cell using a CRISPR/Cas9 system, thereby generating a deleted CTCF interaction site and disrupting binding of CTCF protein to the deleted CTCF interaction site, wherein the Nanog gene is located in an insulated neighborhood (IN) formed by looping of the two CTCF interaction sites occupied by cohesin on the chromosome; and wherein the CRISPR/Cas9 system comprises Cas9 and a first guide RNA complementary to SEQ ID NO: 8 and a second guide RNA complementary to SEQ ID NO: 9, and wherein expression of the Nanog gene is decreased by about 40%.

6. The method of claim 5, wherein the insulated neighborhood (IN) is contained within a topologically active domain (TAD).

7. The method of claim 5, wherein the IN comprises a super-enhancer domain (SD).

8. The method of claim 7, wherein the SD is chr6: 122640118 -122657871.

* * * * *

SEQUENCE LISTING

<160> NUMBER OF SEQ ID NOS: 44

<210> SEQ ID NO 1
<211> LENGTH: 20
<212> TYPE: DNA
<213> ORGANISM: Artificial
<220> FEATURE:

```
<223> OTHER INFORMATION: Target specific oligonucleotides

<400> SEQUENCE: 1

atgacataat gagattcacg                                                  20


<210> SEQ ID NO 2
<211> LENGTH: 20
<212> TYPE: DNA
<213> ORGANISM: Artificial
<220> FEATURE:
<223> OTHER INFORMATION: Target specific oligonucleotides

<400> SEQUENCE: 2

actgaagtgg aaggtgagtg                                                  20


<210> SEQ ID NO 3
<211> LENGTH: 20
<212> TYPE: DNA
<213> ORGANISM: Artificial
<220> FEATURE:
<223> OTHER INFORMATION: Target specific oligonucleotides

<400> SEQUENCE: 3

cgacccacct cctaacctta                                                  20


<210> SEQ ID NO 4
<211> LENGTH: 20
<212> TYPE: DNA
<213> ORGANISM: Artificial
<220> FEATURE:
<223> OTHER INFORMATION: Target specific oligonucleotides

<400> SEQUENCE: 4

cattggctgt caactatacc                                                  20


<210> SEQ ID NO 5
<211> LENGTH: 20
<212> TYPE: DNA
<213> ORGANISM: Artificial
<220> FEATURE:
<223> OTHER INFORMATION: Target specific oligonucleotides

<400> SEQUENCE: 5

cccgtcctaa attatctgcg                                                  20


<210> SEQ ID NO 6
<211> LENGTH: 20
<212> TYPE: DNA
<213> ORGANISM: Artificial
<220> FEATURE:
<223> OTHER INFORMATION: Target specific oligonucleotides

<400> SEQUENCE: 6

cagaagctga caacaccaag                                                  20


<210> SEQ ID NO 7
<211> LENGTH: 20
<212> TYPE: DNA
<213> ORGANISM: Artificial
<220> FEATURE:
<223> OTHER INFORMATION: Target specific oligonucleotides

<400> SEQUENCE: 7

acactcaaac tcgaggactc                                                  20
```

<210> SEQ ID NO 8
<211> LENGTH: 20
<212> TYPE: DNA
<213> ORGANISM: Artificial
<220> FEATURE:
<223> OTHER INFORMATION: Target specific oligonucleotides

<400> SEQUENCE: 8
ttaaacacat cataagatga 20

<210> SEQ ID NO 9
<211> LENGTH: 20
<212> TYPE: DNA
<213> ORGANISM: Artificial
<220> FEATURE:
<223> OTHER INFORMATION: Target specific oligonucleotides

<400> SEQUENCE: 9
tgaactacgt agcaagttcc 20

<210> SEQ ID NO 10
<211> LENGTH: 20
<212> TYPE: DNA
<213> ORGANISM: Artificial
<220> FEATURE:
<223> OTHER INFORMATION: Target specific oligonucleotides

<400> SEQUENCE: 10
cagtctgaac tgcacatagc 20

<210> SEQ ID NO 11
<211> LENGTH: 20
<212> TYPE: DNA
<213> ORGANISM: Artificial
<220> FEATURE:
<223> OTHER INFORMATION: Target specific oligonucleotides

<400> SEQUENCE: 11
aaagctaaac tctcccaagt 20

<210> SEQ ID NO 12
<211> LENGTH: 20
<212> TYPE: DNA
<213> ORGANISM: Artificial
<220> FEATURE:
<223> OTHER INFORMATION: Target specific oligonucleotides

<400> SEQUENCE: 12
ccacgtggga aatctaactc 20

<210> SEQ ID NO 13
<211> LENGTH: 20
<212> TYPE: DNA
<213> ORGANISM: Artificial
<220> FEATURE:
<223> OTHER INFORMATION: Target specific oligonucleotides

<400> SEQUENCE: 13
gaagtgaagc cttctcgtta 20

<210> SEQ ID NO 14
<211> LENGTH: 20
<212> TYPE: DNA
<213> ORGANISM: Artificial
<220> FEATURE:
<223> OTHER INFORMATION: Target specific oligonucleotides

<400> SEQUENCE: 14
gaagagtgtg actgaaaaga 20

<210> SEQ ID NO 15
<211> LENGTH: 20
<212> TYPE: DNA
<213> ORGANISM: Artificial
<220> FEATURE:
<223> OTHER INFORMATION: Target specific oligonucleotides

<400> SEQUENCE: 15
tctcacggag cctcaggaga 20

<210> SEQ ID NO 16
<211> LENGTH: 2545
<212> TYPE: DNA
<213> ORGANISM: Artificial
<220> FEATURE:
<223> OTHER INFORMATION: PRDM14 locus reference sequence

<400> SEQUENCE: 16
ccgtttccct agcacagagc cacccaggac cagaaataac agcttcacaa aagagctcgc 60
tctgtacaca tgggtcccaa ggaagaagtg agattctttc cccctcactg aggaaagggg 120
gccgtctttc ctgctaaaga gaaagaaagt gaagtttcct ggaatcttct ttttctcctc 180
gtgaatctca ttatgtcatc gaaattctag gcttaatcga tgcttctgcc ccagcttctc 240
aattatctga gatttcagat gcccaccgcg tccagctcag aaaatcaaat tgtggttact 300
attctagaca tttccagcag agggcgcttc ggtgcaggta gccagaacac cgaagtcatc 360
cagtttctgg ccgcaaactc agattactag attgccaaca gggtttccag aacgtgggta 420
aaagagactg aagtggcaat ccccacgaaa acaaaaaaaa caaaacaaaa cggtcaaggg 480
tgcttcgtac tgaagtggaa ggtgagtgag gctgtgtggg cagatcgcaa ccgtcattta 540
gaacaaacct gaagcagagc ggtgtaaatg actgtattcc cagcactcaa gagaatagct 600
ggagctttgg ccagcctaca gaggagaccc tgtgctgttc tcagtattca gttatgctac 660
cctctaatga agtacattgt acttcctggt aatttcattt ttatgaaagg caatactgga 720
ttcctgcctt tcttcctttc tgcctgtagt ccgtttttag gttgatcaac aggttgacat 780
tacacttgtg acaattctct tgcctcacgg aacgataacg tttcaaaggg gaagactaat 840
taggattggt accgttagtt ttttgtcaac acagccagag tcatctggga agagggaacc 900
tgagctgggg gtttacctcc atcagatcgt ttgtgagtat gtctgtagga aatgttctta 960
atcattaata tcggagagcc agaccatccc cggtggtgcc actgctgggc cggtagtcct 1020
gggtgataca aggaggcagg tttactggct agtaagcagc actcctttgc aggctctgct 1080
ccactctctc cttcctccct tctgccttga gttcctgtct tgacttccct cggtgatgag 1140
ctgtaccctg aaaaccagat aacttgtcct taatttactt ttggtcatgg tagacttttt 1200
attattgttg ttttgttgtt gttgttgttg ttgttgtttt tatgtgtatg ggtgttttgc 1260
ttacaagtat gtctgggcac catattcatg cacagtgatg cccaatgatt ccagaaaagg 1320
gccgaggatt ccctgggact ggagttacag aaagttagga gctgccatgt gtgtgcagcg 1380
aatcaaactc tggccttctg gaagagcagc cagtgctctt aactgctgat ccatctttct 1440
agcccacttc gtcacgttgt ttatcacagc agtcgaaagc agactaggac atgatggaaa 1500
ggagtcaaaa gcttggtcaa gggatcttta gagatgggaa ggggaacttt ttaaacgttg 1560
gtcctgccat gctctcccag aggcatggtg ccttctctgt ctttcctagt gctttccttt 1620

```
gcaaagcaag caaatatcat ctactttggt gttttaagaa atagtacggg ggggctggtg   1680

agatggctca gtgggttaga gcacccgact gctcttccga aggtccagag ttcaaatccc   1740

agcaaccaca tggtggctca caaccatccg taacgagatc tgactccctc ttctggtgtg   1800

tctgaagaca gctacaatgt acttacatat aataaataaa taaatcttta aaaaaaaaaa   1860

aaaaaaaaaa aaaagaaata gtacggggct ggtgagatgg cttagtgggt aaaagcaccc   1920

gactgctctt ccgaaggttc aaagttcaaa tcccagcaac cacatggtgg ctcacaatca   1980

cccgtaatga gatctgactc cctcttctga agtgtctaaa gacagctaca gtgtacatta   2040

tatgtaataa ataaatgttt ttttttaaa aagaaagaaa tagtacattt ctcaatggcc   2100

tcgagaatta acctgcagga aaaggaaaat gctgtgtttc ttctccaaaa atcctatagg   2160

tggcgcacag acaccggttt caagtgatgg gtcccagctt tgacctttct gcccaagtcc   2220

ggtttgtcgg gaactcttct tccttctgcc tctacccct gccagaatta cagggctgct   2280

cttggctctg agttgttcgg tgtaagtgag aaagcaagca gcacctgcag tcctgaggtg   2340

tcacctagca gctcccttct aacaaggctg cgctcctctt gggaggacat agccaagagt   2400

cactgaaggg caagctccct caaagctcct ctctaaggtt aaatagcagc atgacctcga   2460

cccacctcct aaccttaagg ttcatattct ctctgcaaaa catcaagggg gtctggagga   2520

acactgaagt ccctcctgcc gcatg                                         2545
```

```
<210> SEQ ID NO 17
<211> LENGTH: 118
<212> TYPE: DNA
<213> ORGANISM: Artificial
<220> FEATURE:
<223> OTHER INFORMATION: PRDM14 C1-2 Deletion allele sequence

<400> SEQUENCE: 17

tctcctgcta aagagaaaga aagtgaagtt tcctggaatc ttctttttct cctccacctc     60

ctaaccttaa ggttcatatt ctctctgcaa aacatcaagg gggtctggag gaacactg      118
```

```
<210> SEQ ID NO 18
<211> LENGTH: 799
<212> TYPE: DNA
<213> ORGANISM: Artificial
<220> FEATURE:
<223> OTHER INFORMATION: MIR290 locus reference sequence

<400> SEQUENCE: 18

ccaggcctca ctagtgtcag gtcgtgagtc atgcacagcc atgatttctg catccttggc     60

caccttgctc agttttctgg agtgttgaga ttcaatgcga acaccaccac agctgggcaa    120

aatctaataa cccaggatag gatgggagca ttggctgtca actataccag gtgtgcaaat    180

cttgggtttt gaggcctcat ttgtaaggtg ccttatacct ttagccccag cccacttttt    240

tttccccctg ctgtataaaa ttcaggtgtg agtacaattt ttctttttaa agatttataa    300

gtgttctgta gctatcttca gattcaccca aagaaggcat tggatcccat tacagatgat    360

tgcaagccac catgtagttg ctgggaattg aactcaggac ctctgactta accactccag    420

cccttgagta caatttttga aaaattacct tgtgggtctt tatgctgtga cttggccagt    480

agatggcagt cttggtccat ggaaatgtct aggactctgg atatttttcc ttttctgtgg    540

tctttactga tcttcaaacc tgctaaccag ccaatccccg tcctaaatta tctgcgtgga    600

atctacatca aacccagtga gctccatcaa aggttgagtg tttaggtctc aagcagaaca    660
```

attttgtcaa cctgcactta ctgggcctcc tgacctaaga cggtcccatg taacaggatg 720
accttgagtg atcttgtctc cacctcacca tataccagag gctggccttt aaaagttcca 780
cctcaagtgc ttcaaagca 799

<210> SEQ ID NO 19
<211> LENGTH: 160
<212> TYPE: DNA
<213> ORGANISM: Artificial
<220> FEATURE:
<223> OTHER INFORMATION: MIR290 C1 deletion allele sequence

<400> SEQUENCE: 19
aaatctaata acccaggata ggatgggagc attggctgtc aatctatatc aaacccagtg 60
agctccatca aaggttgagt gtttaggtct caagtagaac aattttgtca acctgcactt 120
actgggcctc ctgacctaag acggtcccat gtaacaggat 160

<210> SEQ ID NO 20
<211> LENGTH: 737
<212> TYPE: DNA
<213> ORGANISM: Artificial
<220> FEATURE:
<223> OTHER INFORMATION: POU5F1 locus reference sequence

<400> SEQUENCE: 20
ctcagccatc tccctgttga gctgtcaagc agagaggccc caacaacaac acaggaaatt 60
gccagtgttc ttgattgccc aaaagaacca gatgaccaga agctgacaac accaagaggc 120
taggggtctt ccagttggcc ttgtactgtt gcaactgtca gggaaaggat gtaaccagag 180
ggcctctggg actcctctca cccttgatag tttgagggat atgagcaaat tacacggtta 240
tcagaaggtg gccatagtga cactgaaaat tggcccattg gcttcaaaga tttaccaaag 300
taccgtccgt attttctacc tacggtgtgc tggagcctag aggacactag gggcgcgct 360 gagctcgcgg aagccaccca gagtccttcc aggagactcc cttaaaggtt gatcaaattg 420
ttctttgcca aactgaattt atcataaaaa ttatacttta ttttgtatta ctttgtgtac 480
atgggtgttt tgccttcaca gatgcgtctg gtgcacctga gaagccagaa aagagaacag 540
gagtgaacag gtttgtgggg gctgacactc aaactcgagg actctgggaa agcatcgagt 600
gctcttaacc attgagccat ctctccagcc catctgtttt cttttgccgg aggaaggggc 660
tctgagaaag gatcttacct gtagcccagg ctggcccagt tcaccatgtg atgaaggctc 720
ctttcaaatc caagcta 737

<210> SEQ ID NO 21
<211> LENGTH: 163
<212> TYPE: DNA
<213> ORGANISM: Artificial
<220> FEATURE:
<223> OTHER INFORMATION: POU5F1 C1 deletion allele sequence

<400> SEQUENCE: 21
aattgccagt gttcttgatt gcccaaaaga accagatgac cagaagctga caacaaatta 60
tactttattt tgtattactt tgtgtacatg ggtgttttgc cttcacagat gcgtctggtg 120
cacctgagaa gccagaaaag agaacaggag tgaacaggtt tgt 163

<210> SEQ ID NO 22
<211> LENGTH: 839
<212> TYPE: DNA
<213> ORGANISM: Artificial

<220> FEATURE:
<223> OTHER INFORMATION: NANOG locus reference sequence

<400> SEQUENCE: 22
tcagttgtgt gtggggtagg ccatgtgtgc cttggtgcac atgtgcaggt cagaacaact 60
tgggtgagag tctgcttcct ttttctgctc tgtatgggtt gtagggatag aattcaagtt 120
tcgcatttga attctatggt ttagcactta aacatcaaaa cctttcccag aacgtcacac 180
ttcaatgcca ttgaggaagg tgtctgtaac gctgtgtgtg tgttgttagt taaacacatc 240
ataagatgaa ggaaagctgg gagtgtcctt aacacagcag cgagcagcaa aagctacttt 300
ctcctcaagc ctggaggagt ctggtccgac agtccaccaa caggggggcgt tatttcccag 360 ccctcgtgaa gcgttgaact gtcctggtga gaagggtgat gtgcagttcc ttgtctcagc 420
agcagatgga gccataggga cgagaacaag ttcctaggtg aaggaaggag tggggggaga 480
cgaagcggaa gaagctgaag tgcatcttgg tcggtcaaat ttttcttatt gatgaaaaag 540
atgattaaag gacactgtga atttgagact attctgaact acgtagcaag ttccaggaca 600
gccagtgtta caaatcaaga cccgattttg gaagaagatg ggggctgggg aaggcgccat 660
gttccccccc ccaccccccca cccccagctc ccatctcatc tgttgctaca tttactagac 720
tgccaagaat tttctctctc agaaattaaa aaaatagtaa agaaataaag aaaaaagcca 780
ggcatgatgg ttcactctca taatcccata attccattac gtaagagaat ctctctacc 839

<210> SEQ ID NO 23
<211> LENGTH: 101
<212> TYPE: DNA
<213> ORGANISM: Artificial
<220> FEATURE:
<223> OTHER INFORMATION: NANOG C1 deletion allele sequence

<400> SEQUENCE: 23
gtctgtaacg ctgtgtgtgt gttgttagtt aaacacatca taagatccag gacagccagt 60
gttacaaatc aagacccgat tttggaagaa gatgggggct g 101

<210> SEQ ID NO 24
<211> LENGTH: 767
<212> TYPE: DNA
<213> ORGANISM: Artificial
<220> FEATURE:
<223> OTHER INFORMATION: TDGF1 locus reference sequence

<400> SEQUENCE: 24
tgagcaacaa gatgtctgca ccatcttttc atccctcgga tttttcttta tagtcgtggc 60
ttgtactgag tagacaggtt cctgtctctg acaaaaacgg aggacagaaa ccccactctt 120
ctccaaagaa gcatgctgat aaaaagtgga cacaaaccat gaactgccgt gtgacagtct 180
gaactgcaca tagccggatg aggctttcgg gtaaagacta gaattgcaag attactaaca 240
ctgttaaact ctttgttttc tgcagtcctt ggtttagact caagactctg aaacctagaa 300
actgagctca aggcttccga ggctttgaca tcgaaacacc tgatctccag taggggggcgc 360 tgcagcctag cagggcggag ctgactcttc tggccagttt tttctcctga tggtcccagt 420
aaaactcatg tcaggctcag attttagact aagggactgg aaagggggaa ttctgagaat 480
tagagctaaa gaattagagg ggttaaagag tgaagcccag gaaaatatat ttgaacaaat 540
aaaagctaaa ctctcccaag ttggacaaac aaaaacaaaa caaaaaccct ccataaatcc 600
tcaatcttta gcttcaagaa attgaatcca aaggaaccca tatccagacc cggtgctcag 660
cgtggaaaag gccagagtgc tgaaagcagc tgactcttca gtacacatgg acaaaccctg 720
gcagagctgg gcaagaaaac agacacacct gggtgtgata atgactt 767

<210> SEQ ID NO 25
<211> LENGTH: 223
<212> TYPE: DNA
<213> ORGANISM: Artificial
<220> FEATURE:
<223> OTHER INFORMATION: TDGF1 C1 deletion allele sequence

<400> SEQUENCE: 25
agacaggttc ctgtctctga caaaaacgga ggacagaaac cccactcttc tccaaagaag 60
catgctgata aaaagtggac acaaaccatg aactgccgtg tgacagtctg aactggacaa 120
acaaaaacaa aacaaaaacc ctccataaat cctcaatctt tagcttcaag aaattgaatc 180
caaaggaacc catatccaga cccggtgctc agcgtggaaa agg 223

<210> SEQ ID NO 26
<211> LENGTH: 951
<212> TYPE: DNA
<213> ORGANISM: Artificial
<220> FEATURE:
<223> OTHER INFORMATION: TCFAP2E locus reference sequence

<400> SEQUENCE: 26
gctatcttgc atctagaagt ggaaagacag ttctttaaat gcctaggcag tgtacattaa 60
cctatgacaa gcaaacactc ccctgtggat tttgctcttc agtttgcctg tatgtatgtg 120
tgcttgtatt tgcactgcat gtgtttctgg tgcccttgaa gatcagaaga aacatcaaac 180
cccctaggac tagagttaca gatggctgtg aatcaccacg tgggaaatct aactctggac 240 ttggggggt gtgtattgag agagtaattt ttagaagaaa gaagacaagc agggtaggac 300
agaaaatttt taaaaagctg gaaagaatgt aatctcatat gattttatag gataaaattt 360
taaggtacaa atgggaccac agaattagtt ccccacatga gcaagatggt cttctgtatt 420
attatttttt ttcctttttat ggtgttttgt ctgcatgtgt gtctgtgcac catgtgcatg 480
aagtgcctga gaaggccagc agagggcatc agatcccttg agatgagtta caggtggttg 540
agagacacct tatgagtcct ggaaattata cctgggtact ctggaagagc agccaggatt 600
cttaacctct gagccatctc cctggcccca atcttttgca ttcttctgtc cgtcagctat 660
tcaatccatt tcaaagtgga agtgaagcct tctcgttaag gatgacagtt atccggaagg 720
gagcatgaaa atgttccagg gccttttctt gctttatgca cactcaaagc tgaaaatctt 780
tcccatgtca atggatgaga ccatcactca atacctaaac agaaaactat gaagcctaat 840
tgcttgtgtg cttgcttaag tatatactgg ttggtgacag cttccaccaa gaaaggcata 900
ccactgattg ataacattgg taacaacatg aacttcaggt attgataggt t 951

<210> SEQ ID NO 27
<211> LENGTH: 223
<212> TYPE: DNA
<213> ORGANISM: Artificial
<220> FEATURE:
<223> OTHER INFORMATION: TCFAP2E C1 deletion allele sequence

<400> SEQUENCE: 27
tgcactgcat gtgtttctgg tgcccttgaa gatcagaaga aacatcaaac cccctaggac 60
tagagttaca gatggctgtg aatcaccacg tgggatgaca gttatccgga agggagcatg 120
aaaatgttcc agggcctttt cttgctttat gcacactcaa agctgaaaat ctttcccatg 180
tcaatggatg agaccatcac tcaatacct a aacagaaaac tat 223

<210> SEQ ID NO 28
<211> LENGTH: 1684
<212> TYPE: DNA
<213> ORGANISM: Artificial
<220> FEATURE:
<223> OTHER INFORMATION: TCFAP2E locus reference sequence

<400> SEQUENCE: 28
tgatccactt ccagctcctt ggttcattca gcatctttca cctggcccat gcccctcccc 60
ttatgcaaaa tgcctccggg atcatggcct tggcccactc caggaatgaa gctgactagc 120
actccaggac tcctggttac ttttcctttc ttgctctgtg agtcgcttca ccagaagtct 180
aaagttgggg gggagggggg gggggaagag tgtgactgaa aagatggctc agaggctacg 240
agaaccggct gctctttcaa aggagtcagg tttcatcccc agtacccaca tggcaggaat 300
ggctatctgt aattccagtt ctgatggatc tggtgagtct gacgccctct tctggccccc 360
acaggcattg cgctgcacag acaggctggc agaacacccc acacataaaa caataaagga 420
atctttaaaa aaaaaaaaaa gtctaaagaa gtcacaagtc gggctggtga gatggctcag 480
tgggtaagag cacccgactg ctcttccaaa ggtccggagt tcaaatccca gcaaccacat 540
ggtggctcac aaccatccat aatgagatct gacgccctct taagtgtctg aagacagcta 600
cagtgtactt acatataata aataaataaa tctaaaaaaa aaaaagtcaa aagtctattt 660
agtactttgc ttggagtggg tcaagcagcc aacaaatagc tactaaataa ataagtaacc 720
aaaaagataa ttacagtttt ccaaatctgt taggggactc tttggaaggg ctcttatgtg 780
accttgacct agcatagcta cacataaggc ccagttataa gtgagcacaa acgagcaact 840
gtgcttattt cttctaggag ggacatgtgc ttcatgagct acttctctgg agaccagcag 900
agctgtggaa taccagggtt tcagactggg cccttctgtt tcaggggcaa gggttcttca 960
cattgtaagc atgcaggtga tgatttctta tggttttatt ttattttttt tttttagata 1020
cagacacctg gatgaaggca tgaggaaggc agagagatac ccctgggaaa acggagacca 1080
caacaggcac agatacactg ataagacata tatacacatc ggtatgcatg ctcaaataca 1140
catggactct cagttgacat tcttggctta ttctcttcca aggctcacgt tttctcctct 1200
ttaaaacaaa acaaaacgaa acgaaacgaa acaaaacaaa caaacaaacc ccaaactttt 1260
ttgtcctcct ttgttgacag agccggattc ctcttcctaa caggtctgtc tgcaaatgtt 1320
tgagatgaaa tctcgcaaaa gatactgacg ccccatctag tggccggagc ttaccactgc 1380
agctcaacac tcccctgcct gtctcagtgg aggcacccag acagagccag ccctgccttg 1440
caagcttccg cttagcccct tgctcactct ggagtctgga accctctcac ggagcctcag 1500
gagaaggcag gtttcagtct gccttctgtt ctcaagcttc gctggccttg gcatgcagga 1560
gagcaactca accgcaagga ccgtggacag taatcatttg ctttgtggcc tttccctcac 1620
ttccccagac tacccgttac tcccatgatt ccaaagaaca cttgacagct cccaaatctg 1680
cctc 1684

<210> SEQ ID NO 29
<211> LENGTH: 97
<212> TYPE: DNA
<213> ORGANISM: Artificial
<220> FEATURE:
<223> OTHER INFORMATION: TCFAP2E C2 deletion allele sequence

<400> SEQUENCE: 29
gggggggaag agtgtgactg ccttctgttc tcaagcttcg ctggccttgg catgcaggag 60
agcaactcaa ccgcaaggac cgtggacagt aatcatt 97

<210> SEQ ID NO 30
<211> LENGTH: 27
<212> TYPE: DNA
<213> ORGANISM: Artificial
<220> FEATURE:
<223> OTHER INFORMATION: primer

<400> SEQUENCE: 30
cacatcttca aagcaaacac tattgtt 27

<210> SEQ ID NO 31
<211> LENGTH: 30
<212> TYPE: DNA
<213> ORGANISM: Artificial
<220> FEATURE:
<223> OTHER INFORMATION: primer

<400> SEQUENCE: 31
tctcctaccc attgcttctc tgctacctgc 30

<210> SEQ ID NO 32
<211> LENGTH: 18
<212> TYPE: DNA
<213> ORGANISM: Artificial
<220> FEATURE:
<223> OTHER INFORMATION: Primer

<400> SEQUENCE: 32
ttcctggaac ctgggcaa 18

<210> SEQ ID NO 33
<211> LENGTH: 23
<212> TYPE: DNA
<213> ORGANISM: Artificial
<220> FEATURE:
<223> OTHER INFORMATION: primer

<400> SEQUENCE: 33
tgatacagca cagctttcct tca 23

<210> SEQ ID NO 34
<211> LENGTH: 28
<212> TYPE: DNA
<213> ORGANISM: Artificial
<220> FEATURE:
<223> OTHER INFORMATION: primer

<400> SEQUENCE: 34
cagatttttt atttccttca gttctgtg 28

<210> SEQ ID NO 35
<211> LENGTH: 20
<212> TYPE: DNA
<213> ORGANISM: Artificial
<220> FEATURE:
<223> OTHER INFORMATION: primer

<400> SEQUENCE: 35
aggatggctc agcggttaag 20

<210> SEQ ID NO 36
<211> LENGTH: 22
<212> TYPE: DNA
<213> ORGANISM: Artificial
<220> FEATURE:
<223> OTHER INFORMATION: primer

<400> SEQUENCE: 36
agggctcacc ttcagtcaag tt 22

<210> SEQ ID NO 37
<211> LENGTH: 29
<212> TYPE: DNA
<213> ORGANISM: Artificial
<220> FEATURE:
<223> OTHER INFORMATION: primer

<400> SEQUENCE: 37
cggcctgtct actttagcct cagactcca 29

<210> SEQ ID NO 38
<211> LENGTH: 23
<212> TYPE: DNA
<213> ORGANISM: Artificial
<220> FEATURE:
<223> OTHER INFORMATION: primer

<400> SEQUENCE: 38
gggagtgact ctctgtccat tca 23

<210> SEQ ID NO 39
<211> LENGTH: 22
<212> TYPE: DNA
<213> ORGANISM: Artificial
<220> FEATURE:
<223> OTHER INFORMATION: primer

<400> SEQUENCE: 39
atttgtgtgg cctcttgttt ga 22

<210> SEQ ID NO 40
<211> LENGTH: 18
<212> TYPE: DNA
<213> ORGANISM: Artificial
<220> FEATURE:
<223> OTHER INFORMATION: primer

<400> SEQUENCE: 40
tccaggcccc gcgtgtcc 18

<210> SEQ ID NO 41
<211> LENGTH: 21
<212> TYPE: DNA
<213> ORGANISM: Artificial
<220> FEATURE:
<223> OTHER INFORMATION: linker

<400> SEQUENCE: 41
ggccgcgata tcggacagca g 21

<210> SEQ ID NO 42
<211> LENGTH: 17
<212> TYPE: DNA
<213> ORGANISM: Artificial
<220> FEATURE:
<223> OTHER INFORMATION: linker -continued

<400> SEQUENCE: 42
ctgctgtccg atatcgc 17

<210> SEQ ID NO 43
<211> LENGTH: 21
<212> TYPE: DNA
<213> ORGANISM: Artificial
<220> FEATURE:
<223> OTHER INFORMATION: linker

<400> SEQUENCE: 43
ggccgcgata tatgacagca g 21

<210> SEQ ID NO 44
<211> LENGTH: 17
<212> TYPE: DNA
<213> ORGANISM: Artificial
<220> FEATURE:
<223> OTHER INFORMATION: linker

<400> SEQUENCE: 44
ctgctgtcat atatcgc 17